(12) United States Patent
Tachas

(10) Patent No.: US 9,821,034 B2
(45) Date of Patent: Nov. 21, 2017

(54) COMBINATION THERAPY

(71) Applicant: Antisense Therapeutics Ltd, Toorak, Victoria (AU)

(72) Inventor: George Tachas, Kew (AU)

(73) Assignee: Antisense Therapeutics Ltd, Toorak, Victoria (AU)

( * ) Notice: Subject to any disclaimer, the term of this patent is extended or adjusted under 35 U.S.C. 154(b) by 5 days.

(21) Appl. No.: 15/007,011

(22) Filed: Jan. 26, 2016

(65) Prior Publication Data
US 2016/0143999 A1   May 26, 2016

Related U.S. Application Data

(62) Division of application No. 14/376,390, filed as application No. PCT/AU2013/000095 on Feb. 4, 2013, now Pat. No. 9,717,778.

(60) Provisional application No. 61/594,532, filed on Feb. 3, 2012.

(51) Int. Cl.
| | | |
|---|---|---|
| *A61P 5/08* | (2006.01) | |
| *A61K 38/27* | (2006.01) | |
| *A61K 48/00* | (2006.01) | |
| *A61K 31/7088* | (2006.01) | |
| *A61K 31/7115* | (2006.01) | |
| *A61K 31/712* | (2006.01) | |
| *A61K 45/06* | (2006.01) | |

(52) U.S. Cl.
CPC .......... *A61K 38/27* (2013.01); *A61K 31/7088* (2013.01); *A61K 31/712* (2013.01); *A61K 31/7115* (2013.01); *A61K 45/06* (2013.01)

(58) Field of Classification Search
USPC ........ 435/6.1, 6.11, 6.12, 91.1, 91.31, 320.1, 435/455, 458, 7.1; 514/44, 6.9, 8.5, 11.2, 514/11.3; 536/23.1, 24.5
See application file for complete search history.

(56) References Cited

U.S. PATENT DOCUMENTS

| | | | |
|---|---|---|---|
| 5,534,617 A | 7/1996 | Cunningham et al. | |
| 7,803,781 B2 * | 9/2010 | Dobie | C07K 14/72 514/44 R |
| 2005/0123558 A1 | 6/2005 | Ross et al. | |
| 2009/0203589 A1 * | 8/2009 | Girard | A61K 47/48215 514/1.1 |
| 2013/0316948 A1 * | 11/2013 | Longo | G01N 33/574 514/7.6 |
| 2014/0296145 A1 * | 10/2014 | Cho | A61K 38/21 514/11.4 |
| 2014/0378379 A1 | 12/2014 | Tachas | |

FOREIGN PATENT DOCUMENTS

| | | |
|---|---|---|
| EP | 1156123 A1 | 11/2001 |
| JP | 11-512298 | 10/1999 |
| JP | 2005-525106 | 8/2005 |
| JP | 2007-524373 | 8/2007 |
| JP | 2009-539803 | 11/2009 |
| WO | WO/2004/078922 * | 2/2004 |
| WO | WO 2004/078922 A3 | 9/2004 |

OTHER PUBLICATIONS

International Search Report and Written Opinion issued for PCT/AU2013/000095 dated Apr. 17, 2013.
International Preliminary Report on Patentability issued for PCT/AU2013/000095 dated Aug. 14, 2014.
Extended European Search Report issued for corresponding European application No. 13743020.3 dated Oct. 1, 2015.
ATL1103 Summary Background and Development Update (2011) Antisense Therapeutics.
ATL1103 in clinical development for diseases associated with growth hormone/IGF-I activity (2011) Antisense Therapeutics.
"Positive New Animal Data on ATL1103: Data presented today at the Thirteenth International Pituitary Congress", report published on Jun. 14, 2013 by Antisense Therapeutics.

* cited by examiner

*Primary Examiner* — Jane Zara
(74) *Attorney, Agent, or Firm* — Knobbe, Martens, Olson & Bear, LLP

(57) ABSTRACT

The present disclosure relates to a method for treatment or prevention of diseases have an increased level of insulin-like growth factor I (IGF-I). The method comprises administration of a growth hormone (GH) variant having antagonistic activity in combination with an oligonucleotide targeted to growth hormone receptor (GHR) to a subject in need.

21 Claims, No Drawings

SEQUENCE LISTING

```
<160> NUMBER OF SEQ ID NOS: 154

<210> SEQ ID NO 1
<211> LENGTH: 586
<212> TYPE: DNA
<213> ORGANISM: Homo sapiens

<400> SEQUENCE: 1
cgatatgttc ccaactattc cactgagtcg cctgttcgat aacgcgatgc tgcgtgcgca      60
tcgtctgcac caactggctt tcgacactta ccaggagttc gaagaagcat acatcccgaa     120
agaacagaaa tacagcttcc ttcagaaccc acagacctcg ttgtgtttct ctgaaagtat     180
cccgacccct tctaaccgcg aagagaccca gcagaaatcg aaccttgaac tgcttcgtat     240
ctcgctgctt ctcattcagt cgtggctgga gccagtacag ttcctgcgtt cggttttcgc     300
aaactcactg gtttacggtg cgtctgacag taacgtttac gacctgctga aagaccttga     360
agaagggatc cagaccctga tgggtcgcct ggaagatggt tcaccacgca ctggtcagat     420
cttcaaacag acttactcca aattcgatac taactctcat aacgatgatg ctctgctgaa     480
aaactacggc ctgctgtact gtttccgtaa agatatggat aaagttgaaa ctttcctgcg     540
tatcgttcag tgtcgttctg ttgaagggtc gtgtggcttc taatag                   586

<210> SEQ ID NO 2
<211> LENGTH: 192
<212> TYPE: PRT
<213> ORGANISM: Homo sapiens

<400> SEQUENCE: 2

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30
```

Glu Ala Tyr Ile Pro Lys Glu Gln Lys Tyr Ser Phe Leu Gln Asn
                35                  40                  45

Pro Gln Thr Ser Leu Cys Phe Ser Glu Ser Ile Pro Thr Pro Ser Asn
 50                  55                  60

Arg Glu Glu Thr Gln Gln Lys Ser Asn Leu Glu Leu Leu Arg Ile Ser
 65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
                100                 105                 110

Asp Leu Leu Lys Asp Leu Glu Glu Gly Ile Gln Thr Leu Met Gly Arg
                115                 120                 125

Leu Glu Asp Gly Ser Pro Arg Thr Gly Gln Ile Phe Lys Gln Thr Tyr
                130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
                180                 185                 190

<210> SEQ ID NO 3
<211> LENGTH: 191
<212> TYPE: PRT
<213> ORGANISM: Artificial Sequence
<220> FEATURE:
<223> OTHER INFORMATION: Somavert

<400> SEQUENCE: 3

Phe Pro Thr Ile Pro Leu Ser Arg Leu Phe Asp Asn Ala Met Leu Arg
1               5                   10                  15

Ala Asp Arg Leu Asn Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
                35                  40                  45

Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Gln Gln Lys Ile Gln Thr Leu Met Gly Arg Leu
                115                 120                 125

Glu Asp Gly Ser Pro Arg Thr Gly Gln Ile Phe Lys Gln Thr Tyr Ser
                130                 135                 140

Lys Phe Asp Thr Asn Ser His Asn Asp Asp Ala Leu Leu Lys Asn Tyr
145                 150                 155                 160

Gly Leu Leu Tyr Cys Phe Asn Ala Asp Met Ser Arg Val Ser Thr Phe
                165                 170                 175

Leu Arg Thr Val Gln Cys Arg Ser Val Glu Gly Ser Cys Gly Phe
                180                 185                 190

<210> SEQ ID NO 4

<211> LENGTH: 4563
<212> TYPE: DNA
<213> ORGANISM: Homo sapiens

<400> SEQUENCE: 4

```
cggcggcggc ggcggcagcg gcagcagcag ctgctacagt ggcggtggcg gcggcggctg      60
ctgctgagcc cgggcggcgg cggggacccc gggctggggc cacgcgggcc ggaggccccg     120
gcaccattgg ccccagcgca gacgcgaacc cgcgctctct gatcagaggc gaagctcgga     180
ggtcctacag gtatggatct ctggcagctg ctgttgacct tggcactggc aggatcaagt     240
gatgcttttt ctggaagtga ggccacagca gctatcctta gcagagcacc ctggagtctg     300
caaagtgtta atccaggcct aaagacaaat tcttctaagg agcctaaatt caccaagtgc     360
cgttcacctg agcgagagac tttttcatgc cactggacag atgaggttca tcatggtaca     420
aagaacctag gacccataca gctgttctat accagaagga cactcaaga atggactcaa     480 gaatggaaag aatgccctga ttatgtttct gctgggaaa acagctgtta ctttaattca     540
tcgtttacct ccatctggat accttattgt atcaagctaa ctagcaatgg tggtacagtg     600
gatgaaaagt gtttctctgt tgatgaaata gtgcaaccag atccacccat tgccctcaac     660
tggactttac tgaacgtcag tttaactggg attcatgcag atatccaagt gagatgggaa     720
gcaccacgca atgcagatat tcagaaagga tggatggttc tggagtatga acttcaatac     780
aaagaagtaa atgaaactaa atggaaaatg atggaccta tattgacaac atcagttcca     840
gtgtactcat tgaaagtgga taaggaatat gaagtgcgtg tgagatccaa caacgaaac     900 tctgaaaatt atgcgagtt cagtgaggtg ctctatgtaa cacttcctca gatgagccaa     960
tttacatgtg aagaagattt ctactttcca tggctcttaa ttattatctt tggaatattt    1020
gggctaacag tgatgctatt tgtattctta ttttctaaac agcaaaggat taaaatgctg    1080
attctgcccc cagttccagt tccaaagatt aaaggaatcg atccagatct cctcaaggaa    1140
ggaaaattag aggaggtgaa cacaatctta gccattcatg atagctataa acccgaattc    1200
cacagtgatg actcttgggt tgaatttatt gagctagata ttgatgagcc agatgaaaag    1260
actgaggaat cagacacaga cagacttcta agcagtgacc atgagaaatc acatagtaac    1320
ctaggggtga aggatggcga ctctggacgt accagctgtt gtgaacctga cattctggag    1380
actgatttca tgccaatgaa catacatgag ggtacctcag aggttgctca gccacagagg    1440
ttaaaagggg aagcagatct cttatgcctt gaccagaaga atcaaaataa ctcaccttat    1500
catgatgctt gccctgctac tcagcagccc agtgttatcc aagcagagaa aaacaaacca    1560
caaccacttc ctactgaagg agctgagtca actcaccaag ctgcccatat tcagctaagc    1620
aatccaagtt cactgtcaaa catcgacttt tatgcccagg tgagcgacat tacaccagca    1680
ggtagtgtgg tccttttccc cgggccaaaag aataaggcag ggatgtccca atgtgacatg    1740
cacccggaaa tggtctcact ctgccaagaa aacttcctta tggacaatgc ctacttctgt    1800
gaggcagatg ccaaaaagtg catccctgtg gctcctcaca tcaaggttga atcacacata    1860
cagccaagct taaaccaaga ggacatttac atcaccacag aaagccttac cactgctgct    1920
gggaggcctg gacaggaga acatgttcca ggttctgaga tgcctgtccc agactatacc    1980
tccattcata tagtacagtc cccacagggc tcatactca atgcgactgc cttgcccttg    2040
cctgacaaag agtttctctc atcatgtggc tatgtgagca cagaccaact gaacaaaatc    2100
atgccttagc ctttctttgg tttcccaaga gctacgtatt aatagcaaa gaattgactg    2160 gggcaataac gtttaagcca aaacaatgtt taaaccttt ttgggggagt gacaggatgg    2220
```

```
ggtatggatt ctaaaatgcc ttttcccaaa atgttgaaat atgatgttaa aaaaataaga    2280
agaatgctta atcagataga tattcctatt gtgcaatgta aatattttaa agaattgtgt    2340
cagactgttt agtagcagtg attgtcttaa tattgtgggt gttaattttt gatactaagc    2400
attgaatggc tatgttttta atgtatagta aatcacgctt tttgaaaaag cgaaaaaatc    2460
aggtggcttt tgcggttcag gaaaattgaa tgcaaaccat agcacaggct aatttttttgt   2520 tgtttcttaa ataagaaact ttttttattta aaaaactaaa aactagaggt gagaaattta   2580
aactataagc aagaaggcaa aaatagtttg gatatgtaaa acatttattt tgacataaag    2640
ttgataaaga tttttttaata atttagactt caagcatggc tattttatat tacactacac   2700
actgtgtact gcagttggta tgacccctct aaggagtgta gcaactacag tctaaagctg    2760
gtttaatgtt ttggccaatg cacctaaaga aaaacaaact cgtttttttac aaagcccttt   2820 tatacctccc cagactcctt caacaattct aaaatgattg tagtaatctg cattattgga   2880
atataattgt tttatctgaa tttttaaaca agtatttgtt aatttagaaa actttaaagc    2940
gtttgcacag atcaacttac caggcaccaa agaagtaaa agcaaaaaag aaaaccttttc   3000 ttcaccaaat cttggttgat gccaaaaaaa aatacatgct aagagaagta gaaatcatag    3060
ctggttcaca ctgaccaaga tacttaagtg ctgcaattgc acgcggagtg agttttttag    3120
tgcgtgcaga tggtgagaga taagatctat agcctctgca gcggaatctg ttcacaccca   3180
acttggtttt gctacataat tatccaggaa gggaataagg tacaagaagc attttgtaag    3240
ttgaagcaaa tcgaatgaaa ttaactgggt aatgaaacaa agagttcaag aaataagttt    3300
ttgtttcaca gcctataacc agacacatac tcattttttca tgataatgaa cagaacatag    3360
acagaagaaa caaggttttc agtccccaca gataactgaa aattatttaa accgctaaaa    3420
gaaactttct ttctcactaa atcttttata ggatttattt aaaatagcaa aagaagaagt    3480
ttcatcattt tttacttcct ctctgagtgg actggcctca aagcaagcat tcagaagaaa    3540
aagaagcaac ctcagtaatt tagaaatcat tttgcaatcc cttaatatcc taaacatcat    3600 tcattttttgt tgttgttgtt gttgttgaga cagagtctcg ctctgtcgcc aggctagagt    3660
gcggtggcgc gatcttgact cactgcaatc tccacctccc acaggttcag gcgattcccg    3720
tgcctcagcc tcctgagtag ctgggactac aggcacgcac caccatgcca ggctaatttt    3780
tttgtatttt agcagagacg gggtttcacc atgttggcca ggatggtctc gatctcctga    3840
cctcgtgatc cacccgactc ggcctcccaa agtgctggga ttacaggtgt aagccaccgt    3900
gcccagccct aaacatcatt cttgagagca ttgggatatc tcctgaaaag gtttatgaaa    3960
aagaagaatc tcatctcagt gaagaatact tctcattttt taaaaaagct taaaactttg    4020
aagttagctt taacttaaat agtatttccc atttatcgca gacctttttt aggaagcaag    4080
cttaatggct gataattttta aattctctct cttgcaggaa ggactatgaa agctagaat     4140 tgagtgttta aagttcaaca tgttatttgt aatagatgtt tgatagattt tctgctactt    4200
tgctgctatg gttttctcca agagctacat aatttagttt catataaagt atcatcagtg    4260
tagaacctaa ttcaattcaa agctgtgtgt ttggaagact atcttactat ttcacaacag    4320
cctgacaaca tttctatagc caaaaatagc taaatacctc aatcagtctc agaatgtcat    4380
tttggtactt tggtggccac ataagccatt attcactagt atgactagtt gtgtctggca    4440
gtttatattt aactctcttt atgtctgtgg attttttcct tcaaagttta ataaatttat    4500
tttcttggat tcctgatagt gtgcttctgt tatcaaacac caacataaaa atgatctaaa    4560
```

| | |
|---|---|
| cca | 4563 |

<210> SEQ ID NO 5
<211> LENGTH: 304901
<212> TYPE: DNA
<213> ORGANISM: Homo sapiens

<400> SEQUENCE: 5

| | | | | | |
|---|---|---|---|---|---|
| atggttttct | ttaatcagca | cttcagtgat | ttacttatta | tgtttattgt | tcattgtctc | 60 |
| tcctaactag | aatgcaagcc | ccatgagggc | agcatctttg | tagatatgtg | gtataaattt | 120 |
| tgttccctga | tgcatgctaa | gttttagaa | cgaagtctgt | catagtgtag | gctcaccaac | 180 |
| atttgtatga | atgaaagaac | atggtgaatg | ggaattcagt | gttagtttaa | aaaaaattca | 240 |
| ttaaagggat | aatattttat | tagaatctta | ttaattttac | cagtaaatat | tgtattaatc | 300 |
| agggagatat | atatatatat | atatgtcata | ttcatgagat | atatatatat | atatatatgt | 360 |
| catattcatg | agatatatat | acagagactt | attttgagaa | atttgctcac | ataattgtga | 420 |
| aaactgaaaa | gtcaaaaatc | tacagggtaa | attggttaca | gatttaggga | atagttgata | 480 |
| tgcagtttga | atccaaaggc | tgcctgctga | cagaattttc | tcttctttgg | ataggtcag | 540 |
| ttttttttctc | ttaatgcctt | caactgatcg | attgaggccc | acctacatta | tgtagagcaa | 600 |
| tatgatttac | tcaaagtcta | ttgatttaaa | tgttaatctt | accataaaaa | tgcctttgcc | 660 |
| aaaaaaatct | aaaataatat | ttgaccaaat | atctgggtac | catggtctag | caaaattgac | 720 |
| acataaaatt | aaccatctca | atgtgtcaac | tttgctaggg | catggtaccc | ggacatttgg | 780 |
| tcaaatatta | ttcaaataaa | tttagaattt | atcacaaatg | tttgatatca | taatttgatt | 840 |
| tacaaatatc | aatctaatac | tttatttac | agctgaatga | tctcagagag | caaccccttc | 900 |
| cttctatagg | ccaagaaatg | gagtcattgt | gagattagta | actaatttac | ccaaaatcac | 960 |
| agaggaccca | cacaggatcc | caaggctcct | gactaacaat | cctatgttct | tcaactacaa | 1020 |
| atgctataaa | acaaaacagc | tataaaatgc | tactttaagt | gttttggcct | cttttgtttt | 1080 |
| gttttgagaa | gaagctttgg | catttttag | tacaacagag | tgactaaagc | catgctctaa | 1140 |
| cctcagataa | ctgtagattt | aggaagttta | tactgtggtg | ttttatggtt | tggggagatg | 1200 |
| gcgatctgac | ctagatatct | gcacttgaat | atatataatc | agaattattt | tctaattgtt | 1260 |
| tctattgtct | tcaaggcagt | ttatatttt | tgctaagccc | tactggggat | gtataaaaga | 1320 |
| ctggggaagg | gtgggccata | ataaggtaag | gccataataa | ggtaaaatag | gttggacaag | 1380 |
| ataagttagc | caatatctga | gtaaagactt | caaggaactg | taggaggaag | caatgaata | 1440 |
| tttgtggaag | tgtgttaaa | tcagagagaa | aagccagcaa | aaagccttca | agttaggagt | 1500 |
| ctgcctggcc | tgcttaagaa | acagcaggga | ggccggtgtg | ctgggagcag | aatggatgac | 1560 |
| ccagtgatgg | ggaaattcat | gggagatgag | gtgtggggca | aaggtacata | gctcacgtag | 1620 |
| ggtctcatgg | gccattttga | attttattct | gatttgaatg | gggaaccatt | ggagggtttt | 1680 |
| gagctgagga | atgacatgat | attaattta | aaaggaatga | ctatgcaac | tgaatttata | 1740 |
| ctttgggttg | ttgttggtgt | tggttgggga | ttaggggtgg | ggtttgtcaa | agcaagcaga | 1800 |
| ccagttgagt | tgagagacta | ctgcagtaat | ctgagaaatt | ctggtggttc | agaccaggtg | 1860 |
| tctctggacc | tctccaagaa | aatagacaga | gttttgaatg | tggaatgtga | ttggcagaga | 1920 |
| agaagtaagg | atgatttcaa | aggtttgtgg | cctgggtaac | tggcaggaag | tagttgccat | 1980 |
| ctactgagat | ggaaatgtca | cccactgtga | ttggagtatg | tttaaggaga | aagaaccaga | 2040 |
| gttcagatgt | ggacatgtca | agtttcagag | gtctgttaga | catccaaatg | gagatacca | 2100 |

```
gttgttagcc tggagctctg tggagagatc tgggttagag atataaatcc aagagataca    2160
acttttcatt caatttgatt atttattgga cgctttataa actctgtaaa tactgggcac    2220
taacctagac attgcaggta cagatattaa gaatatatag tttctccctc agaaatctct    2280
taattaatga gaaaagcaga catgtcaaca aaactgcaat atttaataaa agaagatata    2340
aaggcctata aaggtgctga tacagggaga attaattaat tccaccctgg ggaatagtca    2400
ggaagacctt cagagagaaa gtaaacaatt gattggaact ttaagattaa gaaggatttc    2460
tctgggtgga caaagtagga tcttccaagc agagtggaaa ccatgagcaa atgcagtttc    2520
attcttcaga aggtaaatgt gctctggcat gccttaactt ataacaaatt aatcaactca    2580
atacctgcta cattttccct cacaatttgg aatatataaa gaggcacata ctactatgga    2640
ccaatacctg gtcatatatg agattgaagg acctttactt acgaggctta aaaataaaga    2700
ctgcccttca tgtcagttgc aggtttatat ctagttctat agtattaact gaggtgtctt    2760
ttcctatgtt ttctgtgcat gatgactttt taaaaatcaa agacagagca gcagccagag    2820
tagtctagtt tcatggcaca cagaatggag gatattgctg aacccagatt taaaaaaaaa    2880
aagaagtcaa ttcttatttt tttaagtatg gccctgagct catctcagag cataaacaat    2940
agaatttaga atatctttta tgactccgtc tggcacctcc taaactagat caagattctc    3000
tagctcaggg aagaagggca aaggatgaga aggcacagag aggatataaa cagagaggtt    3060
ggtagtgcca ggctctgaag aaggtccaac ttggaaggtc atttcagaca ggcgtggagt    3120
cagcatttga ggcctgtctg gtctctactc ctgccaggac tacccctgtca gccagcttgg    3180
caggtatgga ccacccagca ggagttttc ttgactgtgc cctaatcttt tactttccca    3240
agtttctcta tatgggtacc tccccttta aaagctccag acacagccaa gcaccactat    3300
tgctccagca aagtatgaag ccccagaaat caatggtttg gggaagagtc ttaggggaac    3360
taaatgcctc cttatttta gatgccatag aacaagagca gttcaggatc aataaccatc    3420
ccaccccatg ataaaacacg cccccttccag aatctttcct ttttcgttca ttctaggtgt    3480
ctgtctggaa cagctgggt atttgagcca cagctgagct tctgaaagca ttctaaggaa    3540
cagtttttca cttatctgat tccctttgaaa ataggggtat cttatgtgat atctgctatc    3600
ccagagtctt tggtcctctg ttccttctca agtcttggct cccgtgtact acttcaaagc    3660
cctatagata ttttattcta aagaaaagaa acttggttcc tttaagttgt ttaaacattt    3720
ctttctgggt ataaacttgg gtttgtgtct gggagctctg ttaaaaaaaa aaagtcttta    3780
gtaagccaaa gctgttagaa gcttataagt aagtgacatt acaattgacc gtcagtaaat    3840
agtggaaaga ttgcatgact agctactcct tcagatctga gacaacctgg agctagattt    3900
ttgtactctc tactcagaaa agcatatagt gacttgggt ttgatgctgt acaaaaatga    3960
catgcttatg cacaacttta actttctgca acactttac aacttcttgt gaatgaagta    4020
ggcagggctc gcatttgaca gatgagctat gtccagcgtg aggcagagtt aaaacccttt    4080
tcctggctca ggaacttcag gctggggcct gtgtctgctc tccctgcatc cctgtcctct    4140
agcagatacc tctctgctaa catgctgagt gtccttggta aattactcat tctctctgtc    4200
tccgtcttct aacctccaca ataaagtcct tcgtagtttt aactatcttt tcactgtgcc    4260
ccagtgagca ggagtttgga acttgattgt tgatggaaag gcaatatttg gatggctaaa    4320
cacgctttcc aaggtatctc gctgatcttc ctctcattcc tggagatagc taaccttttt    4380
gtaagtgttt ctttgagtct gtggactgca cttaacgctc ttgtaggtcc tgctttcatt    4440
```

-continued

```
tggaacgggc aggcggagag gaaggaagtg tattgcaact accaatattt tcctctagga      4500
ggagccgcgc agctcagttg agagtgacac gcaccaactc cagctcctcg ccgggaagac      4560
ttcatcccag caactcggaa tgcttggccc gggcggcact cggcctctcc gcagcagttc      4620
tcgaactggc ctccttgaac gtccgcttcg ccttcgcttc tgcaacctgg atctggggga      4680
ctgcgggcca ggcgcggcgt gacccctggt gaacggtggc cgccttttcc caccccctgcc     4740 ctcccatcct cccttcccgt ttcacccgc cccctctctc ctccccaagc ctgacagccc       4800
gcgagctgcc aagcagggcg cagccatggg aagaggagga gggctaggga gcggcggcgg      4860
cggcggcagc ggcagcagca gctgctacag tggcggtggc ggcggcggct gctgctgagc      4920
ccgggcggcg gcgggaccc cgggctgggg ccacgcgggc cggaggcccc ggcaccattg        4980
gccccagcgc agacgcgaac ccgcgctctc tgatcagagg cgaagctcgg aggtactgga      5040
gtggggctcc gggagtctgg ctttatttttc ctcctgttgt gccagggggc ctgagggtga    5100
accctgggac tctagttgtt tatgaaaacg ggaggatctg tcttatatat ttacacggat      5160 aatttttttat tccggatgac ttggctgtgc tcccctcctc cttgcgaaga agttgttttc    5220
tgctggtggg ttgttgtaac ccaatctagt gtgtgtgtgt gtgtgtgtgt gtgtgtgtgt     5280
gtgtgtgtgt gtgtgtctgg aagttggtga gggcggcagg gagttgcggg cgacagacga     5340
accatcacac tctggcgtct gctctggccc gcgagtagtg tacgtggagg ggtttactcc     5400
ggagacagtt ttgttaaagt cataaaagtt ttgctagtgt gtttctgttt gccatcatct     5460
gcctggctgc ggcaggaact gccgaggctg ctgctgttgc gcggggaaga atccccggca     5520
gcgcgactgg agagactggg gaggtcgagc tgtgcgcgtg gacacagcgc gcagagcgcg     5580
cggtcttttg cgcgtttgtg cgggccgcag ccgcacgttg gcaccgatgg aactggggtc     5640
agtagagtga cagccaccag tccgcatgaa ctggggtaag tggaaattgt ggcgagccga     5700
cctcccccag cttttgacac actagtggtt gtaaaatcaa ccaggcttaa agttttgaca     5760
gaactgccag aggctgcggg tcaatggggt ggccgcgtgt ctagggagag ggcgctggcg     5820
gcgcagaggg tgcggggcag ggcacttgcg agtgcgtggg gaagtctatt tggggcgagt     5880
gctttatata tagcccgagg ggatgcctgc tgagaccgag ctgcggggc tctcggtctg      5940 gcgcggactg tgtgtcctga atgagtgtac gtgtgcgctg tgtgtgcgcg cgcgagtgtg     6000
cgcctgggga ggcgtgtcgg cgcctgagcc agtagggtgt gcagggtgga agaggccaca     6060
gaggtgccgc ctgtctgttt gtgccgccag gagaccttgg aagggacaga gaaaggtaac     6120
ggaaggccaa agtgttggga agtcagagta gtttctgcat aggattaagt attaagggct     6180
ttaaaataac taaacgcatt gccctgagtg gctgaggact ggaagtgagg ttttggggag     6240
ttctcaggag aactgcatgg gagggcgttt gggaggtcta agggatgtgt aatatgtgtg     6300
agtacagaac ttcggagaca gacacaggtt ggagctatga atttgaaatt ttcagggtgc     6360
tgctgtccac agtccaggga ctggctggtt tcagaggtat tcaggctccc tggtgtgtgt     6420
gcctgggaag acactcatct tttcttgcag acatgggata ttgtggcagg tcaggctctg     6480
tttcctgagc aactggtgtt ccaggctagt ttccacctga atcaccctag aagtgtcttt     6540
tttctgatga taaatgttga aacctttcca gaaattaaaa tgctggatag aaacaaaatt     6600
gatgcagcag acaggattgt tgattctatt tattcagtga ttgggagctc ttttcctttt    6660
tgagaaaagc aaagctcagt gttttccagat tagatttcaa ggagtcttca gctatctaca   6720
gcttcccttc tgggcctttg gatggagctg gaaggatgtg ttttggccta aagacctttg    6780
gaagacatca tgtgtagctt aaagaggttg tcccgtctct catcatcttc ttccaccctt    6840
```

```
ataaactttt tgttttgcat taatctaagg aaagttggtg tgtcaacatt tagcttttt    6900
ttattggagt aaatatatca cagtgaaatt atagttatgg tctcctgaag cccatggaaa    6960
gccaacactt aatgggcaaa ggtgtgaaat gaaagtctat aaatgcaatg acaaagtgac    7020
gagatgagtg cattctttt tcaaaatgaa cataactgtg ctcacaaaaa tttgttttag     7080
ccaggctttg ggcccatgtt ttttattatt agtttttaaa cagcagactc cacatcataa    7140
accactttaa aatggatact agaggcctcc tgtatgctat ctctggcgcc tgcttaaaca    7200
gatgtttaca gtgcttggta acctatggga ttgtcatgtt gagtatcttg ttagctcagg    7260
acataatgtt tatagcataa tataataaat ggagccacag ttgcagcgtg cttcttccaa    7320
gtgcatgaag caaatcttgc agcagggaaa caaatcttgc agttggtcca acttggctag    7380
ccttctttgg ctatctcctg gtgagcaatg ttaatgtaaa gataaatgtg agtgacgtag    7440
tgagaaagtg ggacagtaaa ttgtttagct tagtgaaaaa agcatggatt atgttttta    7500
aatctgctaa cctgaagatt acacttctca ggtcgtacca ctggcaaatt gcacaactat    7560
gggaatttgg tttgctttta aagagcaatt tttaaaaagt atgtcagtaa tgaaaataac    7620
ttatatttct taatgtgttt atgtgtgtcc atacaagcca atacttttc ttctttaaaa     7680
agaaccctat aatttctgtg gtaattattt aaatattatg agcattcaaa tctcctaatc    7740
accttttcaa tcttcaattg ataagaatcg aagtttggta agactggagt catccctcag    7800
ccaattgtgt aaacaagaca gtacagaatg tctttctggc aagtaatttt tttcaacctg    7860
aaacagataa tataaataat atgtcccata aaagaattac ttaagatgat aattacttta    7920
gaggtaatta tctggtgcat gaacctctat ctgtgaaaat ggtctagtct atctcttatt    7980
ggaaataatc agttgaaat ctcccttttt cattggtcag tccattctag aaagattca     8040
tttctagaaa gttcttatac tgaatcaaca ttttcttcca tccacttgcc tatccttcag    8100
cagctgacca caatgaatct agtctctttt ccctgtgttt accatacttg aaaacaaata    8160
ttatcctcct tgccgaatcc ccttttgcct actcttggag cagttttca tccactatag     8220
ggttccaccc tcctctgcct tgaacaagat gcccttgatt gtacattctc attgtattag    8280
tctgttctca tgctgctaat aaagacatac gtgagactgt gtaatttata aagaaaaga    8340
ggtttaatgg attcacagtt ccacatggct ggggaggcct cacaatcatg gcggaaggtg    8400
aaggaggagc aaaggcatgt cttacatgac agcaggcaag aaagcatgtg cagggaact     8460
gcccttata gaaccatcag atctcattag acttattcac tatcatgaga acaacatggg    8520
aaaaacccac ttccatgatt taatcaactc ctactgggtc ccttccacca catgtgggaa    8580
ttatgggaac tacaattcaa gatggcattt gggtggagac aaagccaaac catatcattc    8640
cgctcctagc ccctcctaaa tctcatgttc tcacatttca aaaccaatca taccttccca    8700
acagtccccc aaagtcttaa ctcatttcag cattaactca aaaatccaca gtccaaagtc    8760
tcacctgaac caaggcaagt cccttccacc tatgagcctg taaaatcaaa agcaagttag    8820
ttactttcta gatacaatgg aggtacaggc attgtgtaaa tatgcccatt ccaaatggga    8880
gaaattggcc aaaacagagg ggctataggt gcaagtccaa agtctaatag gcagtcatt    8940
aaaccttaaa gttctgaaat gaactccttt gacttcatgt ctcacatcca ggctgttttc    9000
atggctggca ttgactgtgg ctttccagg cacatggtgc taactgtcag cccctaccat    9060
tgggggtgct ggggaatggt ggccctcttc tcttagctct actaggcagt gacccactgg    9120
ggactctgtg tagaggatcc aaccccacat ttcttttcct cattgcccta gcaagggttg    9180
```

-continued

```
tttatgaggg ctctgcccct gcaggacaac tctgcctgga catccaggca tttccataca      9240
tcctctgaaa tctaggtgga agttcccaaa cctcagttct tgtcttctgt gcacctgcag      9300
gaccaacacc acatggaagc ttccaagact tggggctttc accctttgca gccatggcct      9360
gagctgtacc ttggcccctt ttagacatgg ctagaggggc tgggacacag gtaccaagt       9420
acctaggctg cacctagcag gcccagaaaa ccattttttcc ctcgtaggcc tctgggcctg     9480
tgatgtgagg ggctgccata aaggcctctg acatgttctg agacatttt ccctattgtc       9540
ttggtgacca acatttggct tctcattact tatgcaaatt tctgcagcag tcttgaattt      9600
ctccccagaa aatgggtttt tcttttctat ggcatcatca gcttgcacat tttccaaact     9660
tttatgctct tttcacctct tgaatgcttt gctgcttcta aatttcttct gccagatacc     9720
ctaaataatc tctctcaagt ttaaagttcc acagatctct aggacagggg aaaaatgcca    9780
ccagtctctt tgctaaagca ttaacaagag tcacctttgc tccagttccc aacaagttct   9840
tcatcttcat ctgagaccac atcagcctgg actttattgt ccatatcact ataagcattt    9900
tggtcaaagc cattcaacaa gtctctagga agttccaaac tttcccacat cttcctgttt     9960
tctgagccct ccaagtctct agaaagttcc aaactttccc acattttcct gtcttctttt    10020
gagccctcca tactgttcaa acctctgcct gttaccagt tctaaagttg cttccacatt     10080
tttgggtatc tttacagcag caccaactct accattacca acttactata ttagcccatt    10140
ctcatgctgc taacaaagac atacccaaga ctgggtaatt tataaagaaa attaggttta    10200
atggtcgcac agttccacat ggctgggagg cctctcaatc atggcagaag gtgaaggagg   10260
aataaggcac tcttacatgg tggcagacaa taaggcatgt gcgggggaac tacccttat    10320
aaaaccatca catctcatga gacttaatca ctatcgcaag aacagcatgg gaaaaactcg    10380
ccctcttggt tcaatgacct cccactgggt tcctcccatg acacatgggg attatggtag   10440
ctacaattca agatgaaatt ggggtgggga cacagcaaaa ccatattact gactgtccct    10500
cctaatgtgt gttttctaaa caaagatttt ataatttgta gttctgaaca ttctatatct    10560
attaagacag tttaatatta atgaaattct ttagccattt cattacgctc ttgattaatt    10620
tcatacctat aaacaagata acttgttctt ttcagattat taatcatcca tagtcaaagc   10680
attttttataa tagcttcaaa acattttttc atgcctgaat gtactataaa tttatggaaa    10740
gtataatact gtgtgggtaa ataaaattct ataaacagtg caaatagtga cttaatttct    10800
ccctatcaag gaatatcaac cccaaatata ccgaaagtag aatgttccaa agataaacaa    10860
gttgaaacta catgttatag acaggtaggg actatgatgt atttttttca taggcctcat    10920
tgtgtctgct tccatgaaca tgagtcagta ctagcaatca ggcatttatt gaaggcttgt    10980
tctgccaaag tcccagagag tatgccatct ggccttaaat gaagtgaaag tacatcaaat   11040
aaagatactt ccttgggcaa ctgggattta agatgtgcat gcaggacatg tctaagtcag    11100
ccatctactt tttctcagga ggtaaatggc ttgccaatgc cacaggaaag tctaaagtgt   11160
tcacactcca taagcaggtc ccatgtcctg ttgtaggtct ggacaggagc tggacaaagg    11220
ccctgttact cttagcttac caagtcttag ctgccttgga agaagatagc aaatctggct    11280
tatccagagg agaggcctga agtgtgcatt gggcacctac ctggtgtgac tgatttctct    11340
tttatgtatc tgtcttgggc ttccagctaa attgtgaatt cccccttgcca ccaagctaag   11400
aatctgccac agcattgtct tcctgcacac acacacacat acacacacac aaaaacatat    11460
atgttggatg atgaagagac aatgtcagtt tttcagcaag tctgaatgtg aaacaaatgg    11520
ctatgttcct tggtgcagtg gggtgggagg atgagagaga aaaaacaaac ctgtgatata   11580
```

```
aactgacatc tgagcctacc aaaagcccett tgagagacct ttgatcaaga caagggyata    11640
atcatagtgt tgtgcactta gataaaattg tccatgctag tcccgtgtgt gtgtgtgtgt    11700
gtgtgtgtgt gtgtatgtgt gtgtttcttc actttatccc cagcattatg gtctcaattc    11760
atacacattt gcttttttgc tttattctag tctgatatga agggaagaaa taagcaatga    11820
ttcagttcct ttttttacat ttcaaacatt catttcacta ctccccacct cccagtcctc    11880
accccccaaa attacaagag acccattggc aagtacttgg acatgcaatt ttcaaaccaa    11940
aggtttactt tgctataaga aacgtctaag ttaggatgat ataatatgaa ataatagtaa    12000
attagatgtc aagaaacttg ggtcctctcc aagctctgcc tttaatgggc tttgcagttt    12060
ttgccaacta tttaaccttc ctgggcttca tatttcttgt atgttaaaaa caagcaaaaa    12120
ggagaagtaa acaaaatgac cccttagaat tctcttcagg gctattgttt gaatccattt    12180
aattatcaaa tttctctctt cttttaaatg taagcatcaa aaaatgtttg cctattttat    12240
tctctcatca ttaattttta atcaattaaa taaaatagat aaaaatttta tcaaaaccat    12300
gcttcttgct ttcattctaa aacaatgcaa ctcatcacta tctgatgcag aaagtctttc    12360
tgaaatattg tttttctctt ttgttgttgt ttttttcttt gtgctaaaga aaattcattg    12420
atgagtacca ggttcttcaa agaaggatgg aaaagtcatt gttttttagt ctcaacttct    12480
ttcttcagtg cttcttccta ccttttaata taggcaaata aagccttagg ccaggcacta    12540
attttactta gtaatgattc ataagaaggt agtgattttg tcagaaattg ctggctgcat    12600
gcttttaatc agcatctaaa cttaccttca aatactccat tccaaaatca gcagataact    12660
tcttctacag agtctttcaa acttccagat gtgtttactg ttttgattag ggctttcttc    12720
ttttgttgtt gataagactt cagccagttt tctttaggct aacattatta tattcccaat    12780
gaattatact tcttaggttg tgaatttgtt taaagataaa tctatctcca gctggctggc    12840
ttctaagtaa aaagggtat cctagggaag aagtgcactt cacagggatt cagtacaggt    12900
gtagagaatt ccctgataga gaattggaac acatcaagag tttgcaaatt gaaaaggtac    12960
ttttatgtac ttatccatgg tggacaacct gtgtcctagg gaagaagcgc atttcacagg    13020
gattcagcac aggtgtagag aattccctga tagggaactg gaacacatca agattttgca    13080
atctgaacag gtacttttat gtacttatcc atggttgaca acctactgtg ctagacattt    13140
gctgtagtaa ctccttgatt ttttcctcgg ttgtttataa aattaaacat ttgaagtagc    13200
ctattgaaaa gtcttaaaag aagcatctcc tctattcctt tagaatacag tatattaaac    13260
aagtgataaa gtccaaagaa aaatccttat tcttttcttg ctttaaaaaa tgcactttat    13320
tttattaagc attatatcta tcttttaaaa ctttgaattg ccatatcaat gaaagtagag    13380
tgttatcatt acaaaacaga atcgcagata gttctttccc tgtgcttatt gagagaaaag    13440
gtgcataatt gatgctgtaa atgatcatct tgaatttgat gatggctggt gagaaacctc    13500
agtcagacat tcaattttga ttgccattgg tcagaaaggc agcctttgtt cttcgtcact    13560
atgtggcaca tgatcctaat tcaccctatc agctgcttct ctgcacactt tcaagctatg    13620
tgattgttat actagaaagc ctctaagttg gccaaactaa tgaagactaa tctgacaaag    13680
catatgtgaa tgataaattc tgtaaagacc gtggagatag agcctctgca gtggcttctt    13740
cccctgggga tagaagaaga taccagaatc cctgggcaag atgaaataga taaggaaag    13800 gcatcatttt tataccctagg aaatcagaaa gattaaagaa agagaagcaa gaataaagaa    13860
gaactactac tttcatagtt cattctttca atgtagcacc ttatttccca tagagacatt    13920
```

```
ggtgaagcca tgcttttctt tgccatagaa taggtgttca gtaaatattt tgcaggtggc   13980
cttaatatgt agtaaaacat acagaaatat ggaagcattg acaagaagtt tgtggataat   14040
ttgagggcaa aaggatgtag ataggatcag gttcataatg caaatttgct attattctcc   14100
ttagattaat gatgtcactc aaacttcatg acctgctttc aaggtgtat  gctgttcaca   14160 gccttggaaa catttagaag ttttagtac  ttggagcaag atggatatat gtttcacatt   14220
ttatctagga cttagtagga cttgggagac atatctactt tgccagatct tagtatactt   14280
attatggagc atgacatttt aattctcttt gcttttgtcc tacaaagttt agtgttttaa   14340 tttattttc  tcggtgcata tagggagaga attatttata taatctgaaa agtactttga   14400
aaactacttg ggaaaatatg ttgaataaat aagtttttt  ttaaattagc ctacaggatg   14460
taagtctggc caggctagtg gtattttggg tatcattgtg aaaaatcaaa aacagaacat   14520
gtatttatca atccattagt gtgttcccag gaatgtgcta gacactaggg aattaaaaca   14580
tgactcttga ctttagtacc aagcattcaa gctagaaggc aacactatta atgtacattc   14640
atggtgtgat tatggaacag tcgatgactg tacaacttaa tgaaaagttc attagagact   14700
ataaatgcta catttattta gagagaagga caatctgttt ggactgaggg attggaagag   14760
tggccttcat gggcaacatg gctcctgagc cagtacttaa gatatggtat ttttttttt   14820 ttttttttt  tttggttagg tagaagggtt ggagaggttt catgcaagga gttaggaact   14880
gaggaccagg aggcgtatct tgagttcact ggggttactg gtaataggga ggaggcagag   14940
agtaccaggc tgtggatttg ttatccgttg gaagctcttc ccattgctta ttatggtcgc   15000
tgcatatagg ctcatccctt gggtagggct attggagtgg ccaccctgac cctattgctg   15060
attggatagt ggtggctgct gtgtggtatt tcagcacatt tatcttttct gaacattatg   15120
taaattcagt ctgaaaactt cttcttaaa  caatgttcca agaggcctat aaagatgcc   15180 aacaatatga cttccattca agaatatgat cttgaatggg ctttacaatg cagagctga   15240 cctgagatta cctcctctgc tcctgctctc aagccatgtg ctgatgctga cagtcctggc   15300
ccaatagagc catagggcct cacagaactt gagatcatct accagtggct gtcaaccaag   15360
ccactccttt ctgctaggta gtgcataggg acattgggaa atacagttat tataagaact   15420
ggaaagagtt gtaggctttt ggtgcctgaa gtcagaaatg ctaaatttct gtgatgccag   15480
gggcagtcct atataagaaa ttattgtgcc tcctcaaatg ccagtagatc cctattgaaa   15540
tacttgagtc tcatatcctc actttattta taggtgagga aatgggaggc cctgagaagt   15600
gacaaaactt tcttctagga ttaaacttca cagtctcagt gacagattta taactcaatt   15660
cttttagttt tctttcaaga gctcttgttg cagcaccaca gtccctccta ttaacatggg   15720
ctataactat ggaatagcat gttgtttatc tctgccattt ttatagaagg atgatagtta   15780
gctatgttaa ctatctgaat gggtggaatg tgaattgaga taactggtac ttgaccagca   15840
gttctttcgc ctgggaacac acacagattc acctgtaaat tagggttggc agatgcctgt   15900
tgagatgtca accatagcca aagcttacaa attggttgac ttttttggaaa gggcatggag   15960 taggctttgg attcacacaa atctgcttgt ctgaccggat ttgaatacaa cccttcttat   16020
ctttactatc tttgtgactc tcagccaatt aaactctctg agctttatct gcaaaaaaac   16080
agttgattat tcttatttca caagcaatga gtcaaaatag tgcctggcac atattgggca   16140
ctgcagatat agagaattcc ctacagtatc ttttgagca  taaagacttg aaaccttcac   16200
ttataaaaga ccctcttgat aacagtcgct attttttttct cctcctttcc ccaaacaacg   16260
aaactagggc ttcagtgagt ccctgaagtg tttactttgt ttgaactgtt gagatttccc   16320
```

```
tcctccagaa gagtcctgct ggccagagat gagttccttt tgacttctct gtcaacgtgc   16380
ctgtattatt gtcacatagt aaaaatgaaa gatatatcta gatgattatt agcaggttat   16440
gaaacttaga ttttaaagtc aataataaaa gccattcctg ggtagagaag tttttcagag   16500
agatttctac cttgccagcg atgagagagc ctacttaggt gaggtgaata ctttaggcaa   16560
gttaagggat aacacaatat aatttattta agtaagtttt ttatctggga ctaatttcag   16620
gtttgcagaa aagttgcaaa aattttagag gtcctgtata ttcctcacct agtttcccat   16680
gttgacatcc ataatcatga tatatttgtc aacactaaga aaccaatgtt agtacagtac   16740
tattaactaa aatccagact tcatcctaat tcccccagag cttccactca catcttcttt   16800
tctgttccag gattcaatcc agaagcgtgc actgcttttg attttatgat ttttaaatac   16860
tgtgcatgtg ctttttttaat ttgggccctc tcatgtgtta aacttaccgg cctttgtaac   16920
cagatagcaa gttctgtaac agaaaataca atgatgttga atccaacatc atgctgggca   16980
caaagtatgt tctccaaact aattaaattt atcacagcaa caagaacaaa gttttactca   17040
gcgtacatat gtagctgagt cctcattggt aagctaagag gtagtcataa gagtgggata   17100
acttggaaga aatttgattt tgaatgtgtg ccctgaacat tggtataaaa caggacccc    17160 taaatcatat atgaactgag tctgtacact gtgcctagca ttgtgtgtgc atatcacact   17220
tactcctgat aactgtaagg cacatagcct tgagtaactt agctgaggaa atgagaccaa   17280
gggaagttaa gttacttggc cagggattca cagctagtaa cacagctgag attaaaacat   17340
atgtttttct ggcttcagag cctacactcc taatgctgta ttcaattact cccacacttc   17400
tccacttgct taaccctat tcttggtgtc cttttctag gtatacagaa tttgaaaact    17460
atattgtcaa actacagcag acctggatgc atggtataca cttctttgtg agctggatta   17520
agtttcagcc ttgaatttgt ggattatttt caaaacctgc ctaacatctg taaaacatgt   17580 tgtttttta atatgtagat atccacataa attgaccaca atgctcttca gaaagtccca   17640
taatccaata ataaataaat ttttgataca tggctaataa caggcacaga agcatctcca   17700
aaggacagga cattgatatt gtgtaataat ttaaagtatt ttatgattgt ataatgtgcc   17760
tgagttttgg atagttgacc tctatttctc agtctttaca tagttactgc ttttttaagt   17820
gttacatgag ggatgtggaa tattcagtgt aacatttgac taatctttat gttttgagtg   17880
gcccaactga aaattaccct tggttgcctt ggaactctgg gcatgatgtt caaaactaga   17940
aattcttgca aattatttga gctttggctc tgggaagata acaacatga ataactaggt    18000 taaccagggc tgaaatttct ctaacctata attctaaatt cagaaaagaa tgggctttag   18060
ggttttttgt ttattttgc tttgattaca agttgttgga agcctagagt tagtatctaa    18120
taacacaatc tatgtaaaac acaaattatt ggctcagaat gatatctaat ttctaagaag   18180
atatgaggag gcaatcatgt aaaaacgtgc ttttcttcct agaaggaata agctgggatt   18240
ggccaaaagg taatcccttt agagtctaat gtttagagca ttgcatattt ttaaagaaga   18300
catattacct tttagaacat atgtaggaaa ccatttttctt tgcttatatg gctacataaa   18360
gttgtcatgg ttttaaaccg tgaccttaga taccttatag aagtaattac aggcacaatc   18420
tgtgaatgaa gatttgcaaa ctatgcttca ccaagcctca gggactattg gatgtccaga   18480
ggacagagcc atgttggatg tcttatgggc cttcagtcct gcaaagtggt gtgctttcat   18540
gttttacaca cagcagttct gagaaaaattt aagttgaaaa aacagcctct cttcttatta   18600 ttttatatt tatttattta tttatttatt tatttattta tttgaaacga aatcttgctg    18660
```

```
tgtcaccagg ctggagtgca gtggcgtgaa cttggctcac tgcaacctct gcctcccagg    18720
ttcaagcgat tctcttgcct ctgcctcctg agtaggtggg actacaggtg caggccacca    18780
cgcccagcta atttttgtat atatgtattt ttaatagaga cagggtttag ccaggttgcc    18840
caggctgatc ttgaactcct gagctcaagt gatcagccca cctcagcctc tccaagtgct    18900
gggattacag gtgtgaggca ccgtgccgag ccatcctgtc ttctgaaaaa aaaaaaaaag    18960
caaacaaaaa tgtttaagcc tggtatatat tttcttatat tgcataagct acttttctga    19020
ctgcctctct ttagaaattc ctctgatttc tagagaaaaa aaaatcgcat tagcttttg     19080 gtttctaaat tcaggctcac tttagtaact gctagattat aaactcttag aaggcaaagg    19140
gctatgtatt ctctacttgt ggacactcaa ttagtttgct taagcaatta cttctgtgta    19200
agcaacatta atgaagtgct tactatgatc aagggctata ccaagtcctt ttttatatta    19260
tttaatccca cacaaaaccc atgatcgacc taattgtaca cttggtgaaa ctatgatgta    19320
gggaggttaa ataatttgtt caagaaccca cagctggtaa gtcgcacagt gtattcaaac    19380
ccagatcttc ctaattgcaa atgtgtccaa ctcccatgct tctaaccact gcctatgtga    19440
tggttctttg aaattcctcc ctccaagaag tggaatttaa ttccccccgt ccattgaatg    19500
tgggccaaac tcaggtgact catttctatt aaatggagta aagtggaagt gaagatgtgt    19560
ggctttagcg actaggtcat tcaaagtggc tcctgtcttg gttgttctgt ctcttatacc    19620
tattgggcat ttaatctggg gaaaaccagc tgccatgttt tgagctgctc tgtggaaagg    19680
ctaacatgaa aagatactgt ggatcctaca gacagcttca aatgaggacc tgaggccctc    19740
agaccagtag ccagtatgaa actgaagcct cttgaccaca gcctccatga gagtaatgga    19800
atcttgaccc cctagtgaac cacagcctcc atgagagtaa aattcaagat ggagccttga    19860
cacccagtgg agcctcgaga tgactgcagt cttccaccaa cagcttgatt catgaaagac    19920
catcagccag agccacccag ctaaggtgat tctaggcccc tactcctaga aaataaatat    19980
ttgctgtttt gactgccaag tgtttgatta atttgttacg cagcaataga taaataatgc    20040
agcctaacac tgtcctggtc attttttaaa aagaaattgt tttaatttta ctaaatcaca    20100
aattttaaaa cattgataca gcaaggagaa actttccaga aaaaaaatgc tgccaaattt    20160
aagtagtaaa atattaatgt ccaaaaaaca tcatagttac aatgacatct ctaggattga    20220
ggattttgta agtcaaaggt cagctgctta aaaaacccat aatttaaaaa ggaaggatat    20280
taataataac tgcattattg aacatagata gcattttgaa cttttaagaa atcctcatgg    20340
gaaaactcag gaaataatct gtttggtaag ttatcactca taatcttaaa ttgttaggtg    20400
catgtttgca cttttccatga tttgaagagg aatataaagc aaagttgaat tttaacctct   20460
tccctaatga ttttactcag cttttcaaag gggtcctaaa agctcagagg tcaagtcatt    20520
tcttggtttg ctctacctga caaattgcat taactctgct ttatagccac ttgcagttta    20580
ataaatgact tggactttga ttaatatctt tagtgcttaa gcccaagaat ttgtataaga    20640
ctttgggata tagtactgta aatttatcta aagatggaca ctggaaggta gaaggagata    20700
tattagtgtt ggtttgggta catgtctagg tactgaattt ggatcatcat aagtccttac    20760
agaagatact tgttgacttg tcttttaaaa aatatgtgaa agtgattttt taatatattt    20820
acaaagtgat ctaagtgatt taaggaattc attcatgaag tggatatgac tagttcttgt    20880
ttagtattca gaatgactgt aaaatagaaa tgctgatttt ccttgcccag attgtagaac    20940
acagatcaaa ccctcctagt ccttccctta aatgtttttt ctccatacag cttatgccct    21000
gagttctcaa aacattttt atattgaact ggactgtata gtatatgcct gaccctgatt      21060
```

```
catgggatta tgctgcaagg gaatataaag atgaatattg atagcctgag tgtgaaaatt   21120
catcattact ctcatcctca ttcattaatt catttgttca ttaactcata aacacactaa   21180
ttgattcaac agatatttat tgaacgttta cactttgccc agtggagcac tggactaggt   21240
gctagcatag tataataagc aacccagaaa tagcctctgc cttgctgcat tcatagtct    21300 aggacggaga aaggcattaa ccaagtataa tttaaaattg ttttaagtaa tgtgaaataa   21360
acatatatga gaacttgact caggttggta tatttgatgg ttagggaaag cttcaaaaat  21420
gggatatttg agatctaagt aagagggaaa agaaagagca taatgggtag agaaaaaata  21480
ggatccagga agatacttag tacttctgag aactaaaaac agtcaagtca gtgtagtcag  21540
agttcaaaga aggagaaaga acatgatcca agaagaagcc agaaaagtaa gcagggacta  21600
catcttacac gatgatgtag gctgtatttt agttttttact tatcttaaga gcaatagaaa  21660
accattgaag ggtttgaagc aggggagtga cataatcagg tctgcatttt aaggaggtca   21720
cctgctctat tatgaagcat gaatggagga ggatggaaag agatattcag ggagctggtt   21780
tatgagtctg ttgtaggcca gaggtattgg tagcttggac cagggtgatg atgctgaaga  21840
ttgaaaggag ttaatagatt tataatatat ttgtgaagta aagttgactg tacttagtgc   21900
tgacttagat agtactggtg agggatgtca tggtaaactc caaggtactg ggcttcttca  21960
actgagtgga aaacactaga gggagaccag gtaaaggttg aaggaaagtg aggaacagta   22020
gttcagtttg gggatatttt gatttggagg ccttttttaag acttcctcaa agagacacag  22080
tgcagtcttg agtcctggat cagaggagat acctcaatgt ataaatttgt aagacaatgg   22140
tttatacaca ctattaaagc cactgaggta agtgagatca tgtacagagt gaaaatgaag   22200
tgagagaaga aagcataagt ctgagccatg agaactccaa catttaaagg ccaagtggaa  22260
aagttgacaa gagtgggaat tgtgactggg gtagatgcta gaggggcatc tcagaggcca  22320
aggaaagaga atcatttaag gtgctgatga ggggtaaagt aagaaggtcc tgtaaatgtc   22380
ctcttggatt aataaatttg atgttttgaa ggactttagg gagaatgagt ttgttgtagt   22440
gatggggcca aagccagaa tgaagtgtca tgggaaatgg gtggaagtct tgaaagagag   22500
acaatgaata tagataactc aagatatgtg gtcaaggaa acaaaaagga taaggcttta   22560
actagaggag gaaatggagt taaaggagga gttttttttt ttttgagacg gagtctcgcc   22620
atgtcgccca ggctggagtg cagtggcacg atcttggctc actgcaagct ccgcctcctg   22680
ggttcacgcc attctcctgc ctcagcctcc tgagtagctg ggactacagg tgccctccac   22740
cacgcccagc taatttttta tattttagt agagacgggg tttcaccgtg ttagccagga  22800
tggtctcgat ctcctgacct catgattcgc ctgccttggc ctcccaaagt gctgggatta   22860
caggtgtgag ccaccactcc cagccaggag gagtatttt taaagatggg agacttgagc   22920
acatttgaac aataatgggg aagaccagtg gggaggatca ggggtggcct gaagatagac   22980
agagggtgga taaataatca tgtaggattc ctgagaagat agaagaagtt ggatccgag   23040 cacagcaggg ggaattagct ggccttggag aggagagatg atctctatcc tctattctag   23100
aaggaagcca aaggtgatgt gtgcagatgc agaggtgtgt ttgatgtggt gaagccaagt   23160
caaaggagtt tttgttcgat gccttatatc tgctccagaa agcagttgag tcaccaactg   23220
agacagggag agagaaaggg gctggcatac taggaaggaa aggggatcat ttcagatatt   23280
tgaggaggac agagtaagtt ggaatatgaa agggaataaa tgagtgaaat ttagtaggac   23340
tgctagtcac tgcttgaagg ctcagctgag gctgatgatc atgaattcat ggtactactg   23400
```

```
ttagaattat tataaaatat atgagccttt ttggaggtgc tcagcagttt accagacaca    23460
gaaaaacagg ttcatctagg cttaggattt tgtcagagag gtatgatgaa aagattgcaa    23520
aggagtttag gatattggca tgggcaaggg agcttctgga gtgataaacc aggaatctaa    23580
gcctgctagg gagggacata tagacaggag aaggagagta tagagatctt tctgaaggtt    23640
agaggaaatt tgtaatcaaa gtggttgatt aaacaagaca gaagtatagc agtcagtgat    23700
cagcccagga tgctgcaccc cagatcaatt aaatctgtat ttctgggtgt agggcccatc    23760
ccagtttctc aggagattcc agtgctttcc ttaagggaga atattgatat aactgttatt    23820
aagactattg tgaaaaaaca tattagcaat gtgaaatcaa gacaaaaaca caaacacaga    23880
aagaagttag acaaaaacaa aaaacactga aattacacat tttcttttc acaaatcaaa     23940 gtcaaattca cggaccttct tccctgactc attctccctg acattagaag tccaaaggga    24000
gcaagtaaag tctttatggg gaagatggta taattaagca ccaattacct agggaccaga    24060
tgctttggga tttgactgat gaaaacagat tagaagcatg gtgaatttgt tcactactgt    24120 cttttttggag gggcaacact cctggctcac ttggcatgag gtaatgtcag tctggctaca    24180
aagatttgaa tgtggggctt gagtttctaa aaggggactg attggacttc tcttagccag    24240
gatacttgga cttggtggct atatcatggc tcacagtgtc ttggaatggt cttgagccta    24300
gttgaaattt gttgaaatta catatgaata ttcattaatg tattacttgg aactcagtga    24360
gaaggatcat cactgccaga tttcctagtt aggaaaactt accttcattc cttccagtta    24420
aatagaagac cattgtatag ttcatttttgg gctaagtgga gtgtttatga aatgtgtagg    24480
gcttataggc ataactattg ctaaagaaag cccagtaaag cttgacatcc cctctgttgc    24540
ccttgtctgt cattccataa atttaatgtc aagggcattt ttagagaaga tgatcacagg    24600
atgattcagg tagacatgga gcaggttgtg aaaacactgg catgtttcac caatgtatta    24660
gggtttccag agaaacagga ccagtagggt gtgtgtgtgt gtgtgtgtag atttattta     24720 agagattggc tcacacaatt atggagactc gcaagttcaa aatgtgcaaa gtgggctagt    24780
aggttggaga cccagagaag agctcatgtt gcaagtcaag tccaagtccg ctgcagaatt    24840 tcccttttgct tgggaggtca gtctttggct ctattaaggc attcaactga ttggagggca    24900
gtttacttta ctcagagtac atcatttaaa attttaatat catctaagaa cactctcata    24960
gaaacattta gggtaatgtt tgacaacata tctgggcacc atggcccagc caaggtgata    25020
tagatataga tatagataga tatagatata gatatagata tagatataga catagacata    25080
gatagatata gatatagata tagataatgg atatatataa tggatatata atggttatat    25140
aattaaacat tacacctggg aagttacagc actatcttct ctggattaaa caacaacaac    25200
aaaaatactc agtccaattc atgatttgtt gagggtctgt gtagaatata gaaattatac    25260
tacaagtttg gttttctta ggatggtgag cattttataa aatatgtata tataaagaga    25320
ggcattctct tgtaacactt agaatagtcc tgtacacata gaaggcacac agaatgtcca    25380
gtgccagtga catgagactt cataatgagt ttgaagccaa agctttgtgt agtaaaaagc    25440
catgagcagt taataaattt ccatttgatg gcagctataa atattaacca gaagactcat    25500
aactgtgttt tcaactcaca tacctgggtt ggggcagaag caatagtttc agcagctttt    25560
atttatctgc ttttaattcc atctcaccat tgttaaattt acctgaaata attgccattt    25620
tgacaatgcc ctcaaaaatc atcttattgc ctggggactg attttcagat tcctgagccc    25680
agtattcaga atcctatata ttccctcaac ctatctttcc atgtgtattt tctgttgagc    25740
ttcaaactga actacctctt tgctctcaac atattctatt tgttaacttt tgttcatgtt    25800
```

| | |
|---|---|
| attccctcta aaatgacttt tctctaattt ttttcattct ctcattcttc ttgtctttcg | 25860 |
| aggtggaact caaatgccac aacgtcaaat gccacagtat ctgctatgat ccttccctt | 25920 |
| tccagctaca aattcctctt tcctctacca cttctttggc acatttatta agactcgcga | 25980 |
| tttctctcat ctaagtctct tgtgcaatgt cttactgtat gtggcctgaa ttcaggatct | 26040 |
| atgtctacag cctccccttt agcctcactc cagtatcttg caggtgggca gtcctctgta | 26100 |
| aacacttgtt aaaaagtca aaacacattt ttcaaatcag aaagaaccta acatacaaag | 26160 |
| cctcattgtc atttttaaat ttcatcgaag agctatacat tgaattttt gtgtgttctc | 26220 |
| tatagtacct agccatgtgc tggacagtgg acccacagtg acattcagt aattagtaat | 26280 |
| agatggattt attctgtatt taacaaaatt ttctggatgc ttttagactg aaggagattg | 26340 |
| gtttgatgac acaagtttca aaagacaatg ttattgctaa tgcacattat gagggaacta | 26400 |
| tgatatattt tgaagtccaa caaatagaaa aatgaatcaa tcacgagtca gatttattga | 26460 |
| tggaattgtg ccaccatcaa gtcctaaagc attagtagtg atgttatcag aaaatatccc | 26520 |
| actctgagat catctgtagc cagctttata ctctaaaaga atagtctgag tatgttctgc | 26580 |
| ctggaaaagg gctcagtggt ctaggaatta ttgttttac tttttcaaag tttataaact | 26640 |
| tggcatgact gtgcttttct gtggcttcca atctctggtg ataagttttc tcaaaatatt | 26700 |
| cctgatttat cctgatgtaa atcacaattc ataaatatca agagagactg cctacagtac | 26760 |
| catcttctga tttaaaaaca catttgaatc aatatttact tatatataat gcattctgct | 26820 |
| gaataaggaa gttctgactt gttaagctca gtatgcttcg ataagaaagc aaaattttt | 26880 |
| tgttgggttt ttaaaatgta ttttaaggtc cttgtctctt ggtgatagtt ctttacatat | 26940 |
| tgaagtgcca gggaataact gtccagtagc tggacaagag agactcataa tatggcagtt | 27000 |
| gaagccaaag cattaagcaa aaacagttat taatattaac aggctcactg tagagagaag | 27060 |
| ccatagttgt caggggaggc agaactgccc aggaaaccca tctttgtcct tttgtctaca | 27120 |
| caggttgggg caaaagcagc agttatttga actcagcaaa cctgtgttcc atattgaagg | 27180 |
| cctgcataag tcagggacca gggatgtaat gaagaccaga catggacttt aggagcacaa | 27240 |
| agtgtagaga taaaactgca ctcataatgt aagctaatgg gaggcaggaa cgatggaagc | 27300 |
| agcaaagact cgctacagtg ggaggagtta tgagagactt cccagaagat atggcatctg | 27360 |
| agctgattct taaaagttct gtaagaggcc aacaggcaga gaaaaatga aaaatgcta | 27420 |
| ttaaacagta tagcccataa ccgtggggat ataccagagg atgatgtgtt agggaaatgg | 27480 |
| taagtacttt aaagtggcta gatcagagaa tgttcgaggg caggtgaagg gaaaagtagg | 27540 |
| cagggttctt atatttatat cagtgatctt ggactttgtc tggggacctg caggtagctg | 27600 |
| ctaccagaat ttcttatgtc agtaagtaac atgatcagat ttgttatttt agcaagacaa | 27660 |
| cttacactat aaagtataga gaggtgttg gagtgcactg attgaacagt agtgtggaga | 27720 |
| tgtgtttttt aataataaac caaatgagta ataacatgtc ttactcttac ataattagta | 27780 |
| agatcttgcc agcatctttg ttggatgaaa ggaagcctag tgtttatcac caaatctttt | 27840 |
| gagatgtcag tataacacaa cactgtattc cacttttgaa aacagccatc cctatagtgt | 27900 |
| gtgaagagaa tacttaaagt gcagacagac aagtgaacac cgcacttctt tgtcacatgc | 27960 |
| agtcaagaaa ccagacaaga tatttaagct atgattatta gtgttggcaa gggttcagct | 28020 |
| ccagggaaaa taaatacatt gagttagtgg tggtgatgag attgacacga atagagttgt | 28080 |
| attttccttt tcatgctgtt gcaagggaaa tgaagcttta aacataatga aattggttct | 28140 |

```
tgtgaacagc aaatctgcta tttcttcact ttttatggct ttgtcaacag tgatctaagt   28200
tttgctttac ttatttattt taaattttgt tttattttaa tagttttggg ggaagaggtg   28260 gttttttggtt ccacgaataa gttctttagc ggtgatgtct aagattgtgg tgcacccatc   28320
acccaagcag tatacactgt acccagtgtg tagtctttta tccttcaccc cctcccaccc   28380
ttctccctga gttgccaaag tctattatat tattcttatg actttgcatc ctcagagctt   28440
agttcccact tacaagtgag aacatacaat atttggtttt ccattcctga gttactttca   28500
gctccatccg ggttgctgca aatgccatta ttttgttcgt ttttatggct gagtagtatt   28560
ccatggtata tatatatcac attttcttta tccactcatt ggttgatagg catttaggct   28620
tgttccatat ttttgcaatg gcaaactgtg ctgctgtaca aatgcatgtg caagttgtgc   28680
aactgcctcc ctccctccat ctctctctct ttcctttctt ccttccttcc ttcttttctt   28740 cttccttgt tttctccctc cctccctccc tccctctatc tctccctccc tccctccctc   28800
tctctctctt tctttcttc ctttctttct ttcttttctt tctctctctc tctttctttc   28860
ctctttctct agccctgcca cccaggctgg agtgtggtgc catgatctca gctcactgca   28920
acgtccaacc tctgcctccc aggttcaagc aattctcctg tctcagcctc tgggattaca   28980
ggtgcccaca accatgccta gctacttttt ctatctttag tagagatggg gtttcatcat   29040
gttggcctgg ctggtctcaa actcctgacc tccagtgatc cacccacctc agtctcccaa   29100
agtgttggga ttacaagcat gagtcaccat gccccgcaca agtgtctttt tcatataatg   29160
acttcttttc cttcgagtag atacccagta gtgggattgc tgaatcgaat ggtatttcta   29220
cttttagttc tttaaggaat ctccctactg ttttccatag cggctgtact agtttacatt   29280
cccaccagta gcgtaaaagg gttccctttt cactaccttc atgccaacat ctattatttt   29340 ttatttttt aataatggcc attcttgcag gtgtaaggtg atatcacatt gtggttttaa   29400
tttgcatttt cctgataatt agtgatgtca agcattttt tccatgtttg ttgggcattc   29460
gtatatcttc ttttgagaat tgtctattca tgtcctttgc ccactttttg atgggattat   29520
ttgttttttt cttgctaatt tgtttgagtt ccttgtagat tctggatatc ttgccgattc   29580
tggatattag tactttgtca gatgcatagt ttgcgaagat tttctcccaa tcggtgggtt   29640
atctgtttac tattattatt attattatta ttattattat tattattatt gctgtgcaga   29700 agcttttttaa ttaattaggt ccaatttgtt tattttatt tttgttgcat ttgctttggg   29760 gttttttgctc atgagttctt tgcctaagcc aatgttgaga agagtttttt tgatgttatc   29820
ttctagaatt ttaatgattt caggttctag atttacatct ttggtccatc ctgaattgat   29880
ttttatataa ggtgagggat gaggatccag tttcatcctt ctacatgggg cttgccaatt   29940
atcccagcac catttgttga ctagggtgtc ctttccccac ttcatgtttt tgtttgcttt   30000
gttgaagatc agttggctgt aagcatttgc ctttatttct gggttctcta ttctgttcca   30060
ttggcctatg tgactatttt tataccagtc ccatgctgtt ttggtgaata tggccttata   30120
gtgtagtttg aaatcaggta gtgtgatgcc tccagatttg ttctttttgc ttagtcttgt   30180
tttggctatg tgggctcttt tttggttcca tataaatttt atgattttg ttccagttct   30240 gtgaagaatg atgatggtat tttgatggga attgcattaa atttgtagat tgcttttggc   30300
agtatgttca ttttcacaat attgattcta cccatccaca agtgtgggat gtgtttccat   30360
ttgtttgtgt catctattat ttctttcagc aatattttgt agttttcctt gtagagatct   30420
ttcaactcct tcgttaagta tattcctaag tattttattt ttatttttgc agctgttgta   30480
aaaggaattg agttcttgat ttgactctca gcttggtcat tgttggtgta tagcaatgct   30540
```

```
actgatttgt gtacattgat ttttgatcct gaaactttac tgaattcatt tatcagatct    30600
aggagctttt tggaggagtc tttaggattt tctaggtata caatcatgtc attggtgaac    30660
agtgacagtt ggacttcctc ttttctgatt tggatgcctt tatttctttc tcttgtctaa    30720
tcactctggc taggacttct agaactacgc tgaatagaag tggtgacagt gggcatgctt    30780
gtcttgttcc agttctcagg cagaatgctt tcaacttttc cctattcagt acaatgtggg    30840
tttctcctag atggttttta ttactttgag ttatgtccct tctatgccaa ttttgttgag    30900
ggttttatc ataaaagtat gctggatttt gtcaaatgct ttttctgtgt ctagtgagat     30960
gatcatatga ttttgttttt taattctgtt tatgtggtgt atcacattta ttgactcggg    31020
tatggtaaac ctacatccct ggtatgaaac cactatatcc ctagtatgaa acccgcttga    31080
tcatgatgtg ttatctttt tgaaatgctg ctggattcag ttagctacta ctttgttgag     31140
gatttttgca tgtatgttca ttagggatat ttgtacttt agttttctgt tatgtccttt     31200
ccaagtttag gtattagggt gatactggct tcatagaatg atttcctctt tttctatctt    31260
tttgaatagt ttcagtatcc aattcttctt taaatgtcag atagaattca gctgtgaatc    31320
catcgctctt ggactttttt tgttggcact tgtttttta ttactgtttc agtctcacta     31380
cttgttattg gtctgtccag agttcctgtt tcttcctgat ttaatgtagg agggttgtat    31440
atttgcagga atttgtccat ctcctctaga ttttctagtt tgtgtgcata taggtgttta    31500
taatagcctt gaatgatctt tgtatttct gtgatatcgg ttgcaatatc tcgtttcatt     31560
tcttattgag cgtattcgga tcttctctct tcttggttaa tttcactaat ggtttttcaa    31620
tcaattttat ttatattttc aaagaaccag cttttgttt cacttgtctt ttgcattttt     31680
gttgttgttg ttgttgtttc agtttcattt agttcttctc ttatttggtt atatcttttc    31740
ttctgctttg tttgggtttg ttttttcttt gtttccctag ttccttgagg tgtgacctta    31800
gattgtctat ttgtgctctt tcagactttt tgatttaggc atttaaaact atgaaatttc    31860
ctcttagcat cactttgtt gtatcccata ggttttgata agtttgtca tcattatcat      31920
tttgaaagaa ttttaattt tcatcttgat ttcattgttg acccaaagat cattcaagag     31980
cagattattt aatgtccatg tatttctata gttttgaagg tttcttttgg agttaatttt    32040
catttttatt ccgcagttgt ctgagaggat acttaatatg atttgtttt tcttaaattt     32100
attgagactc gttagtggc ctatcatatg gtctgtcttg gagaatgttc catgtgctga     32160
tgaaagaat gtatattcta catttttagg tagactgttc tgtaagtacc tattaagtca    32220
atttgttcca gggcatagtt taagcccatt gttttctttgt tgactttctg tcttgatgac    32280
atgtctagtg ttgtcaatgg agtactgaaa tcccacacta ttattatgtt actgtctatc    32340
ttgtttctta ggtctagcag taattgtttt attaatttgg gagctccact gttagatgca    32400
tatatattta tgattgtgat attttcctgt tggactaatc cttttatcat tatataatgt    32460
ccctctttgt ctttttttt ttccactgtt gttgctttaa agtctgtttt gtctgatata    32520
agaatagcta ctcctagact ggccgcagtg gctcacacct gtaatcccag cactttggga    32580
ggccaagatg ggcagatcac aaggtcagga gttctactaa aaatacaaag aaattagcca    32640
ggtgtggtgg tgtgcgcctg cagtcccagc tactcaagag gctgtggcag agagtcact    32700
tgaacccagg aggtggaggt catagtgagc caagattgca ccactgactc cagcttgggc    32760
aacagagcaa gactctgtca aaaaaaaaa aaaaaaccta ctcctgctca ctttagtttt    32820
ccatttgtgt gaaatatctt tttccacttc tttaccttaa gtttatgtga gtccttatgt    32880
```

```
gttacgtggg tctcttgaca acagcggata cttggttgtc ggatttctct ccattctgtc   32940
attctgtatc ttttaagtgg agcatttagg ccatttgctt tcaatgttag tattgacata   33000
taaggtactg ttctattcat tatgttagct gttgcctaat acttttaaaa attatgttat   33060
tgctttatag gccctgtgag atttatgctt taagaaggtt ctgtttgggt gtatttcaag   33120
gttttgtttc aagatttaga acacccttaa gcagttcttg tagtgctgat ttggtagtgg   33180
caaattccct caacatttgt tagtctgaaa aagactatct ctccttcata tctgaagctt   33240
agttttgctg gatgcaaaat ttttgactga caattatttt gtttaagggg gctaaagata   33300
ggaccctgct cccttctgat tggcaaggtt tctcttgaga gtctgctgt taatctgata   33360 ggttttctt tataggttac ctgatgcttt tgtctcacag ctcttgattt tttcctttgt   33420
cttgacttta gataaactga tgactgagtg tctaggtgat tatctttgca atgaattttc   33480
caggagttct ttgagcttcc tgtatttgga tatctaggtc tccagcaagg ccagggaagt   33540
tttccttaat tattccctta aataagtttt tctaatttt agatttcact tcttcctcag   33600
gaacaccatt tattcttagg tttgactgtt taatatagtc ccaaatttcg tggaaacttt   33660
gttcattttt aaaaattctt ttttctttgt ctgattgggt taattcaaaa gtcttatctt   33720
tgagctctga agttctttct tcttcttgtt ctagtttgtt gctgaaactt tccactgaat   33780
tttatatttc cctaagtgta tcttcattt ccagaagttg tggatgtttt tctttatgat   33840
atctatttct ctggagaaaa tttcgttcat attttgtact agttttaaa tttatttaaa   33900 ttgttttttg ccttttctg gtaactcctt gagtagctta ataattgacc ttctgaattc   33960
tttgtctgga aattcagaga tttcttcctg gttcggatcc attgttgtgg aactacagta   34020
atctttgggg gttttataga actctgtttt gtgatattac cagaattact tttctggttc   34080
cttctcattt gggtagacta ttacttaaaa ttgttttgt ggactgtgtt ttttttttaa   34140
tttcttattt tttctttctt aagaatcaga ctctaatgtt tattttagcc taattggagt   34200
cttggtgctt gtaggggtga agactctgta cgagatcctt agttacagaa tcttcctgca   34260
ctggttttcc ccaatgctga ttttagtagt tacatacttg gtgtgtgggt gaattctctg   34320
tctcctgtga agctggaatg gcagggatcc cttgacgctt atgtcctcct ctcatggtat   34380
acagtttatt tactggtctt ttatttactg agttgatgat tcaggcttca ggacaattgg   34440
ggaggtatcc cccggcaggc accagttgtg gctaaggcaa gtgggtagat gtaataccca   34500
atggcgagcc gaggtcacag ccttgatgag ggtggctgga ggagctctca attaggtgtg   34560
ctgaaatttt atcaaggtga aaagtgggag cttcctcagc tcccctgcca agtcagaaag   34620
aaaactattc acctcacagc ctcactcctg tcctagcatt tcagctattc agatcagaca   34680
ggcatctctt ttcatctata ggaatgttgt tgttccaagt aggga ggaac tgtgactctg   34740 cctctcatgc aggcctgaat ctggggtttg ctcctcttgt gggcgatact caccctggag   34800
tgttccagaa aggctgtcta caggtgtatc catgtgtgtt cctgtgggggg aagccccagc   34860 tgtgtctgca gtggagtgcc aggggaaca aggactcctt ttccaaggcc cttcatggtc   34920
acagaggctg cttgcctatt ggggtatagg tgcagacttt ccctactgca cctggcactg   34980
caattgggtc tctgctgtga gaaactaccc actagcagaa agatctgaaa ctcctactat   35040
tcagattatt ttgtctcact tagtgattcc ttgatgtggt gttctcctct ttcccctagg   35100
gatgggcttc ctgagagcca gattgcagtg actgttattg ttcttctggg tctagccacc   35160
caatggagtt accaggctct gggctggtgc tggcgaatgt ctgcaaagag accggtgatc   35220
tgatcagtct tcaggtctcc tagccatgta taccagcacc tgctctggtg gaggtgacag   35280
```

```
gatagggatg tagactctgt gagaatccct gattgtagat aggtgtagtg tgctggcttt   35340
ctcaaatgct agttatgcta gtattgaagt tgccacgtgg acagactaag gacctctggt   35400
tagccaggat gttgcaggca gtgatattag ctgttgtttt ctccttcctg ggagcaatat   35460
tattgtcatg agtatggcct gagttggttg gcctccagcc aggaggtggt gtcttttgtg   35520
ttcggctgcc aaggcagata gaaaaatacc atcaagtggg ggcaggatta ggcgggtctg   35580
agctgagact cttcttgggc tagtcttgcc acagccacta tgtaggatgg ggaggatggt   35640
tttcaggctg atggggttat gttccagagg ggattatggc tgcctctgtg cacagaata    35700 gttcaccagg gaagtggaga atagccagta gtgaaaggct tcacccagct cccacacagt   35760
tggtgagccc aatctcactc ttgcaatgct gtgttaacag caccaagttt agatccacgc   35820
ctcctgcttg tggaactcag tcttactcca ggccatacac ttccccactg agaaagcaag   35880
caaggctttc aggccacacc cctccctgtc tgcccacaag gttcctgtgc tcatatctgc   35940
tgcagttccc attcacccac cagattctgt tcacgcaggt tcatgccccc tcaaaattat   36000
cacaaaattc atttggaagc ttctttcacc ttgtgccccc tccctaattc tgctggctgc   36060
cttccctgag ggcccctgtg agatatagtc aggcatggct tccctgggtt tgagctggag   36120
actgggagtg cctacaagac tcttcctgct gctgcttcta cttttgtgtt tcacgtggct   36180
ccctaaatct gttccagctc taggtaaggt taaatccttc tctcatgatc tggattttca   36240
gattccccag tgaggatatg tgtttggagg caggttttcc cccattcaca ctttgggaac   36300
tcattgcttt ttgcctgtct cacagagttt gcagcagcct gtcacttctt tcaaaggatc   36360
tgtgaattct ttccatttc ctgatatgat cctgtggtgg ttcttggaaa aaaggttcac    36420
agtctgagtc tccacacact gttcgtgtcca tccaagcagg agatgtatgt tagccctgcc  36480
tgctatctgc catctttctt ctgtccccaa tccttctctt tagatagctg atataccatc   36540
ttttgtttct tctgacttgg ttctattcac tgacattcct ctctatcaag tagattttg    36600 aactttcatg gaaatttatt cccaatttat atggaaataa ttcccaattt atatgaaaag   36660
cttataaagt gattcattaa ccaagtattt actgaggtgc taaaagtata ctctgaagca   36720
ggagtggcaa gtcctttgcc ttcatggaga ttgcattctc ttgtaaatct tacatgatgg   36780
tcactagatt taggaataaa ggactccagc ataaaacact gacacttctg ctggagaaat   36840
attttacaaa ctatatatat tgaagcccaa actctggttt attggtaaag gagtagcact   36900
gatactagaa ttttgtgatc aacatgttgg aataagaagt cagaagactt agatctgtgt   36960
tctttttctc ccgctggcta taggttgctt taatctctga gctgcagttt cctcatctac   37020
agaataggtt agaccagatt agtggtcttc aactttggct gtatattaga attatcttac   37080
tcttgaccaa ttaggttaga aatttcgggc cacacacaat ggcttacgcc tgtaatccca   37140 gcatttggg aggcagatac gggcagatca caaggtcaag agatggagaa catcctggcc   37200
aagatggtga acccccatct ctactaaaaa tacaaaaatt agctgggtgt ggtggtacac   37260
acctgtagtc ccagctactc aggaggctga ggcaggagaa tcgcttgaac ctgggaggcg   37320
gaggtggcag tgagccgaga tcgtgccact gcactgcagc ctggtgacag agcgagactc   37380
cgtctcaaaa taaataaata aataaaaatt aaaattagaa atttcctggt ggagaggaaa   37440
gcagaggtat ttttaaagct ctcaggtgat atatttctgt tttaaggtag gactaaaaat   37500
catgggacta cgtcagaagt tctaattata aatctatagg ttagttttct ccaggcatgg   37560
gtatagtgct taaatgcctt ttaaatttgt taccaacata gaaaaaaaaa ggtttccggc   37620
```

```
ttctcttgaa aaatggaaat attaggcaac agttgggctt atgtttctga gtggtaaaaa    37680
ttaaacaaag taaacgagtc tccgtttcat ttgttcctgt tgccttcctg gctcttgaag    37740
gcattgtcat ttgtgaaaac taaactagat ggtctttaaa atctccaatt atttgaattg    37800
cttatttcca catccagaaa agagacggta aacaaactat acctttatct gtaagctagt    37860
tggtttgtga aatcaaaggg aacttaatct ttgaatatgg aaaaatccca gggtccaatg    37920
gaagagaaac tccatctcat taatagcagg actccacaga ctgctatgga aaagacaccc    37980
acccggggct aagagggagg gaggcggaag aggacttaat tcattttctg ggcattttta    38040
atgaagcttt cccctctttc attatttctt atttgggagc tggatcatta gttgggatgt    38100
gactggcttt ccctggggag caaaaaggag attaacagag gttttgctcg cttcttcctg    38160
tgatttactg tgggaagtct cccaggttct tcccttcgct tctctgtggc cttcatcttc    38220
atggtttctt gctgtgtctc tctgagagca agtacctggg tgaaaaaggc tgagtgtgtg    38280
gttttttggc aactgcctgg cattggattt aagtgggtat atttgaatta ctagaatttt    38340
acattttata ggttcaaaat atgcacttga attctgtagg acctcttacc caaattgaat    38400
aatcctttgt gccttgttaa attttaaaaa gtcacactat caacattatg acatatggca    38460
tatatgatgg caataataaa aataacacac ttattgtcca ctttaatgtg ccagcagtgt    38520
tccaagtgat ttgcgtaaat atcaaatttg ttccacacaa ttatcctatg aactaaatgt    38580
tattatttcc tggtttatag gtgaggaaca cagaggctca aagcagctat ttgatttctc    38640
ttatttcaaa attaggggaa gtgagataca ttaacctgta taaccagacc ttgttaactg    38700
tttttggtaa attccaatgt gtattgattt tcacaaagac aaatcacacc attgttatat    38760
taaatattaa tttttttcata gtccctcaag gtgcttactg gctatattgt tactgtcttt    38820
tgatgttgtt tatacatggt ggattacaga attccatgaa cataaaaaat cttgacttta    38880
tcctagccta tttcctattc ttaccccctg caaagtaaaa agttcaaaat agcgttagta    38940
agccaagcaa actacttact agccacatga acctactagc ctctctgcct cagtttcttt    39000
gttgggaaaa tggacaatac ctaactcaac tcataaggat atttctagaa tcaggtgtaa    39060
tatcaaataa aaatatattt ccttttttcct agaagatacc catgtatatc ttaggtactg    39120
atgtattcat agtgatgcag aacataaaat gtttattctt ttgcttagca acaactatcc    39180
atagagattt ttccacttta gagatttaat cccattaaag gtttttagat tgattggaca    39240
atgagaatgt ttttgtctct ctgaaactga ggctgaaagt tgatttcatt ctctcacttc    39300
aaatcatact acaaggctac agtaaccaaa acagcatgtc actggcacaa aaacagacac    39360
atagacaaat ggaacagatt agagagccca gaaataatgc cacacaccta caacaatctg    39420
atctttgata aagttgacaa aaacaagaaa tggggaaagg actctctatt caataaatgg    39480
ggctgggaag ctagctagcc atatgcagaa gattgaagct ggacccctcc ttacaccata    39540
taaaaaaatc aacttgagat agattaaaaa cttaaatgta aaacctaaaa ctataaaaaa    39600
ccctggaaga taacctagga aatggcattc tcgacatagg acctggcaaa gattccatga    39660
caaagatgtc atgacaaaga tgtcaaaagc aattgcaaca aaagcaaaaa ttgagaaatg    39720
gaaacagatt aaactaaaga gcttctgcac agcaaaagaa ctatcaacag agtaaacagc    39780
ctacaggatg ggagaaaata tttgcaaact atacatccga caaaagtctg gtattcagaa    39840
tctataacaa acttgaacaa atcaacaagc aaaaaacaac ccaattaaaa agtgagcaaa    39900
ggacattaac agacattttt caaaggaaga catacatgtg ccaacaagc atatgaaaaa    39960
atgctcaata tcactaatca ttatggaaat gcaaatcaaa accacaatga gataccatct    40020
```

```
cacaagtcag aatggctatt accaaaaagt aaaagaaaaa cagatgcctg tgaggttgta    40080
gagaaaaggg aatgcttata cactgaaaag ggaatgctta tacactgctg gtgggaatgt    40140
aaattagttc agcaattgtg gtaagcagtt tggtaatttc tcaaagaact caaagtagaa    40200
ttaccattag acccaataat cccattattg gatataaacc caaaggaata taaatcgttt    40260
taccataaag acacatgcat atgtattttc actgtggcac tataacagag acacaataac    40320
aaagacatgg aaccaaacta aatgtccttc aatagtagac tggataaaga aaatgtgata    40380
catatatacc atggaatacc atgcagccat aaaagaaat gagatcatgt cctttgcagc    40440
aacatggatg aagctggagg ccattatcct aagtggacta acacaggaac agaaaaccaa    40500
ataccacatg ttctcattta taagtggaag ctaaacattg ggtacatatg aacacaaaga    40560
agagagcaac agacagtggg gcctacttgt gggtagaggg agggaagagg atgaggatta    40620
acaaactacc tatcagatac tatgcttatt acctgagtgg caaaataatc tgtacaccaa    40680 accctctga catgccattt acctatgtaa caaacctgca tagtaccccc gaacttaaaa    40740
gttaaaagaa aaaaaaatga ttaatgagcg tgataccaga acaatattat gatgcagggc    40800
tattttttgt gtgtttgcta gctgggcttg agatttgata aataagtccc attgtcctaa    40860
tccgctagtg atgatgttct agcctttgaa attcaaacta ctactactcc actttgagag    40920
agactgcatg agaattggac ccagcctggg gctttagaca ccatggttca aatcttggct    40980
cttatcattt tttagccacg tgtcatggac tcaatgtttt tgtctcccag ctccccagat    41040
tcacaggttg aagccctaac ctccaatgtg gctgaatttg agattagggc ctgtgaggag    41100
ctggtaaaag ttaaatgaat tcttaaggat aggtctccaa tcctatagag ttggtgctct    41160
tacaagaaga ggaacagaca cccgagttct ctctctttgc tatatgagga catggtgagg    41220
agtggccatc tgcaagctca gaagagagcc ctcaccagga acttaagtgt ctggcacctt    41280
gatcgtggac ttcccgacct ccagaactgt gagaaataat ttttttgtgt ttaaatcacc    41340
caaactgtag tattttgttg tggcagccca agccaattat tataccatgt aagcaggtta    41400
cttaaattta ctaaatatgt aagttactta aaatttcaaa tcctggttct aactttacta    41460
gctatcactt ttactagcta acacattaca ttttcttcaa cttgccgcat gcttttgctg    41520
tgagttttaa atgaaattgc ttaagtactt tgcttatcat actgctgatc catagtaagc    41580
acttaaagtt agtttccagg aagtttggaa tggatctcac ttatgcaaat ggttgacttt    41640
gacggtgctt gttcctctct ggaaagggtt cacctcccat tagaatagtc ctgtgactgc    41700
agtaattttg tatgttaaac ttacatgtat atctgcagaa tgttaaatct gcaaacacca    41760
tccatcaacc caaaagcaaa aaagagtgt ttcctaatag ttaatagttg gtagcttaat    41820
aggaaatcta gaaaaaaat gtttaataat gaaggctata ttaataccaa gtctcatttg    41880
agttcctgtc agtaaggaaa tagttatctt tcgttgttaa tcaatgaaga ccagttgcca    41940
taattagggc tctggtgtgt tttcttcaca tggtcttcta ggacctaatg taatatcatt    42000
tgagaggctc aaagaggatc ccatattccc aaaggtatct tagagtcctt agctgcccaa    42060
catcccacca ttaatcatgc tttgcagatg aaaaattgaa gactccttgt ctctgaatat    42120
ctgggatatg ctttcattcc taggatggac attttttcttc ttccccaata aggaagaaaa    42180
agggacagag gtgatttata agagcagttc tactgagtga aatgtgggtc ctagcaaagg    42240
aggacacagc tgccccttgt aatagtggag ggaaggaagg aggcaggctg gctgtacttt    42300
gccctcctca accctaaacc ctatctgttt accacagtgg acctttttc tgaactctaa    42360
```

```
cctcattatt tcattcatta tccacgtaat attcattaat gttctccaag gctcttagaa    42420
taaatcttta acatttcccc aaaaagtcac aaggtctgac acctgccttc cttttttccag    42480 cttcctatca taatcctcct ttttggcagt ggccacactg atcttctttc aggttcccaa    42540
gctcagcatt tgcttttcat tgggagcccc ttacatcatg actgtcagcc tgattgtcat    42600
ttctttgggg aggccttccc tgaaccctgg aactggatca tataccccta tcatgtgctt    42660
tcatagcacc atgaatgtct ccttggtggc agtccccagt aggagaattc tgtgtttatc    42720
tgtatggctg tttcataaat gtttatcttc ctcccaatag tctgtcagca ctttggcagc    42780
cagttgtgtt ttgctgttga ttctacctcc agcacagaat gtctcttagt atttatggaa    42840
ggggacatga aaaagaaaa agtccactgc atgaagattt aatccagcga cactgaggcc    42900
tgaacatcta gctttaggga agccagcttc tagcaggaca gactggtagg gactaggtaa    42960
ggagaatgga aaaacacagg gaatgagcat cactttcttt aagactttgc ctctggcaga    43020
cccctccaag taacagattc caaagagatt gtgaatgttc tccctctggt atgcagtctc    43080
ctgtcctgtc agaaacatgg tacccagagg ccaaagctgc tgcataagca agttatcatg    43140
aaactattcc aggacaggtt tcagaagcag ggtcttaaaa atgagtatta aatctaatgt    43200
tcacccagat acatttccaa cccacatata gacaccgaat ttaacgatga aagtggaagt    43260
tactctgttg aggatttatt tgaaatgttg gttttctctt gtccatctga tacaggtcat    43320
agctctgttt ctgtcattag attgattttc atgtttctca gcacagactc tctgtgagtc    43380
agagataagt ttaatttttc agcatggcca taggaatgat gaagtcattc ctcattaaaa    43440
tgaagctaag caaaatttaa tagtacttgt ttaagattcc ttatttactt ttctacacaa    43500
aaagagttgc aaggggaaaa caaaaacttt agctttgagt aatttcctta attcaaatat    43560
agatttaaac cactttgtca taatatgtaa atgaactatt gctttttca ccacaggtct    43620 gttttcaaat agataatgag attatataaa taattacctt atataaacat aaggttactc    43680
attattgaaa gcaattttct tttttgttt ctggtttatt atggttaaga gtgagccttt    43740
gttttagata tttgaaaaca aaatgtgtgt gtgcgtgtgc ttttgtgtgt gtgtgtggat    43800
atgtgtatct agggaggtcc tcaaattcaa aaattataat acaaggttgt aatgtcagca    43860
cttcctattg catagtttta taatggggat atatagctat gcattaaaat gcattattga    43920
aatggaaaat caggatgtgt taaaaatgaa ttagtaatta tattaagatc tgaatggaaa    43980
ctagcataca atgtaactta agcttttgaa aaataaaaaa aaacagaaaa taattaatga    44040
taagttagtt tcagtattac attgataaat atttccagaa taagctataa aaaataagga    44100
ggtagattta ttattttaag gttcatacta aaagattgta atatttactt aacctttctt    44160
tatttaattt agaataagat tactgtcatc tctctaagca tctatgtaat agtgtttttat    44220 ttacttttcc attaaatatt actgagataa ataaggagtc ctggtgaatg aaatataatt    44280
taataagcag agttttctta ggtgaaaact aatcatgtcc tgctataaat gtatattgag    44340
agagaagctg aatagacaag ctccatgatt tagtcaatga tacgacttca gggaaaatgt    44400
ttttatgcct tgttggccat atctttaat acttgcattg aaaataaaat tacatcccaa    44460
gattatgagg gttgtgaaat tttataatta gatatttaag tcctgaattg attagcagca    44520
gtataaacat agacatggat tttgggttaa atctgagaac tattttttg tactaaaatt    44580 tgcgtgcaga tgacaatggg aaaatcaaat gttttcctgg aaaatttca atgggacaa    44640 atagtcatct ttctgaaaat atgaaataaa gggagtggta gtggtggac tataaacctc    44700 tttgaaggcc ttttaatctt tagctgtaat tcatgtttta tcaccattgg attttcaaaa    44760
```

```
cggaaaatac cttagaaata atttagtggg ccgggcgcgg tggctcacgc ctgtaatccc    44820
agcactttgg gaggccgagg cgggtggatc acgaggtcag gagatcgaga ccatcccggc    44880
taaaacggtg aaaccccgtc tctactaaaa atacaaaaaa ttagccgggc gtagtggtgg    44940
gcgcctgtag tcccagctac ttgggaggct gaggcaggag aatggcgtga acccgagagg    45000
cggagcttgc agtgagccga gatcccgcca ctgcactcca gcctgggcga cagagcgaga    45060
ctccgtctca aaaaaaaaa aaaaaaaaa aagaaaaag aaataattta gtgttacctt       45120
gttgatatta ccaaaaaaaa aaaaaagtg ctcagagtca cataacttga ttcagtcaga     45180
gctggtacta gatgctcagt cttctgactt ctaatttagt ttgctttcat tatctactta    45240
ctacctgctg ctgactcaga gctcctcagc tatctgcaag tggatgtgtt tattgaacat    45300
ttacgatgta catgaactgc tctcaatgcg aagctcccat ggtgaatggg agcttacttt    45360
ctgactcaaa aattagtttt ctctctttgt gttctaaatg aaagtgtcct tttgctttat    45420
ctgaagcaga aagttgtaag tttgtttatt ttacttttga aattttggag aattggcagt    45480
ggggtcatgc catcagaaac acatacatgc aatgcatgga tgcacggtgt gaatgagctc    45540
tctggaagat ggtagattat gggaaagaag gaagctcaga aagagagtgg accaagtcaa    45600
gaggaaagag agaagaaaca ggcaagtgtg gagcagagga aaagtaggag ggtcatgaat    45660
ccattctgca ggtgtgtgct gagtgactgg aagaaggaaa agaaccaagg aagtctctgc    45720
catgttatct tagttttgtt aagggtataa agagattgaa gagagtttaa ctaggccatc    45780
tttaacccta ggacatccct agagtccctg gcagaactaa taatctaaat tatgaatggc    45840
tgtgtgtgca cacacacagg atgcacttac taatgtctat cattatgagt atcttctgac    45900
ttctccacta caaagaaagg aagggaatgt gaccctcttt ccaggttaga agtaactagg    45960
gcatagtaac acaaatggat gaattaaact gtttaaatgg tgcactggaa tatatttatt    46020
ttggggcaaa tcatgaagaa ataaaaaagg aagagattct cttttgagaa aaagtttgtt    46080
tcctattgtc aattgagcaa ctctgtgaac atcttaaaga taaagaatga ttattctgta    46140
aagtgctggg atttctggtg ctgtgtgaca aagtccggtt cctttttgtct aagttagtta    46200 taataatctt taatgaaaag cagaggggtc ccatggtttg gaacaagtat ctgagtcaag    46260
agttgacaag tagaatagct gggcgcagag gctgctgtca agttgacaaa gccagaacag    46320
tacatttgga cagaaagaat ttgatttcct tatactgaat gtgatgatct tgaagaacag    46380
attttttttt tgcatgaaaa taaatcttta ttttcagtta ttacccacca gtaagagaaa    46440
gttaggttaa gggtataaag ggattgaaga ggtttctact tttgcccagt ccttattttg    46500
aatagccttc cactcatcca aagtcatctc ttttggaccc tcctctttta cctcttcaac    46560
ttcattctcc ttattttcag tgtctgccac tggatgatgt tcttcacctt caggtgtttc    46620
ctcagtcaca tttgattgat ccaagtcact gcaattataa gatatttgtt tctgaatgta    46680 tttggggac tctgttaatt catctttgac aatteccccag ttgtgagatc tgctacctcc    46740
acgttacagg tcctcgtgct tcaggccact gtaatgtgaa aaaaagatc tatcacttcc    46800 actataccta tcaaattcac gtttgccacg agaatcaaat ccatctcctt ggcccatttc    46860
acgtccactg ccctctcgac ctcttccaag accaccatga cctgaatag gtcggtcaat    46920 aatcagtcta tcaactgaaa attcgcctcc ttcaccccct tcatcaagtg cttttcaag    46980 tcttcgttca caaggtggtc tcctttctgg tcttctatca gttatttcc cttcaccgtg    47040 aagttgttga gcaggtcttc ttccaacttg tcttattcct tcttcttttt gtgttttta    47100
```

| | | | | |
|---|---|---|---|---|
| tttttcctct | aggcaagctt | tattctttga | ttcctctatc | caggaagggg gctgttggtt 47160 |
| gcatcttacc | caaatggaat | gcaatgggaa | ttgggagctt | gagttgtgtg gaggaggagt 47220 |
| tgtcaatctt | aacaaatgac | tatagctggc | gtgtggtgtc | catcaatcct tgagggcttg 47280 |
| gccatgcaca | ctagggaatg | gtcagaacag | actcaacaga | ggtctccaga gctttacaat 47340 |
| atctacaata | tcaaggttca | gggggtatag | acagtaagga | aaaaggccat ttcctgtttc 47400 |
| tgtccatttt | tggtacagta | gacagttaag | gttttttctt | ttgactagct tttaaaaaat 47460 |
| tacttagaaa | atggaaagct | tataaacatt | cataagtgaa | ttgttgaatt gctaccccaa 47520 |
| gtggtttcct | tacctagtca | ccacttaacc | agaaatacta | gaatacacgg ttcaaccaga 47580 |
| attcaaccag | gcagataacc | tgcctattgc | tcaagcaatc | atcagagttt ttaaaaacaa 47640 |
| aattaagcaa | aaaagacctt | tccccaaata | caatcattac | tttgtatgac ccattcctaa 47700 |
| gaaagctaca | ttccatttca | gaaaacatga | ccacttaagg | tacagttaaa acaaagtcgt 47760 |
| tgccttcagg | tgcttacttt | ctgttttctt | taaattaact | gctgaaatgt ttatcttgtg 47820 |
| ttttgtgctg | cattcctgaa | aactgtaact | tttaaggaca | taggcctcat ctttataaag 47880 |
| gaagaagaaa | acagcaaaga | ggtgtctcat | ttgggaggca | gaaggttatg accaatgctg 47940 |
| gaagtcttcc | tcttccttac | ttgttgttca | acaagatggg | ttctgtggtg tcgcatgagg 48000 |
| tgtgagttgg | aaatgaaagc | tgcaccacac | ttcttatatt | catagggctt ctccccagtg 48060 |
| tgggttctct | ggtgcaccgt | gaggctcaac | ctctgtctga | aggcctttccc acactcatta 48120 |
| cacatgtaag | gttttttctcc | attatggatt | ctctgatgaa | taagtaggta tgagctacat 48180 |
| gtgaaggcct | tcccacattc | attacacaca | aaaggaagat | ctccactgtg aattctctgg 48240 |
| tggacaaaaa | ggcaagagag | ctgactgaag | gcttgcccac | attcactgca gtcataaggt 48300 |
| ttctctgcag | tgtgaattat | ctggtacata | ataaggtgtg | aaaaacaact aaaggttttc 48360 |
| ccaaactcac | actcatatgg | cttctcacca | gtatggcttc | gctgatgtac aataagattt 48420 |
| gcaatctgcg | taaaggcttt | gccagaatcg | ttacaggcag | agggcttctc cccagtgtgg 48480 |
| atcctctggt | ggacaatatg | gtttgagctc | ccagtaaatg | ttttccgaca ctcattacat 48540 |
| ttacagcatt | tttctgtaat | gtggagtttc | tggtgccgag | caagttgtga gctataacta 48600 |
| aaggctttct | cacatttact | acgcctaaag | gttttttcta | aggagaggtt ttttttgatat 48660 |
| acagtcagat | ttgaactctg | attgaaggct | ttcccacatt | ttgagcaaac ataaggtttc 48720 |
| tgtccagtgt | ggattctctg | atgcacatcg | agctttgcac | tctgaatgaa ggccttccca 48780 |
| cactcatgac | attcaaaagg | tttctcccccg | gtgtggattc | tctgatgcac aacgaggttt 48840 |
| gcactctgac | taaatccttt | cccacacatg | ctacaatgta | aaagactttc gcccaagctg 48900 |
| ggttttcgga | ttgttaacag | tgtcagaatt | aaggctgtat | tttcccacag atttcttaca 48960 |
| tttctggtct | tcctcttctt | tgaagctttc | aggtaagtga | cagtcattca ctatgactta 49020 |
| tctgaaatct | ttcctttccc | tccttattct | ctgcctcttt | aacatgtttt ctttttcaca 49080 |
| agcctctctt | aactcaggtc | cttaaggatc | agctttctgg | attcttccta atatgatgcg 49140 |
| ggggttttca | gcttcctcac | gtatctcagt | ttttggaacc | agtaactgaa ggttcttggt 49200 |
| ttcagcacct | tttcttcctc | ttctgatcca | tcaaggcctg | tctgacgaaa ctcccctggg 49260 |
| gcccagactt | tgatgttctc | agagtgcact | tgttggctgg | atgcctgatc tgggaagttt 49320 |
| tcttcttcct | cctcctcctt | tttcaccttc | actgggcggc | atgggcctag gccatggct 49380 |
| tctctcaatt | ctgcagtcat | cttctctgct | cagcagggga | acgcctatag ctgggagctg 49440 |
| cccagcacag | gtcaaacccc | atctaagctt | tatgtttcaa | aagcttcttc ttgagttttcc 49500 |

```
tcccagggcc aagatgagta ttgcctacgt gcgcagctga gaggcccgac cagagttcac   49560
tggctctgca gcaggaggct gggggaccag gacctcagct cctactggca cgagaacaat   49620 gaccettatt ccttctttct taagcaccat ggacggctgc gtctcctctt tcctgtcaac   49680
cacgccaacg ctggagggca gcgggttctt gctgtctttc tgggactcct tgcgcagcta   49740
gctatttgcc tgccgccttg gagttggtct gggtcgcagc ctgagctgcc gctcttggcc   49800
ccagagacgc cgcccccgcc agcttctttt ttcttgttct ctcctgcctt cagcacctcg   49860
aaggggtccg attagttgtc aaataactgg tcgaatcggt tggtgaccag gcagctgaag   49920
ccttcctgta actgcccagg catgatggtt gctcggcggc acattcctcc acggattgca   49980
gcgggctgcg ccgagccaag agcgcgtgct tcagctcttc ccagaagatc gaagaacaat   50040
ttttttgaaa tccgcctgta aatgtcaggc aaggtaaatt tcaaaatgaa ttttaaagt   50100 ctctaaaatg gagttatgtt taattatgac tttatgacaa attaaaagat agttctagat   50160
aatactattg tagaaagaag cttctcttgt tctgggaaag agagacagtt tggaaacttg   50220
agacaagacc cttattgtct gtttattat ttactgctaa caaactgcat tctctcactg   50280
ttcactggaa taggtgggtc cagggaactt aggaaagcct aatgggaagt gagaaaagta   50340
aattatttct tatattttta tgtatacaaa tagttgataa aggaggaagt gtagtggtgg   50400
ggtggatcat gcagattggg atacaagaga cagtataatt attcacaatt atagataagg   50460
agatctaggc ttcacatttt cacttctgga atattccact ttgacagaac agtctactgt   50520
ctgcctcagc ctatcctgga gatgtccttg tggtgggaga ggacctgctt tctcccttgct   50580 gtgctcctac agtttgtctc tgccagtcat gtccaagccc cttgtcttag tgcctcacaa   50640
gacctcttcc tctgaccagg attcaggcac cttctcagaa ccttcattcc cctgacagca   50700
ggaccagcca gtctcccaga cccggggtag tgcgaagagg agagcagact ccttagaccc   50760
agagtcccag gacacttggc ctcaattccc gtgacaccta tatcacccag acaactggga   50820
aatggaggtg ctggtgccag aacaaaagca taagctgtgt ttctcaagtt tggactttac   50880
ctgggctgtt gctttatttt ctagctgttt actgattttt agaagcataa aggtttcttt   50940
ctgtgaagtt cctagggaca cttaacggag tggggacagg tattccttt gtctttcaga   51000 aaggcatgtt aagagttagt ctcacagtaa tttaagtctc acctcctaaa tggggtaaga   51060
gtggggagaa atatatgtgt gtatatttgt gtgtgtatat aaataatata tatatactac   51120
taatataatt aataatgtgt gtataaataa tatgtaaata acatattata ttatatgtca   51180
ataataaaat attatattaa tatatgttat tacattaata tactatatat tataatatat   51240
aagatataat tatatatttat atactattat attatatcta taacataata tattatatat   51300
ttatatatca ttatataatg tattacatgt attaatatat attatctata tagtaaatat   51360
atggggtgtg tatttgtgta tacacacaca cacgcacata tatatcctgc attgtttgct   51420
tagaatcatg ctttgcaatt attaactgct ttttcttcct tcccttcatc taatacacct   51480
gaagaatatt tcagttagcc aaaggtgaga atccgaattc atatttgtat tcccaataga   51540
tttcccgcag aatcttgggt tatcattca tcaataacag ttatgcagat gttctattgc   51600
tgtgtccaat gcttgcttcg ttcatatgaa atttgacttt tggccattca aaaagcaatc   51660
agtgccttct tgttgattag cactaatcac cacaagatcc ttccaatagt aaattttcca   51720
gagcaaaatt ctaaacttac agattagttt gccgcagccc ctagccctac actgtaagga   51780
tcttgctttc catgaggtcc attgttaaat ggaaatgttc ccctggctct atgcagtgct   51840
```

```
caggtgtttc ttactcagct gaaggactaa tgaatttagt ttgaatctaa atttggagta   51900
aaaaatgcca ctcaggagag ctgcttctgt gactgcattg ccttccaacc tgcttttcca   51960
tttttcctta ttactccatg tccttgagga gtttattcct ttatagcttt tgtgatctgg   52020
ctgtaattat tttgaaaaaa attttcatta tactggacat tttggattaa gtcctccaaa   52080
ttttcttatt tgtgagagta caagtcacta tttacactat ggtaaactgc atgcaaacat   52140
ctgagtacct ttctgttcct gtcttcagct gggccagcac taagctggaa tagcctatac   52200
tttgatgttt ttctgaggaa gtacattttc cttttccctc agattcctgg tgcctggtat   52260
agcactttt tgatttgctc ttgttctggc aataggtcaa ctggctttca tggtccttaa   52320
cgtttcaggt aaataattcc aacagttgtg actggaagga attcaaatca actcaaggca   52380
tccactctat gttcaaaatg ccatgttttg agtgatttgt cctttggtta gtaactttaa   52440
aaaatatgag gactggaagg agaagctact atttgaggaa ctaatggaaa atcaagcagt   52500
ttttgatgta ctaacatata cacttatgat gcaaggagtg tgatcgttga ccttcctact   52560
tatctaaaca ttatgctctc agagcatgtg gataggtagc atagcctagt ggttaacaca   52620
catagaaaag tcagactgcc tagttcgaat cccagcttca tcacttgcta gctatataat   52680
ctttattaaa ttagttaact ttcctgtgcc tcagtctggt tttcctgagg attaaatgat   52740
tttatatttg ttaagtgcct agaactgtag ctggtctgca acaagtacta tacgtctttg   52800
tttaaataat aaataaaatg acagtattgt tcatatggag aaacaggggt cttaggcagc   52860
ttaggagttt ttctaaagta acagaatcat ttaatggcag gaacaacaat attatcactg   52920
cccagaaccc taatggagaa ctatagctct taagggtgat gtggggagaa atacactgat   52980
gaaaaacaat caacattatt aaagacagga tgggagagag tgggaactcg tcattcattt   53040
atctaatggc ttagtcagca agtaactaat gcctactttg ggccttgaca ctataccaac   53100
attgtgcaga aagtgattaa aatgcaaaag aacattcact taggctggga taaacaagag   53160
gtcttttgca aaatctgatg atgagcttgt tgatgttgag ttgacaaact atgcagcagg   53220
tcagtggggg ggtgattatc ataaaattcc atcccttaaa catctacagg aagatgatta   53280
ttttaagatg ctttacttct ggagatgtat gctttacttc tacttagaga atctggctta   53340
tgttctcatg ttctggtttt atatgtaatt ggtcatgagc ttaatttgag ccaagcattt   53400
gacacagttg cccccagaag ttaactcatt tgtggattgt ataaatgcta ttgcacaaaa   53460
aagaagtata tatatacaaa tagtcatagt agaccacatc tcagttaatg gcttcaagtc   53520
tagatgaaat gttttaagag ggatattgac aaattagaga acattagaag catttgccag   53580
aatactggca gggcaagaaa ttatgccaaa tagtagaaag agaattagat gcctaagtgg   53640
aacatggtgt atagcccata agaatttgaa ggattgtcac tggtagaata agatgttatt   53700
cttggctgct tccagctgag gagtggtgga tgggtgacta aggcctataa gagagcaaat   53760
ataaggaaga gtttctagat attaaaatca atttccaaag aaacagcctg gcctctaagg   53820
gaaagagctt cttgtgagta gatgtgttta ggtgggccaa gatgaacaag ctcctgagct   53880
ctagggatta gactccttct gctggatagg aggtacaacc aggtcatccc agaggttcct   53940
tgtgttccaa gattctgtta ctctatgatt tcatgacttg gatgtcacct cccttaggtt   54000
ggttactcta aataatgtta aaagtcagtg tatgccttaa gattgggtga attgctatga   54060
cagaatgaga tttaccagag aagcagttaa gtctaagaat gaaactactg tttctaagtg   54120
aaagaggtat gaataaccta aagataatat ttttctctgt agatagaaag aatttgtatt   54180
ataagtctgt gttgggtgta tagtagggca tcaccagaat tcaccctaac tgggtgaatt   54240
```

```
catggcagtg atcagtagaa tatgtagttt aacaatgagg ccttatcatt tctaagtagt   54300 ttcttttga gacggagtct caccctgtca accagagctt tgccctggaa ctcttggagt   54360
gcaacggcgc gatctcgggt ccctgcaacc tccgcctccc aggttcaaac aattctcttg   54420
actcagcctc ccgatttcta agtggagagt tatgaatggc ccaaagataa tatttttctc   54480
tatagataga aataatttgt atgctaggta tgtgttggat atatagcagg acattaccag   54540
aattcagcct aactcggtga attcatggca gtgaacactg caatatgtgg tttaataatg   54600
aggccttatt cttaaggcaa agctcagaaa agctgataag caaattagaa aggtctattg   54660
aaaagtgtct gttggccggg cgcagtggat cacgcctgta atcccagcac tttgggaggc   54720
tgaggcgggt ggatcatgag gtcaagagat tgagaccatc ctggccaaca tggtgaaacc   54780
ccgtctctac tacaaataca aaaattagct gggcatggtg gcatgcgcct gtagtcccag   54840
ctactcggga ggctgaggca ggagaatcgc ttgaaccatg gatgcagagg ttgcaatgag   54900
ctgagattgt gccactgcac tccagcctgg tgacagcaag actttgtctc aaaaaaaaaa   54960 aaaaaagaa aagtgtctgt ctagccaggc gtggtggttc atgcctgtaa tcctagcact   55020
ttgggaggcc aaggtgagtg gatcacttga ggtcaggagt tcaaaaccag cttggccaac   55080
atggcgaaac cttatctcta ctaaaaacac aaaaaattaa caggatgtgg tggtgcacac   55140
ctataatccc agctacttgg gaggctgagg tagaagaatc gcttgaaccg aggaggcaga   55200
ggtagtagtg agccaagatt gtgccacagc actccaacct gagcaacaga acaagactca   55260
gtctctgaaa gagagagaga gatgaaagag agagagagag aaagaaaaag aaagaaagag   55320
agagaaagac agacagaaag aaagaaagaa agaaagaaag aaaagagaa agagaaagaa   55380 agaaagaaag aaagaagaa agaaagaaag aaagaaaaga aataaagaaa gaaagcaaag   55440
tgtctgtctg ccaacctgct tccacaaagg cccctcttct gattgtagaa gtgcctggtt   55500
taggatggca gtgtgctcta cctgctgtct ggtgagtagt caggattgga cttctataag   55560
acaccctctg agaggcttgc aaataccttc agaatcaggc agaggtcttt ggccagttat   55620
ttctgaataa agcatatctg cgtgtctgtc tgacctaagc ctgggaacca cgatggaaga   55680
tactgtttga acaacaacaa caacaaaaaa aggcagggaa cttaagagag aaatggattt   55740
tagtcactaa gaacacgaag aggaacattt tgataatatg tactctatac aaacagaatg   55800
cttatacaag acaatcaaag aggaatgggt agttttctaa agagtaaaac ctgtatttt   55860 aggaacatat atttgtttac aatatatttt ttctttttc acccttgatt tttaactatt   55920
taataatttt ctacaacatt ttttttcttttt tttttttg cccttttttt ttttttta   55980 aacagagtct cgctctgttg cccaggctgg agtgcaatgg tgctatcttg gctcattgca   56040
acttccgcct cctgggttta agtgattctc ctgcctcagc ctcccgagta gcttggatta   56100
taggcacctg ccaccacacc tggctaattt ttgtatttgt agtagtgacg gggtttcacc   56160
acgttggcca ggcttgtctg gaactcctga cctcaaggcc cacctagcc tcccaaagtg   56220 ctgggattac aggtgtgagc caccgcgccc agcctgccct tgattttta ctatccctcc   56280 tgtgaaaatt taagtctttc tgtgggttaa agggaactgg taaagagcac tggatttatg   56340
cttgggctgg aatttccctc taggtttgga tgtaatgaag gcagtagaga tttgggttta   56400
taacagaggc agatttgtga aactatagga gttgaagcct gagggtccct cacttgcaga   56460
gaccccttcc agggtcctgg aaggaaccct gctaatgtgt tattatggtc atttttttta   56520
taaaaattgc aaaacataat gtgtttcagc catgactggt taagatcatt gtcttcttcc   56580
```

```
aattcaactt tccctcctttt ctccttccct ttctagttgg gtggcattaa agtggtcatg    56640
cgcattttgt atttgtaatt atgtatttt tttttttctt aaaaaggacc cccccaccaa    56700
attgtataag tttcaggccc taaaaacatg gatcttccac tgggtgtagg aatggaatga    56760
gtaacaattt ggaaattgcc tgtgtagcag aatcagcgaa aagtcagagt cagcagtcaa    56820
aatgtgatgg ggagagtgag agtaaattgg aatccataat cccaacagca tttgacagtg    56880
ggaaaatgga gcttttcccc ccctctttag ggttcatttt aaagaattcc atgcaaagga    56940
tatcatgaat tgagaaatat acatcagatt catcagatta aaaattttt tttttttttt    57000 gagacggagt ctcgctctgt caccaggctg gagtgcagtg gcgggatctc ggctcactgc    57060
aagctccgcc tcccaggctc acgccattct cctgcctcag cctcccgagt agctggaact    57120
acaggcgcca accaccatgc ccggctaatt ttttgtattt ttaatagaga cgcggtttca    57180
ccgtgttagc caggatggtc tgatctcctg acctcgtgat ttgcccgcct cagcctccca    57240
aagtgctggg attacaggcg tgagccaccg cgcccggctt tttgttgtgt ttttgtttt    57300 tgtttttgtt ttttttgagat ggagccctgc tctgtcgccc aggctggagt gcagtggcac    57360
aatctcggct cactgcaacc tccgctccca ggttcaagtg attcccctgc ctcagcctcc    57420
cgagtagctg ggattacagg cacgcgccac catgcccggc taaattttt gttttttagt    57480 agagacaggg tttcaccatt ttggccagga tgatctccat ctcctgacct cgtgatgtgc    57540
ctgccttggc cttccaaagt gctgggatta caggcgtgag ccactgcacc tggcctaaat    57600 tcttttttaaa aatagcaaat tcttaaaaat aatgcaaatt gatgatgaat tatgaaaatc    57660
atgatgagaa actcctgact gaagagagaa attgttggaa aatgattctc cttttcctct    57720
actactttat gtaattataa agccttttc taaagttcct ttctgacaca gaaatactgg    57780
ccaacagaaa ttcaaaggaa agttgagact tttgaagttc aggcaattta tatggtgttt    57840
caggtgttac tacctctaat agtctatcag taaaaccctg ataggggatg gtctctcctt    57900
tttgccttct actccatctc ttctcacaca cacttgtgat tcttttttctt tttttaaaaa    57960 atttattat tataatactt taagttttag tgtacatgtg cacaacgtgc aggtttgtta    58020
catatgtata catgtgccat gttggtgtgc tgcacccatt aactcgtcat ttagcgttag    58080
gtgtatctcc taatgctatc cctccccct ccccccaccc cacaacagtc cccagtgtgt    58140
gatgttcccc ttcctgtgtc catgtgttct cattgttcaa ttcccaccta tgagtgagaa    58200
catgcggtgt ttggttttt ttccttgcga tactttgctg agaatgatgg tttccagttt    58260
catccatgtc cctacaaagg acatgaactc atcatttta tggctgcata gtattccatg    58320
gtgtatatgt gccacatttg cttaatccag tctatcattg ttggacattt gggttggttc    58380
caagtctttg ctattgcgaa tagtgccaca ataaacatac gtgtgcatgt gtctttatag    58440
cagcatgatt tataatcctt tgggtatata ccccagtaat gggatggcag gttcaaatgg    58500
tatttttagt tctagatccc tgaggaatcg ccacactgac ttccacagtg gttgaactag    58560
tttacagtcc caccaacagt gtaaaagtgt tcctatttct ccacatcctc tccagcacct    58620
gttgttccct gacttttaa tgatcgccat tccaactggt gtgagatggt atctcatagt    58680
ggttttgatt tgcatttctc tgatggccag tgatgatgag catttttca tgtgttttt    58740 ggctgcataa atgtcttctt ttgagaagtg tctgttcata tccctcaccc acttttgat    58800 ggggttgttt gttttttttct tgtaaatttg tttgagttca ttgtagattc tgcatattag    58860 cccttttgtca gatgagtaca ttgcaaaaat tttctcccat tctgtaggtt gcctgttcac    58920
tctgatggta gtttctttg ctgtgcagaa gctcttgagt ttaattagat cccatttgtc    58980
```

```
aatttttgct tttgttgcca ttgcttttgg tgttttagac atgaagtcct tgcccatgcc   59040
tatgtcctga atggtattgc ctcggttttc ttctagggtt ttcatggttt taggtctaac   59100
atgtaagtct ttaatccatc ttgaattaat ttttgtataa ggtgtaagga agggatccag   59160
tttcagcttt ccacatatgg ctagccagta ttcccagcac catttattaa atagggaatc   59220
ctttccccat ttcttgtttt tgtcaggttt gtcaaagatc agatagttgt agatatgcgg   59280
cattatttct gagggctccg ttcggttcca ttggtctata tatctgtttt ggtaccagta   59340
ccatgctgtt ttggttactg tagcctagta gtatagtttg aagtcaggta gcatgatgcc   59400
tccagctttg ttcttttggc ttaggattga cttagcgatg caggctcttt tttggttcca   59460
tatgaacttt aaagtagttt tttccaattc tgtgaagaaa gtcattggta gcttgatggg   59520
gatggcattg aatctataaa ttaccttggg cagtatggcc attttcacaa tattgattct   59580
tcctacccat gagcatggaa tgttcttcca tttgtttgta tcctctttta tttccttgag   59640
cagtggtttg tagttctcct tgaagatgtc cttcacatcc cttgtaagtt ggatttctag   59700
gtattttatt ctctttgaag caattgtgaa tgggagttca ctcatgattt ggctctctgt   59760
ttgtctgttg ttggtgtata agaatgcttg tgattttttgc atattgattt tgtatcctga   59820
gactttgctg aagttgctta tcagcttgag gagattttgg gctgagatga tggggttttc   59880
tagatatata atcatgtcct ctgcaaacag ggacagtttg acttcctctt ttcctaattg   59940
aataccettt attteetret cetgcctcat tgccctggce agaacttcca acactatgtt   60000
gaataggagt ggtgagaaag ggcatccctg ttttgtgccc gttttcaaag ggaatgtttc   60060
cagttttgc ccattcagta tgatattggc tgtgagtttg tcatagatag ctcttattat   60120
tttgagatat gtcccatcat tacctaattt actgagagtt tttagcatga agcattgttg   60180
aattttaca aaggcctttt ctgcgtctat tgagataatc atgtggtttt tgtctttggt   60240
tctgttata tgctggatta catttattga tttgcatatg ttgaaccagc cttgcatccc   60300
agggatgaag ccagcttgat catggtggat aagcttttg atgtgctgct ggattcggtt   60360
tgccagtatt ttattgagaa tttttgcatc aatgttcatc aaggatattg gtctaaaatt   60420
ctctttttg gttgtgtctc tgccaggctt tggtatcagg atgatgctag cctcataaaa   60480
tgagttaggg aggattccct cttttttctat tgattggaat agtttcagaa ggaatggtac   60540
cagcttctcc ttgtacctct ggtagaattc ggctgtgaat ccatctggtc ctggactttt   60600
tttggttcgt aagctattca ttattgcctc aatttcagag cctgttattg gtctattcag   60660
agattcaact tcttcctggt ttagtcttgg gaggatgtat gtgtcgagga atttatccat   60720
ttcttctaga ttttctagtt tatttgcgta aaggtgttta tagtattctc tgatggtagt   60780
ttgtatttct gtgggattgg tggtgatatc ccctttatca tttttattg cgtctatttg   60840
attattctct cttttcttct ttattagtct tgctagcatt ctatcaattt tgttgatctt   60900
ttcaaaaaac cagctcctgg attcattaat ttttttgaat ggtttttgt gtctctattt   60960
ccttcagttc tgctttgatc ttagttattt cttgccttct gctagctttt gaatatgttt   61020
gctcttgctt ttctagttct tttaattgtg atgttagggt gtcaattttg gatctttcct   61080
gctttctctg gtgggcattt agtgctataa atttccctct gcacactgct ttgaatgtgt   61140
cccagagatt ctggtatgtt gtgtctttgt tcttgttgct ttcaaagaac atctttattt   61200
ctgccttcat tttgttatgt acccagtagt cattcaggag caggttgttc agtttccatg   61260
tagtagagcg gttttgagtg agtttcttaa tcctgagttc tactttgatt gcactgtggt   61320
```

```
ctgagagaca gtttgttata atttctgttc tcttacattt gctgaggagt gctttacttc   61380
caagtatgtg gtcaattttg gaataggtgt ggtatggtgc tgaaaagaat gtatattctg   61440
ttgatttggg gtggagagtt ctgtagatgt ctattaggtc cacttggtgt agaactgagt   61500
tcaattcctg ggtatccttg ttaactttct gtctcgttga tctgtctaat gttgacattg   61560
gggtgttaaa gtctcccatt attattgtgt gggagtctaa gtctcttagt acgtcactaa   61620
ggacttgctt tatgaatctg ggtgctcctg tattaggtgc atatatattt aggatagtta   61680
gctcttcttg ttgaattgat ccctttacca ttatgtaatg gcattctttg tctcatttga   61740
tctttgttgg tttaaagtct gttttatcag agactaggat tgcaaccect gccttttct   61800 gttttccatt tgcttggtag atcttcatgc gtccctttat tttgagccta tgtgtgtctc   61860
tgcatgtgag atgggtttcc ttaatacagc acgctgatgg gtcttgactc tttatccaat   61920
ttgccagcct gtgtctttta attggagcat ttagcccatt tacattcaaa gttaatatca   61980
ttatgtgtga atttgatcct gtcattatga tgtcagctgg ttattttgct cattagttga   62040
tgcagtttct tcctagcctt gatggtcttt acaatttggc atgttttgc agtggctggt   62100 accggttgtt cctttccatg tttagtgctt ccttcaggag ctcttttagg gcaggcctgg   62160
tggtgacaaa atctctcagc atttgcttgt ctgtaaagta ttttatttct ccttcactta   62220
tgaagcttag tttggctgga tatgaaattc tgggttgaaa attctttct ttaagaatgt   62280 tgaatattgg cccccactct cttctggctt gtagagtttc tgccgagaga ttagctttta   62340
gtctgatggg cttcccttc tgggtaacct gacctttctc tctggctgcc ctgaacattt   62400
tttcctgcat ttcaactttg gtgaatctgc caattatgtg tcttggagtt gctcttctcg   62460
aggagtatct ttatggcgtt ttctgtattt cctgaatttg aatgttggcc tgccttgcta   62520
gattggggaa gttcacctgg ataatatcct gcagagtgtt ttccaacttg gttccattct   62580
ccccgtcact ttcaggtaca ccaatcagac gtagatttgg tcttttcaca tagtcccata   62640
tttcttggag gctttgttca tttcttttta ttcttttttc tctaaacttc tcttctcgct   62700
tcatttcatt catcttccat cactgatacc cttttcttcca gttgatctca tcggctactg   62760
aggcttctgc atttgtcacg taattctcgt gccttggttt tcagctccat caggtccttt   62820
aaggacttct ctgcattggt tattctagtt atacattcat ctaatttttt ttcaaagttt   62880
ttaacttctt tgccattggc tcaaacttcc tcctgtagct cggattagtt tgatcgtctg   62940
aagccttctt ctctcaagtc atcaaagtca ttctccatcc atctttgttc cattgctggt   63000
gaggagctgc tttcctttgg aggaggagag gcactctgat ttttagagtt tccagttttt   63060
ctgctgtttt ttcccccatct tggtggtttt atctaccttt ggtctttgat gatggtgacg   63120
tacagatggg ttttggtgt ggatgtcctt cctgttcatt agttttcctt ctaacagaca   63180
ggaccctcag ctgcaggtcc attggagttt gctagacgtc cactccagac cctgtttgcc   63240
tgggtatcag cagcggtggc tgaagaacag cggatattgg tgaaccgcaa atgctgctgc   63300
ctgatcgttc ctctggaagt tttgtctcag aggagtaccc agccgtgtga ggtgtcagtc   63360
cacccctgct gggggtgcc tcccagttag gctactcagg ggtcagggac ccacttgagg   63420
aggcagtctg cctgttctca gatctcaagc tgcgtgctgg gagaaccact actttcttca   63480
aagctgtcag acaggtacat ttaagtctgc agaggttact gctgtctttt tgtttgtctg   63540
tgccctgccc tcagagaggg agcctacaga ggcaggcagg cctccttgag ctgtggttgg   63600
ctccacccag ttcgagcttc ctggccgctt tatttaccta atcaagtctc agcaatggtg   63660
ggcgcccctc ccccagcctc gctgccgcct tgcagttcaa tcttagactg ctgtgctagc   63720
```

```
aatgagcgag actccatggg cataggaccc tccgagccag gtgcgggata taatctcctg    63780
gtgtgccatt ttttaagccc attgggaaag tgcagtatta gggtgggagt gacctgattt    63840
tccaggtgcc gtctgtcacc cctttctttg actaggaaag ggaattccct gacctcttgc    63900
gcttcccagg tgaggcgatg cctcgccctg ctttggctcg cactcggtgt gctgcaccca    63960
ctgtcctgca cccactgtct ggcacacccc agtgagatga acccggtacc tcaattggta    64020
atgcagaaat cacccgtctt ctgtgtcact tatgctagga gctgtagact ggagctattc    64080
ctatttggcc atcttggctc ctcccccaga tcacacactt gtgattcttg ctggcattca    64140
cacttactct ctctttattt tttgagacag ggtctcactt tgtcatccag gctggagtgc    64200
agtggtgcca tctcagctca ctgcagcctc cacctctgga gctcaaggga ttcgagtagc    64260
taggactaca ggcgtgtacc tccaccoctg gctaattttt gtattttttg tagagctggg    64320
gttttgccat gttgcccagg ctgatctcca acacctggga tcaagcagtc tgcccacctt    64380
ggcctcccaa agtgctgaaa ttacaggtat gagcctccat ggctgggcac ttactgtctt    64440
tttaattatc agcttgcaaa tgagaaatct gcccaaggag cctgagcttg gtgaatacaa    64500
gttcatttca gccccattgg tgagtttatg attctatgag actttaaaga tgtattttat    64560
ttggacatgt taaaaaaaaa aaaaagaac cgtgtgtttc ttcacaacat ccaaataat    64620 tattttattg gtattgataa ttattattga ggaataggga agtcatgtat gttatcaacc    64680
acttcctaaa tgatacctag ttaacacgtt aggggaggga atcgaatctg aaagtgatac    64740
ccatttagtg aagccaagca atgtagcaag agttgagaaa aacttataaa gggacctctt    64800
agcccatgtc cataacattg tcgttaacat aaagataggt tgccagagaa agggtaactg    64860
tatggtcaat ttagccaggt ctgaactctc aaaaatcaag cactctcatt ctgttagggt    64920
gaagtcagag aaaagaacct tcacaaggtt tgaaaacaca gttgtaacat actgggctgt    64980
gttccagggc tagcatttga ctctgatttt tatcttgtgc ttagaaccag cctactgttg    65040
tctctgtgca gagagagtac taagtaggta ctgaataata cttgctgtcc agcacatagc    65100
tctgtgcaga acgagcacta agtaggtact aataatgct tgctggccag cacatggatg    65160
gatcatgttt ataagtgtgt atcataaaca ctttgccttg aggaaattgt tttcttttta    65220
gagttttcat actgtggaca tccttaaaaa gcccagaaaa tgtatcttta tggattgaca    65280
tgtgacttct tacatatgaa gttagaagcc aatgaaatgc tgttctttgg actgaacttt    65340
caagactcat gtgtgtggtg tctaattcat taactaaaaa tatgattcat atttaccta    65400 tgtaggacta caggtatcca catatccacc attaggatat tctttaaatc tggtagttg    65460 gaagatttcc agacattgta aagagtaaat gcatcagaaa taagcatttt ccagaagagg    65520
gaggtatgaa attgtaatga ttagcctgtt gcttagtcct ggaaatgtga atcagataa    65580 aaatgaaaaa gatgctttcc ttgcattctc ttccagaaat atgcagcctg ctgctctttt    65640
gtcttcagtg tgaccatgct gccctgagga gagcccagaa ctgttttaa attcaaaagg    65700 acagctgctt tctgctcact caggtccact gaggcatgct ccaagacagg aaaaaggtgc    65760
ttagcggggc tctttgatag agattcaata tatgaatttt actttgagaa taaaaagctc    65820
acccactttt aaaaggttaa tcaaaagctc attgtagtgt attcttcctt tcctatgcag    65880
tttcctatgg aaatggaatc agtttaaatt ctggcctcag aacagcaata ttttcacag    65940 aggcagtcct tctgccaagt ggctctagaa gtacccgtaa tatccatgtc aggagatga    66000 aaaatgaaag ggatgaacac ttccttcaga aattatacct ttgattcctt tactttacgg    66060
```

```
ccaggcagga agaatcctga gagaggtctt tactgaaagt tcagtattta tgaactacat   66120
actgaaaaat gaaaaacgat tcctagcact gagttgctta ccctgtcaag tttacccatt   66180
attttcaggc tgttgagcat tgtttgaaaa atcgatctga gagctaaatg agactctgtc   66240
ccttaccatg gtcttgctgt tataaattca cactgggcta tttccattcc ctaagtttgc   66300
tttgcccttt cctacccttt acctctatgg tcttccatcc ggtaaatttt ctctcaccct   66360
tcctggtcta gctctatttc atcttcactt atgaaggctt ccttgttttc cttttttaga   66420
attaattgct aattcctcac tgctctctaa gcattaatac ccccatcata gccttcatca   66480
taatatgttt tgtgctgtag ttatttatgt acttacttgt ttttccccct tctttgctct   66540
ttgattaaat gcatgccaga tccaacttta cagatgagaa aaatgagctc tgaagttcaa   66600
taacttgccc aaggctaccc agttagaaga gttatggact tcactctgaa tatggtgact   66660
tttgttctag tgtgttgcct tctctagtct tcttaagaaa accttgtct tcttttcttt   66720
tttccttagg ttgacttatt ctatacatta gaagtttcta aattttaatc aaactgtcat   66780
tccagggtca tagtcagcca catgtaaatc agaatgcagt tttacataga ttcattatta   66840
ctgtgcatgg agattagaag ccagctcaca agaagactta atttggaaag atatgtaacc   66900
aacttcacgt aagtgctagc cttttcattga tttctcacct ccattctata ttcctcctgg   66960
cacttgtttt aaatctgttc tactgaagtc catactctac ccccttgctc tcagccgatg   67020
atctgtttac ctgctctgag aagatttaga tcagtagttc tcaaacttta atatgtataa   67080
aaatcacatg cagagctctt tctaacatag tttcccggga cttttcccag gaattctgat   67140
ttcagcaggt cagggtgggg ctcatgaatg ctccattcta acaagctccc aggtgatggc   67200
aacacagctg gtctgaggac tacactttga gaacctctga tttaggccat cctctgcaat   67260
aggatgtctt ctccaataca tcttctctgg atatttatcc ttcctctcct tctatgagaa   67320
ttcagtcgtt ctattctcag gctgaaccct ctcaccacga gcttttatcc catctcattt   67380
catctatttc aggaccttgc ttcaacttgg ctctctttga atcttttata tcaccctctc   67440
aattgctttt tattctctac tgctttacta ataaaactgt tcctttctca gttgtactat   67500
ttaagataca tctaatgatt gtaagcaaaa ttattttctc taagaatggt cgacaatttc   67560
agattcaact cagctggcta ggaactaagt ttctgtaatt tgggaattgg cttgtagaga   67620
gcaaaattaa gaaccaagt ttggccgggc acggtggctt acgcctgtaa tcccagcact   67680
ttgggagtcc gaggcaggtg gatcacgatg tcaggagatc gagaccatcc tggctaacac   67740
ggtgaaaccc cgtctctact aaaaatacaa aaaattaacc gggcgtcgtg gcgggcacct   67800
gtagtcccag ctactcggga ggctgaggca ggagaatggt gtgaacccag gaggcggagc   67860
ttgcagtgag cggagatcgc gccactgcac tccagcctgg gcgacagagc gagactccgt   67920
ctcaaaaaaa aaaaaaaaa gaaaccaaat ttaactttt ttaatggatg tgagtggaag   67980
agactaatga gataacacaa aagagttaac ttcttacatt tctgtagtct aatacgagat   68040
agtttctcca ggaattaaca cagcacatct ggttcactga cctgagtttg tttcctggtg   68100
aggcattgca gtatcatcca tatctcaggc aaaggtactc cagcattttg tagttaagca   68160
gttggaggag gagtagggag aactgctgta ctttgaaaca tttcacagtg gactactttg   68220
cattctaatg atgttctcct tacttaagga ctttgttatg taaggatact ttgtccttct   68280
gataatcact tacactttc ttctgtgttc atgtcacttc attaatcctg attacttgta   68340
atgaatcata atcttaccca cttattcttg tgtgactcat tcctacttgt attcttaata   68400
gtattttcta tgtctgataa cacattgtca attgactatg ctatttttaa cgtaagcgtt   68460
```

```
ggcaaaaagg tttacttaga gaaaagctct acatttaatt ccccggtgcc tcagttccca   68520
aatttgctaa taaagattat acttagctgt cactccacgt ttcatcagta ggattaaaat   68580
gaatagagat catgaaataa gacaatgaaa aaagataatt ataatggacc agattgagaa   68640
atccctacaa atcaacagaa gcgacctgcc atgtcagatt cctagatgca gtttatttac   68700
tcagtgggcc atatttcttc cttattcttt cttttccat gatgccttcc aaaactatat    68760
tttaaccagg agggaaatac catttgtctt ctgatatagg aagatcctac tgagagatta   68820
tattcatata tttcgtccat cggcctgtag gtggaattgt atttaaaata ctaataaagg   68880
ttattattgc ttatatatct aaaaatgctc caactgtcca aacaaagctt atactgttga   68940
tgatatttat cagtggctct gaacacttgc atatcataaa attctccctc aaaatttaac   69000
cttaaactct ttcaggcttg tcttggtcac agtgggaact gaggacagct gctcatgttt   69060
tttgatagaa cagctcttaa catgcttttg ctcttgcctc ccactgccca acaccagctg   69120
catacacaca gtctacttgc tgtgtgcatg ctctggctcc tgtctccttt tccttcagcc   69180
tagttagcct ggttttgttt ggtttcatca tacaatgtat ctattagtaa aacttttatg   69240
aactctgatt atagtactaa actcataata aagtaatcag aacttcattt attaaaacac   69300
tgtcttgagc ttatttttta atttagtaca catgacaatt tggtaaggta ggaattttca   69360 ttccccttt atagatggga aaactgaggt ccaggatata ggtaacattt tcaaagttaa    69420
ctcgtaagta aatggcttag ctggaatttg aacccaggtt tctgcaattc taaagcccat   69480 cctttaact gctatgctat gcgcacaatt actgtattct tatttgctct ctgaaataca    69540
acaccttatt ctcatttcat ctgctctttc tgccctgtac acttcagttt ctgctctata   69600
gatacctgct cgtattgtga catctcaatt ttttttgtac cttggcaggg ttttgattga   69660
tgtattggtg ttctgaactc tttagcatat gtattaatag ggaagaccta ccaaatattt   69720
catgtaatag ggattatttt gtctacctat tttatctttc tttataatgt aagtttgtag   69780
agggcagaaa ctataaattg ctcagttagg gactccacat tgagccaagc acatacatac   69840
ttgacccaga gaagtcatca ccatcttat cgccacagct aacatatggg tagtgctcac    69900
catctaccaa acatgtgcat ggattatttt atttactctt cacaataacc ctataaagta   69960
gactatgttg ccatccccaa ggttaaaaaa ctagcccaag ttcatcgagt tactgcatga   70020
tagagtttga gtctaaccaa caccaatcta cacgtctgtc aacacagtta actatcccac   70080
acttctcagt ggaatctaga gttccactta tttcctattc cttccattct tcactatatg   70140
tcctctttgc cttcttatcc tgtttctcta cttctcactt tctgccctat acgtatctgc   70200
tcaatcttca atcttctctg ccttaccctc tcttttcaa ttttgttctc gttctgtcct    70260
atcctgcctc cccactcttc ttacctcatt ttcctagtcc tcttttcttc tttttttcac   70320
ctttttacct cttacatatt tcttttttaa aagtaacttc aagcttgata atagattctt   70380
caacgctctt agcaatatcg tatcctaacc ataataaaat gatagtgtgc taggtgtaaa   70440
cagaagtaga atatgaaatt gaaatgaaga atctctttac ttttctatt agaaacataa    70500 ataatgagtg actgtaacat cttggtctcc ataatttcta agtgttaaat aaaacacatt   70560
tcttttttta tttaacacac acacatccac acacacataa acttgtttta tgcattgatt   70620
gccatttatt gagcagcata ttttggaaa tgcaacaact acaaaagaat tttaagtta     70680 ttatcataca gtgacattaa taggctcatc actttgcctt ctttccttgt tctatcatgt   70740
agagggttgc tttagagatc attgtgtatt gatatgaatt atcattgaag ttttattagt   70800
```

-continued

| | |
|---|---|
| ctggatgtct catcttgggc attttgataa atttcttttg ctccaaatcc agaagttatg | 70860 |
| gccattcatc tttataaata agactttta aaaaaggtaa agtcataaaa taaatatttc | 70920 |
| aaagcagtgt tggatatagc cagctgaata aactgcccct tctagttaac tttgaactct | 70980 |
| aaaccttatt taaatatcct ccctttttt ctgtaaagaa gacgagaaaa aaaaacaatt | 71040 |
| tcagtagatt ctaaaagaaa atatagcaag aacattttca taagagatat ctcacataaa | 71100 |
| aagctgtaaa aattgggcaa gtatttgcac ctaaccagta gaacttagaa gagaaaacat | 71160 |
| gaaatgaact tcttagctta tggaatggtg tggataggtt tgcattactt agatgttcac | 71220 |
| agagctctag catttactta ctgaaacact ggaatggttc atatccctgt ggtttccacc | 71280 |
| ttatttcttc cagaaggatt aggttttatg ctgccagaga ccacattgac tcttagtaat | 71340 |
| gggatcacta aattctggtt cacaattttg tgcatagaga gattgcacta atatctcaaa | 71400 |
| attgtagcta tgattataac cctggcatag aaatctgagc tatgctggca gtgtcatgct | 71460 |
| gtacaatcga atccacctga ttatctctgc atttgtgaca gctgggctgg ccttcattgg | 71520 |
| catatgcctc tttgctgtgc ccagggcttt gaatgcaaaa tgaaagatca gcatgatatt | 71580 |
| aggggcccat gatccataga tggagcttca caagtgaaca gcgtctcagc tttaacatgg | 71640 |
| cccccagtat cctgctttat cttctggac tgaagttcct atgacagatt tgttgcttta | 71700 |
| aaaaagtaat tttgcagatt tgtccttttt taaaagaaat aaagattgcc ttccatttcc | 71760 |
| tactgaaagt gatatggtag tatccatctt ataattgcac agattcaaaa ataagccaca | 71820 |
| agtatgtgtg ctgaagtata actgtggact ataaaataca gatatcatag cctataatat | 71880 |
| ggagggtagt gtgatgttat aaagccattt ttctgtgttt tacattatca taaaatttaa | 71940 |
| ctactgaagg gaaagtgaag gttttaatat ttaactaagc ctagcacttg aagagaaaca | 72000 |
| catatatttt acttggaaaa aaaggaagtt ccatttggga cactgcaaat gacagtgcca | 72060 |
| gctgttgtca taatatttct aacatccgct gaggattaat tccaggccca gcaaattcac | 72120 |
| tggatgagca gaaacagcca aagaagtaaa cactggagct tatgctgtga tattattaaa | 72180 |
| ttaggcatga gacttctaca gagttggata tgtagtgaac actggattat catgcctgag | 72240 |
| gatcgtttgc tttgtgtata tctgcagaaa attgaatcct gaacttgctt tcttctgcct | 72300 |
| cttggccctc ttcctctgta gaggtatact cagaaaatgt gatctcattt gaatataaac | 72360 |
| ttttctatta atattcatta agtactcata caatataagc tgaggaaaca aagtggtggg | 72420 |
| tgtaaaacac aggcctcatg taaagagctt actttcacta cagaggcaat gtagcataat | 72480 |
| gaagcagaga tgggtttcag aggcaggtag accagaattc aaatcctact tctcctaagt | 72540 |
| atggccttgg gcccatcact taaatttctg agactcagtt tcctttttcta tgaaaggtag | 72600 |
| atactaatca tgctacagag ttctattaag aattagaaat atttaaagat acttagacca | 72660 |
| ctacaaggta gctattttc tagaacaggc ataccttatt gtatacattc tatgtttcta | 72720 |
| gaacaggcat accttattgt atacattcta tgaaacagaa tatggaaagt gctaaatgaa | 72780 |
| aggcacaatc agagaattcc ccaggccctc aagaaggaag gcggaatgga tgaggaagtc | 72840 |
| tgctgtccaa ggggtgggcc agagctaagg caagatttgt gggtgggcct tcactaacca | 72900 |
| ggcacaggga gagggcattc caggagcaga tgtagatctg gccaaggaat taagacagga | 72960 |
| atgcaagtgg cgttttccag gcaaaagatt aggaagtttt agatcagcct ggatatggag | 73020 |
| accttgaata gcaagccgac tgaggaatgc atgaaagaat gactactagc tggaataaga | 73080 |
| gataaatctc aaggcctctt ttctctttca cctctcctct tgcccacatc atggacagat | 73140 |
| agttctggct tttccttata ctctgtttct gtaagcaatt ttaagaaggc agagtgcata | 73200 |

```
atggtattac ttttatgtct gcgtgtgtat tgccaccatg aagcctatag ttttgctttt    73260
caaactacta gattgtgacc ttgtaatgat ctggcaaaag gctgaatttt taaaagcagt    73320
aaatccatat agtggataat attgggaaaa aattagggct aatactgagg aatgagaaga    73380
ttaggaaaga gataaataaa atatgggtgg tataaataaa aattaaagtg aaaatgtggg    73440
gaaaggactg cttatgattc accttacaaa atttctacct tatggggtct gttttcactg    73500
tcagttcttt ctgtgaatgc atgttcatga agatactgaa ggctgttttt ctataggcag    73560
ctggtggttt tctgctgtag gcagaagtgg ttgaggtaat cctagggagg tgatgctgaa    73620
tggggctgtg gttctacttt atgtaaggtt attatatgtg aaagaaagag taattttttaa   73680 aagtaattaa ctagtggtag attctgaact aacattagca aaggttgatt ataaatcaga    73740 ttttatttt actactgatt tagaaaaaat ctttggagaa atagatttgg aatggttaaa    73800 tatcactttta gggagcacat tttggtatca cagcttaaag gtactcttaa gagaaagctt   73860
tacaaatggg gcaacctgaa aagacacatt tcatgtgcat tcaaattcaa gataagaccc    73920
aaagctctgt tgccaaggta aaggttttga gagttaaatg ggaatttgga aaataatatg    73980
caaaaattga cttaaaatgt agataagcct acaagtattt acagggtgga gacatcagag    74040
aatgtaagaa atagtttgga tcactaacag gaatgtgtaa tgggaagtca aaatctatgc    74100
tgtcaggaaa aattcatatt attggataga aactgtatta tttggtacat ttaagataaa    74160
atgaaaattg tgttttcaaa gggttacgcc tcgcagtgga tgagtgattg ggcgttttc    74220 tggtttcagt gattctgtag gcagaaaaca gtttttactg ccaagtgtgt cagtggaggt    74280
ggggagacag agaccttgct gtgttaagtg aaatctgttg cttaagaata aagctgggat    74340
ttctgtagaa tggagaagga gtttggtatt atcatattat caaaaataac tgctctttga    74400
aaagtagatt ttttaaagtt tgattatcaa gtatttattt aaaatactgc ctaagtattt    74460
aaacactttc aggctctgat tttgtttttt ttacaaagga aacctatgcc taaaaattat    74520
tttaagtagt tatatggata catgagctac acagtttcag acctgtgtat atgactttct    74580
aagaggtcta tggtatccaa taataaatga ttttatgcag ggatttaaca cataatgggt    74640
catgcattat ctataccttg ttaatgggat ctatatagag tgatagcaga aaagaaagtt    74700
aattttagga tcctttaatg cctataaatt tagagcaaaa gaaatatttc taaaagttca    74760
acttttgtat acatatgccc aatcacaagt tttacagaca tttttacacg tttaggcctg    74820
aaatatttga ttccgctctt atttgtcaag atacaatata attacattag taaaatgcaa    74880
acagggcaga taagttttcc ttcttttttcc tatgctatag tcatgctgca aaccctccat    74940
tacagttttt tggctgaggt aggtctagat gtctagaggc caactaatac agttttatat    75000
aatcaacata gggaagtcat ttcagagact ggcattgagc tcttggaggg aagaaaatga    75060
accttaaagc ttcttgggaa tatccctcac tgcagcagag tttatgtgct ctaatggatg    75120
ctccgtaaat gcttgagaga atataagtcc cataggttag catatactta attctaccta    75180
tcatggaaac ctctccatac attctatagc tgaaatattt taggagctca aaaggagtaa    75240
cagaaactaa agggaacacc agctccaaga ttggattttt aggctttctt tctagtgtaa    75300
cacttccctt cctgttgggc catcggcaac catatcctgg ctaattagaa gtgatttca     75360 ggggaaagga agaggtcata agttcttgcc tccctatttt ccttcttgtt gggtgctagt    75420
aacttacctt aagaagtaat gaagtcctag taaaactcct aatattcaga aaccaactct    75480
cattattcaa acatgttgag gaaaaaatgt ctccttgcgt cctcttctgc ttaaaactcc    75540
```

```
cccagtacca tcaagcatgg acggatatat gatagtggca gtatccagaa gacacaccat    75600
ctatgtaaca aaccctggaa ataaagtatg gtataatcct aagcattcgc tcagcactct    75660
tgcttctggg aatttgctat gagtcagcca caggcatctc tgtgtacctt caagcccaga    75720
ttagcacgta tgggaggata agagagaaag tgtacttcct gaatacatct tgggtagagt    75780
aaactaatcc ttagctaggt tgatgacatc cttacccaga atttaaaagt tcagtagaga    75840
ctcttcttga aatgttgaat ttttatttct gcttgttgcc ctctatagat gagtgaaatg    75900
caatgaagat attcatggct actataaaaa tgcattagtt ctttttggtg agctacttga    75960
ctatcagagc caaatatgta ggtagttgga attaaatttc aatttagca tcccccttag     76020 aagggtgatg gaagctccca tatcttggta tttctctttc tgagtatctg ctgtctcact    76080
gaggcaacat gctagcctcc atgttgtatt atttcacagg tatagaacta agtgacacat    76140
tgccaattcc cacgcccccc ccccatttc tttgatggag gtagattaca tttataaggt     76200
gtagatattg cttgaaggta cttgttcttt cttataagta agcaagaaag agagcagcaa    76260
ataatagcta ggaggaagat gtgcccacac cacattcagg ccacttagtc tatctagtaa    76320
gatagagtgt ttcaggcatc aagcatgtac tgggagacat gcatacagaa aaagaacaag    76380
caatagactc ctttgagagt gacatggtag gtctgaagag tgaatgtaac ttttgtctc     76440 catccctca gtgattcatt aattattcat tagctgtttt tttccaccag gattacaatc     76500
attttacctt tgcttgccag cctagtgggt tattaacagt ggttactcta tttatttaca    76560
cattttcctt gtgtatgtta ttcatcctgt attagttcac ccccacccct agtcaccatt    76620
cttttttctt ttgtttggcc tttcatggct accatattac catgtgatca gaaaaaaat     76680 gcactggtgt cagaattagg ccaacacaga catatgggat ggtaggttca tttgggttgg    76740
atagagagct gtttgaaact tgtatacaca ttttcaatt tcaagaagaa acatctgcag     76800
taaaggaaga actgcatagt ttgcagtggt ctaatggagg tgaactcagg aatctcagat    76860
gcatttagct ctacaagtct ccattataca aatgatgttg aatgtttcat ctcttgctac    76920
agattagttt tgggccatca tgaaaaactt tcctgaagat taagtcaaac ttatctatgc    76980
atgccttctt tggatacata gatccaccct tgacagctac tctgtccact aattctgtca    77040
agtaggactg agctttcttg aacacctctc cttttgttaa caagaaggag aagaagaaaa    77100
ttaaacactc ctggcatctg cctggctgtg atttagccct tggtaaaaag tattacaaat    77160
tgagacggtg ccagactgct cctgtgattc atctcttctc ctgtcaagac cagttgaggc    77220
gatgcaattg ggaacctctc tagtttgtga agagacactt tatgttggaa gcaacagcat    77280
aagcacaata gtacttaggc attcaaagca gagagaattg gttcctcctg attgggtgaa    77340
caatcactgc aaattaaggt caaaagtatt gtcaaccaat tcagtgtact aggcttcttc    77400
atcatttccc atgacttgtt ctctcttagg agaaggttta gcaaattgga gcaattttt    77460 tttttaaatc ttggtgcagc gttagtgata aaacacaaga aagtttaagg ctggatatag    77520
catgtgcatc tatatcaaga tgaagatcca tagagagatg tgcttgatct tgggatgctg    77580
gatgaaaatc caggcactgt gttgtgggag cctgatttct gaaagttggg gcatcattgt    77640
ttggcttatg acgttataa gtgtcaggta cgtcttgtcc cacagaatac ttgttatagc     77700
tgttaaagga cagattgtct tcaagacaac tggtacccat gccagagtag ggtatattct    77760
gacagaaaat ccatttactc tcatctgtaa tttatcccct tagttgaaac atgatcccag    77820
tgtagggcat ttacttttca cactccgttt aaatcagtgt ggtttcttcc taccttaatg    77880
aattttacct catttctttg tcttgcaaaa acccagggca gaatggtaaa atttcaaaac    77940
```

```
aaatctttca caaggctgga actagacact ctgttgggtc acatgcaagt tatttgcaga   78000
agaggaacac tttgcatgtg aataagagaa agcaaagcac ttacaccagt attcagtgct   78060
cttggggcca ggagtgaggg gccttccatg tttgcaggac atctgtttgg gccttaagtt   78120
ctgctacagc cccaagtcct tatctcatat ctgcctggtg tcctattttt ctgcttaaag   78180
agtcaaagac tgaaattctt atccttgttt cccattcatt cctaagttac tttagccttc   78240
acatggagcc accatgctgt ggcccacaga gtgtgctatt cacttaaact tatttatctt   78300
aacctttttg tgaaatatgg ttgcattctt tgactttcct tgcttgtcac agtttacatt   78360
aatcctggaa cttttgagtc ttaagcgcta catgatagta ctctttctaa tggtttctaa   78420
tgttacacga atgcctctct ttcccatttc atccctttct ctctgttggt tttgacttta   78480
agctctctgg ctgtttcatg gcaatgatta ttggtgacag tattatctat taccaagtgt   78540
ttcttgttca gttttgcata gtttcaatgt cctttaagc aaggattgcc aaactacagg   78600
ccacctgttt ttggagatgc catttaattg gaacactgcc atacccattc atttacatat   78660
cacctatggc tcctttctca ctacaagggc attgttagt agttgaaaca cagaccttat   78720
gtaccttcac ctcaaaacct agaatattta ctatctgact cttacagaa aaagtttgct   78780 gatctctact ttgaagaaga gaaagtcgtc agatacatac aatgccaaag aactgctggc   78840
tatgaaaggg atattgtaga attctgcaat tttcttaaag aatggaaaac attggaaaag   78900
agtcacctgt ttacaggtga tttgcatttc tataggtatc agaataatgt gggtgcttgt   78960
aggttgggga aggaatggca ggccttctct ctctgtcagt atcttcaggc cctgaagtca   79020
tacaatcaat ggattgcttt tcctcttcac ttttccattt tgccataatt ttgccaaggg   79080
ggaggttgga agtgggttaa tattttgcgt tagaagagca tttggataca tcctgataat   79140
tactttatct cagatattct tagattctct ctagtgaagg ccacaccttc tctgtgcctc   79200
aggctggcat ggcccaactg tgctacttac cttgggttcc tgctgctcag cttaaaggga   79260
atctctttca tatgcctaga gccttgttta ctcagttcag gtctgtacca gttgacacca   79320
agtcaaaaag cactttagac agaagcctgc tttgaaagtg ctagctagca gcaaataagt   79380
ctggcttaat tctcccttga gtctggagat ctgattggaa gggtaaaagg gagaaaggga   79440
tgatttattt gttgactgga ttgactactt tatattagta attatgaggc aattctaccc   79500
acattatctc atttaactcc ccataaaaac cctacaaggg aggtaatata ctttggaaaa   79560
ctgagactca gagaaattaa gtaaattgca aagtccccat gctataagca ttatagtctc   79620
ataagcaaat gtcatgagct tcttctagct ttttcttcat gctcacaaaa tggttgaagg   79680
agatccaagc atcatgtttc tagttaaaaa gaaggtgcag agtaaaaggc aaaaggcaaa   79740
cggacaagcc aaccaagttt gttctctttc ctagatgttc tacttggtga cttcagctta   79800
tatctcatta atgtgcatca taggattatc tctgcaaggg aacctggaaa atatagaaat   79860
ttgtttgtgt taagctgggc accttgccac ctccataaaa atgtgctcta taggtacaga   79920
gcaggagata atcattatta ataggcaact tatagtctct gtttcaagag gtcattctgg   79980
tacctgagaa aattgacaat ctctggtcta aactcttaca ggcctctctt gccttcattt   80040
aagatgaact tgatagaata aagattattg ttgttctcta atctcctggg tatgagacag   80100
agaggtaaca gatggaatga tttctttctg gcttccatag caaaccaaag catgtgccag   80160
tgaagagtgg caactgctac aaatacttag ccaaacgtgg ggaagagtgt tgatgctgta   80220
agtctcctag ctatgtcgag gcagcaggtg tctctgtaga tcagggcagc aatccctttg   80280
```

```
gtaagggcat gaagagggca cttgggacta ctggattgca tcatcttggc agagaaaaat    80340
gtagcatata ctggaactct agctgggtag ggaattgaca agttgaacca caagttgact    80400
actgttcagt cagcactagc ttttatcttc cagtcaccat tccctgtggc tcttcattga    80460
tcgtccacaa gctccaggcc tgggtggtgc ctgttgtgat ataagaaggg aagagtgatg    80520
gtttccaaaa tgtgaacact catgtgtaca gttttcatgt tgataatgaa atgctagaag    80580
gggaacagct agctgatgcc tatgtctttg tccatacctg gctacccatg acaaagttgt    80640
tgttgttgtg gttgttgttt cactccaggc acaggcacag agccgcaaga gtagaaaaca    80700
agaattccat cctgcaaaag aaaactgaat ccccttgct tggtcactta gggaatcaag    80760
ttcaggaggg ctggacatgt tttctgttgc tctgtaatag gggctgaaac ttagttcaat    80820
tatggtgctt agctgaagca ccatgactga atctttttt gagaaggaga aggagaaga    80880
ttttaaaatg aaatgccata agtgtaacat agtacatata gaggtcacaa acttggaaag    80940
cctgtggtgt cttggaaggt cacataaatg tgtgaaacac gccagttgca cacaggcaag    81000
catatgtccc ttctagagaa attattgcca ctgaggaatg ctggttctaa tctccaccct    81060
cccttcccct cccctccact cctgtaaaaa ccagaggttt ggaattttgc gtgaataact    81120
cagtttgtta gtgttgacaa ccaggcatga cagtagctca tttggaccct ttgtccaaat    81180
caggaaacag cagcccttcc ttcatggcag ccctgtagct acgccagtcg agtgtgggct    81240
ggatttcagc ccttactctc ctccttagct gagactttgt gccagacaca agctgcccag    81300
ctgtagacag tgggcccaga agttatcagt gttacatgag caaaacaaaa catatctacg    81360
ggccatactc agcccatgga ttattatttt gcagcttctg tagctgcggt taaaacaaag    81420
ctctggggcc agatcacctg ggtttaaatc tgggttctgc ccttcaggca aatgactcag    81480
tatttcttgg cctcagcctc ctctatctgt aaaatgaaga taaatacttg tacttactta    81540
acagggttgt tacgaggata aaatcaatac tgtggggcaa acacttagct ctacagaggg    81600
tgacacatag cacttaatgt tatataatac caaaatcatg tgaaaatctg attttttcac    81660
acttagagaa tatacagcat ataaaatgat gggagagtgc atgtcagacc ttcatgatta    81720
ttttctgctt cttggggaaa tgcttatgcc tctttggtca ctgtgaagac agagaactca    81780
aaatagtaag catcacttac tagctggcct actaaggcca caagaacaaa tgaagtaaac    81840
actctgcttg aaccactgat tttgtttgcc tgcatgaaac acttgcacag gttgacagct    81900
gacatccgta acaatgacat cctaaaacca ttaagaaatg attaaattaa gttcagtatt    81960
atctgttgca aaagacaaag atgtgtgagg tacgttttag aataacttac aatgaaaaca    82020
actaaaaagt gaggaagttt aaagtggtga gtattcaatt gcttgagttc atcttctaca    82080
ctggctcatt atctggaagc tgggccacag agttaatact ccatctttaa agactgtcac    82140
aggtgtttgc acctaagatg catcaggttc tgcagtaaaa atttggttcc tggcactgag    82200
acaatgctag gaggagggtg ttaacttagt actgaccata atgaaatctg tggttgactg    82260
caaggacctg ggttgaaata agactaaatc cagtagtatt gctccggtag gttcaatcat    82320
attcaagtgt tcaataatga ttataaagaa gtgtcaagct gtcatgctta ctttaaaaca    82380
tatccagaaa agagaatcca aggaagtgta tttagttcta cctgcattta aattagcttt    82440
ttttttatc attacatcaa tgtcattagg ccctaaatga tattaagagt gtctatgaga    82500
ccccaaagac aaagattgtc ccctaaaactt ctattcttat tgtttaaca tggacttggc    82560
ccagctaccc ccaatctaaa gcttcttct ctagagtaag gtatctcaat ctatgcactg    82620
ttgacatttt gggccagata attctttgtt cttggggcta ccctgtgcat tttaggatgt    82680
```

-continued

```
ttagcagcat ctctggtctc tacccactag atgctagtga cttccttccc ctcaactcat    82740
gacaaccaaa aatatctgta tacattgctg taatgtcacc tggggagaaa atcttcctgg    82800
tgagaaacac tactctagac taagaaaagt agccagattt ttaaacacaa aagtgttttt    82860
cctcccagag gcaaaaagtg ccctagagat ggaagaattt tgaaaataag ctcttccaca    82920
aactatactg ccaaaatggt tagagaaaga tcctataatc accatgcttg acaaatggtg    82980
tttttgctaa gcctcacagc agctttgttc atgtattgtg ttaattgcaa ttaaataaac    83040
tagtctagaa gtgcgggtca tcatccagcc cattcatatc cctcctttac agtacacatc    83100
cagacttctt tcagagttttt gcttgcccat tggtgctcac atataaaaac tccgtgggtg    83160
ggagttaggg attcatagag cagagaggga cctcagctct tcatgtccac ttttcttgtt    83220
ttaaaggaca aggcactgag gtccagaaag tggaatttgc agcacaaatt gctatgataa    83280
acctcagtga ttcagcccct gggatcttca atgatatagg cacagaacat ataactatta    83340
ctgagtaaaa tgtttaaaat tatgttctta tggcaatgtt caaggtttta ggcataagta    83400
agacaaagca gagaaaaaat aaaaaatatt tttcaaattg aaggcttaaa aaattaagga    83460
taccctctat gtgccttctg ctttaggatc cagaatctta tgtttgtttg ctctttataa    83520
cacatgactg tgtaatatca gtcaattgtg actggtaaat ttccattaat ttgcctaatc    83580
atatttagaa attatgccta ctaaataaat tatggttgga acttgaaagg aataatggct    83640
taaataagtg atttgttctt tagtcagaaa aatattctca cgctctctct catacctca    83700
tgaagcactg tcatctccat ctagtttata attaaggcaa tgggaccaaa gtcatcctgt    83760
tggcacagga tggccatctc tgcatccaaa tttcttttac taattggaga aaaccactaa    83820
ttgtacattt taaactcaaa atgtctttat gtatatatat atttaaaata tatttatta    83880
tttttattaa tttattaatt ataattatat ttattaaaat aataattatt tttattaatt    83940
tatacatatg tataatttat gttttctcca tgtggctagc tgttgatcta aaggagaagg    84000
agcaaggcag gaaaattatc aggttcagtg tttaactggg agatgaggac atcactaaaa    84060
gaaaggtaca gcaggttcta ctggtatgta caagttttga ttacaaggtg tactcttgcc    84120
acctggtgtg gtgtctcagc taactttagt ttctgattac cggggtctct gagacaactc    84180
tccagggtca ggtatagagc tccttttgcc cttggcatgt tccaaatcgc ttccttatgc    84240
tcaaccttct gagcaataca aggaaaaatt ccttgtattg gcatgttatg aaggttattg    84300
aaatacttta ggaaatgcct ttgaccttgt tttgtactta gaggatgatc tcattcagaa    84360
atgggtagtg tcaaaatatg gaatgtgcta gtaaataag cacacaattc acttaaagaa    84420
acaaaaacaa gacaagacaa aacaaaacaa aacttgtttg ggatgggtga aaggcatggg    84480
gctgcaattc atcctggatt ttaaggttag aagtggttga aagaaatgtg atattttac    84540
ctaaaccgtg gtcaactata ctttttacttt ttagcaatga tgtgaatgaa gaatggcttt    84600
gaagactgtt ggtggatttg acaaatattt atcaagagcc tgctatgagt gtcaccatta    84660
taggtggtag agattccaca atgaacaaaa cagagtcctt tcttacattt tgtgaaggga    84720
gaccacctct aaacaaatat atatcatgtc aggtagagat aagtgccatg gggaaaaaca    84780
aaatagggta aggggctagg tggggcagga tcagaccaag gaatttatat tttatataag    84840
attgtcaggg aatgcctctc taattagatg acttttttttt taatagaact gaaggacata    84900
aaaggacgag gcttatggat atctggggga agatgtcaga ggctgttata aaagttgcaa    84960
caggaaactg attaggactc ttagcagact tatatgtgct tagaatgaaa gggattggga    85020
```

```
taaaagaaaa gagggagct ttgggaaagc attaaactgt ggccatagca ctgattggat    85080
aaaccataac attggattat gggtctgcaa atttcttaca tttttttaa agtgtcagac     85140
ccatagccct agtaataagc aacatggtct tttctttgag catagctgta atgaacatgt    85200
tattcttttg gagttatcct gcaaagctta tcaaactcaa gaagcaatag tttatatgca    85260
ttgcccaggt tgaatattat taatttgggt tgggaagtga tatgaccaca ttctgactga    85320
ctataggccc tagttcagtt tacctgattt tatgcccaat ttttaatgag aagggagctt    85380
gctaggccag gcaggaagaa agaaatgggg acagtgtcaa gcaggaaatg cagaagagtt    85440
gagtgtaggt aaatcccatc tttcctggct ttacgttgcc ttcacatccc tcataatgat    85500
cttctacctc agtcttcagt ataagcagta tgttgttcta aaggtatgaa gtcttggcca    85560
ggcaccgtgg ctcacgcctg taatcccagc actttgggag gccgaggtgg gtagatcacg    85620
aggtcaggag attgagatca tcctggccaa catgatgaaa ccccatctct actaaaaata    85680
caaaaattag ctgggagtgg tggtgcacac ctgtagtccc agctactcgg gaggctgagg    85740
caggagaatc gcttgaaccc aggaggcgga ggttgcagtg agccgagatc gcaccactgc    85800
actccagcct gagaacggag cgagattccg tctcaaaata aaataaaata aaataaaagt    85860
aaaggtatga agtcttttcc aagctaaggc aagaatgctg aaacctcaat catagcactt    85920
ttccaaaaga gtcttacctt atattctgga tctcttcatt atctcaagag gggcttcttt    85980
ctctttaaat gtgaaaagaa gagaggcatc agctagccct attagcccag ggctaagaat    86040
tgctccagat ttttgaatgc ttaaccttaa acaaagtcac atgtaccagt ggaaagtggc    86100
tcccctgttt tcaaggacag gtcagatttt aactacgtgc ctcttaggct tgccctgtct    86160
tcggagttgt taaacatgca tgttgggagc tgttgactgt ttttttttt ttttctttct    86220
ttcttttttt gccttataat ttacttttat tttaaatcta ttatactttg aactgttgac    86280
tgttagagaa agcagtactg gcttaggatc agcagagaat atggttgaat tctatttctt    86340
aaactgagga gaatttctgt ttgagcccag tccaagtcat tacttgagca attttttgcg    86400
cattttgctg cttaagtgtt tatttttttt ttgcttttac aagtaatttt tttaaaaaa    86460
gttatcatac actcagcaaa cattttttga gcacgtacac aatgcccagc cctgtgccat    86520
gcatgttcaa aaaaaaaat aggtaacatt atatctgtgc ttgtgaaatt aatacatttg    86580
ttagaaagat aagacttcaa tcagtaaagc aatccaagaa ggaacaagta caaatccagg    86640
aaggagacat tagctcagtg gaaagagtcc actgaggtag gtagacttgg gtttgagtca    86700
gaagcaagag attgcttttg tgagatttcg cttatcctgt gtgggcctca gcttcctgtt    86760
atgtaaaatg ggataatagt acctattaca ttgtcacatt ggattgctgt gatgacttga    86820
taatatttat atacaaagca accagtataa tgcgtgctca tagtaagcac ttattatatt    86880
attattattt attggacata taattagaag gtctgggtta taatcttgat tctacaatta    86940
tttagttttg gtaagtcact taactttatc ataccattca tgcatattac ctataaagtg    87000
aaaggaacag aggttctaca atttatctcc caaattccat ggtattttga accaaaatgt    87060
attgaataag tatttgatgt ttgcttcccc ttcttgttag tgatatttac aatagcaata    87120
aaacatcaat atttatttag gacttgctct ggagccacga gccgtggtgt gttcttgaca    87180
ttatgttatt tactccatgc tgcatactca gtgagacaga taaccttgtc ttgtttccta    87240
gatcctaggc catattttat ccagtttaat atttctgaaa tcagaatgta ttatgtagta    87300
ttatgtagtt aataaatata tttaatgtgg aattttttc ccaaaagccc tttcaagtg     87360
agatggaccc tcttatgatt taatgaggat gtcttccaag ggaaataaat attttttcta    87420
```

```
tatttctgat ggtaaagttg aagcatagag aggataattt acatgaccaa gattaatgaa   87480
ctaacaaaag caaattcagg acttgaactt aggtttgttt tatttaacaa tgctcaccct   87540
accgtacttc ttgggagcaa aaaatttaaa aagtttctaa catatattca ttagttcttt   87600
ccatttttta tagcaaaata tatttgatct gtctctagaa tcaatgatag attcactatt   87660
tgttaacttt taacaggaat atattttagt ccctctagcc tgactttata ggctatgtac   87720
ccagtacatg aaaatatata gtagcctcag tttaatgttg atgtttattt gatgtcgaca   87780
tcactagtga cactggtcaa gcgtatcctt ttagataaga gcctattaga attatatatt   87840
ccctgtagaa atcttacctt gaccatagta catttaacag cagattttc tcagactttc    87900 aaaatcctga agtctgggt cattacaaga aaacaaggat gtggtcataa acagttgatt    87960
attaagcaaa ttcattgaaa attaacagca gtattctttg acctcactct ttatagccaa   88020
actgctaatc ttgggtaaat tataagatta tattactaat ccattgacat ttagcacaaa   88080
ttagctatca aatgggtcag ttgttactgt tggaaactta tgaaaataca ttaaagttct   88140
tcccatttcc tgtatgtttc tttctctgac acagaatctt agaggctttt attaggctgg   88200
gagaacttcc caaataatct aatgactagt tgaataattg tttatgatat aaaatcagct   88260
ttgttgtcag aatgattaca gtttcagggt catagttaat agaaaaatat ttcagtgaag   88320
gttaccatta gtcgttgtaa gtatcccttg attcaagaag tgaaacttt attgaaaaaa    88380 ctatttgcag agctggagcc ctgatgggcc tttctgaagt ttttaaaatt aagaaatcct   88440
atctctactt ttaacaagac atgaatgtta gtatattcac ccagactaaa tgaatgaatg   88500
aatgatcaca ttacacatgc ttgggatttg atttccttcc tctggtgttc actggactag   88560
cagcttcagt actcaagtgc gattgtaaaa ttacacatgg tggaattcaa aatggtgtac   88620
atcagtcagg tcctggaaag acacacaatc taactcagaa gtttcaagag acttcaaggg   88680
gaaatgtaca gaagtatggg taggattaaa gtagctagca aggaatgctg agtcactcgg   88740
accctagctg ccatgagaag ctattatctc ttctggacct ggagctgcag aagaaggaaa   88800
ccgtgttact ctagtcctga gagggccgga gccatggagg aggggtcttg tgacagaagc   88860
taaagttctg gagagacata ggctaggcca gagcatagga atgtggggaa gacatccctg   88920
acctctctgt caaccttcta atctccattg ttcaaaccca gtaggaagtt atccagcatt   88980
gagcctggag agtcagcccg cagcagtcag cctcctgagt gcagagcaga ggaagacctg   89040
gaatggatat gctataggag gagggccaaa cagagagtaa ctagtccaga tgggaaatgc   89100
tattttagac ctcatacact gccaaaaaag aatggcatat tcaaggaatc caggaccttg   89160
acctcatttg atcttggatt tgcatccatt ttctgatact ttcttccaaa tactcttgta   89220
agcatctgac agcagccagg agaattgctg gtcagttcag cctgtcccag cttcattgct   89280
gaggtacata tgtggttaag gagctgagag aactggtctg atagctcacc aaaggggggcc   89340 tttcccaagg aaaataaaat aaagagaaaa ttcattgaga atctgtccag aaaggacagt   89400
aagtaggcat ggaatcatag tagtaaggaa gcatggagga ggcaggtgca taaaaatgac   89460
ttgtgatatt tttgaagcta tatgataatg ttctgaccca cactcttgcc agcctctgca   89520
atcttctgga ggcttcatat gaaagcagga ttggtatgct gtttattata aatagtgaga   89580
cctgagagat gattactgtc agcataaatg gatattacac attgcaccta tctcccagca   89640
ggaagtttgt ttgtttgttt gtttgtttta gacggagtct tgctctgtcg cccaggctgg   89700
agtgcagtgg cacgatctcg gctcactgca agctgcgcct cccgagttca cgccattctc   89760
```

```
ctgcctcagc ctgccaagta gctaggacta caagcgcccg ccaccacgcc cggctaattt   89820
tttgtatttt ttagtagaga cggggtttca ctgtgttggc caggatggtc ttgatctcct   89880
gaccttgtga tccacccggc tcggcctccc aaagtgctgg gattacaggc gtgagccacc   89940
gcgcccaacc agaagtttgt gtttgatgtc actgttgttt caccaattta aaagaaaatg   90000 aatatttta aaggaaaaga aaaagttat cacactatgt gatgaaattt gtatctatgg     90060
gtggttattt gctacttggt aaataattaa agcctgtact ggttaccttt cctttagcag   90120
ctgacaacaa ataaacatcc tcacctcaca ccttatacac tttactccat ggttcatttt   90180
cagtattatt ttgtacttct cttgcttcat catactattg cctggcaaaa ttccaaccca   90240
gatttaatcc tgctttccat ctatacctg cctacacctg agagttcaat gttactgtgg    90300
aaaatgcaca ctgtggtgac ttgtttcact ttaaatgcat gggccctaac ctcactgagc   90360
catttattag taatgattgg caactctcca tatttcttga atccactcac tttcctagtc   90420
tcctggacaa ctatgtgaca actcctctat cctcaagcct ccaacaatta cttctcatac   90480
cctaactctg cgcagataac cttttttcct atttcactgc aaaaagccca gaagtaatca   90540
aaagtgaatc tacaagcttc caccaccaca tctactcctc ccagtctcag tgaccatatg   90600
gtttgccttc cttctgttaa cagagagctt ctatcaaaga tgaacctctc cacttggcac   90660
tttatttccc tcttgcatat tcaaggacat tagctcagca attttctttc tttctccttt   90720
cttgcattat ttatttctc cctccaccag aagttgtcac cccaacttct attagaatga    90780
cttaggaagt gcaggcctca aaccttttt tttttttt acacgtctac ctctattagc      90840
actccctgct cctatttag gaatccaggc tttaacgcta acagttacaa attaagccac    90900
aagctttgta agtatttgcc tgtgctctag ctgctagtgg gttttggaa aatcagtatc    90960 tgatgggcat ttgaatacat ttgctcttgt ggctttaaac aatgtctgta caataaaaac   91020
ttgagaattt atctcctctg aattctagac atttctattc aactacctag ctggcatttc   91080
cacttgcatg ccttaaaggc cctcaatctt atctgtactg aatcgatcac cccctaact    91140 gcctcatccg tcagttatcc ccattgcagt tggtgacatt ccatcctttg gttgcttggg   91200
ttaaaaaatg ttggagtccc ccttgactcc tttctttctc tcatttccca aagccaattc   91260
tttggcaaat agtaaccatt tatcacattt tccactgcta ctgttctggt ccaagccacc   91320
atcctcattc acttggatta ttgcaaagac ctttacctgt tctatatgct tttatatttg   91380
ctcatttttc tcccttcacc cctatttgc tttcagcaca gtatatcatc tcatgcatct     91440
actcaaagcc ttctaatgcc ttcccatttc atgatggcct ataaagccct ttgtgatctg   91500
gttccctgaa atccttgact tcatttgggc agatgtttct gctataacgc tatttatgtg   91560
ttctgtaaaa cttttggtc tgcaagatgt actttgaaaa ataacaggtc ttatggtaaa    91620
attacgattg gaatagaaca ctcatatctt atacaacata aaaaactgta gcaataacca   91680
aagcaataat agataccttg ggagataaca ggaaggcagg cagctcagat tgactgaagg   91740
cgactcaagg aatattaaaa atgcacaaaa acagtagcat ggagatgccg gctggggagc   91800
tgagatgaga cagatgaatg gagctctgag ccagagggcc taccacaaaa gtggtcatag   91860
gaagaagttc agcctgcctt gagcagatag ctttgcctgg tgggagaggg cgtatttctt   91920
gggagacacc tctgggtgca ggcgctcatc tttaattccc ttaagagagc tgaaatcact   91980
gcagtctgtg cagcagccaa cttcagggat ttttcctttc ctgctaaggt tataattctg   92040
ttcttgctat tcttactcct cttgcctaag aaaaatcttg tttccatgta ataccaatat   92100
tatcccacta tttaccagta gcatatgagc tgcttgctgt tacagaaaca catgctgtaa   92160
```

```
tagaacagac tgcactcctt gggtcatctt tgttatttcc catgtgtcag gtgagcaccc    92220
accttgtgac ttttgctact ggtctttccc tgcctggaat gctttccctc cagaagtcct    92280
cacggatttc ttcttctatt tcagttcttt atttaaaaat attttttcata gtttgaacct   92340 ctctaaccag ctgatttaaa agaacaacac caccccaaca acgttctcta ctttacatca    92400
tagtttaatt ttctccatag tatttatcat catctgatat attataatac tcatgtattg    92460
gctgaaccac atccataagt attaagatcc gtgagggcaa gacttgtggg tttttaaact    92520
tgttttcctc ctttgttttt ctctattata tctttagtgt ctggaataag gttcagcaca    92580
tacaaggcat ttactaaatg ttgaatgaat gaatgaatga agctcaagct ccatctacaa    92640
acagtcctct gttttttgtt tttgtttgt tgtttgttt tttgtttttg ttagctgtta      92700
tctggctgtt tttattaga taataatttg tcttcctttta cttactgatt ttgtttatgt    92760
gtttgcaggt gtgtgtgtgt gtgtttgtgt gaaagaggag aatgactttt atcaaacctg    92820
gttttatgtc ttccttagga tgcatcagag tttcatgctg ttcacactac ccttcggggt    92880
attcagacat ttaaagtctt aatatttcag caataaagtc ttaatatttc tggcctggaa    92940
aaatactgtg atatgggttg aattcatctt tttgcaccccc tctatcatca taaccactcc    93000
ctgctcccat tctaggaatc caagctctta tgctaacaat taaaaattaa gtccacagac    93060
tgcagataga ccctacgctt gagctgccgg tgggttgctg aaaaattaat atttgatgga    93120
aatttgaatt aattgcctct ttaccccta ccaatccctg tgtatggtca aaaatagga     93180 cattccaata ctccacagtg atggccacag tgctggtttg tgctgatgtt ataaaggagc    93240
aggaagatgg taatgaactc cctctggtgc tggacaaggc ttcacaaggg tgctgatgaa    93300
aacaatgtga gaaatggac tcaggggttc tcaaggcaga gaatggtggg gggatccagg     93360
aatccacata ttcaaagaca caaagaagta cagatttctg aggtgttcag ggaatggtga    93420
ttcattaggt atggggctgg gggtggggca cagggtaggc agaggagaga gcagtaggtg    93480
tatatgccat gaagattttg gaatcgatcc aactatacag ctatcaaagg tttttggtga    93540
tacaaccaga ttcgtcttct cactccttac ctttctcacc tgatccctcc ctggcttttc    93600
caaactgtca actataaggc tgtgtgacca gagagcatgc ccctgtcccc agtactcaga    93660
taagtgcctg acatatat atatacatag acaacctact tgtttatgtg tctgaacaaa      93720
ctatcaatat tcatttctgc atttttctttt cagcaatgct tacactgtct tcaaatcctt   93780
tagggcccta cacttgacta tcaggctgcc tattgaaaac taactttaca ggttgttcat    93840
tggttaccat gatggcacaa gtaaccattc agtaactttt ttttttttttt taactagaat   93900 tgaaagcttt gatccattct ctttttctgg tctcatttcc cttctaccag atctgattca    93960
tggtgcaact tttggtggca tcaccccctta atccagcaac attttttgtat accctgaggt  94020 tattactttg atgtcctgaa cttatggctc tgggggatat ttttttaaag gggtcagaga    94080
aataaggttg aattagagag attccttagaa gtttatgatt aaaacactat ccctctgat   94140 ctgagtccca gctctgccat tgacaggttg tgtatcatta gcaatagcaa gctacttcac    94200
atttctgaat ctcagttgat tgagcaaaat ttagataatc aaagactact ggagatgtga    94260
tgctttgaca caaagaaatc tacctctttg gtgaaatttc aattgtgtag gagcagttat    94320
ttgggagaaa agtgccctct caccttctta aatcatctcc tagggctata ataggaaata    94380
cgcagctttt gctgagaacc caaatgacat tgtggattat ccagctctag tcttctctct    94440
cccatataga ggccggttat ctttgtcact tcacagctca ttagcagccc cactcagggc    94500
```

```
catggagagg aaatagatga gatgaagctt aaatatgtca cattggttat ttcttagcag   94560
ctctgataaa aggcttagca ggggccaggc gcggtactgt acgtctgtaa tcccagcact   94620
ttgggaggcc gaggtgggcc gatcacctga ggagttccag cccagcctga ccaacatgga   94680
gaaaccttgt cgctactgaa aatacaaaat tagccaggcg tggtggtgca tgcctgtaat   94740
cccagctact cgggatgctg aggcaggaga atcgcttgaa ctcgggaggc ggaggttgtg   94800
gtgagccaag atcgcgccat tgcactccag tctgggcaac aaaagcaaaa ctccgtctca   94860 aaaaaaaaa gcttcagcag ggtgaggtta aaactcaaat aaagaggtct gaggattatc   94920
tgtgatgtta gctcatgtgt gttaccttcc tgtcttccct tctttgttct tatttctagg   94980
gattagttga ctgcaaacat taatgggtta aatataaaaa tgactgcaaa cattaatggg   95040
ttaaatataa aaaatctttt ctatcctgaa ggtctttgaa aaaatgattt tattacttac   95100
tggaaaagaa aaataaaaca aagcttgctt cacccagaat ttatttttc ttctagttaa    95160 aatgagcaac ttcttaacc agaactgacc ttgaagacaa atggctaaaa taaaacattt    95220
gctgaattca ctgggcgcat cttacaagta atttttggat tctgcattga ctacctacaa   95280
gtgccttctg ggtgcaagtc cacaggcaag atttgttctg caaatcttcc atgaccaagg   95340
tcacctcttt ggattggcag acccagggag tccatattgg gaagataaat tcacacttca   95400
ccccttgttg agatctccag ccttgctcct ctgataacca ggtctctctt ctgtcctatt   95460
ataatttatg accttgaaa agttactat atctggggct attcaaactc ccagctatct    95520
atgaccatat gcataaatgg ttctagattt aaaaaaaaa agaagctatt cagagatatt   95580 gggatacct ataaccaata taatgggta attcagcaga accagatgct ggggttgaga    95640
aatagatgtg gacaattggg gcagggccta agaaagatcg gaggcaaaga cagtgactag   95700
atggggagct ctgataaggt aatgcccagg cctgtgcttg gaattctgcc acagtgggga   95760
cattagtggg ggtctgtagt cattgcaggg tgagaggagg atagaaagaa aagattgtgt   95820
gaaggtcagt ggaaggtccc ccatttcatt gctaagagaa ctatgtatgc acgttttcct   95880
gtgtttagtc tcacacataa ttgtaccttt aagaactgat cacacactgc atttccctgg   95940 cagttttgg catctcagat gaggaagagt gatgggcgac aggtgatggt gacaactatt    96000
aataagatct gaaagtaaac agtctcatga aaggtggcca ggagagggca gtcaccttt    96060 atcaggagca cagactgaat ttgcaaaggg tacttaagct acaagactat aaagcatgat   96120
gcaggcttaa ccaaaatgca gtgtcttgag catagtagac tcttagtgta tgtttgctaa   96180 atataccta gctgctgctg ttccccagag ctcatcagag ttccatagaa acctggtccc    96240
ttccagaaaa ccaaagaatg actaaagaaa agtgattgca aatccagaaa gcagctttgc   96300
cttactggtt ggtaacagca ggattttctt tccttgtag tttatttgg cttaggctag     96360 tgtctctttc atgaagacag ctactattta caattgttgt taacatgttt ttccttttc    96420 atctcccaat atactctctt cctgtcgtta aacacagtca atttaccaat ggaatctgct   96480
ttataagctc ctgcattttc ttttccaca gatgggatta atgccattat gttctatgtc    96540
atccacatag tcttggcttc taggcaccaa ggtgttgttc tagaggaaag aagagtaatg   96600
gtcgacacag gcaggctgag ggctaaccta atgatttcat gcatttagtg gtaattctta   96660
attaagatcc caattttatt ctgttggatt tagtctataa cccgctgaaa atcattcttg   96720
aattaacact gggtggatat aaaagcagaa agccaaggac tttgcactgt tctcagctgt   96780
agctgtttat ttagctggag aaaatttagt gggtggtcca accttcataa ccaggaagaa   96840
taaaatagag gtgtaaaggc cttggtggaa ggagggcagt agcaacccttt ccatttcttc   96900
```

```
agttttatcg cagcctatga aattagttcc ttaggtatgt tgatcttgta ggagctagta   96960
ttttaacatt tgctccatca agttgtttgg tttaaatcta agaataagcc cactgaaaac   97020
tattcctaat ttgtgaaacg aataacaata atagatgtta atagaaacaa agacttcatt   97080
tggttagttt ttagagggggg cacagagaat gtagtaacat aataagttag atttttgttg   97140 ttttctttt  cttagttctt tgtagtcttt ataatctcta attggcattt gctcctgact   97200
tttctcagtg tacttccaca tggaagagac aaaagtctca aagctggtgt agaaaaccc    97260 ttaataaatt gcccattaat tagccacctt gatttccacc tttaaagcag ttaattgaag   97320
taagaatttg ttagatttt  ctcaagcata gcagaaatta agattaattt cttaggtgtc   97380
attgctactt gcctacttaa accaccagtt catctttatc ataaatactt aagccaaaag   97440
tcacattaga ggcaatatgg cacagtgatt gtggaccccg gagtcaggtg agctggttga   97500
aatcctggct tggctacttc ccagctatgt gatcctgggc ttcagggttc ccttttgcaa   97560
catgacatga ttgctgagct gcttcttagg gttgtgtgtg gctccggtaa gataatacag   97620
gaaaagagct gaaagcagta tctgaccctg agagaaagt  agggaagaga caatagagga   97680
aagaggacaa ggaagtggga gatgaagaga aagttcaaga aggaaagtgg aagaatctca   97740
aatagaaagt taattttcag ttttttcctga gaagagatat atagacatct tcatgtggct   97800
ttggagagcc ttggagccca tcagcaagac ggttggaaat tatactgaaa cagaagtgta   97860
gacctatgtg acttatgtcc tggccagttg cctcatgtcc tctgtggtca ggttgatctc   97920
tactggcact gtcaaaagat ttttatggga cagctggttg gggtaaactt tgaaacctga   97980
ttgtttgcac ttgagtgcca gagtgtgtaa ttatttaccg gtgttcacta aggatgtcag   98040
tgtagatttt taggggggaga aaaaacttaa atttaaaatt tggaggcatc tttttcagtc   98100
tgcctgccct ggtgtttgtt ataacactta gtttggcatg taacagctga agctactggt   98160
taaatcatta agcatttatt attttaaaac tcctcttctc aaagcaaaaa ataactatca   98220
tgttgaagtt cttttcctcta agaatgacat ttactgtgag ttttatacca atggactaat   98280
tggagggttg agaaaataaa ttttggaaag acaacaataa cttcagaatt ttccttggat   98340
ggaggtttcc tttttaaaac ctgaactgag ctttatcaaa acagtaactg aactttgaaa   98400
cgaaacaaga gtgctgaatt gaaagctcca ggaaggcagg gatgtgtctg tgttgtttat   98460
gactataacc tctgggccta aatcagtacc tatcccatgg taggcactcg gtaaatactg   98520
aaggaatgag tacagtatga aaattagcat ggctgatcct tggaaaaaat ataagtcaaa   98580
agggaatagc atgcatgtgt aactaaaaca tcagtccaca tgcttgaaat gtcatcactt   98640
ttttatggtc aggacctgtt ttttctgct  ccaattaaag aagaaattg  taatgtgaaa   98700 gaagcaagaa gtgaagtatt tggtattcat gtgttttgac atctgcagta agtttaaaat   98760
aaatttctaa atcttattgt attgaaattg tatgagtttc ttaagtggta ttattcattc   98820
agacttaaag tgaagttagg ttgctgtcac tcatagtgga ctttttttt  tttggcatta   98880 ttaaaacaac atgtcttctg ggtgttgtct tgtattacaa aagcttgcgt gttttctctt   98940
gatgctgtgc cctgtctgtt gccattgagg ggtctaagga ccaaatgagg tcttgtttcc   99000
ttcctgatat tcttttgacc agtttagaat atgccaggtc cattcacaca actaagcggc   99060
tcagttctct cagttccctg gtcttctcat attagattgt tatctatgag cttgaagttt   99120
agacatgaaa aagaatggtt gtaatcctct tccttctctc accctcttcc ctttttttct   99180
taagttagcc ttttgaattc atgattctaa taattaaatat atattattat ataatatagt   99240
```

```
atatattcat aataatgatt aatgatagta ttaataattc tgtgtgtgtg tgggcagcta     99300
ctcatacaga ggaaaacaga ttgattagtg gaaattacat taatttcata acttcttatt     99360
aaaagagttt gtgtgtgtgt tgttggttgt ttgttcccct tgcaactcaa catggtcttc     99420
ttgaggtgta gggaaaacat atgcttagga aacagagcct tcttttctcc ttttggtatg     99480
gaagacatat gcaaaagaa tgaaggaact aattgtctct agccagggct ctgcaaaaat      99540
agtactggta gagaaaaagc tctaaaagaa gtaaagtttt atagtgcttt ctcctggcag     99600
agttaacctc atcttcatca gctttccc tgcctcagag aggcagtttt ggaatgacca       99660
aagcagagtg cccaacctct ctgttcagag ttagcgagca tttggatcac tctctctctc     99720
tgcctcagta tgagtggaat attgcatgac catttctgat ttctgccatg agcgcactcg     99780
gcctagatga ataaatcctc cttgaagaag gcggggcatt ttggcattca caagaaacca    99840
tgttgatatc tgatcctccc actggagaaa tgtggcaaag tgagaaagac tcactctttg     99900
ggactccaaa aatgtaaaca caagtaagca tgcaagctga agaagtcact tgaaatagaa     99960 aaaaaagtg ttaaactctc tgttagtcat gtgactttt cttggtattc gagagccagg       100020
aggctcttgt ggtctaatct ggaaagagtc gctaatcgct gtgtcacctt ggcaaattgg    100080
ttgatctccc tgtgctggag tgtttagtcc agctgctgga tgggatgaaa gcaagacctc    100140
actgaaacca gatgctgtct ctctgaaaag atttcagcaa taaataatat cgtatatact    100200
ttgttcctgg cagcaaatac tgaactgcta taaccctctg ttttcacttg cttctaaatt    100260
tctggaaata tctcctttgg gcttgaattt ttccatgctt gtcttcagcc caaaactttt    100320
tggaaagttt gaccaaaatt tcacttagct gttttcctg aattatggga gaataagggc     100380
aatgcattgt ttttcagctc ataaattctc attttcc  ttattcctca gaaaaatagc      100440
tgctacattt aaagtgttta gaactagtaa aagaatcttg gtatggtaaa gaatactggc    100500
agaagacaaa tttaagtctc tcagtatttc cttctaactt taaacatgac tgcacacaat    100560
cagggcacac ataaaaagct ctgatgtagt tttatagatg gccaaagaga agattctgca    100620
aattctctca gtaactcatc ccaagttacc aagaggcaac tttagctacc atcagttgtt    100680
acctttctca accacttgct ctgtctgtgg atctgatttc taaaaaaatg tcatggttat    100740
atgttggcat tgaccccta tctacatttt aaataaagtt gaccatttct tttaggtagc     100800
cttcatgtgt gatgacctca gtcatatctg ctgacctact agactcaaaa ttccttaca    100860 gcagggccta ggtctgtcta cctcaccatt gacactgtag tgctcagcag ggtatgacac    100920
atgtagtaaa aactgattgt tgaatgaatt aaatgaacat aagtacagtt gttttgctg    100980 caatttgttc attgatttgt ccactaagac atgcatgcat gtattcagtg agtatcactg    101040
agtctctact ttatgccagg tattggtatg aatgttgtga atatttcttt gctttgatgg    101100
ataacacaga gttttgctg atacacaaca aaataattat attatttgag tacaattact     101160
atgcctatag ttggaatatt agtccaatat agctaaaggc aatccagggg aatttatcac    101220
ttactgagcg tccatgatgt gcctggccct gtgttaggta ctgagaagag atcaattaga    101280
cagtttctgc aggaagtcac acataggtta acagtgccaa gacaaatcct aaagtaccta    101340
ttatacaagg ggaactataa taagagcca ggtgagttga aggcaggaga ggtatcattg     101400
taccacaaga taccttgtga tcttgtgtaa atcccctgaa caatcaggaa aagctttatg    101460
gcatagcttt atggtcagag atctcatggg gacaggcagt tagttgcaat gccttttata    101520
gccacatcct tcactcctta accctgcact gtctgccatt cattctctct gtgctttcag    101580
ccttgagaag ctggccaaat ttctcaggac tggaaaataa actggaatga cactcaggca   101640
```

```
cttgatatca agattattag ggtcatgatt gtgtttaaga ccctaagacc tcttgatgct    101700
tttacaagaa tgggtacttt ttttgtccct gttttcttct tttgcccaa gtttcaagag    101760 catgttacag cagcagtata agcatacaca atcaaaggtg attgaagtga ggacaactgg   101820
ctcaatgagc tccagccact tcaactctcc tcctagtccc tgtccccttg cccggaatgc   101880
ttcaccctca gactttgaca tagcaggctt cttttgtca ttcagatctc agctcaactg    101940
caaggatttc tctgacctga agttacatat gtgtcacccc ttctggtctc cgttgctctc   102000
tatcacatca cctattggac tacctttata gcatttatct ccacctgatt gtgtcctttt   102060
cactgttttt ctttaaactt tttattgtca attttctttc actagatgcc agttccatga   102120
agtaggaaac ctttaccact ggtcttgagt gctcttgaaa gtgtacgtgt gcaataggca   102180
ctcaaaaatg tttatggaat gatcagctgg atgcgtatat ggcaagtggc gagaagccaa   102240
gggaatagga caagagtcct attgtgctcc ttgcctgaag aaaacctctt gcaagaatca   102300
taggctgttc ttgagggtgc ctttgccttg gattcgccaa aaattcttct gtttcttttg   102360
tgtgaaaatt ttcccctcat acacagcaat gggcactaag aatgcatata tccagacttt   102420
tcaggttaca ggatggcatc tcagatatag tcttcctttg atctatatac tatgaagcca   102480
taattgctta gccagtatct ttttcaggat ttactccata tttcttattc taggcctttc   102540
aggtggcagc tgcactggct ttcagatata atttagaatt tagtttcgga tttgtaaagc   102600
tactcatgct gcagatcttc tctgaaacat ttctgtcaca ttttagaaag ctttacattt   102660
tcatctgcta acgattttca tctgccaaag agcccatcta cttaaaaagc agatcactga   102720
agccacactt ggcacatatt actttggctt attttctttt gattttttg ctttgctggg    102780 attacttatt tatgaagaaa gagagaatat tgacttctta ttttagaaga gaggatatta   102840
cttgggttga gagttctagt tatataaaat gtatttatct aagttgttaa ctatatcaaa   102900
aatggagcag tcaatctttg gaaatagttc agggtgaaat gtttttagca tgttcacata   102960
ttctctttgc tgtttttaaa taatttggca aagcttattt gcatttccca aattaacaat   103020
tttggccaag aggaaaagct aaagtgttgg tttttctcag ctcaactttt tgggtgtaat   103080
taatttataa gcaagatttt atgaagggag aacagatagg acctttctac aaagtccctg   103140
agccaaaata aacaccccat tgttccatcg ttttgtattg cacataggaa aacatccatc   103200
cctatcatta ttctgttaaa gggacacaga ttaccagatt tgtaattta aaaaaggcca    103260 tttgttgatt gagccacttt gcgtataaag ggtggtatat gttgcctgcc gaatttctgt   103320
acaagaaaaa aatcatatat caaaaaaatt tttctcattc atcatataag aaatttatgc   103380 atttagtat gtaccagaag aaatggcttt ggcattttct gttttagca gtctgttgaa     103440 atttcttcat taaagacatt ttctgtttga aggttaaaat gaccatataa atacagatta   103500 attcagttttt aataggtgca tcttcctgtc atttaccact ttctctcctc aatatcagct   103560
acagtgatca acatatattt agcagtgaaa ctgatatatt ctgtttatct tcaaatcata   103620 agcttttgt ttaaatacaa aggaaaatct tatacctctg attttaatat gacaaatcaa    103680
aaagtccaca ccaaactccc aactcatccc aaaaaagaga ttgctatcta ctcatcactg   103740
ttctctgctt ctaagatttg tttcccttgg ggttactgtt tgagcaactt tcttacttc    103800 caagattgtt tttgtggttt taagaaagaa tctgaattcc aagattattt ttctggtttt   103860
aagaaagagt ctgaaaatct agagattact taccttgtgg tgaggtggtt gtctatgctt   103920
ctgttcaaca aaggcctcat gtactgaatg gaaaaaaagc atcaggacct ataatttct    103980
```

```
aggcattatg caagataata gaggagacaa aaatgatgtc ttgcttcaaa gtcttagatc  104040
tatttccctt tgggggttga ggaatgaaaa agagatttttt agatgaaaaa caggaagccc  104100
aatgaggacg tgtggcaata gttcctaaaa tgagcaaaga gataaattta ctcttttata  104160
tgattacaac caaatcacac actggtgagt ttcaaaacag tagttttcat ttagaaagca  104220
aattaagtgg aataattcaa ctgagtttca ctgcaatggg attcattcta gatggttcaa  104280
ctctggaatt agaaacaata tctaaggatg ttgctgatag tagtcagcag ataaatacca  104340
gtaagtcgta tacaggtata catcatttta ttgtgatttg ctttattgtg ttttgtagat  104400
aattgtgttt ttacaaattg aaggtttgtt gcaaccctgt aacgagcaag tcttctggct  104460 ccattttcc aatgacttgt gctcattttg agtctctgtg ttacatattg gtaatccttg  104520
caatgtttca aactttttta ttattattat atctgttttg gtgatctgtg atgagtgacg  104580
tttgatgcta ttattatgtt gttttggcac accatgaatt gcacccatat aaggtgggga  104640
acttaatcac taaatgttgt gtgtgttctg actgcttcac tgaatggctc ttcccctatc  104700
tctctccctc tcctctggct tccctattcc ctgaaacaca acaatattga aattaggagc  104760
gttaataatg ctacaatgac ctctacgtgt ctgatatggt ttggttgtgt ccccaaccaa  104820
atctcaactt gaattgtatt tcccagaatt tccatgtgtt atgggaggca cccagggggt  104880
ggtaattgaa tcatgggagc cagtcttttcc catgctattc tcatgattgt gagtaagtct  104940
cactagatct gatgggttta tcaggggttt ccacttttgc ttcttcctca tttttctctt  105000
gccaccacca tgtaaaaagg cccttttgcc cccagccatg attctgaggc ctcccaaggc  105060
atgtggaact gtaagtccca ttaaagctat ttttgttccc agtttctggt acgtctttat  105120
ctgcagcatg aaaacaaact aatacagtaa attggtacca gtagagtggg gtattgctga  105180
aaagatcccc aaaaatgtgg aagtgacttt ggaactgggt aactggcaga gtttggaaga  105240
gtttggaggg ctcagaagaa gacaggaaaa tgtgggaaag tttggaactt cctagggact  105300
tattgaataa ctttgaccca acagcctgat aacgatatgg acaataaagt ccaggctgag  105360
gtggtttcag atggagatga ggaacttgtt gggaactgga gaaaatatga ctcttgttat  105420
gttttagcaa aaagactggc agcatttttgc cctagagatt catggaactt tgaaagtgag  105480
agatgattta gggtaactgg cagaagaaat ttctaaacaa caaagcattc aagaggtgaa  105540
tgcttgggtg ccattaaaag catttcattg tgaaagggaa acagagcata aaagttcaga  105600
aaatttgcag catgacaatg cagtagaaaa ggaaaaccca ttttttgagg agaaattcaa  105660
gccggctgca gaaatttgca tgagtagcaa ggagcctaat gttaatcccc tagaccatgg  105720
ggaaaatgtc tccaggccat gtcggagacc ttcatggcag acctcccatc acagacccag  105780
aggcccagga ggaaaaattg ttttttctggg ccaggcccag ggtccctgtg ctgtatgcag  105840
cctaaggact tggtgctcta tgtcccacct gctccagctg tggctgaaaa gggccaacac  105900
agagctcagg ctgtggcttc agagggtgga agccccaagc cttggcagct tccatatggt  105960
attgagcctg tgggtgcaca aaagtcaaga actgaggttt ggaacctcc gcctagattt  106020 cggaagatgt acggaaatgc ctggatgccc aggcaaaagt ttgctgcaga gttggggccc  106080
tcatggagaa cctgtgctag ggcagtgcag aaaggaaatg tggggtcaga gccccacac  106140 agagtccctg ctggggcact gcctagtgaa gctgtgagaa gagggccact gtcctccaga  106200
ccccagaatg gtagatccac caacagcttg cactgtgctg ctggaaaagc cgcagtcact  106260
caatgccagc ccatgaaagc agacaggagg gagactgtac tctgcaaagc ctcagagtag  106320
agccgcccaa gaccatggga acccacctct tccatcagcg tgacctggat gtgagacatg  106380
```

```
gagtcaaagg agatcatttt tgagctttaa agtttgactg ccctgcggca tttcagactt  106440
gcatggaccc tgtaatccta atcctattgt tttgtccaat ttcttccatt tggaacagct  106500
gtatttaccc aatacctgtt gtatctagga agtaactagc ttgcttctga ttttacaggc  106560
ttataggcag aaaagatttg ccttgtctaa ggtaagactt tggactgtgg acttttgggt  106620
taatgctgaa atgaattaag actttggggg actgctgaga aggcattatt ggttttaaaa  106680
tgtgaagaca tgagatttgg aggggccagg gccagaatga tatggtttgg ctgtgtcccc  106740
acccaaatct caccttgaat tgtatctccc agaattccca caggttgtgg gagggaccca  106800
gggggaggta attgaatcat gggggccagt cttcctgtg ctgttctcat gatagtgcat  106860
aagtctcctg agatctgagg ggtttatcag aggtttctgc tttcgcttct tcctcatttt  106920
tctcttgccg ccaccatgta agaagagtct tttgcctcct gccatgattt ggagggctcc  106980
catacatgtg gaactgtaag tccaattaaa cctcttttg tttccagttt cagatatgtc  107040
tttatcagca gcatgaaaac aaactaatac agtgtccaag ggaaaggaaa agtcacatgt  107100
ctctcacttt aaattaatta agcttagtga ggaaggcatg ttgaaagcca atataggcta  107160
aaagctaggc ctcttgcacc aaagagttat ccaagttgtg aatgcaaagg aaaagttatt  107220
gaaggaaatt aaaagtctac tccagtgaat acataagtta ttaaaaaaaa aaaagtgaca  107280
cagccttagt gctgatatgg agaaagtttg agtggtctgg atagaaaatc aaaccagcca  107340
caacattttc ttaagccaaa gcctaatcca gagcaaggcc ctgactctct tcagttttat  107400
gtaagctgag agagaaagct acagaagaaa tgttggaagc tagcagaggt tggaaattta  107460
agaagccatc tgtgtaataa cataaaagta caagatgaac cagcaggtgc taatttagaa  107520
ggtgcagaaa gttatccaga agatatagct aagatcagtg atgaagatta ctaaacaaca  107580
gattttcagt atagataaaa tagccttcta ttggaagaat acgtcaatag aagatctaag  107640
actttcatag ttagaaagaa aaagtcaatg ctgggcttta agacttcaaa acttcaaagg  107700
gaaggctgat ccttttttta tgagttgatg aagttggtga ctttaagttg aagccattct  107760
ccccagcctt gctagagaaa ccaaaagtca aattcaggaa atacagagaa ccctgcaag  107820
attctacaca agaagatcat accccagaca cataatcatc agattttcca aggtcaaaat  107880
aaaagaaaga atgttaaaat cagctagaga gcaagggcag gtcacctaca aaaggaaccc  107940
catcgggcca acaacagacc tctcagctaa aaccctataa gccagaagag attggggggc  108000
tatattcaac attcttaaag aaacaaatct tcaaccaaga atttcatatc cagctgaact  108060
aagtttccta tgtgaaggag aaagaagatt cagagaagca aatgttgtgg gagtttgtta  108120
gtaccagacc tcccttataa gagatcttga aaggagcact aaatatagaa aggaaagaca  108180
gctaccatct aatactaaaa cacacttaaa tacacagacc agtgacacta taaagcaacc  108240
acaaaagcaa gccagcataa ccagctaaca acacaatgac actatcaagt tcacacatat  108300
caatactaac cctgaatgta aatgggctaa atgcctcact taaaaggcac agagtggcaa  108360
gctggataaa aaagaaagac ccaatggtat cctgtcttca atagacccat ctcacatagc  108420
ctcaaaataa aggggtggag gaaaatctac caggcaaatg gaaaacagga aaagcaggg  108480
gttgcaatcc taatttcaga caaacagact ttaaaccaac aaagatcaaa aaagacaaag  108540
aagggcatta cataatggta aacggttcaa ttcaacaaga agacctaact accctaaatg  108600
tatatgtacc caacacaaga gcactgtatt cataaggcaa ggtcttagat acctacaaag  108660
agacatagac tccctcacaa tattagtggg agacttcaac actccactga cagtattaga  108720
```

```
tcatcaaggc agaaaattaa caaagacatt taggacctga actcaacatt ggactaaatg   108780
gatctgatag acctttacag aactctccac ctaaaaataa caaatatac attcttctca    108840 tcaccacgtg gcacatactc taagattgat cacataattg gaaacaaaac aatcctcagc   108900
aaatgcaaaa gagctgaaat catacaattt caaaaatcag agggccctta agaattatgc   108960
taaatctact ctgtctatac tctataaatg gaacacaata catgtgtaat agtacacctg   109020
tttacagtat ggcttgctga atattttaag gccacagttg agacctcctg cacagaaaaa   109080
aaagattttt ttctaaatat tagtcctcat tgagaaagca cccagtgacc aaagggctct   109140
gatggagatg tacaaggagg ttaatgtagt tttcgtgcct gttaacacaa tgtccattct   109200
gcagcctatg tatcaaggag taattttggc ctttaagtct tattatttaa gaaatacatc   109260
ttgtaaggct atagttgcca tagatagtca ttcttctgat ggatctaaga aaaatacatt   109320
aaaaacctta tggaaaggat ttaccatcct agataccatt aaaaacattt atgattcata   109380
ggaggaggtc aaaatatcaa ccttaacagc agtttagaag aagttgattc caattctcat   109440
agattacttt gaattgattc aagacttcag tggagaaagc cgctgcaagt gtagtggaaa   109500
tagcaagaaa acttgaatta gaagtggagc ctgaagatgt gactgaattg ctacagtctc   109560
atgataaaac ttgaacagat gaggaatcac ttcttatgga tgaacaaaaa aatagtttct   109620
tgagatggaa tctactcctg gtgaagatgc catgaacact gttgaaatgg caaagatttt   109680
agaatatgac ataaacttag ttgataaagc agcagccaga tttgagaaga ttgactccaa   109740
ttttaaaaga agttctgtgg gtaaaatgct gtcaaggagt atcacatgct acacagaaat   109800
cttttatgaa aggaagaatc aatcagtgtg tcaaacttta ctgttgcctt attttaagaa   109860
attatcacag ccaccccaga cttcagcaac caccaccatg atcactcaga aggtgtcaac   109920
attgagacaa gactctccac cggcaaaaag attatgactc actaaaggct cagatgatga   109980
ttagcatttt tagcaataaa gtatttttaa attaaagtat atacattgtg ctctttttag   110040
acataatgct cttgcacact tactagacta caacagatta tacacgtaac tttttttttt   110100
ttttttgaga cagagtcttg ctctgtagcc cagtctggtg tgcagtggtg caatcttggc   110160
tcactgcaag ctctgcctcc cgggttcacg ccattctcct gcctcagcct cccgagtagc   110220
tggaactaca ggtgcccacc acaatgccca gctaattttt tgtattttca gtagaaacgg   110280
ggtttcacca tattagccag gatggtcttc atctcctgac cacgtgatcc accctcctca   110340
gcatcccaaa gtgctggtat tacaggtgtg agccaccgcg cctggccaga cataactttt   110400
atatacagta ggaaaccaaa aaattgtgtg gcttgcttta ttgagatatt tgcttcattg   110460
cagtggtccg gaactgaact gcagtatctt caaggtatgt ctgtattcaa gtttatattt   110520
tgacatacat tcttctttac ttgttaaaat catggtcacc tcattattat atgactgatc   110580
agaatttgca gggttgcttt gaccatatac cattgttcta caactacgca gatgtctgag   110640
tcctaaaggt gaatctgtct ggccagttct gggtttaacg gcctatataa aaagtagatg   110700
ttacacacct tgtataactg aagcgcccta tcacggacac agcttaactc ttgggtgggt   110760
cacttagtct gcttggttga ggtttcagtg cttttcacat ctacagaaat gtcctatttg   110820
tctaaggcaa tttatgaag taaatttact cttgtcatcc tttccaacct gaaaatagag   110880
gatatataat ttttagcatt ccattattac ctaggggatg gtcttcagtc attcttccct   110940
gaatttatta cactgccct atcttcttca cctgaaataa gttaaatgta gaattagcac   111000
taaagagaaa tagaatgaac ttcttccgga atgggaatag gaaatgaaag agagtaaatc   111060
agaagtgaat cacttctttt tttttttttt tttttttttt gctttgcaaa tctatatttt   111120
```

```
tttccagctt tatttaggta tgatcagcaa ataaaagttg tatatattca aggtgtatga   111180
catgatgatt tgatatatgt gtacatttta taatgatcac catgatcaaa ttaattaaca   111240
catccttcac cacacagtta ccatttgtgt gtgtgtgtgc aagaggaggt aagggagttt   111300
aatcattttt gaacactagc tacaacataa ttcaattaaa attctgagaa agaagaaaaa   111360
ttgtcatgca gctgtttaat tttagaagca ttaactgaca aaatccaagt cttatgatga   111420
atactcagtc aaattttcat gaatgaatgg gagcctttac ctctgaaatt gttgtcatgg   111480
aagaaaacac taacactgtc ttacacagta attcaagtta ccaattgagt taaagtagca   111540
agatgagcca tggttgtaat tgagaatggc aactatggtg ttcttatcta atctgctacc   111600
tagtttgcct ttttgctcta aaatggtgac tatgttagaa ttcaaagaat aaaaggcctt   111660
tatcctttca ggggaaatac aagtaacaag cttaattttt ttttcttaa cactgatgaa    111720 actcatttgg ggctgtggaa attgctgcta gcattgaacc tcttattaac attcaaggtg   111780
tgccagtttt gcacaagctg tgtcatattc agagatagat tgttggcaca aactaaggca   111840
cttattctct tgtttttca cttctttcaa taagaacaga taaatatact atttctagat    111900
aagcagttga aactgttctg ctcatctctt tggaataggt ttgtgggggt atcactgtat   111960
gacatgccga agaaatatac aagggaaatg ctcccgcata cattgagata taaatgaatg   112020 cctatttag aatacgtcat ttcttaaaag taaaataagt tttggctggg cgcagtggct    112080
cacgcctgta atcccagcac tttggaggcc aaggtgggtg gatcacctga ggtcaagagt   112140
tcaagactag cctcgccaaa acagtgaaac cccatctcta ctaaaaatac aaaaattagc   112200
cagacatggt ggtgtgcgcc tgtaatccca gctactcaga ggatgaggca ggagaattgc   112260
ttgaacccag gtgatggagg ttgcagtgag ctgagatagc accattgcac tccagcctgg   112320
gcaacagagt gagagtccat ctccaaaaaa aaaaccaaaa agtaaaataa gtttttaaag   112380
tcactgattc tgttctaag gaattctcag ctggggcttc tgagtcaatt ctcgatggtt    112440
agaacttatg agtagcagaa aaagaaaact actatggatt ttctctacaa tgatttgaga   112500
cagtgaatgg ggcttctgg caggttagca gttaggaact cagatgacca tagactttt     112560 tttttttaga gtgggtctcg gtctcactct atcacccaag ctggagtgcc gtggtgtaat   112620
catagctccc tgaagcctcg acctgggctc aagcaatcca cagatttttg aagttcaccc   112680
tggattgttg tgttctacac agaggttcca ccttttgctg cctttatgg ttactatatt    112740 attattttga tgtttcttaa ccagctgaat cacattgtag tatatgaaat atgttttggc   112800
tcttgtttta atggttattt gctagcagat ttcacaatgg cccaatgaaa caacccattc   112860
attgctattt gttgcaattc atggtgacta acatgactc catggtacgg ctcaccaaag    112920
tcttggttta tgtgtgactt ccaggggaga gagattgaga accatctgtt aatcattttg   112980
tccctaaact agagttttttc aatggagtac ttgggcagtt gaattagtat gtttctcgta   113040
ggctagtgag aaaaatagct tttttttttt tggcattaa tcagactgct gacccacatc     113100
tctgggaata cttgtgacaa gatccagcct gacaatatca catatgattt gcttttcttc   113160
ttggaaggga cacattgtgg cttttctctg gaatctgtga agaaaatgct cctgagccta   113220
gaaactggaa ctgagaaagc tcttcctgat catataacaa taagtcttgt gagggtcaac   113280
ccttgagcca tgagggcagc ttgaaggaac atggggttga gagtcaagtc atcagaactt   113340
ctgtttattt ttctgtgtaa tatttaggga cttgttatgt ttaactctag gcaaaggtat   113400
agatttggag gtctttgata tagatgatag atagatagat agatagatag atgaaatata   113460
```

```
ttttagcata caaaggaggc tacaatacac actcatgtac ctgtcactcc aatgaattca    113520
tcaaatgtaa acattttccc caaatctgct tcttagctgt tattcgtaaa gaaacaaatt    113580
gtacagaaaa atttgaaggc ccccgtttta ccttccccag tctcattatt ttctctgcca    113640
ccccagagaa aacaactgtc ttgcataggt atttatataa ttctgtttta tactttgcca    113700
cttttactac atatatgaag catgcttgtt acatacatga acataaaata tacatgtttt    113760
actgtaagtg tggaatgtat tctagaattt gctacttttta ctacaaatat tttattttca    113820
gaatttaccc ttgttattat ataaccctag ttcatttttt aattgccata tattactcca    113880
tcttatgaaa ataccacaat ttatttattc ccatactaat cagaatttga attgatacaa    113940 ttttttaatta aaattaataa tgctgaaaga aatgttcttt ttatacattt ccctcagggt    114000
gcatgtgata gagttcttct cacatatata tcagtgtact tgctgtgtct taggatatgt    114060
acaattgcat gtctattaga tatgccaaat tgctctgcaa agtactcata ccagtttcca    114120
ctcctaccag caatgaatga gaactttgtt tcgcaggtca ttgccaacac ttgattatta    114180
tcagatttaa ttatttgcca gttgatggat gtgaattgct ctatcactgt tttaatattc    114240
attactttga ttatttataa cattaggtat acttttcata gggccattta aatttcctct    114300
catctgaatt gcctatttct cctcttcgtt gattcttcta ttatcttttc ttctcttttat    114360 taatttatag aaatgtatgt gtgatcctaa tatgtgtcat aatatctatg ttcatatttc    114420
atatataaat ataatgaaat acttgtctct gttatatata ggttgaaaag tttgctccct    114480
atctgctgat tgcattttaa ttttgttcat ggcatctttt aacacacgtg attttttaatt    114540 ttgatatagt taatattttt tattactcta gatttttgaga attgctcaag aaatgacttt    114600
attttgcata gtcatatgct ctaattttt taatctactt acaatagttt tatgttaaat    114660
atgtcaacct ttgtttcacc cggaattttt tatatgtatg gtataaagca taatcaatt    114720 tttttttacta ttgagaatgc ttttattata ttatatctta ttctattcta ttttttatttt    114780 tccataagtt attggggtac aggtggtatt tggttacttt agtggtgatt tgtgagattc    114840
tagtgcaccc atcacccaag cagtatacac tgcaccatat ttgtttttctt ttatccctca    114900 tccccctccc acccttcccc caaagtcccc aaattccatt gtatcattct tatgcctttg    114960
catcctcata gcttagcccc cacatatcag tgagaacata tcatgtttgg ttttccattc    115020
ctgagttact tcacttagaa taatagtctc cagtctcatc caagtcactg ccattaattc    115080
attcctttct atggttgagt agtattccat catatatata tagtatatgt atgtatatat    115140
atgtacgtat gtatatatgt atatatgtaa gtatatatgt acgtatgtat atatgtatgt    115200
atatatatgt acatatgtat atatgtatgt atatatatgt acatatgtat atatgtatgt    115260
atatatgtac atgtgtatat atgtatatat gtatatatgt acatgtgtat atgtgtatat    115320
atgtatatat gtacatgtgt atatgtgtat atgtatatat atgtacatgt gtatatgtgt    115380
atatatgtat gtatatatgt acatgtgtat atgtgtatat atgtatgtat atatgtacat    115440
gtgtatatgt gtatatatgt atgtatatat gtacatgtgt atatgtgtat atatgtatgt    115500
atatatgtac atgtgtatat gtgtatatat gtatgtatat atgtacatat gtatatgtgt    115560
atatatgtat gtatatatgt acatatgtat atgtgtatat atgtatgtat atatactata    115620
gtttctttat ccactcgttg attgatgagc atttgggttg gttccatgat ttttcaattg    115680
caaattgtgc tgctataaat gtgtgcaagt atctttttct tataatgact tctttcctct    115740
gggtagatac ccagtagtga gattgctgaa tcaaatcgta gttctacttt tagttctttta    115800 aggaatctcc acgctctttt ccatagtggc tgtactagtt tacattccca ccagcagtgt    115860
```

```
agaagtgttc cctgatcacc gcattcatgc caacatctac tgttttatta ttatttttt   115920 tattatggcc atccttgcag gagcaacatg gtatcacatt gtggttttga ttgcatttcc   115980
cttatcatta gtgatattga gcatttttc acatatttct tggccatttg tatatcttct   116040
tttgagaatt gccttagccc actttttgat gagattgctt gttttttat tttcttattg    116100 atttgtttga gtttgttata gattccagat attagtcctt tttcagacgt atagattgtg   116160 aagattttc tcctactctg tgggttgccc atttactctg ctgactgttc cttttgctgt    116220
ccaaaagctc tttagtttaa gtcccaacta tttatctttt gtttttattt catttgcttt   116280
tgcgttcttg gtcatgaaat ccttgcctaa gccaatgtct agaagagttt ttccaatgtt   116340
atcttctagt attttatag tttcacgttt tagatttaag tccttaatcc atcctgagta    116400
gattttttgt atgaggtaag agatgaggat ccagttttat tctcgtatat gtgactagcc   116460
aattatccaa gcaccatttg ttgaaaaggt gtcctttccc cactttatgt ttttgtttgc   116520
tttgtctaaa atcagttagc tgtaatattt ggatttattt ctgggttcaa tattctgttc   116580
cattggtcta tgtgcctatt ttcataccaa taccatgctg ttttggtgac tatggcctta   116640
gagtatagtt tgaaatcagg cagtgtgatt cctccagatt tgttcttttt ccttatttct   116700
tgctttggat atgcaggctc ttttttggtt ccataagaat tttagaattg ttttttctaa   116760
ttctgtgaag aatgatggtg gtattttgaa ggagaaggtt ttgaatttgt aggttgcttt   116820
tggcagtgtg atcgttttca caatattgat tctacctatc catgagcatg ggatgtgttt   116880
ccatttgttt ggtcatctac gatttctttc agcagtgttt tgtagttttc cttgtcaagg   116940
tctttcaact cttttgttaa gtatattcct aagtatttta ttttttattt ttttggcagc   117000
aattgtaaaa ggggttgagt tcttgatttg attctctgct tggtcgctgc tggtgtatag   117060
aagagctact gatttgtgta cattaatctt gtatctggac atgttgctga attcttttat   117120
cagttctggg aactttctgg aggattcttc agggttttca agttaaatga tcatatcatc   117180
agcagacagt gacagtttga cttccttttt accaatttgg atgctcttta tttctttctc   117240
tcatctgatt gctctggcta ggactcccag tactatgttg aagaggagtg gcgagagtgg   117300
gcatccttgt cctgtcccag tttccagagg gaatgctttc aacttttccc cattcagtat   117360
tatgttggtt gtgggtttgt cataaatggc ttttattaca ttgaggtatg ccccttgtat   117420
gccaattttg ctgagagttt taatctgaaa gggatgctgg attttgtcaa atgcttttc    117480 tgcatctttt gagatgatca tgtgattttt gtttttaatt ctgtttatgt ggtgtatcac   117540
atttattgac ttgcatatgt taaaccatct ctgtgcccct ggtatgaaac ccacttggtc   117600
atggtggatt atcttttga tatgttgtca gattcagtta gctagtattt tgttaaagag    117660
tttagcatct atgtttatca aggatatcgg tctgtagttt tctttttgg ttatgtcctt    117720 tcctggtttt ggtattaggg tgatgctggc ttcatagaat ggattaggga gggttccctc   117780
tttctctatc ttgtggaata gcatcaaaag gattggtatc aattcttctt tgaatgtctg   117840
gtcaaattct gctgtgaatc catctggtcc tgggcttttt gtcggtaagc ctttaattac   117900
catttccatc tcactgcttg ctattggtct gttcaggtta tctaattttt cctgatttaa   117960
gctaggagag ttgtattttt ctaggaattt atccatctct tctaggtttt ctagtttacg   118020
tgcacaaagg tgttcatagt actcttgaat gatctttat atttcagtgg tgtcagttgt    118080
agtatccccc attttgtttc ttaatgaggt tatttggatt ttctctcttc tattcttggt   118140
taatcttact aatggtctat tgatttatt tatcttttaa ataaccagc ttttgtttt     118200
```

```
atttatcatt tgtattttt cttttaattt tatttagttc ttctctgttc ttggttatgt    118260
cctctcttct cctcggtttg ggtttggttt gtccttgttt ctctagttcc ttgaggtttg   118320
accttagaaa gtcactttgt gttctttcag tcttttgac ataggtgtta gggctatgaa    118380
ctttcctctt agcactgcct ttgctgtatc ccaaaggttt tgataggttg tgtctttact   118440
gttgttcagt tcaaagaatt ttttaacttc catcttgact tcatttttga cccaatactc   118500
attcaggagt aacttattta gtttctatgt atttgcatgg ttttgacggt tccttctgga   118560
gttgatttcc aggtttattc aatgtggtct gagagagtac ttgatataat ttcaattttc   118620
ttaaatttat tgaggcttat tttatggcct atcatatggt ctattcttgg agaaagttcc   118680
atgcactgtt gaatagaatg tgtattctgc agttgttgga tgaaatgttc tgtatatatt   118740
tgttaagtcc atttgctcca agtacagttt aaatccattg tttctttgtt gtcttttgt    118800
ctggatgacc tgtctagtgc tgtcagtgga atattgaagt ccccactatt attgtgttgc   118860
tgtttctctc atttcttagg tctattagta attgttttat aaatttggaa cctccagtgt   118920
taggcgcata tatgttaggg attgtgatat tttcctgttg cacaaggctt tttaccatta   118980
tatagtgtcc ctgtttgtct cttttaactg ctgttgcttc aaagtttgtt ttgtctgata   119040
caagaattgc taccctgct ggcttttggt gtccatttgc atgaaatgcc ttttccacc     119100
cctttacttt aagtttatgt gagttcttat gtgttaggtg agtctcctga aggcagcaga   119160
tacttggttg gtgagttctt atctattctg ctgttctgta tctttaagt ggagcattta    119220
gggcatttac attcaatgtc agtatgagat gtgtggtact gttgcattca tcatgctgtt   119280
tgctgcctgt gtaccttggt tttttgtttt tggtgttgg ttttaactt gtatttttgt     119340
ttataagtcc tatgtgattt aggctttaaa gaggttctgt tttaatgttt ccaggatttg   119400
tttcaagatt tagagctcct tttagcagct cttgtagtgc tggcttggca ggggccaatt   119460
ctctcagcat ttgttcgtct gaaaatgact gtatctttcc ttcatatatg atgcttagct   119520
tgctggatag aaaattttgg actaataatt gttttgtttg aggaggctga agataggggc   119580
ccaatcttat ctagcttgca gggtttctga tgagaaatct gctgctaatc tgatagattt   119640
tcctttatag gttacccagt gcttttgcct cacagctctt agaattcttt cttttgtctt   119700
aactttagat aacctggtaa caatgtgcct aggtgatgat ttctttgcga tgaatttccc   119760
aggtgttctt tgtgcttctt atatttagat atctaggtct ctagcaaggc tggggaagtt   119820
ttcctcaatt attccctcaa atatgttttc ccaaactttt agatttctct tcttcctcag   119880
gaacaccaat tattcttagg tttggtcgtt aacataatc ccagacttct tggaaccttt    119940
gttcatattt tcttattttt ttctttgtct ttgttgaatt gggttaattc aaagaccttg   120000
tcttcaagtt ctgcatttct ttcttctact tgttcaattt tattgctgag actttccaga   120060
gcgttttgca tttctataag cttgtccaat gtttcctgaa gttttgattt ttttctta     120120
tgctacctat ttccttaaat ttttctcctt tccctgcttg tatcatttcg ttgtatcaga   120180
tttccttgcg ttgggcttca cctttctcta gtgcctccct gattagctta ataactaacc   120240
tcctgaattc tttctcaggt aaatcagaga ttttttttctt ggtttggatc cattgctagt   120300
ggactagtat tacttttggg gggtgttaaa gagccttgct ttgtcatatt accagagttt   120360
gttttctggt tccttctcat ttggaagctc tgtcagaggg aaggtccagt gctgaaggct   120420
gttgttcaga ttcttttgtc ccttaatgta gtactctccc tatttcccta tggatgtggt   120480
ttcctgtgag ctgagctgaa gtgattgtta tctctcttct gggtctagcc acacaaccag   120540
tctacctggc tctgagctgg tactgagggt tgtctccaca gagtcctgtg atgtgaacca   120600
```

```
tctatgggtc tctcagccat ggataccagc acagtatttg gggtgtctcc tgcatcctgc   120660
aggagcagtc cacttccttc tgtgggtcct ctcgggattc ctgtttcatt cttgaagtct   120720
agatctattt tttgacagtc taatcctaac accatttact gaggaacact ctttttttca   120780
ttgttctgta atgcctcctc tgttgtaaat taagatccca taaatgcctt ggtatttgct   120840
agactttctt tttcttctgt tgttttaaaa ttttctctcc caacaagata aaatattgtg   120900
taaatattat atgtttatac taagcatttt tatcttgtac tgaataatag tgagaatgct   120960
tcaaaatttc actgttttg  ctattaagta tgatattaag tacgctatta agtactgtat   121020 aggttttgg  ctgacttatt tttgtcaggt taagaaaact gctctctatt tctagtttat    121080
taagacagtt tatcacaagt attagcctat aaataatggt ttttctgcac attcgaataa   121140
tcatttgatt cccacttta  aattattaat gctgtagatt atattgatag atctgcctga   121200
tattaaacta tccttgcatt cttgatctaa atcttacttg aatgggatgt gttactgtat   121260
tctctctctc tctctctctc tctctctctc tctctctgta tctctcttcc tctcttcatc   121320
tctcttctgc aacatcttaa agcatatttt ggtaaatttg cttttatag  ttattgattt    121380 tcagaaatat ttctttgaga agctaaaaat gcaaaggttt tatttcacct tgtttcaaat   121440
atagtaatta tctaggaata agaattgtcc attttctacc tattgagaat caaaacattc   121500
acagaacata aacctacttg tttcaaatat ggtagttatc taggaataag gattgtccat   121560
tttctacata ttgagaaaaa aacattcaaa gaacataagc ctaaaacctc tctttctttt   121620
gtttctaacc tacgggaagc ctgtcacttt tctaaaagtt atgatcaggc tgagcttcac   121680 tccccttcc  tgggctctct ggtagaatat gccctcccaa gtcctcccta gtgtgagtcc   121740
gcccctgtcc ccacccatcc cctctatcca ccaccgcccc cgctctcagg ctgccctgca   121800
gttgtttctt aatgcagcag aaggctgcaa caaccacaaa ctacattgcc catgatcaac   121860
ccatgcccat gtccttctgc accccccagt cagactaccc actcccacaa caaccaatat   121920
cagtgttccc atatttcatg cattatctat ccttctctca aataaagcag atctagcaca   121980
ttttaattat cctttgtgac agtctctagt attttccttg tttttttttt tttgtctaga   122040
atttactttc atcttctgat tcacaggaaa tttgttccat attgttttt  tacaagcaat    122100 atctagttga attacccacc atgttttact ttttcctca  ccattagttc attcacctaa   122160
taaattctta ttgcatgcct tgtgttttcc tgctattgta catgcctgga aatataggag   122220
tcaaccaaat cgtctctgag ctcatgtagt tgacaatcta gttagagaac agagatgata   122280
aacaagtaaa tatatcaa   aaataattgc catggagaaa aattaagtag tataaggatt   122340
attatttatc taggttgtca ggcaagagct tacagatggg tgacatttga atgcatactt   122400
gaaagaagtc tgggagaaaa gtatcccagg tagagggaat agcatatact atttgggatc   122460
ttcaaggaac atcaaagagg ccagtttgtt ggagcaggat gagcaagaag aacgtagtgg   122520
taaatggagg cagagatagt gggtgagagt ggggttggga aaaatcaga  taggactttc    122580 agaccactgt aaatacttgg tcatttactc taagtgagat aggataccat gacagtgtcc   122640
tggaaaaaaa aaagggacat gttcttattt tagtgagacc aatttgggtg ttgggaataa   122700
ggagattcaa aagcaaaagc aggtaggcca ttaagaaact gttataataa tccagataaa   122760
tgttggtgcc ttggttaagg gagataaaga tggagatggt aagaagtgat cgcattctgg   122820
atgtaatttg aaggcatgtc tgagaggatt agttgatgga gtgttactta tggggtatca   122880
gtgaaagaat agaggaaagg cctgagaatc tggaaagatg aagtgatat  ttactgaaat    122940
```

```
ggcctacact cttgaatgaa tagattagga agtaaaattg aaagtctggt tatgggtttt   123000
ataagtttga gacgcctata aaacattcaa agaaattatt aaatagtgaa ctggatatat   123060
gagcctgtag ttcaagaaag aggtctggat taaagttatg atttggacaa catcatcata   123120
tatgtggcat tagtgtcatg attccaaatg agataatcca gggaataact atagagaaaa   123180
gaggagagga ggataattc tggtgatatt tcaatgctaa gtggttggga aaatgaagag   123240
aacacagtga agttgaccag gatgaagtac ttactgaggt ggaagaatca atggagaagg   123300
gtgttcaaga tacaaaatta agacagtgtg tcagagaagt ggggagtgat ccattgtggc   123360
aagtgttatt cattggttaa ataagatgat taagaatttg ccacaatgtg aagtcattg   123420 gtgactagag caaaagctat tccattgatg tagtggagat taaagcctga tttcaataag   123480
tttaagaaat tgggcaagga ggaattaaag aaaggagaat aagacaattt cttcaagaag   123540
ttttgattta gaggggagca gagaaatggg tcagtaactt catgagcagt aactgaaata   123600
ggagaaatta tcctttttct aaaggagat aatttagtg cacacttaag gtgattctta   123660
tcttcctgca aaaatagctc ctttaggtat ttttcaaaat tttatacatg tatatttcta   123720
ttccaatcat ttttggggta caagtgattt ttggttacaa ggttgaattg tatggtggta   123780
gtgaagtctg agattttagt tcatccatca cccaagtaat gtacattgca cccaatatac   123840
accttttttt atccctcagc caccctacc ccctcctcag tctccagtgt ccattatatc   123900
actctgtatg cctttgcata cccatagctt acctcccact tacaagcaag aacttcatgg   123960
tatttggttt tccattcctg agttacttct tttagaatag tggcctccag ctccatccaa   124020
gttgctgcaa aagacattat ttccttcttt tttatggctg agtagtattc catggtgtgt   124080
atatatcaca ttttatttat ccactcattg tttgatgggc atttaagttg tttctacatc   124140
tttgcaattg tgagctgtgc tgtgataaac atacatgagc aggtatcttt ttgatataat   124200
gacttatttt ccttaggtc gattcccagt agtgagattg ctggattgaa tggtagatct   124260
acttttagtt ctttgaggaa tttccatatt gttttccatg gaggttgtac taattgacat   124320
cactaccagc agtgtataag taatcctttt tcactacctc tacaccagca tttattgttt   124380 gttttttggga ttttttttgtt tttgtctttt tataatggcc attctggcta ggaaaaggtg   124440
gcatatcatt atggttttaa tttgcatttc cctcctttag gtattattta atgagagtct   124500
tttggtggta aagtatctta gttttcatgt gtgctcacac acacatacac agagtcttta   124560
gtgacaggct agttgggtat caaattctga attgatgttt ttttctctaa tacttttaaa   124620
gtttatttgt gttctggcat ctgttgttac taaataaaaa tcttccacca gtccatttga   124680
gttcattagc aggtaatctg cctcttattt taagcacttt taaagatttt tctgtatctt   124740
gatgccatat gatagatcta cctttattta tactttactc agtaattact gtgggctttt   124800
aatctgcaaa ctcaatcaat tattcgattt tataaaatta tcagtaataa ccttttctat   124860
aactgattat ttgcagttga attaaatcct ctctttctgg aattccaatc atatgtgtgt   124920
tggagcttct caatctgccc tccaaggctc gtaactgctc ttttaaattt ttcagtacta   124980
ctctcaattt tttttttaaa aaacaacct aatattgcag tgtttggcac agaagaagtt   125040
caaagtacaa ctttgcactg ccacgttgac cagctattct ggcactggtt attctttaaa   125100 gttatttta aggttaacgt accttatcag gcagcaggtc tcaaaaccta gggaagctta   125160
aaagcctaaa ggcagcctgg caaaaatcaa gctgattaaa atgctctttc ccatttttctt   125220 gtcctcctat gccctcatcc ctaaagaata gtgagagggc cttccttaaa aagatatgta   125280
taaaatagca gaaagaaaaa ggggatccag caagcgtgag aagacatact tagataattc   125340
```

```
acagtaaatg ttccaaataa tattcagcct cactaattct caaataaatg taaaacaatg   125400
gcagatcatt tttatccatt aaattagtga aataggagg aaaagaacat tttgctgaca    125460
attgttaaca gtgaaactga aattctcttc ttgtctagtt tgaatctaaa ttaggacagt   125520
ttgaaagcaa ttgggtgata tctatgaaaa atctcataaa cattctaccc ttccatgtag   125580
caacattgct tctgtgaatc aaccattagg caaataaatg gaataacaa accaaatttc    125640 cccccacctc ccaagagatg tttattgtaa cattactgat aatattgaaa aactagaagc   125700
gatctatatc agtgatccac ccttgttttg actgtcactc accgtaagaa aatattaggt   125760
atacaaagta acccaacaga cacacccatg catcaaaaag ttccatataa ggaaaccgtt   125820
caatccattc catttattta aacaagccaa tgaacaaagc tggctttgat ccactaaatt   125880
gatcctacaa cctaagagta ggttatgact cagtttgaaa agcaccaatc tgaatgtcct   125940
ataaaagata tatgatggaa tatgaattaa atttgatatt cacaattttt tactttttt    126000 tgtttgaggg tagttggagg ggtactatgt ttcttcagcc agcaaggaag ataatgtttc   126060
tagataactc catataatgg agatttactg taatgatacc agatctgttc tactatgccc   126120
agccattctt atgtatctgt ctctcaatgc atcatgggtc ctttatggat tcttttgtga   126180
tgtcctcaag cttcctgtcc actccctagc aacttgccca aactgataga accggcctga   126240
atcagtcaac atctgatttc aagcattttc tcttggtcag cctttggtat taggacttta   126300
ttctcaatct aatcaattaa tattagctga gctaggttga tttcatttga atcaacaaag   126360
aattgctaaa agctgcattt cctagaaaat gtggcaatat aattggcagg tacttgagag   126420
tctttaatgt taaatggaaa aaaaataaaa aataataaga gacaactttt tatacggagc   126480
atgttttcgg ttttctttag atattttgtt agagacaaaa aaggaatcca gaatttattt   126540
tatactacat tagtacttaa cagatttcta cataagcaag tattatgcat ttgtaatcag   126600
aaaaaaatat caaaattagc tctgtggaaa atgatcatct tgcaagcaag catcatgtac   126660
ccctactttt gatttagctc atcttcttga tgtaaatatg aagtgtctgc gcttgaaatt   126720
ctgtttgaag tggaaatctt catgtttgtc ttacaaatac catctcagag tacattgctc   126780
agtataaaac ttgttttggg gggttgggta caaaaacctg caaagatata gtccaggctc   126840
cttttcccaa agtccttcac tttcctactc ttagtataac cattattttg taaaatttaa   126900
taaggcccct aataacttgg ggtttgggaa tttgatttga ggtaacatgc ctcagagtat   126960
cacctatttt ttattaaacc aacaaatttc tatctgacaa agatgtgcat ttatgtgggc   127020
cttaataatt cccccaaata aaactattcg taagttctaa cagttccaaa tacttttggt   127080
ttcagcacac taataggatt tatagctgtc ttagataagg agcagtatct tctaaagctc   127140
atgaaaaagc catatcagaa tgccatgtgt tcaggtatat ttccttttct ttatggtatc   127200
aagaataaaa tctcagctta tgttttcact caagtgttgt gtgattactt tttcccatta   127260
ctctttcgat tgagcctgaa aaatgaggtg aaaaaatctt tctctttcaa ggatgaacta   127320
gaaggatcta ggctggctgg tcaccaaacc actgactagt tggccctttg tcttttata    127380 acccctcatt gtctgggatc caacatcata gtgagtctca gacatgttcc acaagtctag   127440
atagccctca tccatgtgtt cagtggtcca gcccatcagc atccaagcca gcagggtgag   127500
gaggggaagt gtaggggatg ctcattgccc tgaaggatgc atatgccact tccattcagg   127560
tcctgcttgc cagaacatag tcatgtgacc acagttagct gcaaggttgg ctgagaaatg   127620
cctttcactg ggttctatta ctaactgaaa atgggaagag tgaaagttgg ggataactag   127680
```

```
taaatattag ttagtccaag tcatggattg tggtattaat tccatgtgct aggaaggtca    127740
tttaaatgtt ttatgcagaa ggatgccatg atgataatta tgtttcaaag catatttgtg    127800
tgtgagagag agagactgaa agagaaagtg agataaatgg attggagaga atttgtctga    127860
gtgttaagag gccattctca aacccaagtg ggaaatggtg gctagtaaca gtagtgagga    127920 taaagggggga tggaatggac tcaaaagata cagaagagat aacatcaaaa gatgaaacag    127980
gggcagagga ggaagaaaag acatccagat aactcctagg tttctgattt atactgcaaa    128040
ttctggggat caggtgttta tggaccactg agtttagttt tagaaacgtg atttagaggt    128100
atttgtcaga taggtggttt ctacacattc aaaataagat ttcaaaacat attagccaca    128160
attcacaatc agcaaaattc tcaaatctag tcattgtcaa ctaaactatt aaaatgaatt    128220 ttccctcta agtgtttctc atcttaaagg gtttgtatgt attacatgtc acagtatggt    128280
ttattgcata taaacatggg aaagcaagcc aggcagaagg agtcttgtaa ccagctaaag    128340
gcccagctaa ttcttgaagc agtcataaat catgaacggt cttcttgtgt aatagtgtg    128400 gacaggactg ttggtcacac acaggaaaat gagtcacaca gtcttgtgtg tacagcaact    128460
cactccacac tcaatgatgg gaatggtcat gattgttcta actgtgtgag cagctacaag    128520
aattatggca aagctccaga gctagaaagc tggtttttt tttatgtcac ccgagtatgt    128580
aattcactaa atgtttagta ttttatacct tttagttgac ttgtgagccc tttctaaagg    128640
agatctattt ccctctacta gaaggtaatc agaaaaaccc taaactacgt tttctaaatg    128700
ctgtgttctt ctgcccaatt gaccaaaata tacttagttg attaggactt tgaagggatg    128760
agatgagggg actaaattaa gatgcaggaa tttcagtttt ctaggggttt tctgtaaact    128820
actttatact gctgacaaat ggttaaatgt ttccaatgaa actaagtatg ctaggatttc    128880
taatgagcaa tgaaatttta gaattcattt actcattaat ttcttcattt acaagatgta    128940
caatgtgcta tcttctgggc atttggggta ctttaatgag gtagcagtga gtaccacaaa    129000
tggtcacttc tgcctttgtt cttatactcc ttagagaagg gaaaggacca gattcagata    129060
ccctatcact gctttctacc catccagatc agagcctttg ctgagttcta acgcttagcc    129120
ctcttctcag ctgatttggc tgcctccatt gtaataggcc tcatgagact ccagcctagg    129180
cctggccttc agttcagcag gcagagccca gagatgtact gggcaaaggt caggggattt    129240
attatatgag acaatggtct gatgtgattt aatttactcc tctggtacca gatatgtgtg    129300
tgtgtgcatg agagagagag attgagaatg actgatttgg gagggatttt gtgaaggttt    129360
atatatcaaa gcagaaagac caagaattta gagattaata catgccaagt ggtaaccaag    129420
aaacttctgt gggatcccac ctccaacccc tccctctctg tcagatttta accaaatcag    129480
tgtgatgtga tctgcttgca tatatgagtg aaagaaaaag gaaatttaaa aagttcttga    129540
tataaagcct ggaggaaaca atacgaaaat ccagcctcta tttcagcaat atctgccgga    129600
ctattggtta gtattccctt actgttactt attgtttgat taaaaggctg atagtcaggg    129660
tttttttttt cttacttttg catttttttag atataaatct ttaatatatg gctgtggcca    129720 gatgtttttcc tttctcctcc cacttcgttc ttccctcttc tgggttaatt tctcattgtt    129780
ctctcttccc cttacttctc tgccctttc ctttctactc taagcgaaac ttctttttt    129840 ctgtgctgga gtttataaag tattctttta ggcaaagaaa gcctttggct gccttcctcc    129900
ttgtctggtc accatcaaga tataattttg gttttcaaag gttgttctct gaaggaagga    129960
ctagttttct gagcatttag agagcagata catttttgaga aagtcaacag agatagtaat    130020
ttgcactcag gaaatactta agggttttaa ttctgttcca tgtgttacat ttcaacagtt    130080
```

```
tacattaaga aaagtattgt aaagagaagt gataccacaa ttgcatgttt attttgcatc    130140
tttagtctga gagatggtca gtactttgaa ggaaagagaa atagggcttt gtctccttct    130200
gcttcttgct atacctcttt tcagattaac tctgatgctt tgggtttctt actgcatgcc    130260
tgattaaaac ccatcccata atgcctgatg tgatgggaac caccacttat tctatctcaa    130320
tggaaagtat tcacatgagc tttcaacaga aggacattct cccacctctt ccaaacacct    130380
ctttgaaaac cgtgtccatg ggcctttatt catgtcttca acaatttgtt taaaactggt    130440
tgtgctaggt agtgggcaat ataaagatga gccacaggag agagatgaca atatcactga    130500
ttccttatag tgctgtaata agggtttatt aaggctgtga tagaagtaga gaggagaggc    130560
acctgacttc acttgggagt ggggttgttg ctaaggtgtt tctaagttga aatgtccttg    130620
agctgaggtt taggggaatg agtagcaaag atggattaag tgagaagagt ataggaggca    130680
gcagggccag aggtgtgaat agcccagaac cttctgagaa gattcctttg tggacggaag    130740
aaaggggagg tttgtggaaa tggtggaaga taaggtagga agaggccaca tcagatcaca    130800
catggctgga tgtacctctc taaaagtact gggggttttg aaacagaggc tataaattgg    130860
cagtttaaga aaatcactgt ggtgtcagtg tgaagaatac attttttgcaa gattctaacg    130920
aggattattt tcagaaattt aggcccaatt tagtccagat gtcagggcta gtttggagta    130980
aatttctttc tttaattact ccagggctct tgtattgctt caaagaaagt agaaagtgga    131040
actcaccctc attcagggag ggtgggcaag cgaccagcca gctggggaag gccaaagagc    131100
caggtcacct tgtgcccgca cttgttatga tttgtttgta ttgtctgcct gatgatcaat    131160
gatattagct atgacagcac gtatgagcct ggggtaagtg tgtcttcttg ctacttgaag    131220
tgcttcttga aaatagtggc aggctgaaga caacaaggaa tactgaaaaa gcccattgga    131280
ctggggacag gagacctggt gctgctccca gcttggccgg caccagctcc gggggcttag    131340
acacattact tcacctctct gggcttaact taccccattt gtaaaatgca acctttagac    131400
taacactgtt ctcggggcca tgttcagcct ctggcttctg tcattgtgat cctgcctccc    131460
caaggttccc ctgggcccca tcactactaa ccctaggctt ctagacattc tgattcatag    131520
agaaatagga aagcccattt atcttaagtt aatgtcagcc agaagtacag ttgtgtctta    131580
aggaatctaa tctagtgaac atggaaaata attttctaag gaaaaaaatt gtgattggtg    131640
ttctgtcctg aactgatggc aaaagggaag cagaaccact tcacacatct caatctctct    131700
gttttttcct ttttatcctc ttgaattttt ctgcctgttt gtctttcaaa agtagagagg    131760
agtttgaatg gggatgctga ggagactgag ggtagccacc gatgggggaa gctggactgt    131820
gggaagccga gttctgccac ctgacaaagg ggcacgtgtt tagtgtttat ttggcatagc    131880
agctgttcag gtggagccca ggcagaattt tgatgtcgtt gggaccttcc atacctttct    131940
gaaattctct tgcaccaaca cccggcaccc tcaggttatg ttctgctgcc caaagcctga    132000
ggctcaactt ctagccctct cttttctctt ttaccggaac taacttctaa aaatccagaa    132060
atgacaagta gatggtggtc tggatgttcc tgaggtggaa agagaacctc tagtgcctct    132120
ggctgacatt atatccactg acagatcccc tcccgcacgc atacatgtca catgtttctg    132180
ctcatttatc aaatacagcc catgctttgg tgattgagag cagagtgggg attataagtt    132240
gatgcagtag gcctgtgtct tgcccttaga agtttacaaa cagcaacaca ggcaccaaga    132300
gctcatctgt tacacccaca gggatttatc atccttgtgac ttggatattg tggaatgttt    132360
tatagtaaag gttaaaaaaa aacaatgtag gcacagagga gttaacagct aagttgcggt    132420
```

```
ggggagtctg gaaggcttca tggacgtggt gatatttgaa cgtgactttg aagggtaggt    132480
agagtcctga tttgtctaac agtagccttg aaagtaaagg aaacttgacc atgaagaagg    132540
ctgttgaaag tctggagaaa agagaaggta ggagactaag actctaggag aaggtactac    132600
gttccaggga gaatgcagag gtagaatcct ccctcatggt gacaagttaa atgtgagaag    132660
ggatggagta accaactggg tgaaccctga tctcattaag caaaataaga aatagaagaa    132720
atgaatctgc atgctcataa tgtagggatc agaagcaggt aggaaatgct gactttattt    132780
tagacagagg ttattttagg tacctgtgga catccaggtg tattatttcc ctatgtctga    132840
agcacatgtc ctttggttct ttagcatttt gatgatgatg ctccatgtaa actgccccct    132900
aggattttct ataagttttc ttcctcattt gagagtaaag ttttaactgg taacatgatc    132960
acaagtggtt gaaagttaaa atgttattc atatagcttt ccaatgaggg gagcatgaat    133020
ggtttggtac tgttttacaa gatgtgaaaa ctgatttcac ttaagtagac tgtaacataa    133080
agtttatgtg tctgtccctt tggcttcctg gtaggtggac agtctctctg aatcaatagt    133140
ggctcaggct tctgatttca aacctctttg gccagccaac tggttagga gaaacatggc    133200 caggtcattg aattataatt tcctgagtta tgttgtggtg gtcccgtagg acagtaaaca    133260
taagcctcct gggaactgaa cttttaattc aggaggactg aaaacaagct cttctgagcc    133320
aagatttgca aggacatgtt acaaagatag actggccttc ctgcttccac accatttttt    133380
cctccataaa tacatgctcc ttttccgtat ttttcttcta ccctagtctg ttgtagattt    133440
tgaccttggc tgttactttc ctaccaacac attgcctatt tttaagtttc ctggtttgac    133500
ctgatgttaa gatggaaagc aaagctagca aactgatgga gatagggcct tccagccttt    133560
ctaactttcc ctgggatcat cttatgttga tttacatgtt caaaaatt ttaaaaataa    133620 ataaattgta tcagttgatc cagaagtgat tagactctag gggcctgatt tatcttagcc    133680
aaacttaaga gatgagccaa tacaccaaaa tgccaatata tttgtttgtt ctctatggca    133740
ctgtcaagca atttcatttc atctgattac tgtgttcatt ttcctgaaag atagtgaacc    133800
cagaaaacaa gaatcagaag gtcatttgac aactgtggag ttggaataga gggaactgaa    133860
tgaccctcta ttgggtcatg agggagagca tcatcaagct ttgagaaatt attgcacctg    133920
tctctgtgtt gggacatttt tttggtccca ggtagttgga agagacaaag ctgtaaatta    133980
tttactagtt tttcaacatt tccttatcac ttatcgttaa ctgatggaac taagttttct    134040
ctaaagtccc ttatgaataa aattgctaga cattgcaaaa atgcccctct caatattgac    134100
atgcttcagt ggtgattatc ttcctgatta atgtttacag tcaatctcaa gctctataat    134160
ggactcttaa aggctgtagt agttttctat tgcttccata acatattacc acaaacttag    134220
tggcttaaac aatacccatt tattgtccca cagttccata tgtgagaagt ctgggcacac    134280
catggcccaa ctgggctctt gcttagagtt tgcaaggcag aaatcagtgt tgttagggcc    134340
tctagggatg aattttcctc caagctcatt ccagttgttt tcatgaactg agttccttgt    134400
cattgttgga ccatgttccc catttccttg ctggctgtca gctgggagcc agttttgct    134460 cctagaggct atctgcattg catctcatgg tttctgtgtg ccccttcca gcaacaagat    134520 tctatgtacc cccttccagc aacaatattc tatgtaccct cttccagcaa cagaagatca    134580
agtccttttc aagtttctag tctctctgac ttccccttct gccatatctc attctgcttt    134640
tacaggctca ggtgattaca tcggtttgtg cagataatcc aagataatct ccctgtttta    134700
aagccagtgg gttagccatc ttaattacat ctgcaaaatt ccttcacagc agtacctaga    134760
ttagtgtttg aataacccag gatggtaatc ttgcggggga tcttttagca ttccatctac    134820
```

```
ccagtctcat cagcaacact ttgaaatatt gtcgttgagt gatcatttct gtggccggct    134880
gatttcatct atacaagtgt attcttttta tttgccattt tataggataa tattttctga    134940
tcttaattcc atatttcagt attaaaatta cttgacatag atccataaat catcatctgt    135000
tgcaaaaaag cacattaatt gattggttga atggggagat tgagatattt cttttctctt    135060
cttctgctca ggtgggggca acttttgggg gcagatgagt tctgttgcca caaaagttat    135120
atagcacatt tggtttgcac tgaatcagcg attctcaatc ctggccatgc tttagaatta    135180
tacaagaaaa atcttcaagt atcaatactc agtccctatc ctactgatcc aattcatcta    135240
tgataaagcc agagcattga ttttttaagtt ctgcaagtga ttctaatata cagccaaggc    135300
taagaactac tgatatgttc caaacactct attttggaga taaagaagtt gaggctgagg    135360
atgagaactt agtcacataa agttccataa ctagtaacag acagaagttc tgtcctacaa    135420
aaaaaaaaaa atttgatgct ttaattgtat gtagagttca gtgctcagta attatgtaca    135480
aagtgagtgt tgagacgatc tggaacaccc tacttcttgc tttagtagga agactatttc    135540
tttctactac tttaaaaaat tatcagatct tgcaaaataa ctgtatgaag gtctcttctc    135600
agcagctttg gcctgccttg tgagtaataa taaacacaga tctattctac actaactagg    135660
gagctggccg cttggacttc tactacctct ctgtgttcca gagcttcatg gtacaatgca    135720
gtagccacta gccacatgta gctattaaac acttgaaatg gaactagttt caactgagat    135780
gtatgtgagt gtaaaaggca tactagaatc aaagatccag tatgagaaaa aaggtgcaaa    135840
atatctcatt aatacttaca ttgattacat gatgaaataa tatttgaata tattgagtta    135900
aataagatac attattaaaa ttaatatatc aattttaac ttttttaatg cagttgctag      135960
agaatttaca actatgtatg tggttggcat ttgtggctca cattatattt ctgttagcac    136020
ttttctaggg agtattttct attaaagcta ttaacaatga atggtccaag tccaagctat    136080
tacacctcct ttgatcctga agagtgaagg ggtacactgt aaacttcctg gagatgagac    136140
atgatattga tctgccctgt gtttgccatc tatctggcag ccagtcagtc tggccaaata    136200
gacttctatt tttacataga agcttaaagg aggcaggata atgccccatg tcatggagag    136260
agcacactgc atagctcttg agtaatgtac ccaaaagtag accaggtgct attggaggtt    136320
ctaaggcata gcgataaata ttacatccct tgagcaatgt aatacagccc ttgaagaaac    136380
tgccatgtca gcacttatga attatcactg tctttgacag gccctatgca ctgaaaatat    136440
tatggtgtct acctctcttt ataattcaca tccaaatatt actctgtctt tttcttgctc    136500
cctgtagttt gttctgattc actgctaccc tgattgtgtg tttagtttgc ctagttcaca    136560
attgaagaag catgggaaag taaaggcagg ccttggaaag atcaagcaca gttcgaaacc    136620
ctacccagaa ttattctgtc tgtgtgagct tgggagattt acttaacctc tctgagctcc    136680
tctaaacttc cattttctca tttgtgaaat gagcctttct cttgcaaggt ctgtctgagg    136740
gttgaatgaa ataagaaggt acctggcaca cttatttttt gggtagatgt tgtagtgaac    136800
atctactctg tggcaagcct atggctaatt gttaggatgt aatcgtgagt gagacacagc    136860
tactgcttcc agctaagaga agagaaagac aaggagcctg gtaacgtcgg gacatgaata    136920
gccgtcaatg aaaggcagct attattacac tgcacagtgc aggatttggc ttataacaaa    136980
attttagaag ggtgttcagg tgagggaatt gagacccata gtgattaaat gactacctga    137040
gtcaccagct cggacaatgc tgggctgatg tcaggttacg ggattgctga ctcctcctct    137100
agtaatgcct ttcctgggag atcacattgc ctcactcttg gtttcccaac ttgtttacct    137160
```

```
tcaaagaata actttaccat gttggactcg ataaaaggaa agaggggttt cctccaattt 137220
ttgctccatt tgttattagg gcatgctagt aactaactgt cttttgaaaac ctacgcttct 137280 gttaactcca aagaaggcag gaatacatgc acttctttaa gatataaaaa gtatttagta 137340
tactataaat tattatagta atcattgtta gattatatct caccaagata atgaatgttt 137400
ttgtttgaag acttcactgt atgagaaatt gtctcctata ccttatttat ctccttttag 137460
attaggtaaa acaaaatttt caaatttgag tctgaagaaa attccaacat ctttaaattt 137520
gtttaaggaa cattttccat gatctatatg atctatcata gtaatttaaa aaatcagatt 137580
ttagaatgag ccacgtgtag aaagagaaaa aaagtagaaa gtcaataaga ggtttcattt 137640
ttcaaatttt gttttggaaa aaactacttg gtagggacaa tggtgtaaag taagatataa 137700
gaaggaatat actgttcaaa taagcggcca tgcaattgat tttctctttc atgtaacaat 137760
cacatctgca ttgtgaatcc gttagtgcac caagtgaatc aagcttagtg agttgacaaa 137820
catccacagg gatagttgcg gggaggcatt ataaagtgca atgtggtcct agtgaaacag 137880
aatgcttcgt tctttgagaa agttccactc tgaatagaat aacggtgcat accaatatcg 137940
gagtatggcc aagcatttgg ctactgacat gccccttctt ctttcactcc tccataaagg 138000
aagagacaga gactcaggtt cttgtaactc agttgccttt tttgagttct cccaagaaaa 138060
gttctaactt caagccaagc gtcttgtcac tgggatttct gtatctaatt tttagttcta 138120
gaaatccatg atttcacaaa acaaattatc caaacctaac gacaaccaca tagaactttc 138180
ttaaagtaga cgagggagga attagccccct aaagtatttc ctgcacaatt ggaactcact 138240
atagaagatg tacaattgcc tgtacaccca agcacaaata ggctgtatta ttgccttatc 138300
ctaggagata tacactttac attatgatgg tccttccctt tcctggacct tcatatgatg 138360
taagtgcttg atttaggaat agggtcttac atattgtggc tggcgaagag cacatttgct 138420
gattgctcta ccacatgcct agatgtcctc ttcatgatat ataaatgagg gtccctactc 138480
tcaatatacc ccataggaac ataataaaac ataaatagtc tatttgttac tactaccaag 138540
aagacttcag taagtgtaat aactaacccct tttggataca tgcagaggga atgccaaatg 138600
ctttaaataa attatctcat ctaatcctga ttttttttatt aaaaagggaa aatcttatca 138660
tatgaatatt agagatgagt aaactgaggt ttggtagagc tgggatttga acctagccct 138720
ctgtgactcc aaagcacatt cacttaaccc caagcccacc ctctctgtaa atgaagatta 138780
atgatagcat ctgtggtaga agctaatgtc tcctgacctg ggaaaatatc tttcaatgat 138840
tattaactaa atgtgatcag ctgccagtgg atcagatgtc atcaaataaa atcgagtgtc 138900
cagggtttac tcaacagtac tgtctcttac attttttatc aatgttagta gattgcttaa 138960
tctttgtacc tgttacctca catgaagcct agatagcatc agtcccttcc ccagccagtt 139020
tgtgctgggt tcagcttctg gcttgtgaat ccagtcagtg aattaatgtt ggtagcttaa 139080
aaacagccct gagagaggta tttacatcac agaaattggc aaatgataca aatcatgacc 139140
ctttttttaa attccaggga gacaggtgtt aaacatttac cagtacacca ctgtctatga 139200
ttcaaatcgg gacataataa ttgtatttct gaaggtaaac aaatgcacac tgagtaccct 139260
tggaaaaaag caaccttcca cagatacaat cacacctaag tcacctaagt ctttagtgaa 139320
ttttttgtcc ccatcattct gcatttggga ggacctttta caacataacc ataatgattt 139380
tatatgtcat ttgaaatttt aaaaaattac tttatttgtt catttttgtt atgaaagcaa 139440
atatgcccat agtaagcatt taatgttttt gaatgtaagt gcagacatat aaaccataaa 139500
atgtatatac gaatgctacc agtagaaata aaatgcaagc cacatatgta atttaaaatt 139560
```

```
ttcaactata gtcatgcacc acgtaatgac ttttcaatga tggactggtc ccataaaatt   139620
ataaaatcat gtttttatga catcttttct atgtttagat atgtctagat acataaatac   139680
ttaatattgt ggtaaaattg cttatactat tcaatagagc agtaacctgc tgcacaggtc   139740
tgtagcccag agcaataggc tatcccatat agcctaggtg tgtagtaggc tataccatct   139800
aggtttgtgt aaatacactc tgtggtgttc acagaaccat ggaattgcct aatgatgcat   139860
ttttcagaat gtattcctgt cattaagtga tgcatgactg taatcacatt taaaaaataa   139920
gaaatatttg ttttaataat ggattttatt taattcagca gttaaaaata tgatttcaac   139980
ttgtagtcaa cgtgaacatt atcaagatat tttgcatctt ttcttcttgt actaagcttt   140040
caattctgtg tatattttat acttatagca catatgaatt tagatgctaa attttaatca   140100
taaatacttg atctgcattt acatttcata aaatgtaaag cttaaaaagt gggttcatat   140160
atccaatctg ttatagactt acatatttaa ttaaattaaa tttaaattgt cattgaattc   140220
ctcaattgca ttagccacat tttaagtgct caatagccac atgtgactta ttgtaacata   140280
attggtcatt gcaggtacat accatatatc cttattttat aaaattggaa acctaggctg   140340
gatgtggtgg cttatggcta taatcccagc actttgggag gccgagacgg aaggatcagg   140400
tgaggccagg aattagagac cagcctgggc aacacaccaa gaccttgtgt ataaaataaa   140460
caaataaata aaaatagcta ggtgtgttgg cacatgccta tggtacaagc tatttgggag   140520
gctgacgaag gaggatccct tgagccaaag agttggagac tgcagtgagc tatgattatg   140580
ccactgcact cccaacctgg gtggcagagt gagacccatg tctcttcaaa agtaaaaat    140640 acaaataata taacaaataa ataaataaaa ttggaggcct actatatata caactcccaa   140700
aagtcttttc cccctcaca cgttacacat ttaaaattcc catcctgcat tccctgctgg    140760
atctccaaga ggagagaaat ctcagcaaaa gtagttatat caaaactgtc tgtgagcttt   140820
ttcttcctca ctcataggaa ggaaataaat tcacataagg cattttggat ctgaccattt   140880
tccaaattat catcaccata aaaagttggt aacaacatga actctgaaag caagctgttt   140940
caatgcatgc ctggtgctaa tgaaaaccag cagttttaaa tgccctttg ggttagcttc    141000 ttcctttttc tgtgctgtat tattagaaaa gcttcaccaa ggagatcaac tagatataat   141060
ttcacaatat ttcttagtaa tcaatgttgg catttactct tcccatatat taatttatta   141120
acatcatgct tctaaggatg ctttaatcac tttttaaaa aaaatacttg atacaaatta    141180
gagggtgtta gttattttag gtggtgattt gttttgtttc tgcaaaatta caaaccagat   141240
atgagcatat tattccctgt gtggcttaat aaactgtttt ttcttttttg agacagagtc   141300
tcgctctgtt gccaggctgg agtgcaaggg cataatctcg gctcactgca acctccgcct   141360
cctgggttca agcgattctc ctgcctcagt ctcccgatca gctgggacta caggtgtgcg   141420
ccaccacacc cagctaattt ttgtattttt ggtagagacg gggtttcacc atgttggcca   141480
ggatggtctc aatctcttga ccttgtgatc cacctgcctc ggcctcccaa aatgctggga   141540
ttacaggtgt aagccaccac gcctggccaa tacacttta atataatttt tgataaaggt    141600
gttatggaga cttgtcacca aatagtctag tcttcacatt aaattcacat gatactcctc   141660
atctctattt agctctctct cacctccagt aatgacctcc cttgtctctc agtctttggt   141720
ctcttacctt cagcttccca ctagccgttt ctcacatttc caaaagtctt gtaattgcct   141780
taaaacacca agtatccaaa gcagtcctat gaccttctcc tcctgctaac caactcagat   141840 cccccaaatcc tgatttcttt cactagcact atctctcatc cacacatact cagttatttg   141900
```

```
tgatagacat gtctctatca tctctcatat ccaatcatca ccaaatctta tcaatacttc    141960
tcagtgatat taagttaaga agtcatgaag ggcggctgta ccctaaggaa aacccacttt    142020
tgcacaaatc tgagtttctg atcaatctga gttcagaatg ctgttttaat ctggtcctac    142080
ctcgccaatc taattttagg ccctttatt cgtgaatttg aaccttgttc tctattcacc     142140
agcttcctca gaatattgtc caaaacatac tcagaattca tactcatatc cagaacattt    142200
gctctgagct tttaccatac aagttcacca cagtttctct ccctttcca tatccaccaa     142260
agccttatct gtcatttagt tttaatttta agcccttcag tttgatagct gattttccc     142320
tagtctgacc ttctatttc gggtatgctc cttctttca cagtttcatg tgtttgtact      142380
gccttattct tgaagaacca ttattttgat tgcttttgca ttaatctcca tagtgccttg    142440
ctcagtgtta gcaggaacta gtagtttaac aaatacttgc taattctaaa ttaaagagca    142500
tgaaacatat tgttttcttt gcctggagtt ggttatagca tgctggaaaa agtattatat    142560
ctaaccttca tcttttctca tgtgtttatg aactgtttta tagccaaaga ataagttagt    142620
atatcatggg cctaattatg taatttggag gcctcctctg ctgggcagtc tacagattta    142680
aaattcatgc cagctgcatt acgctggttt tgaacttgct ttttcttgag aaagatgggg    142740
agcagacaaa atgcctcagg ctttgagggt agaaatggtg tgagttccat tatgcaagaa    142800
tagaacccca ttttttaatc cctcctgctg aaaatcttgc catgaggcta tagccaaaga    142860
atgtgtaaat atcaaaagaa atttagagag ggattttccc taggaaaata ttgcaagctt    142920
aaaaaaccca gtgggctaag gtccaattta gtagattcct ccgaacaatg ccatcctcta    142980
cttagattgt tacagaactt cttatgacag catttgagta gactcctgta cctctgggtt    143040
aaaaggtaca tgtaataagt ttaggtacct gggcaaaaag ggcttggcag aggggaatag    143100
agggactttc ttattctcac atctagtata tcattacatt gtaatgttag ataacattaa    143160
agttccaaac ttcatgtgtc cgcactctga cgtttcctag ggacattttg tctcagctag    143220
aatctaatag agaaggattc cctcatctag aagcttccat atggggctct gtgaagatga    143280
tgtggacagt gtacaatcca attgaatgtc acgtctcgtg gcctggctca tgtgagggca    143340
ctagagagag ttctccagag gagtgcagat ggggctactt ttggaatcat tcccactgag    143400
ccaacatcag tggaagagaa ggggaggagt tagattctaa taaagcccett atcttctgct    143460
gaatccatcc acatttttt atcctcctcc tggccctgc acttagttag agtcgggtcc      143520
ctatgcagtg ttccaggcgg cagtgaactg cattcacctc ctgtttggga gcatggcaat    143580
tttaaatact ttttctgct gtaagagtat gcaaacagat ttctggttaa ttttgtgttg     143640
aggattcttg tttgttttt gttttgatag agcacattct atggacatat gttcagcttg     143700
taaaggaagt gttatagttc ctttttttt ttttttttt ttttttggaga tggagtcttg     143760
ctctgtcacc aggctggagt gcagtggcgc gatctcgact cacttcaacc tccacctccc    143820
tggttcaagc gattctcctg cctcagcctc ccgagtagct gggattacag gcatgcgctg    143880
ccatgcccag ctaattttg tattttagt agagacgggg tttcaccatg ttggccagga     143940
tggtctcaat ctcctgacct cacgatctgc ctgcctcggc ccccaaagt gctgggatta     144000
caggcatgag ccaccacgcc ccacctagtt ctttatttgg aagaagtgaa gttcatttgc    144060
aggcagctgc tttcaaaagt tgggggattg gaggaaggtc atcttctatt caactgaagc    144120
aaatgccact tgttttgtggc atctgccagg catccttgag atgtctgaag aggtgacttc    144180
caaaccagag gatgcagcct tccgagaaat gcaaacctgt tcacattctt gctcagatgg    144240
gaagcagaaa aggctgcgtg ggaattgggg atttactgtt atactctggc attggaatag    144300
```

```
caggtgctac tggaaacttc tttacctgac actaagtgtc ttgggagata acaagtaaaa    144360
ttaacacagc atccagttct tcagtgcttt ctccacttaa aaagaatcag gctgggcacg    144420
gtggctcata cctgtaatcc cagcactttg gaaggccaag gcgggtgggt cacttgaggt    144480
caggagtttg agacaagcct ggccaacatg gtgaaacccc gtctctacta aaaatacaaa    144540
aaaaattagc cgggcgcggt ggcgggcgcc tgtagtccca gctactcggg aggctgaggc    144600
aggagaatgg cgtgaacccg ggaagcggag cttgcagtga gccgagattg cgccactgca    144660
gtccgcagtc ccgcctgggc gacagagcga gactccgtct caaaaaaaaa aaaaaaaaa    144720 aaaaaaatac aaaaattagc tgggcatggt ggtgcacacc tatagtccca gctacttgga    144780
aggctcaagc aggagaatcg cttaaacctg ggaggcggaa gttgcagtga gctgagatcg    144840
tgccactgca ctccaggctg gcaacagag tgaaacaaaa aaagaaaaga gacagaatca    144900
aatgcaaagt aaatatttag ttaccaacag gatggcattt ttagcctata acttttttc    144960 agccttttaa tatatttctg ctggaggttt ccagctttga ttacatagcc tgttcaccta    145020
ggagtaaagg acattgggag ggagagatgc tcagtggttc tcatttgcaa agtagacgag    145080
gatgatgaaa ggccatcagc tcaaggcctt ccaggttagg aattaaaaac atgaatgttg    145140 taaaaccac aactcatatt tatttgaaat ctcacaaagt gtgagattta tttgaaatct    145200
cacaaagtgt gagatttatt tgaaatctca caaagtgtga gatttatttg aaatctcaca    145260
atgtgtgaga tttatttgaa atctcacaaa gtgtgagatt tatttgaaat ctcacaaagt    145320
gtgagattta tttgaaatct cacaaagtgt gagatttatt tgaaatctca caaagtgtga    145380
gatttatttg aaatctcaca atgtgtgaga tttatttgaa atctcacaat gtgtgagatt    145440
tatttgaaat ctcacaaagt gtgttcatct gcatgtttct cacgtgaaat ctcacaaagt    145500
gtgttcatct gcatgtttac actcaatcct atgaacgact ccatgaagta gtgtatgaag    145560
gagagttcct catgcatgtg gatttgcaca tggggattca gatacaagaa gacaatttag    145620
tttacataga gatgtgcttt tttaaagaaa tttttaagaa tacaaaatta tatggaacaa    145680
aaaagatagg tcctctgctg tctagaaatt aaagtacgtc aagaatttta tcctatgta    145740 gaattacaca gccattgccg ggggccacat ctgtaggccc atggaaaaaa acatctttgc    145800
tcattatttc agcctgatta gggataccat gaagggctat tccattaggt caggtttgca    145860
cagtaataaa aatgaagcca gtagaggatc tcgtggagct cctggtatga tgataagtct    145920
ctgagtaact tgtaaatagt gcaattttat ggaaatgttg cagctaagct ttaaagtagt    145980
tggcattagt tgtcagacac agcaacagct ctacaaaagg caatacgctg agttcatttt    146040
caaccagccc aaacttgcct cagaagatcc gggatgtgga caccctggta tatttttct    146100 agaaaagctt atttccttcc tccagataaa ggtgtatggt cactgaggtg ttgtgctgac    146160
agaagtgttg atctactctc tccgttagac tgaagggctc caggtgtggc cacactgggc    146220
ttctaaatgg ctagcaaagc cacagacgca tccctcttgg tgtctgaggt gttcacattc    146280
ctgggtcttt cagatctgta ttcctcatga aaataaaacc tctctacgac acactgtgtc    146340
cttgtgggtt tttagtttta ctagggagtt tttgtttcct tttgcttccc tccttctttc    146400
tgcttccctt ctagttaaac ctctttagga tggctcatta gcaactcgtt ttgagtggtt    146460
tgagctcttt tgttcactgg gaaacagatt tatgaaatgt tactattacc atgattgtta    146520
tgtttttcct tttatggcct gtccagctca aggcccatg ctttctgata ctgctgataa    146580
ggttttctat ttccagatca aattaaagca aaccttactg gccctgttac tgaagctgtg    146640
```

```
catgggggtc gtttgctgtg aggtgtttct atggctttga gccagggtat gaacatctct    146700
agtgttcatg ttatttcctg agactagcac tcacgggaag tagaatttat tacaacctgc    146760
tgtttgagtt catgaaaagt aggacaatat gagactctgg ggcagtgaaa gacttaccag    146820
gattccttct ggaactgact cgtcagctca ttcatgtctt acccagtctt taaacagtat    146880
ttcatgataa tggtctgctt ttaattgctg ggctttacct tacccttttt gtgattgcag    146940
gtcctacagg tatggatctc tggcagctgc tgttgacctt ggcactggca ggatcaagtg    147000 atgcttttc tggaagtgag ggtgagttct gcttttccat ttccaccctc agtgttttga     147060
aacaacactg aactgtattc gctacatcca agttttttgg atgattttat taaaagatgc    147120 aagtttaca tagcagcaaa aaggaaactt gacttagctt taaaatcaga aactagtagg     147180
acttttctgt ggatgtttag gaggaatgca gtagtcagtc aactttggca tctgatgttt    147240
tcatatcaaa aattaatact acaaatcatg ctgaggacat ttatgttgaa gacaagccag    147300
gtctcttgtt ctcaggcttt gggagagata ttgaaattac actgaagggt tattagctta    147360
ctgttcactc agctcatctg tgactaagga tatctaatct atttccagag ctcagaattc    147420
aggcttgtta atcatattct cagagaaaag aaattgcagg tttcaaatga atttcacttc    147480
tcactctctg ggtgattacc atttggctaa gttgaggaaa gagacacctg aaatagttga    147540
atgatatacc cagaaattat gagcttcctt ccccatctct ataattctcc ctcccttttt    147600
tatatccctc tccttgtaga gaagtctcaa tatgtttaaa ctatgtttca tagcagacct    147660
aactaaaaca aggaagagta atagaaggga aagggaagag gaactttttct gtcagaaaga   147720 aaactgtgct ctctaacggg tgggagactt ttttttttt aatgagtact tgatgttttt     147780
ccttgcctgg gcttctacag aagaaagaaa gaatatattt ctcccatgct atgacactga    147840
atttagttgt tgctttaaga gtgtcagact ccccttctca ccattcagct catgttggaa    147900
aacacagttt aacagcagac ttagcgcctt aagatgtcct ccctgacctt ctagccaaaa    147960
ataaatccgt agtagtgagc tgctgagggt gaccacagtc acttagaaaa tgagaagagt    148020
aaaatatgtt atttttatctc ttaaagcaat ttaaaaatat ttatagaaaa gagtcataat   148080
tgttggaaat attttttggt ctctctggcg ttataatgtc aacattatgc aagtcaaaca    148140
tggagagaat tgcaggctcc atttcagcag cttttcccat ggctggtttt agaccttggt    148200
tctgagccaa agaattgcag ctgagatcct ctgctgttcc aaagtcatgg tggcttaatc    148260
tctcgtttct tcattaaggt gactttcact ccactgggca agatttgagg aatttaaaaa    148320
acttgtgaaa tgaaaagtat ggcataggaa atctttaaag aaaattaaaa atgcatcccc    148380
agctgagaga ttagagctca aattacattt tagaactaga aagtctgcaa ggagcatctg    148440
tttcagctgc ttcgacattt tactaaaact ttgagttcct gagtgaagag aaaacatcac    148500
tagttgcttt taatgtttgc ttttttgttt tcttttttaat agttttgttt gattcattta    148560
tttgttcagg gagagcagaa tataagcaaa tgcaatagtt tatactaaac acaaatcaca    148620
tatcctacca gtacttacgc ataagaagta atttaacaaa gaagaacatt tttgtctctt    148680
ttttttttgt cttattgaac taaccaatat ttctttttcc tttggaatat gtgcatattc    148740
cagaatcctt tcttaaaatg gtctaaggat taaggatggg gcatgatgtt tatgtaagaa    148800
ggcatatgta agcacgttcc agtgtgtgtg tgcatgcttg gctctgtgtg tgtgtgtgtg    148860
tgtgtgtgtg tgtgtgtgtg tgtgtgtgtg ttctagttct ggccacttat ctaatgaatg    148920
ggttcatggg ttcagccaaa gttactgcat aacatgacat gggtcagtct cagataatat    148980
ttatggacca tgtgtttgtt tttctgccag gtctggattg tagccaaatc attttatttt    149040
```

```
tattgtgtct cctattgaat aaggcagact aaaaatatag attaaatttt taaaaagaaa 149100
agatactact attgaattca gtttgttcag tgaaagatgt ggcattgatg ggtaagtgat 149160
cttggaagca tcacctggag aaaagtcacc caggagctgg tagaagatga cagacctgta 149220
tgcgtaggga agggtagcac ttgagcaggg attttcttgc ttgggcagat gagcaattag 149280
aaatatactg gccctgaaag gattttttt tattaaatct aattgccctg tgggaaattt 149340
aatgagaact aaatttgaac agtgccgtta ttgtgttagc taaagtgttg taatagatgt 149400
tttctgtctc tcatccttaa tatgaagttc tcatccttaa tatgaagctc tatatctgct 149460
cctcaaagcc agttacatag tctagaggag aatttttat tccaaaatca ggaatgatcc 149520
acaatgcctt gttttcaaag ggcttcacat ggttgaccta tcaactgatt gtatcaaaat 149580
tgctgctgct ggaataatgt tgctaatgag aaatgtgcat aaagatctaa tggatataag 149640
tattcttcca aggagtgcct gttataaatt aggtcgtata tctctactat ttcaatcagt 149700
ctacccttga atatcccctt tgacctcagt aacctaaggt ggaagtaagc aagcccctgc 149760
cttgtagttc agtctagctg ggacatgagg aatgtcttga aattaatgag agcctgtata 149820
cctttaaagt ctagattgtg tgatgaagag aaatggtcaa gatgccctga aaagaaatag 149880
atcaaggtgg actagaatag ttaattcaac aaattcagtg tactgataat tcttaagagc 149940
ttcctatttt caaagcctgc acctatggct atgaggaata cattgattct tccctcaagg 150000 aactttttcat gggttaataa atcaggcatg tacaccaaga attacaatat caggcattgt 150060
atattaacta tcaaaatggc ttgaatcaca ctttatagaa gtgatgatga cgtgagggat 150120
acctcagctg tggtgaatta cagcttcatg aaggaggttg acattgtttc tctagagact 150180
agaatgtcag gtttaagatt ttaaaaggct gagaagaaca gaaggctatt acaggaataa 150240
cttatgtgat aaagcaacaa cataaacaga agtgtacaga tgtagatatg agatgtctat 150300
ggacaacaat tcattcactt actgtgctag tcaatggatg gttctatttt atgcatttaa 150360
cattcaacaa gcatttcttg agcacttact tcgtggaagg cataggatta atttggccag 150420
ggtgtgtggt acataggtgc tatatttgta attattccct ttggaagcaa acttaggtca 150480
gtaggtttga gtcaaattat agaaggccca gagatagcaa aggcattatg gaaaaggcaa 150540
gacttgctgg gcccttgaaa aatcggtagc atttggagag gaagaaaaga aagaggaagt 150600
gtatgccata tccagccagt aatagtcctc aatattggag gccagacaaa agcgctacct 150660
gcatgatgga atagtgtgtg tgtgtgcata tgtgtgatat tcatatgtaa catatatagt 150720
atctacatgt aatattgata tataatattt acatacaaca tatttatatt tgtatgtgtg 150780
taatacatac actatatgta cacatataca tatacatgta tatatatgta cactatatgt 150840
atatagtata tgtatgtgca caccagtgag gtgtggcttg caggcaaagc acataattga 150900
catcactcaa attctgcaaa aggtgttata tcattctgta ccattcaaag taagagactt 150960
aggaatgaga tgccacatcc taagggaacc aagagcccca aaataatttt ttctgtatat 151020
tttgaacatt tttcataaac ctatgcacac tgacaaaaca cttacttgaa aggaaagaca 151080
cccctgttct cattgctatc agacagcaac aatttatttt ttaaaataaa ctctattcca 151140
ccacagttga ggttccacag agctctgaga ggatgtcaag acatgtcaga tatatttcac 151200
acaagtatta gagtcatggt ttcagttagt aaacagtaat gaatgcatct gttaaatgtg 151260
ttcaagaatg aacacttcaa ggcttttccat tcacagtgaa ggtggggaaa aaagccacag 151320
agcttttgat tgctgctgtc ttcaccataa tccagaggca agaagaaatc ttatggtgtg 151380
```

-continued

```
ttctagtgca atggcctgcg tccatgtaca tcagcaatcc tctgtccct tgtcctcctg   151440
atattgcaga atttatttga tgttggagtt cagcaggtca cagcaagctg gattaatcta   151500
gatggtgcca atgtagataa tgacacataa aaagtctttc aagaagcttt tattaagtca   151560
ttttacagat tcaaggagga atttcatgta tttatttatt tattcattca attttgcatg   151620
catgcattta ttcattttt tgttttagag ataggaactt gctatgttgt gcaggcccca    151680
aacagttcta ctagcttcaa acaatccttc ttcagcctgc agagtagttg gcattatagg   151740
tatgagccac tgtgcccagc ccaaggaaga attttgaatg tatattcctg cttttaagga   151800
gctcacagtc tttagaagag aaaacagaga aataaacata atttaattgt gatcctctta   151860
gattattaaa gggttttaat ctaggtaata atactgttag atttttactt tgtcagtaat   151920
actagtaata ggataaaagt gaatttgaaa gggatgaatt agaggaggaa gttgatgaca   151980
ataggtcagg agagagataa tctaagtgtg acagggatga taaaaaatag atggatcaca   152040
aacacgggga tgttaagaag acagaattac cagtactcag agtctaatta acctgtggat   152100
ttttgactcg gggaactatc agtgccttct tttccatcca tttctaagtt tctgcatttt   152160
taattaatgt gatcatcagc aatgactcac gtttaatgca gtgaagtcct ggtgcacagt   152220
tcagcctatt agcactaaag tggcacttgc acagaacaac tctgtagggg aggaaacatg   152280
ctgaggctgg atgacagcag agtgtctaag ctacgcttct tttgtactat ttctctgaac   152340
tcctcatgcc tgtgtctacc ctgggtcctg cagctgtctg ctcagctctg cagtatggct   152400
gtggtatggc tcaggctact atgcagtgag gtctacagc aaggacaaag gtctgaactc    152460
cctcctcatt gtagtctctg acatgtgtg actctatccc aaaaccttga caatccccca    152520
gatattttgt cattgctaga gtatgtactt actcatggga tacaataaaa tatatgcagg   152580
atgagttgag aacagcagag ccatgtgctg ggcagagtct gggaggttgg ttaggctccc   152640
acggaaaatg agtgacctac ccctacaaag aagctggcag tgtgagtgat tagatttgtg   152700
ccacagctaa ttagtaaatt gaaggagtgg gaccacccaa gaatactcag acccctgaat   152760
gttagttaaa ttcacacatg ccagtgatag agtatatttc tggtcttccg ccttagatgc   152820
cagctcttac gggaacagag ccagtcctgg ttatataata gaatgtttcc acaccacttt   152880
ggttcagtat cctaaattgt ggctcttgtt atggggtaga caggaatgag gttgacataa   152940
cgtatttggt gtttggtgat ggcaaagagt acctgttcat agacacacct ggttgtccac   153000
ctctggctag agaccaaccc aagttcaact gtgcagaagt ccatgttggc ctttactggc   153060
ccagccagcc tctacctgag atcattccct acaacaaggg gcccaggatt cctcagtcac   153120
cccagcagct tttcccaagg aaaaccatct catgaagaat tgccattga tgattttctc    153180
ctcactgtgc atcgaagtca atgggtttat tactgagagt tggttccttt taaaccttaa   153240
ccttacactg tatatgatat agaactgtag gcaggccagg gtcatcaata aagacatttt   153300
tgggcctct acttggcttg taaccacctg cttatccaca gtactgtgca cctagccttgt  153360
catcaggcag agtcaccagc agccacaaca aaagggtgca ccttcgtctt ttccaagcag   153420
caggcaatgt ggctccattt taacttttct ggcaatactc acatggattg ttaaataatg   153480
ctgtcaacag tgtcatcttc aaacccaaag caaacttcct catcatctgt agttagcagc   153540
atgaagacgg tgatgatgtg taacataaac acactttgaa atctgatgca attgacccta   153600
cgaagagagt attccttagt gccctgtctg gcaacttctg gacagaccag gaggccttgg   153660
ggcttagagc acttcttcag cctcagctgc aaatccattt tttcttgtcc cttgttccca   153720
ggatgaagcc acagtgtttc atcaggtaca tttatcagga atctctgttt ctgtttatat   153780
```

```
aacaatttaa cttaagcctc aaccttcaca gtgtacgcat cacatttcca tggaaggatt  153840
gcaggtatta gaagatggtg gatcatgtct taaccacagg ggaaatgttt caggatgttt  153900
ttatagaaac tttcactaac aagcaggaca caggattggc agagaggtgg gggtaggagg  153960
caggtgaagg gtggcatttg ttgtgtttcc ctcttctaaa tgaagttata atgacatctg  154020
tgtttcaaga gtgtggcaag tttggactga gcttgaaata aatacagttt aattggtttc  154080
aaataactga acaaaatgac cattccatgc cctgtgtaat aaaatgttat agaattaaaa  154140
cttattagac gttaaaatcc atgaaggata ttttgctgga tgcccatcct tcagcattct  154200
gatgaggatc ttcgtgtatt tgttcaatga ataagtgaat cagcagctaa atcctgacct  154260
ttgatttcct cagttctctc ctgcaattgt cactgatgct ctcatctcca gtcctgagca  154320
aggcaggagt tgaattagta tcccttata gtgggagggg tctagaaata gctgtgccac  154380
tttagaagct aggctttgtg ggcttttccg ggggatggaa tgatttcatt ttcctgcttt  154440
ctactccaca taccaccaag atcagaattc tgccctaaac actaatgtgt gggagcctga  154500
tgtcctgcct aagtcttgtc aacctctttc caggtgactg aactccgaac cccatgcacc  154560
agtcactggc caacattctg cattaagtga cccggtcacc cagcaccatc cccctgacac  154620
cacctttatc tctacaccac ctgcctcctg cctgattaaa tctcctcaaa tattgacaga  154680
cataatgata cctgaagatc ccaaatccaa attttctttg cccctttgga cattgaactt  154740
tagattacaa aagaccctga ctagggatcc tgtggatagc tgagtcaatt ttcttagccc  154800
cattccttaa atatcaagtc tttctaattt tccaatgaga gcacatgaaa ctctcaaggt  154860
taaaagtcaa tttatattaa taaaatcttt aatttcttga tttctgaata tgaaaaaatg  154920
atactttgtg tattttttaa ttttttggca aaaccttcca aatttgtgga aagagaaata  154980
atattgacta ctggataacc atgtgctatg tgtaaatatt aacggattca ccttagtggg  155040
cactgacttg atgatgtttg ccacattata ttttccagag ccttggctct cccaaaaaat  155100
gagaggtcat ttttcagggg aggaccattt tgtgtttggc taacatttag gacatataat  155160
ttcttctcct ctacatgcca ctgacccact gcatccctgg ttggagcaag aagagccatg  155220 cttttccttaa taatagctaa tggtgaaagg atgtgttgta acaagagcag aggaataggg  155280
aaacaggaga aagacagtca gttgaagagt cctgccctgt gtcagggcac cgtttggcca  155340
gctgggcttg ctaggagtag aatatagaaa gtacatgaag tgccatactc agacagctct  155400
ggctacgttg acaaactggt atatcatggt gcccaacttt ctttgttagc tgggccagca  155460 tcatacccctc tagtatttgc tctgaacttc gtaagcacgg ttgactagct ttcttttcct  155520
ctgcagttat cattcagact gaatagtttc taagaggctc ttaatgagaa atagaaggaa  155580
gtaagttaac ttctgtgcat accttggcca tatttgcttg acaaactgat gtgtatacta  155640
aagccattat gggtgtgaaa ggcaaaagta aagtgctcc ccagtatgac ctggctatt  155700 tgtcttactt ctatatttga ttgctaaaaa tatatgttct tgggtcaaaa aactcacttt  155760
aagggaaaaa aatggaagaa tattaataac caaaatagaa gaatattaag aactttaaca  155820
tgagatgtat ttagatcaaa accatctctt tttggatttt tgcgggtgat ttctccaaca  155880
tgtttagaac tgggttgcta ttcacccaaa ggtggaaact tttgatgttg gggaatacca  155940
ctgatgcctt aaagcagagg gtaaaaggaa aagactgaaa ttccaggcta aaatgaggag  156000
agcatggcca ccactgagcc caaggtagca ttcaataaat actatataaa ttactgattt  156060
atttctacag ttggttgata gaagcttact atgatctgcc taagggtgca tcaaattcct  156120
```

```
ctggtactta tcctattctt gactatcact tccttggggg cagcagttaa tcaggtagag  156180
gcttatcctg tcaagagagt aaagggagct atggaggaac tcgctgggag gagaagctgg  156240
tcctcagaga tgcttagggt ttaggaccag taagaggcag tctccacacc acccacatct  156300
gattcttgtc tccttcttct ctgctgtggt caggagaaac agtttagatt agggatttca  156360
gagcagtggt gttgaacttt gtcaaaactg catttgaatc ccatttatga attgtgtgat  156420
tttttttaagg ttgagttccc cagaagtagg atgctgagac aaggattcct atgaaagtga  156480
attattagaa aatggtccag ggagaaagcg ataggagagt cagaaaatga gacggggaag  156540
gtaaagaaac cagacaagga tacaatatca agtagaatcc aacagtggtg tgggtgggta  156600
gaagtatctg tctcagcaga ttttgagttg tccagattat cctcagttgg tggttaaggt  156660
taaatttgca tcctcacgag gatgcaaatt tctacacact atcagttgtc caagtgcagg  156720
taaagctggc tccagcagcc tgagggcagc cgacagagag acacgggtcc tgggtgtggg  156780
agtgaaacca cacatgaagc ctgcatgtaa aaaaaaaaaa ggtaaagagg ggctgggcgc  156840
gatggctcat gcctgtaatc ccagcacttt gggaggccaa ggcgggtgga tcgagaggtc  156900
aagagtttga gaccagcctg gccaacatgg tgaaacccta tctctactaa gaatacaaaa  156960
attagctggg cagggtggcg ggcacctgta gtcccagctg ctcgggaggc tgaggcaggg  157020
gaattgcttg aacccaggag gcagaagttg cagtgagctg aggtggtgcc actgcactcc  157080
agcctggtca acagagcaac actctgtctc agaaaattaa aataataaaa taaaataaaa  157140
taaaataaaa taaaataaaa taaaataaaa taaaataaat aaaataaaat aaaataaaat  157200
aaaataaaat aaaataaaat agtaaagtaa aataaaataa aggcaaagag atcaatctac  157260
atcaccaaag cactgacagc atctgctaca gtgactttgg tagtttctta cattctctga  157320
gcctcagttt tcttatctct taagtcgagg gaaaatgact tgtttaaaaa ggcttcaatg  157380
aggtaacaca agtaaagcat gtattgagat tactacacag gaaaagcagt tgctgaatac  157440
aattagtcaa ctggtaattg gtaataatta tgtaaaattc ctataattat agggagcgct  157500
atacaattat tatatataat tcctataatt ggaattacca ataggctaat tgtattcagt  157560
aactactctt attgtcctca agttgagtta ttattgcaag ccctgagggc tgaataaaca  157620
tgcaaactaa actgacatgt agaattttat ttataacaat atatgcctaa agaagcggt   157680
ttatttgcac aaggaaattt tggaagctac agataatttt aataatgact acagaaaact  157740
atcttgaaga tgtttctaat gtttaagaca taatagcata agcctttata aaatgggata  157800
ctgttatgta gttatagttg taagaatcag tgtttaaagg atgggtttga tgaaattgta  157860
ctactctagt tcctgtgctt ctaataaaat taaatctgat taatacagca agtaggtctt  157920
tggtgagttg attctgatgc tgggagtgat tttcttaatt cttgctcaga aagccatcca  157980
tgagaattaa atgagatagc atgtacaata cctggtatag ttactggtaa gaggttttca  158040
gtagagacca atctcctctt tgtttaccttt ctcatcaaga gaggaagaac aaggaaaatt  158100
aggttgcttt tttgagaaaa tacttttaggc caattacaat tatctgaaag tagaatgaat  158160
ttctaggtta ggcaagacta gagttaaaac gtgggtgtgc agggctgacc tgccagggta  158220
ctctgtatgg aagtacatgg aaatgtatgc ccaaatacag cttcatataa ttgttttgat  158280
catacacagt ttccacatga gattatattt gaatgactaa ttcagcaaat ataaaaaagg  158340
agaaaaccag tggacaagat gattcctaag gttcctttct tcctggtcta tgccctagtg  158400
tattatgaat tgatattcac tggaacacac agttactgct ggagattgag ttataaaaac  158460
attcaaatgg gttactccat tatatctact taggaaattt ttttttaaaa taactgatag  158520
```

```
atgttcagtt atgcgaaacg aaaggtattt ctggctaccc ctttatagtt gtgtacatga 158580
ctgcagagcc atcatttcat gcttacttcc ccacattcat gtaccatttt ctcaaaggaa 158640
aattattgaa tgaacttgct agttttgatt ctggggtttg ttttaaacaa ctgatattta 158700
aatccaccta gtcctcttta gctgttctcc taggaacttt aatattaaca aacagctgaa 158760
cttatacatt ttgtaaaaga gttcagacaa tgaattcatt cttcttgaaa tgcatggaag 158820
tacccaggtg ctagctacac ccaagagcct tttctaaata caaaaaggat tgacaaacca 158880
agcattcatc ctgtctgcgt ccaacagttc ggaatcaaac catgaacttg ctgttcctct 158940
gtttgtggtt agcttgtttg tatattttta aggaagatga ttcaatgcaa gaagtagttt 159000
tatatagtac gttaagtaaa tttcctatac gatatactta atcagaaaaa tattttgaa 159060 ctagagctca cagaacatat gattacaata gttttcagaa agcaaggggc taaatgagga 159120
tttctcaacc ttggcactat tgagattta ggttaattta tctatggtgg gaggcgtgtc 159180
ctgtgcattg tagcatattt atcagcagtt gtgacctcgt acccactaga taccagtagt 159240 ccccctctc agttgcaaca accaaaacaa ctatagacat tgctaagtgt tctctagggg 159300
tcaaaatggc tcctgcttga gaaccacagt ctagatctgg tagttgcata ttgaactgac 159360
agtccccagg attgttgtgg ggatcaaatt agataaaact tgtttatatt ttttaaaaag 159420
taaaactaat acatatagtt acattacacc tcttcttttc atttgttact catctaagat 159480
tttttgagcc agatgatgga gacccataaa taaattaacc ttaagaggct caaaggtttg 159540
ccaggtaaac aaagagttag aagaaaaaga gagatcatgt cagatgtgcc ttaatgaatg 159600
tgtgtgtaac atgtacaaaa agttatggga accccaagaa agaaaagact ccttttgaat 159660
gaaatcagag aaaccaact ggaccataca gttgaagctc tataacagga attaccaatt 159720
aactaattgt aactaaatac tcttttatac aatgtcatat attcatgtag tttttaaatc 159780
tagaagtagt taaggttcat aattgtcatt tctcagggac actactgaag tggtatcaaa 159840
tctaaatgag caacttaaga attgaagttg tcagacagct gttaattccc cttttcata 159900 cctgctccaa tgatagccaa caatcaaaca aaaataataa aataaaaacg aaagcaaaaa 159960
atacaactca gatttcacta cgtacagcaa taaatatcag agacattagg gaataataat 160020
aggtcaaagc agaaattcat tcctcagcat gttcttcaag tggaagaatt aggtctgttt 160080
tagttctgtt gattctaaaa gaaacattca ggctatcaag aaaacctgtt ttaaactcta 160140
aatctgacac tatagataga tagatagata gatagataga tagatagata gatagataga 160200
tagatagata gatagatgat agatagatat agatagatag atagatagat agatagatag 160260
atagatagat agatagacag atagatagat ataattctgc ctaagtaatt atctgctggt 160320
accaaagaga ttgacaaaga gattcactaa cctaccagaa tttcccaacc ttgttccagg 160380
gtattctaca ttaaatactc attccaagg aaattccaca taaaagctgt catgcttgat 160440
ggagccatat ttacatgaaa cgttgcagca ttttcttctt taaacctctt ctacaatttg 160500
accaattcca tgttccaggg agtactcaga ggctgattag gacatgagtt gttagcatgt 160560
gctgcactaa tggttatgag tcacatttgt tttggaagat caccctttaaa gcctgtcact 160620 catgcttgtt tatgggaaat acaacaactt aaacatcagt taacaaatcc ccatgaatgc 160680
atggtcatat ttgagtgctt ctaacaaatg cttcctttca tttctcccctt gacagcccta 160740 agaattaaag gctggtagag caaactggga gacatccatg aacatttatt aaaggaagca 160800
taggagagta tgataactgc aaagccagct gtttatatta ttggtgtgag attaaatttc 160860
```

```
atcagtctta aaacctgctt tttaccacta gagaaatcaa tctgccatat ttaaggttac    160920
attaacgtgg aacattccac gtactgaact gtcacatgcc tttaaaataa ccatgccatg    160980
ctgttttttt tttttaaaat cattacacat gaaacaaaca gctgacaggt ggggatctat    161040
tggtatattc aagttttcca tgtgaaaatt tcccccaata ttagtggtaa tcacaatttg    161100
attatgagaa acaaacatac catatatagg cagaactata tatcagtagc ctttatattt    161160
gacagctcac tgtaaaatcc atactatgat tcagtgaaca tatttatgtc ttatatctgg    161220
gttgatctgg ttgccttcag ctttcctcac ttgaaaaaac tatacttaaa aaactgtaat    161280
ttaatgttaa agttaattaa cacagcaaat acttattgat gacctattat ttactgggta    161340
ctattttcgg tgcttgcaat gcctcaatga acaaaagaga taaaaacctc tatggtcatg    161400
ctgcttgctt tagtgagata tatgtgtgtt tgtggggtgg aggacatgaa tgtgaggcag    161460
acaataggct acaaaaataa taaattatct agtattttat aaggtggaaa gagctatgga    161520
aaactgcccc atttgttcct catctgagta tacccaaaag ttgatcttta atattttata    161580
tgagtctcct aggttctaaa tgttagaaac taattaaaaa taaattgaaa ctaaactaaa    161640
tatctttgtg atctctctgg ctagaagcct caggaccagt cctcactgtt tactgatgag    161700
gaagccgagg cccagagaat taaacgatgt agccaagatt tcaagcagtt actgtcagag    161760
gtaggaccaa gacacacaac ctccttctct agtgtgtttt tctcaatcgg ttggcattta    161820
acagcaagtg ttttagttga aaaaattat ttgaaatct gtttgaaaca tgacaaaata    161880
ggaaatacct gcttattccc tcactgcaga gtggtcctca gcagaaagaa gattttgaag    161940
tttatgaatt atgttcagac aagacccctta taaaatcact ctcctctctc cagtggcaga    162000
agcgtggccc ctgactcctc acccaccttc attcatcttt cgtattcctt gaaaattacc    162060
actgagtatt ttccttctgc ttcctgcagc accagcagaa aagatgagga tgcgtctctt    162120
gattgccatt acaaatctct ttcttatgct tgtttccatt cttattctgc ataaacttg    162180 gacttggcca tcattcttag agctcctcta aattgtttga ttaaaagatt gtttataagt    162240
ccagagtcag aacggaattg aaaaggcact gcacattatg atggagagga ataaactcca    162300
gtcaaaagtc atggcttctg gactcaccac cctaaggcag cctcactgga acttgctttt    162360
ccaactgtca gtggagtttt agaatttcc tacttgcaag cttgttgtga ggattaaacg    162420
gttaagagag attgtgtctg ttatggaatt gtgaaaactg taagttgcag tccacactgt    162480
agaaatctta gttacctctg ccctttcttt ctctagagac aggttgctag tggaatagac    162540
aagtttgcca ttaatttgaa ggttgcatta agcatatatt atgttagtga agttggtctt    162600
ctgaaagttg gaagggacct cagaggtcct gtattagacc aactgtggct gttccttaga    162660
ataagctgga agttttctga aaaatacaaa ttctgaagcc tcatacatag agattctgat    162720
gtggaagatc tggaattgat ggcagcagcg gcccatctgg agccgctgct gtgaagatgc    162780
cggctgtagt gggggaggtg cggctgtggt tgtgccctcc acagagctgc caggtgggaa    162840
gcctgaccct tctgagttgg caggtctgaa gcccagtgct cttcaggcac agttgcagct    162900
gcccatctgt gcctctagac ctgggcatcc ccgtgctctc gggggcccag gaagcacccc    162960
ctgctcctgc aggcttggaa gtgcctgcta tcactccctg gcctctccct gcacctgcac    163020
ccagcacccg ctccggggtg aagcaaagtc atggccaagc ctggatgctg tcatgacctg    163080
gtcaggtgtg cacacactcg gagcagtgct gacacaccag ccccctggca cataggcact    163140
ctctggactt tggacaccaa ccagcatggg agggagactg agagggcact aaggggtggt    163200
tcagcgcagg cctgcaggcg ccccttggca tgaacagcct gggtgctgtg gatgacatgt    163260
```

```
agatggtggc agaaggcaga caggctcctg ggcagaaaga ggccagtccc cagtgaagct   163320
ccaccttcaa gccagggatg gccggaagcc ttgtggctga gctatcagtt ccaggtggag   163380
tccttggctg ggagtgagaa cttatggtgc tttatccagg ccttcccata gccacccatg   163440
gaccaataag cacaccttc ctcccttctg atctcataaa atccctggac ttatccaaac    163500
tcgggcagat gtcgggatga cctgcctatg gataagagct acccacttca ggtctcctga   163560
gaactgtact gtcactcagt aaagtatttc ttcaccttgc tcaccttcca gttgtctgtg   163620
tatctcattc ttcctggatg tgggacaaga actcaggacc cacttaatag caggactgaa   163680
agagctgtaa cacgaacagg gctgagacat gccttccctg cccaccacat tgtaggtgac   163740
aagaacagaa gagctacagc cctttgggga gcccagacct gtgtgacacc ctctttgggg   163800
gctctgcggt ttctgtcatc tccatgctcc caggcgtcac cacattcccc tcgtccagat   163860
gcagttgccc acggtggaag ccatttgcgt acatcagatg cagccgcagg cttgcatgga   163920
gctggtgcct gtgctggtgc ctggagctgc tcaccccacc acggcagctg gtgtacctgg   163980
ctgtacacag tggctgaacc ccatgcttac ccactcacgt atccctcatt gctccacgcc   164040
tggcttgccc ttggcaggca tggggtccag gctggtagcg caacccgagc atagcctacc   164100
aggccgttgg cagaacaagc ccattgggcc cgagcaaaac ttgggcaaat gtgccaccag   164160
ccacaaaaag gaaacacaaa agtttccagc tggaaaagca agacctgaag aatcctgcaa   164220
cagaatgatg ctctggagtg ttttctgtgt taggtgtgct tgtttgtttg actaaacctc   164280
caaacatgag tctgaagatt aaccagtttg ggaagccttg cttcagcttt ctactgacat   164340
taaactcctt ctcctctccc atttctgtct tcacttagaa atggaaaccc actaattact   164400
caagatctta ccttttccat tcagtcaact aggcccttgc accccatta ctttgcgttc    164460
caccttgaca attgctattg ccaaacatcg gcattaatct attttgacat cttctttcca   164520
cctgctgccc tctagtggaa gtgctgacaa gcagcaaaat atttaactgg gaacagcagg   164580
aaagtgacca gtttgagctg ccagttcac acaagtcagc gcaggtcccc agcatgatgt    164640
ctacagacta cagctatgcc agaaatcgtt aggatggcct ccagctgttt ggacactatt   164700
tgcacacaag ttacatttag agcagaactt tgtaaagacc ctggcattta ttcaagggct   164760
ttttaaaggt ttcaaaaatc tacctggaaa acattaccct tgggatattt ttgtttcttt   164820
gtccctcatt ttcttctttt gtcatttacc caaattcttc ttcttgcaaa agaaggtggt   164880
tctttcctgc cttccctaac ctttgaattt tccaaatctt gcaaaaaata aagatatata   164940
tatctttaaa taaagatata tatatatata tataaattct tacagtttag aagcttccag   165000
tcaccaggtg aaaggaattc acatgaactg aaaattgaca atgtaaagga cactgtgttc   165060
tcctactgtt cctccaagtc tctttgcggt ccgttagtag tcttcttttt tccaggagac   165120
actgaagtta agagagttta agaagattgt agtatgtcac aaagcaagtg gaaaagctag   165180
cactagaact caggtctggc tgatggaaaa cccttatgta ttttttttaa tgtgcttctt   165240
tggtgtttag tgattattta gtcttccgtg aagtaataaa taataacttg catggtaaat   165300
gttattaagg ctcgaggtac taaatttata gcaaagtca ttcagctttt ttttaaatga    165360
atgtttaata atcagtgtgt ctctgcataa tctccaatta ctccttttag cagaggaaca   165420
tggcaggaat gcaggtaagt ttgggtggga ggaaaagaca gcaaaagcca cagcactgat   165480
gcaaagttga gactagattt cacagggcag atgccgtata ctccctcaag ctttgaagaa   165540
actaaatagt tatctatgtt aaccaatagg gcagaactcg tactccaaac accgacataa   165600
```

```
accgtgtgtg tgttttgtgt atgtgtgtgt cttcccccac agcattctgc acaattatta    165660
accctttttg tgtagtggtt tttcataatt ttatccttga ttgttaatat catggtaagt    165720
gatgtgttat aaatatattt ttccttaagt atcataaaca atctaagatt tcatttggct    165780
gattttttctt ttcttagtat tgcatatcat tattgctgtt agaacactca tacagattat    165840
tcagcttctt aactagaatg tatacacaca cacacacaca cacacacaca cacgtgcatg    165900
tacagaactg ccttctttct ctttgatggt agaaaataca gctctctata gtaagcaaat    165960
ttgctttcag tctcagacat acccttcatt ctctgcatga ctggtaaaga gcggaaagag    166020
taatacttag gatctggatt ccagttccct gttctctgac catttaaaaa tttttgttacc    166080
ttggccaggt aaatacagtt ctatgaacgt cagttgtgcc tcaattgagc aggcttgtcc    166140
aaaggattcc tcaaggatga ggtatccttt cagctgtatg agctgaacct tgatttgtgc    166200
aatagtttaa gcccctgaat agtcagataa aaatcatgtt aattaaaatt aaatagctat    166260
tggtaggatc tggttttcca ctggcttgca tgaatgatgt tttgccctcc tttctgatac    166320
tcagctcaga ggattccttc cattgggttt tctttcttgt agttttttctg gttcataaat    166380
agcctataga caaacactaa actgttacag gtaaaaggac cctagattaa gccttttata    166440
aaacaaatag tcctgtgtaa ataatgacat cttatttttat gtgtgtgaat ttgagtttta    166500
ggatgtaggg catgtctgac tagatagcta aaggctgagc tccaggcagc cagctgctat    166560
ccaatctcca cacctggaat gttccaaaaa acctcctgtg ttttctttct gcagctaagc    166620
actgatgagc aggatttaag aagtacagcc acacatttt tgctgcacgt tttttaaagt    166680
ttgttatttt tgtcatagat tacttgtttt gaatcaaaaa ttttttaaaga aaacttaatc    166740
tcccaaattt taaccccctt gaagtttcag gattccaagg aatattttta ttttaagatg    166800
cataaaatac tcagtacatg tacaaaggta atgcttataa gaaacttaga aaaaaaaag    166860
gagctagtaa gattgagaag gggaagaata tctaagctaa cattactaac ctggcaacta    166920
ttataggtgg ctggatagca tgaaggcata aagctgaagg cagttaagaa aatagactgg    166980
atttgaatcc tggctctacc tggattagtt ttgtgacctc agagaagttg cttcccttct    167040
ctgtgcctca gtttcttcat atgtaaaagg agataactat agtgtctaac acacagaatt    167100
attgtgagga ttaaataagt taatacatat aaagaaagtc caaaactatg gcacacaaat    167160
gtttaatata tgtaagctat tattgttata aaactaaaga aagagaaccc agaagacatt    167220
cagtttggtg ggattcagat atatgttttc ctttcctcct cctcctcctc ctctccttct    167280
ctaaccccac tatgcttgcc tcccaatcta tccctgactc ctatttttct tcctcccaac    167340
ttaagaattg tcactaaaaa tatttagaag aaaagaaaat gtgcatactt caggggggtgc    167400
caagcttttg ggtaaagtac acttttcagc taacatgact gtatccaaca gtaatgggct    167460
ttatggcaag aaaaagcttt tttctcaata aatgggtttt aactttgtaa tggattattc    167520
tctttgcatg ggtaattctt ctggaagatg gaaattggct cgatgataag ataggacagt    167580
tggatttagg gatctagatt aagggactat catgtatgct tttaggagag aagtttaatc    167640
tgcaaaacct acttgtctta tttaattaat tgttgctctt agctgctcaa tttgtacag    167700
gtgacttgca tgaaagcaaa atgtatgtca aaatccaaaa gcagagtgaa gcctcggac    167760
ttcagtgctt ttgggtgtct ttccagacct ctgctcttcc cccaccctca ccaaggcccc    167820
actgacctca aagggccctt cttgccaggc cgtgaattac gtctgagcca gagggctggg    167880
actacagcca aagccaaatg aaggtgcaga atttaggact aaaaaaagcc tgagcacgtg    167940
gcactgggta tagcagataa atttgttgga gaaatggttt ataaataaca tgaaaaggga    168000
```

```
aaggggatag agggtcaaaa tattgagctg ttgagagttg ttcaatattt gaggtcagtc  168060
tcaccatttt taatactgaa cccaaaagta atacacactg aaaaaaaaaa aaaactcact  168120
gaataaaatt aactacagct gggcttattt tttcttatca agacatttgt aagtttggca  168180
gcaagcattt ttaaacagga tctctattat atgaaataaa tttaaaaaca tgtgtctaca  168240
gtcaggacaa acaagtgaac aaaaacaaag caaaagcaat aaagaagccc catgaaggca  168300
ttatgctttt ctgaggacag tataaggcta ggatactgca gaaactgaaa tacttaggga  168360
tcttattgaa atagttttct tttcctccaa acaaagcaac catctcagag ggatagatgg  168420
gctaaaagac aaggaataaa gtaaacagaa gattggtaac ttgggaggtt ttcttttccc  168480
ctttctcttt ttggttttga tttgcttttc ccttgttaaa gccagaaagg ataaattttg  168540
gtccagaact cccaagacca gagggtcagg gaaagccacc ccgaggctgg aagctatgaa  168600
cttatcgcta gtctaaactc cacctccttc ttccctggga gtcctgcaca aatataactg  168660
cctgatcttt ctgttactg gcaaaggttt tgctcccttc tctttcgtat cggaatgtga  168720
acttggggaa agatttgggg ttttttttgt tttttttttg tttttttaag aaacagagac  168780
ttgacttatt cctcccacaa actcttaccc tggcacaggg agaccacaaa ctaagtgaaa  168840
acaaggtaag aagcttagag aaatgggacc atatgccctc cccggagctg aaccgtgttc  168900
cctgtccacc atcaccttgt cttcccatgc tactactcca ctcctgtctc ttccacactc  168960
tgggtcacat gtctaccct tactgtgagt tataatcgcc caggaagggt aacccattga  169020
ctgagggcca agcttctgat aagtgaatga acttgtcttt tctcctggcc agatatctgt  169080
ctttgccaga gagggctgag tcagggagac taagattttc aaggtcaaat tgtatattgt  169140
ttaaaattgt gaaaatttgc tttgtgcatt gaatctcatt ttcaaaataa aattatgcct  169200
taagtcagat catactgatg cagattctgc agatgttaag aggcttccat gattgtattt  169260
gccagctgca ggtcaggcag tggtggatgg tggtaagaag taacctatac ttttggctgg  169320
gagctgtggt tcatgcctgt aatcccagcg ctttaggagg ctcaggcggg cagatcacga  169380
gatcaggaga ttgagaccat cctggctaac acagtgaaac cccgtctcta ctaaaaatac  169440
aaaaaaatta gccaggcttg gtggcacacg cctgtagtcc cagctacttg ggagactgaa  169500
gcaggagaat cgcttgaacc tgggaggcag aggttgctgt gagcgagatc gcgccattgc  169560
actccacact ccagcctggg cagcaaaagc gaaactccat ctcaaaaaaa aaaaaaaaa  169620 aaaaaaagt gacctatagt tttgcagtag aattttgaat tcaaactcag gctttatatt  169680
ttctccaaag taaattgtat tttgttcatt ttaatccatt ggttgactct aatgagatct  169740
ttctgactgg aaattctgcc cttttttttcc tccataactg tattaccagt tatctctcat  169800
ccatgtgttt gataaatcca tatgaatgtc ttttttttgtt ttctaccaaa acctttataa  169860
caaaacaaaa ttcatagctt tgtcaactac acttgaaaat tatgccccag cttttcagg  169920 attctgtaat taacttattg agtcatttgt ttaaccattg gtgaattcat ttatctttac  169980
tcgggccaca gtaatgtatt ttacttacaa catattatga gaaactacat cacctgcttc  170040
accgaaattg aaaaacatta gatgaacaac actgccctaa accatatttc aataatcctt  170100
tcatgaaagg aaaggaagta catttcctat aatgatttgt tcttagtgaa gccatgttga  170160
ctccaagtga cctgttgttt cctttctggg ctcatagaaa taatctaacc attctaaaat  170220
attgatgggg attcaggtca aaggtatagt tttaaaaatt caccatattt aacctgttaa  170280
acattcagta tctcctacct tctgtcttcc aaaaatccaa agaataaacc atttattgtt  170340
```

```
ccgtttatgc tttcagtgtc taggacatag ctaatctgat actgaacatt tgaacttatc    170400
gttagctttg aaaatatgcc ctattgtcct attggcttta tactaaagtt ttattaatac    170460
attccctcaa tagtctccag tctttgccca agaagaagaa aattctgtaa gagtttcttt    170520
ttaccttcct ttcttctctg agtggaataa tcttttttgt tgtcttcata gtattttaga    170580
gttttgtgag atcagacaaa atttacctca gcttataact ttatctttta agtggaaaaa    170640
ctctgaacta ttgattattg tgtcatcttg aaaaaatagt ctatggaata tatataagta    170700
gttgtgttat ttttttcagt gttaagttga ccttttctt ttagtgcatt gtgaatattt     170760
aaaaggtcat ttgtgcaaca tataagagga ttgacaggtt tccatgcatg atgcttaatg    170820
tggagatgat ttcttttccat caagttatta tgcttggaat aagtaacaca tcttaaaatt   170880
acaaccttga tgtagcaaat catcagatgg gttaccatta catggaaaga gccagtgaaa    170940
taaagaccat taagttcagg tagacagaga tggcggtgag aaattcacag ccaaagaggg    171000
ccatatggag gtgaaaacac tggtaaatgg ctctgggacc ctaggagtct acagtaagtc    171060
attgggaagt tggagtggag aaaggcaaca ttagctaggg attcattca ttcctccata     171120 aatgcttatt gggagcatgt tgtgtgcctg gcatcatcct agcttcactg aaaagaatga    171180
ggaacatata aaatgtgaag gtgagaataa gtgagaagta attgctcttt actctcaatt    171240
atagctgggc aagtacatat atgaatatgc ttttgtgttc tgaacacaca ctaagcagtt    171300
ggtcaaagta ttaagctaga gacaacttct actttcaaat gtagtgtttc aaaataataa    171360
taataataaa gatttcagga cagtttacat ataaccattt agagatttaa ggattaaaat    171420
caggagggaa ggagaaatgt ctctgctggg gaaatttttt taaactagtg ttttctactc    171480
agctactcaa tgtgatttct tttattttct tccttccatt gcttattggc atttattgtg    171540
gggaagactg ctgtgttggc agcatgagag agatgggaat caagaaaatg gaaacaccat    171600
tcaatattca aaagccacta tcccccttaaa agcaaccaca gatcattcag ttttgccaca   171660
tactcagatt gcacactaac tggaggatgt taaaaagtgt tctattacaa ccagttatcc    171720 agttttttgcc acttaaactc tgctgtgaga aatgtgactg tagagcagcc ttaaaaagag    171780
atcatcttga tattaagcag tgttactcat acatgcttgt tgacattcta acaggtgact    171840
ttgaatggat cttcaggctc agaaacatgg ttgtgtccct agaactggtg aggctggaac    171900
aaggtgtaca gaagtgaaat gaccacttgc tttctctatt ggatttcttt atccagctgt    171960
gcaattgttt cagggactac agttgatttt cctgatgcaa gcctagcaac ttgttttttca   172020 gttcagcaca gtaaaatatg aacaggagag aactccctgt tggccaccca cctcacaatc    172080
tttaaagggg aactctgtac agaagcattc tgcattaggc aaatgtacac ttctgcaatc    172140
aaaatgaaaa acacttgagc tgaatcgttt ttcgttagct ttagtttcca gccctgatta    172200
aaaagaacac agggaaccct gcaagtttaa gcggttttgg cagccgagga aacagctgtg    172260
acattgtcaa gggttgtctg taggagctgt gcaggctgct gacagcactg ataatgccca    172320
gaaatggggc agacgctttt cgcatttggt catcaaagga gtggcagcag ctaggttcaa    172380
gaagtgaact tttgaccctg tctgagacaa ctggctctcg tggatcttgt tctgtcattc    172440
tccagtctga ttttctcttt cagaacaagt gggtaggatc tttggttttt aaactgtttg    172500
actgttatta aaagtaagct agttcttata gctgcgattg aagggatgg aagtgagga     172560 agaagagctg gtatttccca ctatcctgca ggggtgggga aatctatcaa cgactgttcc    172620
actaatctgc ggatgagtta tctagggaat atcatgcagt tgccaaagtt ttcagcatct    172680
aaaagcctcc aaagttctct ctgtgagggt ctacctcccc tgtctccaga tccttcccat    172740
```

```
gccccctcaga ctcagcactt gtccactgtc cttgctacca gggaatccct ctgcagcccc   172800
cttaccctcc tgcccctccc aaaagagctc cagactttga cctttctctt ccacctcaac   172860
atctgtttgt gtcttaaact gatgtccatt gaaagaaaca gataaactaa ttaatgctga   172920
gatatgactt atgaagtatt atgaatgtgc taactctctc aggggtatgt gcatttttaat  172980
agaggaccag cagtccaaag gccggtctca ctccactgtg ccctctaac agcaccgagt    173040
ctatttccag gcagccagag accaggcctg agaacttgcc ccagaccacc agcgtcccca   173100
ctgagaaagc aagcagactc aacagttttt cagtgtttca gggagcctgc agcagcaata   173160
cagttccttc aaagggtctg tggattctct cagctttcct agtaggttgc tgtggtagtt   173220
tttggagcaa aagttcacga tgtgaatctt cacatgctgc tctttgtgcc gagcaggtgc   173280
ttgcaagcta gttctgcccc tatctgccat cttaatccta acatctccca tgttttttta   173340
atttaacttc tattttggtt tcagaggtac atgtgcaggt ctgttatata gataaattgg   173400
atgccatggg agtttggggc atacatgatt tcatcaccca ggtaataaac atggtttcca   173460
ataggttagt ttttatgtcc tcacccgcct cccatcctcc acccccaagt gggtgccagt   173520
gtctattatt cccttatttg tgtttatgtg tactcagtgt ttagctccca cttataaatg   173580
agaacacgca gtgtttagtt ttctgttcct gtattagttt gctcaggata atggcttcca   173640
gcactatcca tgtggctgca caggacatga gctcattttt tatggctgca tagtattcca   173700
tggtgtatat gtatcacatt ttctttatcc agtctactgt caatgggcat ttaggtttat   173760
cctgtgtctt tgttattgtg aatagagcct cagtgaacat acgtgtgtgt gtgtctttat   173820
ggtagagcag tttatattcc ttggattgtt gggtaaaata gcagttctat tttaagttat   173880
ttgagaaatc ttcatcctgc tttccatagt ggctgaacta atttacattc ctacaagcaa   173940
tataaatatt ccttttctc tgcaaccttg ccagcatctg ttattttttt gagttttaa     174000
taatagccat tctgactggt gtgagatggt attcattgtg gttttgattt gcatttctct   174060
agtgaatagt gatcgtgagt attttttcat atgcttattt tccatgtgta tgacttcttt   174120
tgaaaagtat ctgttcaggg acatcattcc tatgaaaatg ctagttaatt atacaagtat   174180
tacttgtttc caataatcga tttttaaaa aaccttataa tcaatattgc attaaaattt    174240
tcagctgtgt gattccttat cattttcttg gatgcaaatg ccttgtgtca cgtactatat   174300
ctcataaatc tatattgcat ctaacaaagt gctttgtgta aagtaggcaa ttaataaatg   174360
cttgttttaat gagtagattt gtttttgttt tattttgctt tctatgtttt cctaaggatg   174420
tggggcatta ggccaatgga aactgtctct caaaagttct tatatataaa tattgatgtc   174480
aaagtcacta tttttgtaca aataaacaca tttacctaat ttggtgagca tttatagagt   174540
cctgcctata ttcaaggtcc ctgtgctgat cagtgggcaa ctgaagaagt atgaggcact   174600
gttactgctg tcttccttcc ctaattgggt cctatacctt atcttggtac agctacctcc   174660
taaggaggcc catctgtgct gttgagggta catctgaagg cagtgcactg gaatgtatag   174720
cctaggactg gaatttggag tgaggccctg agagatcata cacatttttc acttgtgggg   174780
gaatgtcctt aagtagaaat agatggtgat ttcagatatt tgatccaaac ctaacttcct   174840
catttgaatt gagtatgcta ataactattc ttgaggctct ggaatagtga tgacatttcc   174900
tggttgggaa atcagatgct gatttctgaa gcagagtttt aaagttgaaa gatgaaaagg   174960
gaacaaaaca ataaacacaa ccttagactg aagggtcatt tttctagtcc aacttccctc   175020
cacctagctg ccacccaaga ttgtccctca gccatcctta gaatattaaa ataaatccat   175080
```

```
tgcagtgctc aaatgacttg tttctatttg aaaatccttg ccattggaga attttttctat  175140 atatcttacc ttaatggctc tccacgaatt ttgtcaacag tttgtcagca atgtactcat  175200
gaaaatatct catatctatg tatattctat cactttagcc tccttgactt ctagaccagc  175260
agttcccaaa cttttcaaat gtgaccccct ttagtatcaa cttctgttta taaaagtaca  175320
aaagccctca catcttatac tttcttttat gcttttattt attgagatat tagacaacac  175380
atacttgtag gtgacatgga ttcttagatc taaataactc cactctccat ggtcactgtc  175440
acttcaacac aggttgatgc agtccttagt ttggaaaaca gttttggcat aaataatccc  175500
aaaccttcct atcacttctt ggagcttttt tcttcatgct ttccttgcat ctttcttaaa  175560
atgtgaagac tacattggat atattattaa aataatgtca ttattagtgc tatgtttaaa  175620
gctgaccttt tcttcctagc cactgatata gcagtgccaa ctgtggactc tctttagaat  175680
gaacacttta gtaataataa gtccttagaa cacaaacact gtcacttgta aaacactttt  175740
ctatacttgg taacctacac agaacagcgg ttcccagact ttttcttttt tttgtcttgt  175800
gggtccttta tatattctta caaattatta aagactccaa agagctttg tttatgtgag  175860 gttttgttat tgatacttac tgtcttagta attaaaacta agaaaattgt aaaacaacac  175920
atcccattag ctgtcagagc atcatcatgt cttgtaggct ctggaaaact ccactgtaca  175980
ctcatgaaga atgagtgtga aagagccaaa tagtagctta atattattat aataatagtt  176040
taactttgtg agctcaccaa tataatacat attcatgaca cagtccctaa catctaaaaa  176100
cttacaatct aaggcccaac ataaatacta atagatgatg ctaaattctg gcttcacagt  176160
gcttcctaca ataatactaa aaatatatga atttagacag aggccaaaat gtgtttatta  176220
accacttggc tttgcttagt attttgttac ccaccttgga gaattgcctc tgctgattta  176280
cactttataa gaagcagccc tatgaaattt tttatcataa gtttaacaat gatgtagaac  176340
atactgtttc attttataat gatccttggg caaaatgtat aatatctgtg ggagaaatgc  176400
tcaatgctgc agtaaaaact atacttctcc tcagaatcag gtatgttctt atatggtcag  176460
tataaatctt ataactgtgc tttctgatct cctttggcca ccaggaagac aggagctgac  176520
aatccaactt actataaatt cttcagggtc tgatgtcatt atttctataa gattttccct  176580
ggcattatct tatttctcag gtctcacttt tcctttgttc tgatttattt ttcttaatat  176640
gttttattgt gtatttgtta atatgttttg ttgtgtattt aattgccaat ggggatgaat  176700
gaataagtga gaaagaaaga tacttgatcc atttgagtgg gactgcttga gtacctggag  176760
tggtgcagac caagcagggt aactgtatca ggtttcatta atgaaatggg tcttaagtgg  176820
agattaggaa ggaaaggaag tgggttgctg gagaggcggg gtgttttatg tgacagattg  176880
gctgtaataa agatgcagct gtggagtgag tgagtgatgt cctgagcaca gtaaggagat  176940
ctggctgacg tggcactgca cctcattgcc ttaatatctt ttcatttgat tgaagaggca  177000
gctgagggat aggtgctctt ggaaagtgga gtaaccattt ccaattaagg aaggactctc  177060
acttcagttt ctaaaataaa ttagaaggga gaaaatatga agtctgagag atcaattagg  177120
agaaagttct ggtgctacat atagaaatag gcttatccgc atatgcaggt gagagtacga  177180
agaagaatct gtgaatggca gtcattttt gtagctggtt ccaattaaaa ttgattctct  177240
ataatgacta cttattggct gctgctcacc aggtctgcct ttttcatcat tgtctgcaga  177300
acatatcaca gtatacagca tagagtaggt gcttcataat gtgttaaatg gatgaaatgg  177360
gttcctacct ccaaaggaga tggaaaaaaa aaaacaggca agtaaataaa gtaaaatatg  177420
tataaattgc tttaagaatg tttataaaa aaggacagta gcccaacagc attcacagta  177480
```

```
ggctggctgg agtagcagtc attgaagaaa cccatgaaaa cagcggcaga agcaaatgtg  177540
cagctgctct gccttttcac actgtagggc agcacacgaa tagtcctgga gcaccagggc  177600
ccttagactg tgggattttt aagttaccta gttggcacag cattgactcc tcctctggtg  177660
tgattagggg ccaggataca ataaacatat gttatgttgg aactttgatg ccagcctaaa  177720
cttgccagtt cagtgtttgt ggttgcaggt agtatcagct cctctcctga tatgattgag  177780
agactgaggt ccaaggcttc aggttgaaca gaattgatgg ccctaaggat tgggttagaa  177840
ctcttccaaa gcacttagca ggaagccagt ttacttttct tggatgccag cttccaagaa  177900
aagatcagtc ttgagcaaaa tagtccttca ctctcagctc agaagcctaa ttgagagggt  177960
atcctataag taacacagcc cactctgcta gtaacctgtt ctacttcaac ctgtaaggcc  178020
catgaggcta gccagtgaca tcactacagg acacagtgga ggatgtttag gaatggctgg  178080
gtgatgacca gggtgcagat tgtgtttact caaggctgat tgagaaatac tgttttcagt  178140
ggtgtgctta taaatgttta acagtggtgg gtggaagggg ggctctggct tgtagcattt  178200
ttctagtgcc catggtgtaa atactcccaa catgaccaac tttaagttac caatgtgatt  178260
gaaagtagag tttggaagcg aggcacagta gcccactgtt atgtagtatt tttgccatac  178320
agatgcataa gagacataag taacctgaag aacatagata attattaaat gtagtaaaat  178380
gatcatgaag tgacagatct tgagtgtttt atcacatttg tttttaatat aatttaattt  178440
taagttgcca taatttaatt tgtaattaag actatgttaa taattggctt atggaatttc  178500
tgagaattca aaaccagtg cccataggtg gatccagtac accactaggt aagaacagcc  178560
tagaagtact tctaggctct tgttctgaaa ggtgccaaga ctggcatcca tggttccagt  178620
gccagggtcg aggaaagact tactaggtcc tgcagtattg ctcccaaatc tctttcagtg  178680
gccagggaaa ttatcagcct gaaggcaggc tgaatggctt gcttacattc aggtcccagt  178740
atctacgatt gacaatcggc ttcatttgta agtaccagat agtgcaactc catgtatcca  178800
ggaggctggg aggtactgag agcagactga tagtgtcaag agacactgaa atgactgcca  178860
gctctctcct gccatatcca ctactaagtg agaaattcag tgacatagtc actgaggact  178920
ccaccactgc tgggtgttgg ggagggcaca ctgagtattt caagacaatc cgggtaagat  178980
ttttcttgga gggattcaag tacaaaatag ttaatatgca gaaatgaagc agaaattatt  179040
atacctcaga aatgagtcag ataatactaa agaaggaag aaaggaaagc atgacttgat  179100
tcatgtcttt aatgatgacc aaagaagttg ggtctttaaa gatgacaaga gaagactgat  179160 cagggtagcag tgaggtggaa gggaaagat gagagagggg acattcctgg tagaggaagc  179220
aaggtagaca aagtgtagga atgtgaaaga gcataatgta tgtaagtatt gttcaggtga  179280
cttcttgggt acctagatag tagagagaaa ttagaggtaa gaatggagga aggggagact  179340
cagggccagg ttgttgaggg catttatgc catgctaagg agtttccaat ttttcctttc  179400
agtaatagca agaaacttaa aatgagcagg ggtttgtgtt tttgaaagaa ctgggaaaac  179460
acctctgggc aatccattac ctggggataa tgggtgaaat ttcccaagtt agtgcacagg  179520
ctgctgggta gggcttgagg ctttcctctt gcctcctatt tcaacactgt ggtcttttag  179580
gacttgtcct caacatgttc ttaaaaggaa tgtttgctaa ctgccaaaac agtagtcttc  179640
atatttattc tgttcctttc caaaggtaa attgaaaaag caacataccc tcagccaaga  179700
gaattaatct tttatcacct aagttactgc ccactgcctt tcagttttaa agttaattta  179760
gtgtgcataa atggctatga gcccctggaa ctctctttat gtttgcatct taaatttacc  179820
```

```
agaccctcct tctgcctcta gttccagaat tttctttgtc ttatttttctt caagaaatgt   179880
atttctttaa attggattgc aaatttggaa tacacacagt caaagccttt taaaaccatt   179940
cttttaaaaa aggacaagtt tcttgagaac attttaaag gaaaagtta aatagatgt     180000
caatggaaga tgcaaatatg aatataaaat atgaaaagca tctataggct ggagcttctc   180060
agtagagctc tacttcattt aaagtcatat tatctggcac catttcaaag cttttggtta   180120
cttgattttg tagttagaaa aaagtataa agttgaaata ttgggctctt tacatgacca    180180
ttttgctagt agcagtggat gaagcttttc tctaagagat caatagcttt agtgtaaact   180240
tggtcaatac cttattggaa gaggtgacta tgtcagatta ggtagaaact ttaaaagcca   180300
gcaagtttcc aaatgtcctt ctggaattgg cctcctaggg ccatgtggac cagagagatc   180360
ttatcacaga agtcataaac tgatatccgt gagccaaatc tagctcatgg gcatgttgtt   180420
tggcctacag cacatttttt tttttttttt tttttttga cagagttc actctgtcac      180480
ccaggccgga gtgcagtggc acaatctcag ctcactcaac ctctgcctcc cgggttcaag   180540
caattccctg gctcagcctc ctgagtagct gggattacag gtgccacca ccacacctgg    180600
ctaattttg tattttagt agagatgggg tttcaccatc ttggccaggc tggtcttgaa     180660
ctcctgacct cgtgatccac ccccccgcct cttggcctcc caaagtgctg ggattacagg   180720
cgtgagccac cacgcctggc ccacaccaca tttgtaagca gatgaattgg ttatttttaa   180780
aaatttgaag aatttaacaa caaaaacaac aacaacaaca acaaacttttt gtgtccagct  180840
tcttttttttt tattgtccca atagttaagg acaatcctgg gcctgcattc tttgaacagt  180900
tggctagact taagtagctg ctgccccttt tagatggggc aaacattctc tacttttca    180960
cagtccccctt caagggtgct tcagccattt ttgctactca cttgtcttca ataaaccaag  181020
gtcatgttta aaagattaaa taacagttat tgcatgctca ccaaaccgtc acaaggaacc   181080
agacttgtgt accagaacag agtcctggag catatctctg ttaggctaga catcactctt   181140
ttagttatgg gatcatggaa aggtgcagaa agttccaggg aaggggtcgg gagggatttg   181200
gtgagtgagg cacttggagg catgggtcaa tagcttttca ccagctagca tggaagtact   181260
tttagtgttt aaaaacctat ggcacagtgg gatcttctag gaaagtagac cctggagatg   181320
gagattcaca tgtagcacat ttattagggg atgccactag gatcaatatc tgtaaaagag   181380
agagaaagga tgtaagagtg ggcagaggga gaagttgagc tgcaaagcag gcccagtgcc   181440
agcctcaact ggctccataa ggagctctgg ctctggaatg ccctttata tttgtttccc    181500
atgggaccag gatggctagg ccattctact ctgacatgca tcactcactg aaagtgggaa   181560
gagtcttgct cttgagtgag gaaatcccct gctactgagg caatccctca aggagtaag    181620
aagtgaaagc tcctggcctg gagcacctgc aacatctgaa acaagaaatc cttcattgaa   181680
caggatctgg gcagcacacc agagtgatca cagtcagcag ctataccagt gacaacagat   181740
gaatatcaac tctgccttta gccccctaggg tatgacacct ggcctaccaa ggctgtgcct  181800
aaactctttg gactgattca gaatcaagca agtcctagcc taaagagagg agtttaatgt   181860
catgctacgc tctagcccaa tatttgctga cttgtaattc agtcattaaa aaaattcttt   181920
ttatcttcac atagttttag attgtcaaac tgttaccgtt ctgtgtccag aaattaaaat   181980
ctattctttc tattctttttt tttttttttt tttttttttt gtgacggagt tttgctcttg  182040
atgcccaggc tggagtgcga tggtgcaatc ttgtctcact gcaacctccg cctcctgggt   182100
tcaagcaatt ctcctgtctc agcctcctga gtagctggga ttacaggcgc atgccaccat   182160
gctcagctaa ttttgtgtt tttagtagag atgaggtttc atcatattgg tcaggcttgt    182220
```

```
cttgaattcc cgacttgagg tgatccgccc cgctcagcct cccaaagtgc tgggattaca   182280
agtgaaatct attcttatat tttattgtaa cctcagaaaa gaatgctttt ttgaggacta   182340
gagttctgtc tcttttattg tcttctcctt tctctttccc aaacctataa ctctattttg   182400
cttagcacac aatgaataat cagatgtctt aaattgtggc ttacataatt actagtataa   182460
cttttttgct ttttttatt tcattttaat ctgttcatga ggactgttac ccaggtattt    182520
aaaaaatctc actccattgt tttaaggtta gtggttccaa agggatttta gagaccctga   182580
cccaataata gttatatttt tctaagtggt tctgaagcaa tggtcacaag taagaaactg   182640
cagttcaaaa cacatcatag gtttgttatt ttccaaattc ttattaaagc attaatgcaa   182700
atggaatttt cctactagta ttctgctttc tctaatcctt gacaggacta attgctaaac   182760
tataatatga tttattataa ttttatgttt atattaaaaa tatagaatat gattgccctt   182820
tgatgtcaaa tactaaagat cctgctacta ttttagttgt gctggttctt ttcttcctta   182880
tctttcattc accttttcaa ttcatctcat aaacatttaa tgaaaaactt attgtgtatc   182940
aagggttgtt tattatatga tttgtaattc aaaaactttc tttctctggt ctgagaattt   183000
tagaaacatg aaaagaaaga gggagggaga ccaactgaga gtaaaaaat aaatctggca    183060 tttattaaca gttaaccaat ttctttttc tataataatt tatctactaa actgtatttt    183120
ttaaattatt gttttagttt ttgttgcata tatttaaggt atacaacatg atgttttta    183180 taattactag agtgaaacaa attaacaaac tcatctccta catagttatc ttttgcgtgt   183240
atgtgtgtgg taagagctcc agaaatctac tctattaaca aatttccaat atgcaataca   183300
atattattaa tgatagtctt tctgctgtac gtcagattcc tagacttatt catccttcat   183360
aactgctact ttgtaccatt tgaactacgt tttcacatcc cctgtgaaaa tgggaggggg   183420
gccgtaccat ttgcatggaa tatctttttc catcacttac cttttactgt atgtatgtac   183480
tcagatctaa actgagtttc ttgtggaaac catacagttg gatcttcatt ctttacccat   183540
tcagccattc tgtatctttt ttattgagga gtttagacca tttacaattt aagtaattat   183600
tgatagggac agatttaagc ttgccatttt gtcaactgtt ttctatttgt ttataattct   183660
tttttctctt gctctcttct tcagtgtttt gttggatttt tatgctgata ggttttgatt   183720
tcttcttttg tgtaacttct atatattttt tctttgttgt caccaaaggg cttacataaa   183780 atatttaga gttgtaactg tccaatttat gctgatagca acttagcttc ctttgcttat    183840
aagaactctc tgcttttacc tcttctcccc cattatatgc tactaatatc ccaatgtaca   183900
tctgtttata ttgtgtatgt agtaacataa tttagttata gttgtttaa tacttgtctt    183960 ttagttttta tagtagaatg aacatattta cctaccactg ttatagtaat acagtattct   184020
gtattatttt ttaccaatgt gttccctact ctgctgcttt cttttttgttt caattttaag  184080 agctatcttt ggcatttctt ataaggcaaa tctagataaa ctctctcaac ttttgtttgt   184140
ctgagaaatt atttatcttg cctttatttt tgaaggacag gattgctggg tatagccgtc   184200
tttgttgtta ggttttgtgt tttttttttc tttttcagc acttggaata tatcattcaa    184260
ctcccttcag gcctgcaagg tttctgcaga aaaatcgtct gataatacta cagagatttc   184320
attataagta gcaagtcact tctctcttgc tgctttcaaa attctctttg tcttcaactt   184380
ttaacaatta taatgtgtcc tggcgtgggt ctctttggat tcatcttact tggtgtcgtt   184440
tgggcttcct ggatctggat gtttattttc ttcccgggac tggaaaatat tcaaccatta   184500
tttctttgaa ttttttttctc tctctcttct ccttttgtat attccgtaat atgtatatgg   184560
```

```
gttcacttga tgttattcca aaattccctt aagctatctt tacttctctt cattcttttt 184620
tcttttgct  tctctgactg gataatcatc aataatctgt ttttgagtta gctgatcttt  184680
tcttctgttt gatttagtct tctcttgaat accttctgag taaaaacaaa caaacaaact  184740
gttttcctc  tgctttcaca gttcaacagc aatcagtaaa gaagccctt  gtgacaaaat  184800
gtgtgtttag ggaaggggtg gtttccttca cacaacaagt aagcaatcag ttctgcagta  184860
aataccagtt tggtgtcctc taattcaatt ccaacacttc tactgagaga tcctacagat  184920
tggggctca  gtccccgaga ctgtcttcct caaccaactt ccaatgccaa ttgcaaaccc  184980
caggttattt tgcctgtact tcttactgac tggctataaa ctgaggttcc cacaaccccc  185040
ttctgaggtt caattaattt gcaagagtgg ctcatggaac ttggaaacac ttgcttatgt  185100
ttatgagttt attataaagg atattttaag ggatacaaac aaacagccag aagaagagat  185160
gtctagggta aggtcaggaa gggtcatgag tacaggagct tctgtccttg tggagttggg  185220
gtacacaacc cttcggacat gtagatgagt tcttgttcac cttcctgtaa gccttcacat  185280
gtatagctgt ctagaagctc tctaaatcct gtactctttg gccatttatg gagacctcat  185340
tggataggca tgattgacaa tcatgtggaa atgtgattgg acaaaaagag tattagctag  185400
tgctaacaga ctgaatggaa aacccagaaa ggcctgtctg ttcagattct tcctggtctc  185460
tctctgcagc attctttcct ccagggaatg gggcaggacc ttttttgaaa tgaaaatctt  185520
atgacctaca atcagacaaa gtaggtcaga gaatttcttt atggccagag gcaggggaag  185580
acttaagtgt attttagtt  tctgttgcct gccttatgga gaaaaggaa  caggtgaata  185640
gagggtaaga gaaagtcata gagagatttc tgtttttga  ggcctgcttc taatgtctaa  185700
agcaccccag cattataata aaagactgta ataagagcta aggaagttat gagccaggaa  185760
ctgtggacaa agtaatatca caccctcta  tttttttttt ttttttagtt tacttactgt  185820
attatttatt tccatgattt ctgtttggta cttttttaata ttttctatct ttttgttgaa  185880
atctcacttt gttcatgcat tgctcacata aactcagtga gcatctttat ggctgttatt  185940
tttaattctc tgtgaaatca gttacctcca tttcattagg gtcagtttat agaggattta  186000
tctagttctt ttgtttgaaa tatattttcc tatttcttta ttttccttga ctacctagag  186060
ctttctttaa attatatgaa atagccatct ctcccagtct tgtcaaactg gctttgtgta  186120
gcagaggtac ctcaccaatc aacttgacca gagatttgtg gtgcctcttt tttttttttt  186180
ttttttttt  tgagacagag tttcactctt gttgcctagg ctggagtgca atggtgccat  186240
tcagctcacc ccaacctcca cgtcccgggt tcaagtgatt cccctgtccc ctgtctcagc  186300
ctcccgagta gctgggatta caggcatgca ccaacacgcc cggctaattt tgtatttttt  186360
ttagtagaga tgggggtttct ccatgttggt caggctggtg tcgagctccc gacctcaggt  186420
gatccgtctg cctcgacctc ccaaagtgct gggattatag atgagagcca ccgcgcccgg  186480
cctggggtgc ctcttaaact tttgtgctta ttcaaaccac cagttttgtt cttagtggcc  186540
ctcggtagga atgtcccaag tcctaagtta gtgaccaagg tagagaaacc tgtccctcaa  186600
gaagcagcta gaaatattgg ggctctagat gagtggtcca tcttcctctc tcctcaggga  186660
taagctggga gctggacttt ataccccact cactctgcag tccagataga ggatctgtgc  186720
caaatgcttg tgctctattt cagacaatgc tctctttaaa catttacttt gctctctcaa  186780
atggcaggtc tcattagctg tcctggataa gtgaattagc tggaagcttg gttatgtttc  186840
tggagtgagg agctgcagga agtgcccctca tgcctgttca gactcccgga gttctactaa  186900
ttgcctgctc catcagctcc ctgatgcagg ctaattaata gcttaatcca cggacagcag  186960
```

```
ctaggaaagt cagaatatta tgtatgcagt ctaactccgt ccagggagaa actgagagct 187020
gggtgttttt gcttgctcac tcttcactga gcttggggaa ctagctgctg gtagtgcaca 187080
tgagctcatt taaaaccact tctttgttcc ttgtggtctt gggggacaca taaatgccag 187140
tcccccatag ctcccagagc taggtgattt cagagccagt ctctcaggtg ggagctgtaa 187200
aagttggggt gctcaatgta tggacaaact ccttccagga gagattagat gcttgatttt 187260
atcattggat tgagctgggg gagaaggcac aggaagtgcc cacacactag tgcccacata 187320
catacccttt caagctccca gaggtcttac taattacctg ccccactggc tcttagtcca 187380
cttagtaatg ctataaggaa tacctgttgc tgggtaattt atgaggaaga gaggtttatt 187440
tggttcatgg ttctgcaggc tgtacaggaa gcatgatgct agcatctgct tccagtgagg 187500
gcttcaggct gtttccactc atggtagaag gttaagggga gttggcatgt agaaatcaca 187560
tggcaagaga tgaggcaaga aagaaagagg agaaggtgcc aggctctttt caacaatcgg 187620
ttctctcgta gaaactaaga ctgagaactt aaccactgcc ctgacaaggg caccaagcca 187680
taaatgagag atcattctta tgacccagac acctcccaca aggtccacct cccacactgg 187740
ggatcaaatt tcaacatgaa gctttctggg gccaaacaaa ctgcatcaaa atcgggctcc 187800
cagttttaga ctatgtagaa ctttaatcct tgggcagcag ctgggaaagt gcaataaaac 187860
ccctaccaga gagaaactag gagttgggca atatcgcctg ttcactctgt actaagcctg 187920
agggaattgg ggtaggaagt tcttgcacac ctgtttaaaa ttgccacctt gttctctgtg 187980
gtccagagat aattgcaaat gctgagccta tctgcttcca gagctaggtg aattggtgat 188040
tatggtttgg ctctgtgtcc ccacccaaag attgatcatg gggacggttt cttccaagca 188100
ttctcatgat agtgagtgag ctctcacaag agctgatgaa gttttaaagg tgtttggcag 188160
ttcccccttt gctcactttc cctctctcct gccaccatgt aagatttgcc ttgcttcccc 188220
ttcaccttcc accatgatta taagtttcct gagccctccc cagccatgtg aactgtgag 188280 tcaattaaac ctctttcctt tttaagttac ccagtctcag gtagtttctt tctagcaggg 188340
tgaaaacaga ataatataag gagcaagtcc ctcagggagg agctgtaaaa gttgaggtgc 188400
tatatgtgtg gtcccaaccc tttaacttct aagaaggtaa agctaggagt tgggtttcct 188460
tcctgattac aaagtgatgt gcctgggtgg tgctattggt gtgaattaac caatttctta 188520
aacatcaact aggtgttcca aactgtgcta agggctaggg aaaaggcttt gttatcctta 188580
ttctgagaga gcttatagtc tgattaggaa taagaaaact gacacaaaat aacagcaaat 188640
aacaaggcaa cataatcagt tgctacatgt tatggtggta tataatgat ggtagaattt 188700 agaaaactga aggggacag gatagacaag agtggtcagg aaggctgcat ggaagagaag 188760
gaacttgatt tgggatagaa gaaggggctg ggatttggga agacaaaaca aaagaagagg 188820
gccattccag tatccaagta atgacagata gaggcacagg gcatgtatta acacgagaat 188880
agcagaagtt tgatgttggt tagaacttac taccaacttc ttacagaact ttcctctaag 188940
aattatgagt ttgaaaacat tcaacacctc aatctacttt caagatttcc tggcaaagtg 189000
aaggaagcaa ataccttat tattttacaa ctgaagttac ctgttttgtc agttatgatc 189060
taggctgatt ctaactacct atgggcaacc tagaacagtc aaaagagcta ggaattcatt 189120
caaaagacca aaatctgcat tgtctggtag tgtgagcatg agcaaatcac ttcatctcct 189180
tgagccccag ttttctcatc taggaatgaa aagtagagcc ttatctatct gaccaggtta 189240
ttatgctatt aagttatata agtaaatgtg aaaattcttc ttaaacaata aaacaatata 189300
```

```
aattttagtt ggtacttttg ttaacatcta cactagacca cgtttatata ggtaatttaa    189360
aaataaaaaa gaatggggaa ttcattctta tgtcatggat ttatattttt tttgtagtac    189420
aaagttaatc gctcagcagt gtttgttaca tttcaagtag caaccatcat attgccatga    189480
aatttattta gtaacccta actactttt ttaatgaa atagcataga atgaaagtat    189540
agtgtatatt gtactttta gggcagtaga ttatatcatt tgtcataaag atgagtgtcg    189600
tttagtgaca cacaaaggca taagtgacat acacactggt caaaatgtaa aatatatttc    189660
tttttgtgga ttgttgtcaa agaagattga aagacactaa ttaataatat agtatttcaa    189720
atataaaatc ctcagtcttc atattttgaa ccctcaaatt aaactaacca aaagataaa    189780 tttcagagaa aagttatttt atgtaaagaa agtgagattt tgatgaaatg agacatgcta    189840
ccacatattc tttattttct tcttatgtct cttgctgaaa cccaaattct gtcttcactt    189900
ctgctgccca agtatacaaa gcaaagggat tttttgtgtg tgtttccatc aaaagctaca    189960
tgcctagaaa ctcattgtac tctattttt ctggtagctc ttgagttgtt tattttaact    190020
atcaatcaat attatataat ttaaaaataa aaacttaatt tgtgacaaag taagttttca    190080
gtctgggttc aggaaagaaa gggatggcat atgcaaaaat gatgtaacca ggaagaatgc    190140
aataatatgt ctatgtacaa gaggggtgat agaattaagg aaaccaacca aagatggtga    190200
agaacccaga gctaagaaaa gggtactagc tcccaggcct gaaaggtcac agtgttctag    190260
gttccagaag tgacactgag cagtgggaga ggagcaatat tactagtgcc atcatggaa    190320 accagtcttt tcaggaaaga gagaggcatg gaggggacag gtgccaatgg ctgaacccaa    190380
tgaagaccaa gggttctggg caatgtcatc tgtaatggcc aacttcctgg ggcacagagc    190440
agggaagacg agagtggaaa atgagtgtgg agcaacaaat ggggagtaac cagcaaccta    190500
ttatatgaat gatcatttt catgtcagat ggtggcatat agcttttcta ctcaaattca    190560
gtttccttcc tctgtttgct aactggccta gaccaatcct gatctagccc atggtagttt    190620
actttggttc ctagctgttg ggtagccaac cagtggtgtc ttcctgcagg aacttcttag    190680
aagggccaaa gataaaggat gaagtgtcct cattgatttc atagacacaa ccagttctag    190740
atcactggtt caaagagggt aataaaattag taaagtggga gaacacgaaa ttaggaagat    190800
tcatttctgc tttattgtga actgggtcaa tttttgcttt cttaatatta atcttgaaaa    190860
agatatcctt tgaaatctca aaatcctttt ctgtaattta aaaacaacct taccatctgt    190920
gtcctctgtc atatggtaca atattcaaga gggtgaaata atggtccagt gactaagaaa    190980
aaccttaaag gataaattgg ccttagtgac tgtcactaaa atgtaaacat ggctttaaaa    191040
agtaaatcag gaggcatgaa agggccttga cagctaaggc tctcaggaag ggtctagaaa    191100
gacatgaagc acaattttat aagtgtgata taggagttac tcttcttttt ttattcatgt    191160
gtcatagaag ggaaaggaaa tttctaaagg agtaagacca gccagatatc acaagaatat    191220
acaggaatgt aaggatagca tgttcaaggg caacatgagg agtcaaagaa aatgtcctgg    191280
atgccaagac tagctgtgtt cttgcagctg ctggctcctc cttggcaaac acaccattgg    191340
caatgaactg atctgatgtg aaccctcta agtccttgag actctctttt tattgcaaag    191400
cttgccagcc tctttaccca gtacatgtac tccactctaa gaagaaaaaa caaaactaag    191460
tgactgctaa gctcatggac aatgttttg ggtctctcca gcagccagct agtggctgac    191520
taggtaaaat catttatttt tctcaagatg ttgtgattct gggaatgcag ggtttggctg    191580
ccatgttagc ctggattttc tgagatgcat ccctgcaaga gattcactgg gaaattagat    191640
gtgcaagaga tttatctggg gaaatgccta tgagggaaaa tggagaagga gctgcagaag    191700
```

```
gctggaagag atgaccactg cagtacaggt ctaatcccag tggaaaaaaa aaaaggagag   191760
aaggaatgag aaaagggaaa gagagaagga gggaagaaag gaaagaggta gggagggagg   191820
gaaagtctta gacatcagtg cagtgccaag aaagttttgg caaggctgat ggggagtctt   191880
caaaccaaag tcacttgaaa gaggaatccc ctcatcatcc ctctaggaat gggcctgcct   191940
tggtgtcctt gtcatgcaaa gtcactggct gggtggattt cagagcatag cagctgaggg   192000
cataggccag ttacactctg ccataggagg cttgagagat gcattttcat agctgccaca   192060
tttgccactg aaaccttctg ggagtgatgg gttgtgctgg aagaatttga agatactatc   192120
ttatgctcca gataaagaaa tgcattgatg aaggcccttc actattagat ttattttgt    192180 gtgtcccaac tattatataa attccccctat caaggaattt tcagtgtttt ctccttgccc   192240
ttagatatgt gatcttatat cccaggtttg ctgagacatt cctcttacag atagttctac   192300
tggctcatga gtgtaatgtg tctaaatgta tggttggaaa aatgtggtta ttagatctaa   192360
attttaagtc caaatttcct tagcctgaag tttagagtct tccacagtct agtcccaacc   192420 acttttttcca accttaatta ccattgcact ttatcctgta tttcaattca tttgaaatat   192480
ttgctccttt ctaaattact cttgcttacc caccactatc tctttgttca tactgttctc   192540
ttcaactaag gttaattaat caacatgtat ttattgcccc cttcccatgg gccaagccct   192600
gtgcttagaa ctgtatgtta ggggacaaaa cgcacatggt ttctgtcttc ttagagtttg   192660
aatttagtag aagaggaaca gacaaataca caggtcaatg gacagtgcat gcttacaaat   192720
catgtgacag tgtcaaaagt aaacaaagag ggttccctga cagagaatta gaggaaggtt   192780
ttattttaga tagagctatc aggaaagaaa tggcatttca gctggaactt gaatgataaa   192840
gggaatgtag ttactaagga cttaagtcct gcaggtacca gttccatcat cttcaagata   192900
ttgccatgat cttcacaaaa tctttactga ctcatcattg gactctcaac caattttagc   192960
cctgtgctat ctgcatcttt tatatcacag aaagtgttga agttcatact atatactaaa   193020
tgtgtttgtc tccaatcaga ctataagatt gtggaatgtt agacccatgt gtgatgtatg   193080
cctttgtatc ctatcagatt atatgatttt ggaaggttag agctatgtct gtatccagca   193140
taatatttat ctctgtatct gcatgatact taggataata gtatgtggcc acatccaaca   193200
aatacttgtt gaatgaataa acagtattcc actctctgca aatttggtct ttctgacatt   193260
tgtctgaatt atagaaggag aaggaggctt tacataatag ttgaaaatta ctgttcatgt   193320
aatacagagt tctgaacttc aaccagaagc aagtctacag cagatgaaaa catttgtaat   193380
gagggaatta gctgtggata actttcggat aggatgttat aagtttagca tttgtattaa   193440
aatccattat tatatgcata attaagtttt aggaagaaaa tctggctgaa tagtaaacaa   193500
ttactatttt caaacagttc ttcagcagtt agttaccact ggcttctaga atttaactgt   193560 tgttttttt  aatatatcaa actagcatgt gggttgagac acaacatcac attacaaatg   193620
ggtagtccct tcacttgtag atcaatcagt aataatatag atactgattt ttacagtttg   193680
taaaattatt gtcatttctt tctcttatta tctgtattct cagaaacaaa gagtataaac   193740
aaagagaaag ggcatgatgt atttttgata ggctaccatc tcaaattttc atttcaatgt   193800
ttatttggag aaacactttt atctaaaatg gaccttttcc attttacaat tgcacttgct   193860
ctcagaatga gaactgcacc ttccaggaga gatttcaatc tgactccaaa gccttgaccc   193920
tcacaaacag tgttgtttgt aatggcccct ggttagaaac tctcagccta acaagcatgc   193980
agcatagccc ctgaagtctc tcctcctatc tgcataaatt ggggatgtag aactcctgca   194040
```

```
tatccagcct cacttactca taaaatgctg ggaatcattc caaattgctc ttccagagga   194100
gggtttgttt ttaaaattat ttcagataga gatgtttcaa attctacata aatgcataat   194160
attatttctg attgtgcttt cttggtattt ctcttcctgt aacacctact tagccattct   194220
ccagggacca cttcaaggac ttttgtaatc catatagctt tcctaagctg ttctaacttt   194280
cagcaatccc aaccacatca ctgaccgagt tgtaatgac tcaccagaca atgtgttggg   194340
tcctctagta atactttgtt aattccaagt tatccttgct gctgttgttt ctccgtgtgt   194400
gtttctatct gcgctctcca gttaagctgt aatcaactta accactgggc tttgtcttat   194460
actctacttc tcacaaccct tgcctcttaa attggttaat gtatgtttga tgactaattg   194520
tacacataat agctacttga taaatgttct taagaaaggg acaaattaag tattttccct   194580
gataatcctc tataccaggc atcgctgtgg aaagctgcac agttgggaaa gcgtcatttc   194640
aaaaacagga aaaatcacct gtaaattatt tcagggattt gactttgaca ttatgttgac   194700 ataaagagg cttaagaaca gctattagaa aatagaaaca gataaatgaa tgagtgaatg   194760
gcatacctaa atggcatgaa atgtgaaaat gatacaaaat gttaaggtaa tccttttttc   194820
ttctctaatt aatctccact gggtatgggg aatagggaac aactggggta ttcgtaacag   194880
gcaaacattc ctgattcttg ccctactaaa ggtagggaca ttaggagaaa ggatcatcta   194940
cttggaaaat aaactggcat tgctaagtct aaatgattga gtcaagtgca aattttatag   195000
gccaaataga atttcacaa gtccattgac tgttgaaaac tacttgtacc ctggctcaaa   195060
ggacattttc ttgctgtctg tagtaagcgg tctgtaaact gtgtttagga cctgaaccga   195120
atgctggcct ttcacttctc aaactatagc ttagtaatcc cagctcagaa gtccctccat   195180
acacaattta gtaaaattaa catcagagca taaccatgct tgttccctc cagaagtaaa   195240 atgtgaagtt tcttcccatt ggaagtctat ttattattag tttcagatgt tgtgacaccg   195300
ttttcatcca aatgttagag aacagaaaga agcctttttt aaaagcgtaa ctttcattat   195360
tcatctaggt tttttcagg gtccttgaga atgctaaga ttatgccttg tgtttgaaga   195420
gtagaaaagg aaaagggag gaaaaccacc tagagaagtg cttctcaaac tttaaggcac   195480
acatgaatca cctggggacc ttgcagattc tgattctgaa ggtcagaggt ggggcctgac   195540
atcctgcatt tctaacgagc ttccagggga tgctgatgct gctggcccac agaccatact   195600
acctagagca gcaagcttta taggccatag aggacatttt tttttttttt tttttttttt   195660
ttttttttgc atggagcaca gattactgct ctactctagg ttacaattcc aaggaaataa   195720
tgactaaaga aaaatactgc tgtttcaaca tttctgagtc atttagtaag aatgaaggt   195780 taacattagc aatttaacat tcaaatgtg gtgggagtat ttattgatgt actaatttgc   195840 atttgttcc tgccaaatct ttttactctg ttggctccag ggagtttgaa agtctaggac   195900
agaatttttc ttcctaggtt tgtttacata ttgtggaaaa gaagtgagca tctttggagt   195960
taaggagagt taagacccaa ggagaagaaa gaaaaagact atgaaagatt tttaaaatgt   196020
ttatccctgt gtaagatctc caaagcccct cccttgaccc agtagtagca aatggagcca   196080
cagtgatggc tgaaattgaa tatcccacta acttggtaaa agttgggcag gctcccagtc   196140
agacttaaat catttttagag aagtacaata atgtggcatt ccttgcaccc tggtgatatg   196200
cagaaaatac atacctgctt ccgacgaaat ttaaacatgg actgttaaca agaatgtacc   196260
cttaaagttt tgtaaactct acagcaaaga aaaaaaaaac tgctacagaa aaaataagga   196320
ttttttttct agctttacca gcgacctata cttcatttc ttcatgttac taattacaga   196380
aactttcagc agaaatgtat cactcttggg catcagttag ttctaaacat tttagctctt   196440
```

```
aggagcctct gatgacatct gttctgttgt tagttttgct ccctgactag attgtaactt  196500
ctaagctcag gaatcatgtc tgcaactact tttctttagt cctaacctaa ccaagagcta  196560
ggcatttagg aaatgctcac tataaatgta ttgacaaatg attatgtata attagctctt  196620
catcacaata tttttcatca tcaagaaata gatttaaagg agatattttc aaacagtatg  196680
gatgtatcat cccccttacct ttatgtatgt gtctggttgt gaatagtcag cacatattat  196740
ggttaaactc aagaaacaag ggaggttatt ttctaagcct gcatcatagc agtagaaatt  196800
tggaaaaaaa caaaaaacaa aaaaaaaaaa acatagaatt aattgagttg taatcaaaga  196860
aaattatgtg actataaatt gtaatatttc taaaatatac ccacatatgc caatctattg  196920
taagaaaatg ttcgcagagg gaaacaatg gaaattccta gaagctttag atagattcta  196980
atgattggaa ataagtatta caaatggtcc acattttaat gtgacttcta gaattttta  197040 gaagtcatag tatcctttca cgctcttatg ctgcttgctt acaacataca cttgggtcac  197100
gtttttctgt taggaaatat catactaatg atttgtgatc atatttacca cttggggatc  197160
ttggtggcca tgataaggaa tttggacttt attctgatta catgggaagc cactagagaa  197220
ttttagccag tgaggtagca tgatcttact tatgccttaa aaaggttaat tgttttggta  197280
gttaattgaa ggaaggcaaa agtggaagta ggaagtctag ttaggaaact atttgattgt  197340
tcggaaaaaa ggtgctggat gcatgggcta taataatagc aaaggagatg gagagaagtg  197400
aatggattga gatggaactg aaagaacttg ttgatggtta aatgagttgg aaggagttag  197460
agaaagcaaa gtgacaaaga tgactcagaa gtgtttggct taagtacctg agtggatggt  197520
gaaacaattt tcagacatag agaagaattt aggaagaaca gttttttca gacattgctc  197580 gagagttctg tgttaggatt gagataccta ttagatacca actgaagata ctgaagaggc  197640
tgagtagagt ctgaagttca atggagaggc tcagactaag atagaaattt ggaaccatca  197700
atgtgtagat gatatttaaa gccatgagac tcgatgagat tcccctttgca ggggaaaaaa  197760 aaaaaaaagc tagaatattg gagggaagag ttttgtaaca ggacaatatt tatgggtcgg  197820
gcagaggaaa agaagccagt aaaggagacc aagaaagaac agtcggtgag ctagaaggga  197880
caccaagtgg ctcaggcatc ctcaaagcta agcaaagagc atattttaa aagacagtaa  197940 tgtactgggt caaatgcctc tgagaagtta agtaatataa gaaataagaa gggactattg  198000
aatttgatat gaacaggttt agtggaatgg aaggattaga agtaaaacca aagtagattc  198060
agaagaggag aaattaggaa gtagagacag ccattcagac aaggacttaa aagatccagg  198120
aatgaaaagg aaattcctgg gagcgcaacc cctaagaagc caaaaataga gtatgctttc  198180
catgtaggtt tttaattctt ttttggtggt gttctttaga aagagaaatg tctgttggga  198240
ttattgtttg aaatggtgtt gggggcccaa ccatttctgg cttctataga tccccttttt  198300
gtacatgctc attcccttaa aaaaaaaaaa gaagaagaag actagatttt ctaatttagg  198360
gcaaggggct aatagcaaac caaactcatt tgtaatctaa atggtcacat attatttttgg  198420 ttgctcttca gtggcactag ctgctgctag gaagttcatt ttacacacac acacacacac  198480
acacacacac acacacacac acagcatttg ctgcagatcc taaacttgaa gccctggatc  198540
ttccttacat catttacccca gaagtatctt tgtcaacctt cttaacttac atccaccaga  198600
aagtagaaca aggcagaagt tgtgtgggag ttctgttcct ccccatttcc cccctcacct  198660
gctggcgtca gcacaataaa tactgtgttc agaacttggc taactgcttc ttttcccaca  198720
ttcgatcagg gaatacttaa agccatacag tgtccttgtt ctgccaaaaa gcatatgggg  198780
```

```
caggttgccc cttcaggctg acacaaagac acactgtgca agacatctat ggccagtgga   198840
gtggccgtgt atgggttatc aatgagactt ttgactttt tctttatgtc atattgtcat   198900
cacattaaat agaattcaaa caaggaaaca aaatttatat tctagacttt taaggcattg   198960
cctgccctat agctatgaaa cttttctttt tcatacctgg tataattttc cactttaaac   199020
aatgttgtgt gatttgatta ccgttttgac tctcatttaa ttgtccattt taaaaatttt   199080
aactgaagtt agatttagat ttaaagttca atacccataa aggatacttc tcaatagagc   199140
cgagaacttc agaaggcaca acaaaaaag ggcaaagttc aaaaaactaa gcatcaggta    199200
gctactttt actgcccagg gacatgtcta ggtaaactgt caccatatcc atctacattt    199260
gcttgctagt agagcttcca ttttctactg caaaatagtt tctggaacca cttccatgtt   199320
ggccaaaaga gagtgtcaac aattcctttc caaaattgac ctttagaaag tgaatctaaa   199380
atgtttgatt caagtatgtg aggggagctg catcaaagtt ttcatttta ctacatacaa    199440
aagtgacaga taaatccgta aaatgtatgc atttttctgc taagactgct aattaattta   199500
aaaagagatt gttagaataa aaggtcagag agtaaacata ttacagatat ttattgagag   199560
cctgctgtgt gcagagttgg aaaaaataaa atgaggttgc tcctttcaac agacttacaa   199620
tctaattgag ggagcgacag cataaatgta tgcaaagcaa ataatgcaag atacagcata   199680
agacataatt aactatcaga tgagtgacat atataataaa taccattaat tcacaggcaa   199740
tcgtaatcag aagcacttaa cttactatgt gccaggcatt ctgctcagta cttcacatac   199800
attatttcat ttttttgaaa tattatttct actttataga tgggaattgg ctctgatctt   199860
cccctattc tggagaaagc aaggataatg gtgtaaggta gacaaagacc caagcagaca    199920
tgttggtctg gggcaaaggt ccattaagg gaatggagag aaatgaaccc tggggccagc    199980
attagtctgt ttacaaccat atcccagtgc ctagtatagt gccttgcaca taataagtgc   200040
tcaataatat gtcttgaaaa aacaaatggc cctctggtct gtgcctgtaa tccagatcaa   200100
gtaccatgga ataaagttaa ttagtgaatt aaagccacat accacatagc ttaaggaccc   200160
atccccaaga cctcccaatt cccaactatg acaataaagg attgcagtgg aaaagataca   200220
tcataagggg aatagcaata gcaattccag ctcactgggg tctatttcat ggaatctgac   200280
atggtgaaca gttcataagt ttatttccag gctgcaagac cctgcaacat ctggcctctt   200340
gcacctccac aacctcaaat ccttctattc ttctctcact ctctctactc ctgccacaca   200400
tacctccctt ctactcctca aacccatttc agggcctata ttcttgcttc atattgcctg   200460
gaatgttctt ccacaaaaca tctgtgtggc tcattaccat accttcagat ctataacagc   200520
cactctcccc acatcttccc agctgcctga cattataata cacatctatt tccttatgtg   200580
ttcatcccg tacacactag aacatgggcc caggaaggca gaattccatc tgctgttttt    200640
gccattgaat gcccagcaac taggacagtg cctggcacat tgtaagtact cacacacagc   200700
aactctaact caggattact ttttctagct ctgaaatacc tacttccaag agaacgaaat   200760
ttattcaaga aatgttggat ggaaattgaa gagtgagctt ggaaacgaga cacagagtgg   200820
caggagccca gaccaacctg tttatgaaag atgcctttgc ccatagaggg aaaaatacac   200880
cttaaaacct ctgccaaagt atatgctttc ttaggacacc tctgacatgc tgaattgcac   200940
ctggtctgaa caagatctat gaatttgcca aaacaactaa ttcctgtgat ttaagagtca   201000
ctactaccag tatcagccta gtaaacaagt accagcaac gagcaccaca tatgtcagta    201060
tccaaagaca aacatgctgc tgcatgcaaa accagacaaa tgcattcacg cgggtgacag   201120
tgagtggaag aaattaatct tattttatt atttttccc ttatcaaaca ctagcaaggg    201180
```

```
actagatgtc ataaatctag ttaaaatatg ttgactttgc ctcaaatttg agcattcatg   201240
gttccaaaag gacacttgtt ataggatctg atgatgtact ttagaatctt cttttgtgca   201300
aattgagact tcagagaact caaaatatat ggtaaattca agtaatatt ataagtaaaa    201360
tcataatgcc tcacaacatt ttttgaaagt taaatattta gtaattttac aaatatgtat   201420
tgagcactcc ctatatttaa ggaactatgc taatgctgtg atggatcaaa aggagaataa   201480
gccatgatcc ttaccttcag acttcaagct tattattcat tgggcagtta gataactaac   201540
atatcagaca tggaataata agtgccattg tccagatatt aaaaacaaaa ttggtgttgt   201600
ggaagcaaaa agaatgtaga gatggatccc aactaggaga agaaaaatt gcttcctaaa    201660
gaagacacag attgaccatg aaaggtggat ggttctacac aggactagaa ggtaggaatt   201720
cttcatttgt tggacttgct aatttttttt ggtgtaaata tacccactgt tgttgattta   201780
aagttgataa cgtgatgcaa ctgaacacag aactgggaag agaaggtggc tccagcacgc   201840
tacctatgag tcaccagctg agctccagac ttaattaaat caacctcctc actactattt   201900
tgaatgagtg aattcacaag tcttaaaaag atctatgata acattataag ggaagagata   201960
gtcacttctg tcattctccc ttacatctcc atctcacctt ccaatattct gtttgaatat   202020
ccttccaatt tcagtcatat gttcctggct ggcctaccta ggattaatat tggcccagtg   202080
ccaaaatgtg attctattta ttccttttag cattgctgtg attaatctgc gctcctgtta   202140
tcccatggca tagcaaactc tcttactgat tatggcctgg tattgacacc tctgctgttc   202200
tccataacga aaagcagctt ttggggtggc tagctgggca ggatgttttg ctgctcttgt   202260
aacagtagga aggaaaagct ggaggaatta ctgggaagct ttgcagaagg aagatacagg   202320
ccagctgaga gccagcattc atattgcctg ttcctttcag tattctttgt gaaaacacca   202380
ccaccaatgt gttccctgga cgtcactact gcacctttaa ctggccttat tatgctaggg   202440
actgcatttg aaaagccaaa ctctagtatc tgtctgtaat tgcaagcgga tatctcagca   202500
catgcacaag cttatgtcag gaggatgttt atgaaaaact caccaagcag aacactgcta   202560
gacaggaaat aaatatgtga agcttgaagt tgttaggaaa cttccacatt tgtccctcta   202620
agccagagat aggacctgtg agaaaagaag gtctttatca ttgcgcattg attcttgctg   202680
aaccctgct attctcaaaa tacatttaca gcaaaatgtg gctactgcag atgtatttaa    202740
acatgtgctt ttttaaatga cactggttta tcttccaagt ttgttatcta ctatttact    202800
gtaaagcatt aaaaagtgtt tgaaaccacc agcaccattt cacagttcct gttttatttg   202860
tttaaattct ctagctcatg taatatgctg tatgatttac tgttcaagta gagaagaaat   202920
acactccctc atggagatgt ggggaggtaa tactgtctct tggaagggct cagagatttc   202980
ctgtttagat tacacaggct tctttagagc tgccaagagt cataacatgt acgagataat   203040
acactttggt tcaggaaaaa ctatggatag gaatgtaatt aattcactga gccacaaaag   203100
atattccagc ttagaaatgt cactgcactc aggcctggtg gactcagtat gccaaggggt   203160
agccatgacc aaaaagagga ttgctgcctg aggacccact gagtagtatc caaccacaga   203220
gcaaaaggag ggggcctggc tgctaaggac atcacgtc tcacctgctt ctttgagaat      203280
tgatccctga agggtatttc tgcccaaagc ctcagcaacc tggcttcatc aatataactt   203340
tgtgatgctt gtgacattga gatcaatcaa tcagcatgta ctttatcaag tgcctcctca   203400
tgagtaccaa ttgtggcaca tagtggggaa accctagagg cagagccctg cagaggatat   203460
ggtgattctg accagagcaa gaaggtatag tgaaaagttt cctaaatata ttttgtgtct   203520
```

```
tgtcataaga atcacctggc agggaggggt atggaagggc aaggtaagca tacacattcc    203580 caggacccttt ccaaaatgta gagtgaccag ggacttagag attcagactc tatcaatctg   203640
gggcagggcc ctagacttgg tatatttaat aactgctgtg tgaggcccctt tacatgcatg   203700 acctcctgta attgtatagc ttggttgctg tatatggtac tatgtttact tgtgtttgca    203760
ctgtctattc aggggtgttt ctaaatgcca ttgctacaca actggtgaat tatgattctt    203820
gccagaacat tgattctcct actcttgctt ccttaatgac acactagaga actgggattg    203880
gctgcattta gtctcaggat gaatcattgc cataagtaga tttccatccc ctactccacc    203940
aactcatttg ccaaacaccc ttaaagaaca gaacccactg cctacatgca gcctgcacca    204000
ggagggccta aatggtctag ctgggtttat gacaacatcc cgtcttcaca tcagcaaaac    204060
cctaagtgca caaagtctaa tgtaaacaca atgtcaagtt ctccatagga aaagacatgt    204120
ccctgctgtc aaggtagtga ctagcaataa taataatgac aaaaacaata acaatgataa    204180
gcatatataa cacttactta tcactaatta tattgtaaat gaaatgattt gcatgtacta    204240
actgatttaa atcttatata tatatagata cttttactct ctcaattta aacacagaga     204300 aaccaagacc tagatacgtg tttctgttga gaagttgagt acaaggttga gtgtaagtag    204360
ggaaagttca actgcagtca gttctagtct tggtaagtac actgtgaggc gctccacccc    204420
aagcatagca aattaatggt tccccagtgt ttgcagaatc aaaattaagt tctttggcta    204480 ggttctcct gatgtgcccc tgcttcttcc ctaattcaac acatccccag ctccatccat     204540
gcattcccaa cacatcacag ctctttacat gcccaggctg tgtcttctgc acctttgtac    204600
cttctgcacc tttgtttcct tggccccaac tgcccttct tttcctccac attacccttt     204660
atcccaaatt tagcacctgt ctcaaggagt caccttccca aggaagtttc tccaaatttg    204720
ttaacagata ttccattgtt cctccaatgc ttgaccactc ttcctttata gatccctgcc    204780
tagaaaaatg tgggctcact gaggccaggg gctgcagcta gtttatttta taacccagca    204840 tttaaagtg cctatttatt gatttgttgg gaatagttaa taaatggagt ccttgcagat     204900
cataaccaag accacagttc gtaatggttt cattaacttt gttactattg gatgtgattc    204960
tctgcttatg gtcttccttt acttgttttt cccttactgc tcagcaccct tagacattag    205020
gtacatggct ctgatgctaa ttaaaattga tgactgagaa tgacacttcc atttgctaag    205080
ccagcgcagt tttgttcatt gtgctttact ttttaaccag caccccttagc ataaatctgt   205140 agtctttcca tgagggtacc atttgttcct tttatgtctc gattcattac atattttcag   205200
gactgttagc tgactaagac ttttgctttt gtgaaaatgt caccaaatgc acgataaagg    205260
caaagtcaca agatgtctgt ttgcaaaaag aattaaatgc tggtttgtga agattcaagg    205320
ctggccaggg ctccccaagc atttccaggc cagagctttg gctctgcact ctccttagga    205380
tctcataact gaccccaca ttccatttct gccatcgtgg aaaaatttgt caactttact     205440
gctgatgtta ggcctggaaa ttgtcatcca ttagttttct cagattcaag ctgaaaattg    205500
agacaaactt cctacgtaat tttgaccaaa ataacacata tgtttatgtg ctatcccatg    205560
attaacatat ttttaaaacc actttattga ggtatggttg gcatacaaaa atctgtgcat    205620
atttaatgta tacagcttca tgaatttgga gataagtata catccatgaa attattactg   205680
catgtatgcc ataaacctat cacctacaaa aatttccttt cactttgtta ttattttgat   205740
taacttaatt ttttttcttcc tttgaactat caaaactttc tcaagtaata catagttgtc   205800
agttatacaa acttactgaa ccttgaccaa aggtcctctt ttagtgctca tcttagagaa    205860
agaattaatg aaacaaagtg ttctctgatt tgtagcaaag atctgtgatg gtggtgggaa    205920
```

```
tggttctaga aaataatggt aataataaaa acttagagta tcaaagcagc aagtagattt   205980
gaaggaattg ttacaatgca atttttgcttt cccgccactt taaaatcaag gtgtagtact   206040
ttatttactt taggaaaatg tttgcttttt gtcataattc cttattgcat atgagagtaa   206100
atgatctata gatgaagata ataataaaat ttagagagag aataaaaaag aaacactttc   206160
acagctgaaa ggctgcttcc cagttagcta actgggagga gttactgaaa aagtacattg   206220
aaaagcggct caggggcagg tgaattggac tcaccaggct ctgacattca gagagatggg   206280
aatgagtcag ctcactgtcc agcacatctt tattttattt ctctttcttg ttttatatca   206340
gaaatagatt tcttggcatt gttactgtgg gtttctatta aggactgaaa caaaagtatt   206400
aataatctga gagtatgtaa aaaaaaaatt catttttctcc tactatactc tcataacaca   206460
gaatattttg gtgaccagag atcaccaaaa tgtgtgtggt gtcaacgaaa agagtcaaac   206520
tctctaaaat atttgaagag attttttctg agccaaatgt gagtgaacat ggcctgtgac   206580
atagccctca ggaggtcctg agaacatgtg cccaaggtgg tcagggtaca gcttggtttt   206640
atatatttta gggaggcata agacatcaat caaatacatt taagaaatac gttgatttgg   206700
ttcagaaagg caggacaact caaatggggg gcttccaggc tataggtaaa tttaaacatt   206760
ttctggttga caattagttg agtttgtctg aagacctggg attaatggaa aggactattc   206820
aggttaagat atgtttctta ttggacctaa aactgtgcct ggctcttagt tgattactgc   206880
ctggatctgg gaaggaagga aggaaaacaa aggggggaagg ggattctcta tagaatgtgg   206940 attttttccca taagagactt tgtagggcaa tttcaaggca tggcaaggaa atatactttg   207000
gggctaatat tttttccttg tctcataatg ttatgccaga gtcatattga aaagcaagtc   207060
acaatataca aggtcaaata aaacccatcc tgatgagaac ccatggtttg tagggcatga   207120
ctccccagaa cccttaggta ggaatttggg caagataaaa aatcggaact tagtcctcgg   207180
tgggaatctc tccccacaca aattctccaa cagattcttc agtgggacac caactgggtg   207240
ttctcaaatt caattcaatt ctgacaatct acctatctac ctggaaatag catcagataa   207300
ccacaggttt acggctcatt ccaacaatac tgtcccccac ttcagatgcc aactgcaagt   207360
aataggttgt tacctatact tctagccagt cagctgtaaa ttggtgttcc cacaacctcc   207420
ccctccggtt tgataatttg agacagcttg cttacatgta ccagcttatt agaaaggata   207480
ttacaaagga cacagatgaa gagatggata gggtaaggta tgtgggttgg agttgcagag   207540
tttccatgac ctctctgagt gcagcatctt catgtgttca gctatccaga atctctcgga   207600
ttaagacatt ggccactggt gatcaaatta accttgagtc cctctcccct tcctgaggtt   207660
ggagagtggg gctgaagtgt ctcaacctct aatcaactct tggtctttcc tgtgaccatg   207720
ccccatcctg aggctctcca ggagccccca ggcatcagtc aactcattag catacgaaag   207780
acacttatca ctacagagat tcgaaggatt ttaggaactg tgtcaagaaa cggagacaag   207840
gtcaaatatg tatttcacaa tatccaccagt agtttcactg ggaggtaaaa ctcagtgttt   207900
actgtgggcc tgagccatgc tgaccctcta agaataactt agaggtaacg tgatcagatg   207960
tggggaattc tggagaaaca cctttcacca ccaagcccag acaagagatg catactttc   208020 tagctgggat gcttacaaag caacccactc taatacttca aggtagagtg acactacatt   208080
catcattttt cattttttcc tgtttttat gccatctact actaatgtca atcaaattac   208140
gactgtgttt atagtggatg aattatggac catctcacac cataaagttc tgtttctctc   208200
atgttgagct tttcacctcc cttcattccc tccctacttc caggatcatt cacatgttta   208260
```

```
tttctaaaaa taaactttttt ttactgaact ttttttcata ctgtttaaaa agaatttata    208320
tttctcttca ttcttacaga taagattcaa gtttaaactc aaataatgta ggaaatcttt    208380
ttttaaaaaa ttgttcccta ctgtgtctag gcgtgagacc aaaagtaatt aagaccaggt    208440
tttcatttgc tgtgatttgt gtgagttctt tttagaggtt aggtgcaatt ttaatttta    208500
aaaggggat tattatgaga ggagaaatca tactttatca tttgaaaatg atgccataac     208560
aggtgttagc agaaaaatca aactgtaaaa tattttaaag agatttattc tgagccaata    208620
taagtgactg tggccccatt gaaatgagcg agttccctga tccctctcac agagcttgcg    208680
acagggatgt ggctcacctg ttcagttgcc ccactgctca aaccctagg gggagaatac     208740
agacggtcag gtgcaaaggc tggggcaagt gccttggccc cttggcccct tagcccgag     208800
gtagtgtcta ggggtggggt gcctgcaacc ccagtgttac aaagttcttt cagctttgca    208860
gtccacggac agcttgagtg ttaatcagct caatggaccc tctgccttat agcaaaggca    208920
gagggccagt gtgacagctt tctgtatccc aagctcttgc ccagtgtcct agaaaaaca     208980
gatcatacag gggctcgaag gatgagtgca aggttttatt gagtagtgga ggtggctctc    209040
agcaagatgg atggggagtg ggaagtgggg atggagtggg aaggtgaact tcctctgaag    209100
tcgggcagcc cagtggctgg actcttctcc aacctccccc aggcaagctc ctctcagcgt    209160
ccagatgttc ctcttccctc tctctctctg ccgcatcatt tcaccatctg tctgctggtc    209220
agctggcttg ctggtgtgct ggtctgttgg tctgctggtc tgcttctgga acctcaggtt    209280
cagagtttat atgagtgcac gatagggggt gttttgggcc aaaaggtagc ttttggaca    209340
tgaaaacgga aatgcctgtt cccatttagg gctgcaggtc ttcaggcttg agggtggggc    209400
ctttgcccag gaactaccct cttctaccca gtgtttccct gtctcctgtc catatcacca    209460
gtattcacag tctcaaggag tcttgagaaa gtgtgcccaa ggccgtcaga ttcagtttgg    209520
ttctgtatgt ttcagggagg caggaattac aggcaaagac ataaatcagt acatggaagg    209580
tatacattgg ttcactctga aaaggcagga tgtcttgaag tggggacttg caggtcatag    209640
tttggttcag agattcttta atctgcagtt ggttaaagga acaaaactgt acagaagctt    209700
cgagttagca aaaagaaata tttaaattaa gataaggatg ctatgtcaga gtcagccaca    209760
aaatgacctg tttagcaaga ttaatggcct ataggtgtga cttaacccttt gccttgcatg   209820
gcctaaggtc ttgtttataa tttagtatct tattgcccaa agagtctatt tagtcagtct   209880
tatgatctct acttaacat taatgctggt cacttgtgcc taaactccaa aggggaggta    209940
tatccaacct gccttcccat tgtggccagg aaccttctc tggagtcccc ttggccaaga    210000
aggggtccat tcggttggtt tgggaagctg aggattttgt ttttagttta cacagggtca   210060
tatcagattg ttttgatggg gatgactaat ggttttcttc tctttctgtt tcagccacag   210120
cagctatcct tagcagagca ccctggagtc tgcaaagtgt taatccaggc ctaaagacaa    210180
gtaagaattt cagtccttt tcttccttca atgatatttt ccatgttta gtgtaattaa     210240
gctactatcc tttctctatt ttatttggga tggtagtaac tggaatagtg actgagttga    210300
aattttatag gcaagcaaaa cattttttaa ggatttattt tttaacttct gatatagttt    210360
ggatgtttgt cccttccaaa tctcatgtaa tccccaatgt tggaagtgga gactgggagg    210420
agatgtttgg gtcatgtggg cagattcctc atgaatggtt tagcaccctc ctctttgtgc    210480
tgtcctcacc atgagtgagt tctcatgaga tctggttgtt taaagtgtg tggcacctcc     210540
cccttcaatc tcttgctccc actctcgccc tgtgagacac ctgctccgct tcaccatgat    210600
tataggcttc ctgaggcttt caccagaagc agatgctaat acagcctgca gaactgtgag    210660
```

```
ccatttaaat cattttcttt tataaattac ccagcctcag gtactttttt atagcaatga   210720
aaacaaacta atacaacttc tgtgcaaggc tgctttttt tctattttt gcttgtgctt    210780
ggaggttaag taaggccaaa ttaatgaagg aggaaaaaag aggaaatgat acatcatgga  210840
tcaacaatta tttattgaat ttaggaaact gcctctttt ataaattctt tttaaaatta   210900
ttttcattat tatcttgaag tatttatcta aggtttacac tggtagaaag ttaaacttgt  210960
ctctccaacc aaattgcctt aagcttcaaa attatgcctt attgtaagct ctttcttaac  211020
cttaaaatga ctttacacat tccccgctgg tcctttgaca atctcctctt caaccacaag  211080
acagaacccc accatcaact ctgtggggaa gcgtctccaa attctctagt cctgaacaac  211140
attctgcctt ctctgcttcc atggaacttt gtcctttaca acatgatagc gtttgcctcc  211200
tgacatttta gtgtgtgtgt tagccctgca tatagaactc accagattgt gtggactgca  211260
tgaatgaatt aattctattg aactttaagg caaagcctaa actttatgct tcttctaaat  211320
cccttacatc tcctaaaaaa attctgatcc atagtagtag gtacttgttt aattaaattt  211380
tagggatgga tattttcat cagtggaagt atatgctaga gtccatatta tgcaataagg  211440
gaagggaaga cagtgtacct aaatcagtta agatattgct attcttgttg ttattctaga  211500
gtcacgaaat cataatttga attttatgac taaattgcag aattaatttc caatgtgaga  211560
ttttaacatt atttccttgg aggtgaccaa aaaggagagc tggtactgtt tttaacaact  211620
gtcattcaat tgtcagttgt gccagaccac aaatcctta tagccctcct gtttaagaag   211680
catctgacat gttaagctgc tccctaatta acacagaggt tgtaaaagaa gtggctgttt  211740
ggttctgttt gggtttccca gccagtatat tccaaagcct tttttcactc aacagatgag  211800
ttatgtgctt tatattctgt aaggaaatga gaagtaatca gttgaaaatg tgttactaat  211860
ggtacatgct tcacattgaa accatcctcc tgacacaaac ataatacttt gccctccact   211920
gtcccccaaa gtggcagtag gatttctcta agtaattttc tttacttata tgagtgcagg  211980
atagggggtg ttttgggcca aaaggtagct ttttggacat gaaaacggaa atgcctgttc  212040
ccatttaggg ctgcaggtct tcaggcttga gggtggggcc tttgcccagg aactaccctc  212100
ttctacccag tgtttccctg tctcctgtcc atatcaccag tattcacagt ctcaaggagt  212160
cttgagaaag tgtgcccaag gccgtcagat tcagtttggt tctgtatgtc acagggtcta  212220
agaagcgtaa acattgtgtc ttgttgaaat acagcctcta ggtatggagg atgtgttgaa  212280
caacttccta ccagtcattt ggcatatgtt gatttcctgt cttcatgata cgtaagacga  212340
ctagctaatt atcattcata tgtggtaagt cacatagata ctgacttccc ctatctttcc  212400
agctttttct tatcaaaagt cacctgctct ctgtcccagg aacgactggc taaagtaacc  212460
tatatcagtg tctgtaacag tgggcaccta tcatagtgca catgcttgaa catatcattg  212520
cctttttatca tcacgagcct cacatccaga tgtgacagac tcaagtgctc acatcacctc  212580
actctgtcac tgtatacatt gttaccgtgt cacaaatatt taacagtctg ctgtgtactc  212640
agtctttagc tgtgtgccct gagggagaca gagtaagata ctgccttgac atcaaggagc  212700
tcacattctc cctaaagaga taatttcaca tgaaaagtta tgtgtttaata tgaaaagtta  212760
gtgtttaaca tgaaatgtcc tgagaatata caattataat ttacacgttt cctgtgtgta  212820
cttttctaag ttctcagact caaaacaaag ccccatggaa gaaaaaatga aataaaaacc  212880
ctgtcaggac aaatcctagc cagaactgac caaacataaa aataaatgc cactgccctc   212940
tccaagctac ctttactta tacttgggtc caagaagccc aaacattgtg cctcattgaa   213000
```

```
atataacctc taggtatgga ggatgtgttg aacaacttcc taccagtcag tgcagtgcag   213060
tgaccattta gcagcatctc cctcctctct ccttccaccc cctgcccat  ctctccttcc   213120
ttgcatctat cttccctgc  caacaataat tttcttatgt tctaagtaaa tatctttagt   213180
gctctcccta ctacctaaac attaaacttc aaacctttcc caagaccctg aacacccacc   213240
ccagcttgta agttcaggct acttaccatt ccccaggcac actgtatttt ccctcctctg   213300
gtacactgct catgtcatcg aatctatctt cctcccaccc catcctggat tctgtaaata   213360
taaatcagtc ctgcccacct ttaagtttca gtcaaaacct gatactcatg gcctgaagca   213420
atccctccct tctccatgct ggtctgagag aggtcatgat atttcagtag ctctggagag   213480
acacatatgg tcaaaccaga ccagctaaaa ttaacccatg ctatgcacaa cctaaagaat   213540
cacctcttgc tgtaacctct ttcttctctt gctcaccaaa aactgtctgt cacatttgct   213600
aagtaagccc ttagggcttt gctgtgctgg caaaaggtct taatccatgt gaatgtgcat   213660
ttttgtgtta gtgagcacat gctaacatgc cttccacaga ttagtttctt aagaaacatt   213720
ttctggggga aaaagacct  gttttttggtt agtaaccccca aaaggacctt tcagttcaca   213780
tacgtggtag cagcatactc cacttatgca aaggtcagcc cagggtaaat atgggcaaaa   213840
acacagactt aggataagaa gaatgttaag ggagtttaca gtttaaagag atatccaaac   213900
aactttttta tattttaaag aagtaatgct ataattttac tacaaagaaa acttctttat   213960
atttctgggg agaagaatag gaagagttac aatctcctag agaaaagcaa aacattttta   214020
gtattcccaa ataagacagg cacctcaact agggtgctgt ggttgcacgt tctttgtagt   214080
ttttcaagaa ttttatttct ctgtcatgat tatttattgg cagaagattt gttgggccaa   214140
acatgtaaga ctttcttaaa cacatataga gaaaaaaatt agatgattgc acatctttct   214200
gagggagatt tttccctat  ttttaaagt  cattgctttt cactgaattt gtcttgtatt   214260
cctataaaag tgtaaatttt gtgattgata gcatttttac ctcaaaatga aatgaatatc   214320
caactggagc aagttttatt gactgcttat tggagcataa attagtctaa gttttcatga   214380
aaataggcat ttgaacatga gtattaatgg ctgagatcag aggcaagttt tgaaaggatt   214440
ccaaaatatt atcatattag ataggcaagc aaatgaattg cttgaatgct agaagttcac   214500
aaacattcaa acaattgtga gttacattaa cttcaataaa aacttttgca ggacaaaaat   214560
ttaatatagt aaacttcatc ttgccttgtcc aggtccgtat acattcttag ctggactctt   214620
gtcctagctt cctaattttt cttcctatct cctattttc  cctattccaa gccaccatac   214680
tctgttcttg attaattctt cctgcctacc tctgattcag tgattcatct gcccaatcat   214740
ctatagtagc tccaaactct tttctaaatt atgaataaac ttatctccct ggcattcaga   214800
aaattcaaca gcattcatct tacacacttt tctagcctta tctccctttt ctcttatgta   214860
ctcctatgtt tatattccct gcagtcttgc ttcattatat ccatttacaa tgacccttt    214920
accagtaatt tcctcttctt tcctctcagt ctgaaacaat ccttcataga ttttgtcctg   214980
tgagccatat ttcaaataca actttatcca caaagctttg cccagttccc acaagaggat   215040
tctgcttttg ctttagaatt gtagccttttt ttcctctct  cgcaaggaga gagagcgtag   215100
caccgcagtt taagtactca gcctctggag taagctttag tttaagaccc agttctactg   215160
cttacttcct gtatgatctt ctctaaattt tatgatctct ttgtcttttt ttttttcatct   215220
ctaaaataaa gatgctaata gtacctacct cataagatgg ttgtgagaat tataagtgtt   215280
gatatattta aagtagttag aatagtatct ggccctacag taagcttacg tggtatttat   215340
tgtattctct tatggctctt attttattcc aatgtgtatt aaattgaacc gtatgaaatt   215400
```

```
gcccatgtca actctatatt ggaccctaaa atcattatgt cttttggttc aaccaaatgt   215460 agtgctttt  gcaccccccc ttaataaatt gaactatctc taaagatagg gacaatatct   215520
tacacatcat tatatcctac agtacctgct acatacttga catatgctga gtatttcacg   215580
gatggttatt gaattttgca cacacacaca cacacacaca ctgcaaaaaa taaacagaag   215640
ccaagccctc cccagtatct taagtactct ttggctacca gggagtttac tccatgctgt   215700
tcagcagtca tttatgaaag gagagtgata aagatataga ggaggagaat tttatcttgt   215760
ctattgctga gtataaatac tatgcctttc cgaaaagcct tccacagaac ctttccttca   215820
ggtcagggac ctagtgtcat gggtcggtct tggataacgt tgcaggacat atcagttcaa   215880
ctgccaaggg aatcataaat agtcctactc ctgcctgcgg cccaccactg cctctctgct   215940
ttcattcttt tttatcagat attttcaaca tcaagaactt attagctgat aatttaacta   216000
aattaagtat aacataaggg aaatgtgtcc tggcagagat ggcatcttag agtgaatgca   216060
cagtctttat tggttaccaa aaacaaaaaa aaaaaaactt gagctttgga caagcagtag   216120
agagcagatt tgatactggg ttctgacatg gaagctgaca ttaaattatt gacagtctac   216180
ttgtttataa actattcaat aaacaattta gtaagtaaac atagattctt gcaatccctt   216240
ttaaggaaac agtgtttatg ttggctctct cttgtaccca acctagtgct cagcctttcc   216300
tgactcacat aagcactaat ctccagataa caccaagcac cctagggtta ttatttatcc   216360
cccttccttg ttctctgaaa taagagaaag gcaggttaaa ttatgcactt tatgtaagaa   216420
gaaatggagg tacagagaaa acagcttaag tctcttaaca gcccaagaga gtgaagaaga   216480
tattgccaat gcaatgagtt gtatctgtcc ctaggtaagt aaaatattaa ttaaagcata   216540
caactatatt aataattaaa acaacagtct ttacttatat ggactttgca gtgactttt    216600 tccagcctga aatactcaga taatgactgc cattagtttc acacgttagt gctttattat   216660
atactgcttt gttttcacac aaaatcgttg agaggtaaga attttttgaa agaaatattt   216720
ggtcttaact tttttatccc ccttcaactt caagcaattt tctgagcaat gataagtggt   216780
aagtagatat ttaccactta gtttacaaga gacctgtttc tctctgtgca ttgacttagg   216840
cactattaat gaaacctttg gaatgcaggt cccttctggt tgtaaacata tactgaggtc   216900
ttctatttct tttggaactc aaacaataag aaaatagtta gaaatctgtt tgtgggcata   216960
ggtctctaaa agccttaatc ttagaagtga gtaaaaaaaa ttttaggcca gacgcggtgg   217020
ctcatgcctg taatcccagc actttgggag gccgaggtgg gcggatcacg aggtcaggag   217080
atggagacca tcatggctaa cacagtgaaa tcccgtctct actaaaaata caaaaaatta   217140
gccgggcgtg gtggcgggcg cctgtagtcc cagctacttg ggaggctgag gcaggagaat   217200
ggcgtgaacc cggaggcgg agcttgcagt gagccgagat ctcaccactg gactccagcc   217260
tgggcgacag agcgagaccc cgtttcaaaa aaaaaaaaa aaaaaaaaaa ttagagccta   217320
agaaggatga ttaagcatct tacttaaatt ttcagtatgc ctatgtacac tctatatact   217380
gacttctagc atggtttctt tgccaaagca taacacacat tttttaaagg gataattcaa   217440
gacaaacatt ctttcaccct gggtgacccc aatgggtggt gaacactttt tagtaactct   217500
tgaaagttaa agcatccaac agttggttgt gaccttttg gttgtgacct ttgagttctt    217560
ctagcttgta gcccactgat ttgctgctta attccacagc ttcaaaacca actctaatca   217620
ctgctcccga gagagccta gcttctgcac acatgagtct ctcaccagga aaggatacct    217680
gaagtccaga aaagcccttt gttcacactg gctcctccta gtggggaaca gttttttaa    217740
```

```
ataatgtaca tttatgcact gggaaaatat cttgaattta ttatttaggt gtaaccagac 217800
tttaatacaa cttaacctac acactgagaa agcagacatt tacaaaaaga tttatggctt 217860
tgacaaagcg ttcaaatgta gttaccatta aatagtagtt caagtaattg tgtgtctcat 217920
ggcaaatcaa tgcaatataa ggtaatatat atttaagcca aaaataacaa gaggtgatca 217980
tttgctaaac aaagaactta ttacttagga aaaaatgtta cacaactttc aaaggacttt 218040
tgaaaatata gtatgattta taggaaattt atttgcatat aattcacaat atctggtaca 218100
aggtaagcta cctctgtgtt ttttttcttt aggtcaacaa atatttaaac caagggttgg 218160
caaacaggcc ctcagaccag atgcttgttt ttgtaaataa agttttattg gaccacaccc 218220
atgcctgttt gtttcagatt gtgtttactt tagggctaca gtggcagagt ggagtagcta 218280
agacacagag cataggtcca caaacctaaa atatttactc tctggccctc taaaaaaaag 218340
tatgccaaac cattctaaac agcaaagcaa ttaattcttt tttttcaact cttatttag 218400 atttagggg tacacgtgca ggtttgttac atgggtcaat tgcatgtctc tgaggtttgg 218460
tgtacaaata atccccttac ccaggtattg agcatattac ttgatgtttt tcaactcaca 218520
ccccgctccc aatcttcacc actctagtag tccctgtgt ctactgttgc catctttata 218580
cccatgttta tccagtgttt agctcctgct tataagtaag aacatatggt atttcgtttt 218640
ctgttcctgc gttaattcac ttatgatgat gacttccaca tacatccatg ttgctgcaaa 218700
ggacatgatt ttgttctttt ttatggctgc atagcttttc atggtatacg tgtaccacat 218760 tttcttatc cagtccacca tcaatgcgca tctaggttga ttttatgttt ttgctgttat 218820
gaatagtcct gtgatgaata tatgagtgcg tgtgtccttt ttgtagaatg atttattttt 218880 cttgggtat ctacccagtt atgggattgc taggttgaat ggtagttctg ttttaatttc 218940
cttgagaaat ctccacactg ttttccacag tggctgaact aatttacatt cccaccagca 219000
gctataatat ggttgtttgt ttgtttgttt gtttgagacg gagtctcgct ttgtcgcctg 219060
ggctggagtg cagtggtgcg atttcggctc actgcactct ccgcctccca ggttcaagca 219120
atttgcctgc ctcagcctcc tgagtagctg ggattacagt cgtgcaccac cacgcccggc 219180 aaatttttt tatttttagt agagacggga tttcaccgtg ttggtcaggc tggtctcgaa 219240
ctcctgacct cgtgatctgc cccctcagc atcccaaata ctatactgcc ccctcagtat 219300
aatatagtat tttaaggaac taatcatcaa gtttgtactg gttaccctct tttagtctcc 219360
tgttatcttc aatttcataa ttggcattaa tgacaataca gtgttcactt tataaatttg 219420
cttcatagta aactcttctg aaataaatta cagtcatgca tcacttaaca gtggggatag 219480
gttctaagaa atgcataatt aggtaatttc atcattgtgt aaacatgaag tgtactcaca 219540
caaacctgga tggtacagtc tgctgcacac cagcctttat gatatagtct attgttccta 219600
ggctacaaat ctatacagca tgttactgta ctgaatattc tcagcaattg taacacaatg 219660
gtaagtattt atgtatctaa acatagaaaa tgtacagtaa acatatagta ttgtaatcgt 219720
atgggacgac tatcatatat gcagtctgtc gttgaccaaa acatcattat acagcacaag 219780
actatagttg aaaattttaa attacatatg tgggttgcac tgtatttctg tttgcagcat 219840
tgatatatac atttaatggt ttgtatgttt gtgcttgcat tcataaatat taaactgtta 219900
cagggagcat attttcttgt gtaaaaaaat aaataatttt tatttctaat gacatataaa 219960
attattatgg ttatgtttaa agaggcttga agaggtatta tggttatgtt tgaagaggca 220020
acggaaacgt caccctttgtc attgaccaaa acatcattgt gtggctcacg actgtaatag 220080
tgtaaagtaa ggattcaatg tatcggctaa tcaatgtgga catatcattc agtattatta 220140
```

```
aagatactcc atccaatgaa gactgaacac ctgtaaatgc ttggtgatgg atggaaaggg   220200
caattatttg cagctggact gtctgagacg tgtcatcatt attgcataat atttatttaa   220260
tgaaggatca atgcaccata cagctccagt ttgagaacac acttgacatt gtagtttgta   220320
gatcttttat aaactaactg ctatcactga atttttgctg aagaataaag acaaaagatt   220380
ctctctttag gaaattgtgc actttaaaga ctcataaacc tgaaacctca cagaatcata   220440
atagatgtat tttcagagac aatttctgag tccttgacat attctcaaat gtcattcatg   220500
tcttcactgc cgcaggttat ctttttattt ttatctgtca tggaaaagca gccttttttc   220560 ttttttatc tcctactatg ccttaataaa tagaatttaa aaccccgaat ttgaattatt   220620
gtgaaagcca atatttgtag caaatccatc tatgctctgt gttgtcagca catatggttt   220680
tgtgtacctg ctaccatgaa actctgccag ggttatcctc agagaaatgg agagacacct   220740
gatgccatcc ttactctgac agaagttttt cttctgtga attccaaaaa cttttgaagt   220800
tatgcatctc ttgcattgaa cttcagtggc ttgtgtacac atggtatctt cctttctaga   220860
ttgtaagttc tttgagggca gggactgaac cttttctcatc tttatatgct ctgctcctcc   220920 accttggtt tagccagggc cttacaaaaa gtagaagctt aaataatgtt tattaggtga   220980
atatcatact aagttccaga aattacctga gagcaattga agaagggaag tgtggaggga   221040
gaggtgttag catagatttc atagtgtttg agtttggcag tttggcatcc ttttcctcaa   221100
cactaatact gacacagata agtaacctaa ctgccttctc aaatctgaga gcagtagatg   221160
cattttctct tttgggactt ttctatctca tgtgggaaaa gcaaacaaga aggtcctgca   221220
aaagtcttgt gggtatttat tcttatcagt ggttgtggca aactctctta ctggtttcaa   221280
ttggtcccac aggctatgtg atgaggactt tggggtttgg ggagctggga accatgagtt   221340
gtctcttaag tatgacctaa catactgcta ataccccaca agcttcaatt tatccatctc   221400
gaaatggaga tactaacatc tatctcaaag ggtcattgtg aggagcgagt aggaacatag   221460
aaaagttcct agcacaaagt agatatggaa gatatggaat aaggtgttag gtattttatt   221520 attttttactg ctgctgctgc tgttactact actgctatta ttattactac tcctggaaga   221580
gtaggacttg cctgggacac tgaccctact taccccttca cctcattcac caaaactat   221640 ctcctatata aattcatgta tatttttctg gaaggataag aaaaatcctt catctaggta   221700
gcgtattttg tatttgaata gtttatgttt caaatcccag agaaggccta tacagccaaa   221760
tttggaaaaa aaataaattt aaaaataaat attcagtgtt tcatatataa taaaataccct  221820 aacatcttat tccatatcat atatgtgtgt gtgtgtgtgt atcttttaat tgccatgtat   221880
ttctaccaaa aaatacaaaa cttaattttg cgtcctgaaa accctcgtt tgagaatccc   221940 tgcttttatg ttctgcttta gtccaggcaa cagatagctt aggttgtcac tttacaactg   222000
gagcagcagg tagggctgag aggctcgcca tactccaaat taccagtgcc agtcccatgg   222060
caccaagaca ggaaaggcag gcactcaaac agaaaggtag tgcaattaat tgcttcaaat   222120
tctttactca gggctgccct tagtcatgat caaataaaat gtacacattg tttggcactt   222180
ggtaaaatgt tgtttccttt ccttcctcct tcccctgata gactctcctt aggtacaaaa   222240
aagatgaggc tgtacacaga gctaaaagtg tacacctttg aaaaaggtgt cttttcaaa   222300 gagcaccttc accccttact ggactaaact caatccaaag ctctttctc taagctttat   222360 aacacttact gcctggatga gtcatttgtc aataaataca gaatgtttgt ataggtgggg   222420
ttcttgtata tatgtacgag ccctagagt ctctaactta aaatttattt ttgctttaga   222480
```

```
agttcaggaa taaggaggct tgatgatca atttttaacaa ccgcaatata taatacagta   222540
actaatggtt aggtgtccag gctagcccag ggcagcctgt gtgattcatg ctgctggtga   222600
accatggctg gctgggcgaa ctagatctgg aattctgtgg tgcctaaggg agggaaggga   222660
atatttccca cactatctca tcctgccctc actatcgcta cccccaatct ctctctacat   222720
tctaccccac ctactttgct ttttctgtga aagaccagct ggggcaaata ttttggatta   222780
agtaaaattt gtcttgggta acttccctaa aatttagttt ttaattgaat aatcttggtt   222840
aatccatgag taaataagct tgtagagtat agtcagcctc actgtgagaa gctgacaaac   222900
cagaaaacca gaggaatata caccaattcc ttcctgtcct gcaaacctct gcttcttgag   222960
gtttttaaag agtgggtgcc taattgatta gtcattagtt attgacagga ccaaagagat   223020
atgcctggct cctcttggaa aaaccaaaag actgagaggg aaaagtacac caaaaagata   223080
cctaaggagg cagactgcta taaagaaaat aattaggaga agaaatcata tgttttcaga   223140
tgaaaagaat ctgaggatga aaaaagcagc cttttcaggc cgatgatgga aagatagaaa   223200
ctaaattcag aaggatcaga agacgattag aagggcaaga agtcatagaa gaccaagatt   223260
tcccaaatta ccaaaagaaa tcaagcccag tcttgttcag gctgcagaat gagaacgccc   223320
ttctagtaag atccgtacaa tgaatttcac aaatgttgat ttctttctgt cctctttgag   223380
cccataatca cctccttcta cttgcacaac cttgaccatc accactacct ataactaata   223440
accagttctt atgttcccct caaggcataa cacaaaaata ttttctttat gattactttc   223500
tctacaaaaa agagggagag agagagaaac aagtcagggg acttcgttgg tgagtgtaga   223560
ccacagcaag aacctaaaat cctagtgggt tgttagtata gacaggctga aaccactatc   223620
ctgaagtggt ggttctaggt aggtatgccc atcagaatca tctgtggata agtattttca   223680
gtaaatacac atgcaggacc tctacctcaa atgtactgaa ttgaacttca ttgctggagc   223740
ttaggcattt catatttgtt tcctaagctg ctataacaaa ttaccacaaa cttggtggct   223800
taataagaga aatgtattct gtcacagttc tggaggccag aagtccaaag tcaaggtatg   223860
accaggattg gttccttctg gaggctctga ggaaattctg ttccatgcct ctctcctaga   223920
ttttggtgac tgccagcaat cttttggtgtt ctttgatttg cagaaacatc attccaatct   223980
ctggttctgt cttcacttga ccttccctat gtctgcgatt ggtctccttt ctgtctcttt   224040
taaggacacc tatcactgaa tgtagagcct atcctaatgc acaaggagct caattatacc   224100
ttaattatat ctgtaaagac cctttttcca actaaagtca tattcacagg taccaaggtt   224160
taggacttgg gcatatcttt ggaggataca gttcaaccca ttacacatat gcattgaagg   224220
gaaaaattca cgccacaact gattatccta taaagaatgt tggcttaact taacgcattt   224280
aacgcaccat ttctccagca cttaggaaat gctaggagat gcaaagctga agctaaatag   224340
gcttctttat tgcagaacct ctcagaggct ctcatctgtt tgtgtgcatt ataaatgtcc   224400
aagagaaaga aaagaatcac aacatttcct ggaaatactt gaccagggaa cttcttttca   224460
agggattacc tgttaactac ctcaatggac actaatgact aaaggaatac atgctgctgg   224520
tgatcatggc acttccaaac tatgctcaat ggtgtgggca tgagtctacc acagtgtcta   224580
aacactaaga ttgttaatgt ctacacgacc tctccctgga tatgagcaca catccttcat   224640
caaatatcca cagtggtttc cctagaggat ttgcatatgt gcatggattt ttagatgtct   224700
agtctctact cttgtcttca gccattttttg tagagagaaa ttggcaaaat attagcatga   224760
atggaaggga aaggtggcca agataataca ttatgccttt tttttttttcc ctgaaaacag   224820 cccagaatat ctgaaaaggg agaagtgact taatcatttc tattcccaca attctggtcc   224880
```

```
tacaaaattg atatcagtat atgattcatc cagagaagtt cacagtggta ttttttaaa  224940 aaaaactttt agaggttacc agggcatctc actattttaa aatttaatac ctcaagggaa  225000
ataagcaact accttgaatt tttgcatgaa ttgcatttga gaataactga atagttggtg  225060
gaataaagtt gttttttaa aagtaggcat attctagtta ataaatataa aagaaatggt  225120
aggattagaa aaatcactac attacaaact ctaatgacat aatagattta agcaagatga  225180
tcagtgaatg ataaaatatt taggtatgct gtcttctagg tgaatcaagc tgacaatacc  225240
ttggacccac gttaatctta ccacatgata ttatatgtct cctgatactt aaaataaata  225300
tcaaataaat cttgataatt gttgaaaatt gttgatgaac atatagttca cagcaccacc  225360
catgatgtat tctttccatg agaattgatc tgaatcaaag taagcctcta ggtctaactg  225420
ccagtgtgta ggaaatacca gggatagaga aacatttta aagtctttaa gattgcagta  225480
agctgaaaga aattgtctgg tttctgcaat aacagcaaca aagttatgta ataagaagag  225540
agagggagaa tcacggattt atacaaactt aagagacact gtgtgaatct agtttgtatc  225600
ctgatcaaac aaattaactg tcaaaagatg tcttttgaaa catgatggga aatttgagca  225660
taaactaagt attctacgat attcaggaat cattaccaat ttgttagata tgatgttggt  225720
atgttttttt aaatgagaaa gttttagct tttagagata catacctaga tagttatggg  225780
tgaaagcata tcattaaaaa aaagatagtg gaagtacaca aaacaggatt gctatatgtt  225840
gataattgtt gaaccttggt gatgaacata taggaattaa ttaaaccata ttttctattt  225900
ttatgtttat tttgcaaatt ccaaaataaa aatagaataa tccctcatga acagatggtc  225960
tcaaatttca tcctcaagta aacacaattc acattctcag gggaacccat gagaatatta  226020
tgaagtatat gtctatctca tttcattata tatggaatcc taccattcct tttgtcttta  226080
ttactagtgg ccagagttct atcttgaaag gtgggaaatg tccttatatg aacagattag  226140
tttagagaat tattgtgaga aaaccagaaa atatttgagt tctagctaac tggatattga  226200
atgagttgtg ctgaagtatg tggtcataaa gggttgataa tgaaatactt gctttccagt  226260
ggcaaggaaa aataaatgtc ttagaattta caaggtcatt cttgaaatca atcaacgtgg  226320
gctgaagatc tcattgcttc tgttatctgg cacgatggta tttgtttgtg cacagctctg  226380
ttgatgtgag ctatcaaata tttcttagag ctgaaatcat ctaatagcaa acattgctat  226440
gtcccaatgg agattccaag actctttggc catgaacatt tacattcta tcccctttca  226500 tcactcctga acaaacaaaa acaaaaaaag gaaagataac caataggctt tttatttaat  226560
tgaaaaccaa agagagagag aggaaagaac cagttagttg ccatttctta aatgcaggct  226620
tttgtttgtt tctgccttct aattctttgc tcttgaagct atagctttca agcttgtgta  226680
tacaggccca gagagaacat ttgaaatgtg gccaccctac ccatgtccat gccactcttc  226740
ctgcctttct ctctgcctac ttctgctcca ccatcccagg tcaggggctt ggaggctgac  226800
agcattacaa gtaatatagt cgttcaagct catataaaca agatgaaatc caaataataa  226860
ccaaaatgta ttttatttca aggactggac tactcagttc cctcagtttc gctgaccgat  226920
ttctaggagc cctaggctca gctcttggtt gtctcagaac tgaggagagt actcatttgc  226980
accatatgca tctgcttgtt agcctgtgct accaaaattg attcattact tggccttctc  227040
tgaaaagaaa aatgaaaaca aaatgcact cttaaaaata attattaaaa tacaaccagg  227100
aggtatgtgc ctagacatgg ctcaccttct accaaatcat actttatgat tttccacaat  227160
attatcttct attcctcctg cccctaaggt tccatggagc agagcaagtt gaagaatgtt  227220
```

```
aaggttttac taaactttta gaacagaggc tttggggaag caagagagag gtacactgaa  227280
aatgaagtgt ctgtctctgc ttctattaat gtcataggac tagaagttga cctcatagct  227340
gattacaaat gaaccctgca aattgaaccc cagcacatgc ctctcattat ccattcttct  227400
ctttgcagga tggggtccat gctcacatat caagaaaatg gtgggtttca gtctggctca  227460
ctgggtgagg ttttggcatg aaaactaata cgggttagtg tacatcaccc ataataaaag  227520
taaaagcttt ttttttttatt tacccaggta aataagcaaa aggcagatct aaaatacatt  227580
agagttaagt tccatgggga cagaaatgtc tgctttgttt gttgttatac aattgacacc  227640
tagaatggtg gctggaccat agtgactaca aataaaatat ttcttagggg aatgaatggt  227700
tctgcaggat agatgttctc tgcatttgga taagtgatga tactatagac tcagagccta  227760
gatagaaaat attgtcccac tttcagttct gcaaactgac ttgaggtgct tggtgacgtc  227820
ctgcagcaag caaaccaaat gaaggcatct ctgagacccc atagtcacca ccagcatgct  227880
agcctcccat taccttgccc acctagatt ttcaaattgg gaatcactgt ggtaccagac  227940
tgggaatcgt gacttgcata cttttctcata ttggggcttg ggattttgag atcttatttc  228000
cttttttggc ttcttgagat ctgaaattgt tgttcagaga aggatattaa gacaatgact  228060
cttccattac catgcatttc tgttaccaac agaggaggta agtgaatcac ttaaaatgat  228120
acaattccat ccacttcagt acaccataaa catatcctta gctttgacta taattatagt  228180
atgtgggtga tgccgctgag aaaatggtat aattataaca ttatggttga gaattgtctg  228240
agtagaaaac actgagctgt actgtgcaaa gtttaaggcg gaattgtggg tccctttta  228300 atatgaataa aattgattag ccaattgcaa ctgagagctt tgtgcaatga tattaataat  228360
ataaaaatcg gccgggcgtt gtggctcaca cctgtaatcc cagcactttg ggaggccgag  228420
gcgggtggat cacgagatca ggaaatcgag accatcctgg ctaacacagt gaaacccctt  228480
ctctaataaa aataaaaaaa tatagctggg cgtggtggca ggtgcctgta gtcccagcta  228540
ctctggaggc tgaggcagga aaatggcatg aacccgggag gcagagcttg cagtgagctg  228600
agatcctgcc actgcactcc agcctgggcg acagagcaag actgcgtctc caaaaaaaaa  228660
aaaaaaagtc aagggccaaa gtaacaatgt aggaaaaatt tgatgacttt aatttcattt  228720
acttctagga gtcttacatg caagcctaat gcagagtaga gaagctcacc aacttgaagg  228780
aagcatgaat gaaattacaa ggaaatctag cttagaaaaa ttaaccctgt agcttggttt  228840
ttccactctt tgctcttggc aaaaggatct tacgtatgta taccaaatgt ctatttgaaa  228900
attttgtttc tctgaatata gctttctttt ctctttaaca cactggtcca gtggttctag  228960
attttatgct cccataaatt aagtaagaca gcattctata tcatgactga ggtgttaatg  229020
acattatgca gttgtcacat tttgaaatat aaacttaaat gcgagctttt cactgtgtgt  229080
aaagtttctc tgtattttt taaaaaattt ttaaagacca gagattttca gcaacaagaa  229140
acataaagaa gtaaaaagag cgtagaaacc ctgccctaga ggacctgctc caccacttaa  229200
aagccatgta cctcttgaag cctgtttcct ttatttccaa cacaggaatt tttatattta  229260
caccctaacc atcacatggg tcacatgtga taacaatgtg caagtttctt acaagtgttc  229320
taggaatctg taagtcttag agttctgagg tttattccca aaggacagga aattgtgggt  229380
tacaccaaac agttaaacag ggtggcaggg aatccctgtc acgtacccag gcctttgggt  229440
tattttctag ggtgagggga catggccagt agtacaaaga gcatgtgaac gcatggatgt  229500
gggtgtgtga ggtcatgagt gggtgtgtat gtttatgtac aacacatgta ttggaggata  229560
aaagggaaaa taatttgtct tcctgacttc ttctctattc ctggctttc ttagattgtt  229620
```

```
attcctctct aaacaaagct tcaaaacaga aacccctccc cttctttatt atatcggaaa   229680
tctgggaatt cagttatcct tgtcttatcc tactccctgt tctgttctaa atatataata   229740
acaataagta atagtactac tactagtact agtagtagta gtagtagtag tggtggtggt   229800
agtaatggta gtaatagtaa gaggatgaaa agatggagga ggtgaattgg aaatagggag   229860
gtttcctgta gctgactgac agtttatata gcaaccgcct gcagatttag gttttttctg   229920
actgcgctta ttttatagca acctcaacaa gctgtgacaa cctgcaatat ctttagccct   229980
taagatactg tctcttaaac ctgaccaata tttcttattt ctcaaagagt aatgatagtc   230040
ttttctgtct gataagttca aaaggcacaa ctgattttcc taacattttc ctcaaatgaa   230100
gggagtattt gaaaatggaa actcaaatga ggagccacct cagaagccta actggagcat   230160
tcagactgca tcagacagac ttggcttcag ttctgacact gatacttact agctgtggga   230220
tttttggaca agcttctcat ctgtaaacaa gtataaatac tacctacttt ataagctcgt   230280
atgaaaattc ccacaaagtt tgatgttagt ttcctttctt tttgtgctca gctctaaaaa   230340
tatgcagtgt agtgagtcac taatatttca ttaacataag ggaaaactat atcccaacc    230400
caaaagctga gattcttcag aacatttttt aaagaggttc taattaggaa ttttataaat   230460
ggaatacaga gtacttttta aataataata acaatgatta atttaagtta ctaaacaaaa   230520
taccttaatg aattgagaa aaataaactg aagataaata ttaattatta aaagagaaaa    230580
ttattaaagt aataacatgc aagtcacttg atacttgcaa agtaacacag aattagacat   230640
aaagccacat ttaagaggca gcaaagccaa aatggctggc ccccttttaaa aggctcttgg  230700
caacagacat atggaaaact gtcatctctt ccctgggcct ttcttcctac tctggataag   230760
cagcatcctt cacacaaaag aacatccagg ataactaaga aagagatgaa atgatttatc   230820
ggaactagtt aaaataatta aatcttaaaa gcatgttctc ctgggcatag agtggggtga   230880
tttctgcaaa cattttgaaa ataaagtacc cctaaaacaa ggatttggtt taactgctag   230940
aaaacaaggt gacaggttga gaaaactgaa aattttctta aaatcttgtt tacttgaatg   231000
gtgagccagc cacccaggga agaaaccaga gctctttcct ttaagaaata tagacttcag   231060
ttggaagaaa aaattagtag gttttaacct tcaaccttct agtgaagtga gaatattgat   231120
tgagcaccta ttattagaat aaatttatct taagtgaccc agggaagggt cgtgggtgac   231180
gggaactgtc aagaaagaaa aaaaatatgg ctgtggatct taagtactta aaatctactg   231240
agggctcttg tctccatttt ccttagaccg tgatgttgct caaagtcaca taagagggca   231300
cataaattta ctgaatagta ttacagaaag cagcagtgac actgaaatgc ttgcattata   231360
ttcactatcc cagtcatctg cagttgcctg agggatttgc aagcaaggac aggaaaatgc   231420
tagtaccaac cagttctaga taagaattt atttgctcca aaaactttca ctgtattaaa    231480
ttaaattaga ttggctggaa ttaaaaggta ataaggccca ttttcttatg taggtcatca   231540
attaatttaa ctctaaagat aattccaaaa gaagaggttt aaaaattgtt tgagtagtag   231600
taacatcatt ggaatttatg taaaacttcc caatgtactc acttttacag ataacatata   231660
tatatatata tatatatatg tatgtctatg actgctggca taatgatcaa aatgatcagt   231720
tttattactt tgtaatcaca tcaggcggca ctgatggttg aaataaaatg tgttagatga   231780
gtgaatgcaa agataacata tagcaaatga aagtctttgt ctatgaagca catgattgtt   231840
ataattgttg ctgcccttt gggatcctga accagattcc ccaaataagt aggtaacaca    231900
gaatttgtct tgagcacttt ttcaagcatt gtaatccatg cattgaagta ggctttatca   231960
```

```
gcctacagct ataaactcca aggtgatttt aaagtctgaa ggtttatagg tcttcattag  232020
gataagctgg gcttaccata taaatctatg aggactttgc tagaaaaata gtggaattgt  232080
tgaataggga aaagagataa tggtaacggg atttgcctga tgtcttcatc ctagaaaaaa  232140
agatttctgc ttgggcatta aggacccccag tgatgattct gggagacttt caggaatgct  232200
gacaaggctg gagctactca ggatttgatg ccaaagaagc cacactgcac atgtgttcct  232260
ctaaggtgta cttggttctc atctgagagg caaaggctct acttcttttt aattgtttgg  232320
tcctaagtta ccttcaaact ccacctaacc acatctctaa tcctgtgtat agcctttcca  232380
acatcttgta aattccaagg ggttggggga acctttaggt tccaaggctg agctaagtta  232440
taaatgaata ccctgtgcag tgttgagaat gaaacagaag ctttggtgcg tggtagccca  232500
ctgtgagtgg ggtttcaaag gagcagtcca ggggccctac atgaataggc atatatgggc  232560
caagagacag gcttctctca gccataccat agtatactgg aacaatgaga aatgggagag  232620
gacatacttc ttaaagtgac acactgacct gttttcattc tctcctctct ctgcttctcc  232680
atttccactt attgcccta ttgcatctgt ccagtaactg tttctttaac agtttccaa  232740
actgacatta ttaatccaga agatggatgg tggttttta attaaaagag aaagctgatt  232800
ttatttggtg agacttctgc tatcatcttc agtgttatat cccaatatga gtacttttt  232860
taatgttcta ctaaatccaa tagtatattc acctcactct cgagttaaac tcttggcttt  232920
aaaaaaatta gccagaaaaa cttcttaaga aaaatacag tattttaaat tctataaatg  232980
aactatatct taaaatattt gggggcataa ttcaattgta tccattttac tttaagatca  233040
tgcaaaaagg gaaaggtata gatgctattt tattgatatg ctgctccatg gatttcaaat  233100
tcaacatcat aagccaagat ttgtgggacc agaggaatgt tcaaaagtat aatctgatac  233160
attatctgct gcaggaatta agtaaaatat tgcatacatc tcacttccta taccaaatag  233220
agagaatgaa agtactagat tttgtattac agatagttta gacaactata gggaattctg  233280
aactttcaaa cttttatatc ctaaactcaa gatttgggcc ttgaaaaata aaactgataa  233340
aactgctaca gtgtagattt ttaaaattac attcatgtgg tgaagttgac actttctgtt  233400
ggtatggcta gaagtcagat agatgcttaa tttgaaagac catgttttta ttcttctct  233460
ttttcttacc ctatgatttc attgacctga agtggctttt agtgccattc aattcacaca  233520
gaagccaaaa ttggttactg tgttaagaag aaaccaagat gttttatta gtttatgaaa  233580
cactagcaaa attactattt gatgcaaaac tgtgaggaag ttttgtagtc attgaaagga  233640
gcaagaatat agactgcttg cagttccagt gtcgagacat tcattatcag atttaccact  233700
tgaaaatatt atcaagatag tatttatatt gtgtttacca ggtaaactaa gcactttagt  233760
tctgagcact ttacatattt taaatcatta atagtgctgt aacaagcctc tgaggtaggt  233820
actgttatcc ctcttttaaca gataaagaga ctgaggcaca aggaagagaa gtgacttgct  233880
gaaatcacac acagctgaat gtggaccctg attcaaatcc acacatcctg actcaagcat  233940
ccttgctctg tactactgtg ctacagtgcc tctttacatc ctcctgatgt agaaatcttc  234000
ttctagaata atgagaagca gtgtgaactt tgaagtagga cttcctgggc atggtgcttt  234060
ccatctctgg gccaaagttt tctcatcttt acaaaaggat tacgatcaac ccccatctca  234120
tactgtggtt aggagaattg agcaagacca tatactaaaa gatgtcagaa cagggcctga  234180
cagatcatag tgcccaataa acattggctc ttgttatcat cataaatatg ttaaaatgag  234240
ctttagtatg tggataatag tagcagaatt tcctgaatga gacatgttaa acatttatta  234300
agcaggcact ttttggagtt tatcttataa taattcagta aggttactct tgtcatccct  234360
```

```
atttcactga atttgaggaa tctcaggctg caagataacg tattagtttt ctagaatcaa 234420
ataagcaagg attcaaactc aggatatatt gaccccaaaa cctcagatct ttctgccatc 234480
cctatcttgt tctaaacccc aggtttgctc atccgggccc tagtcattga tcaaaaagca 234540
ccaatacaaa tcagagtaga gaaagtcata ttgagcttgt gaggttgtat tatgggcatg 234600
gtaacaaatg taattcagct gtattggcac agtgcataac aaccacactt aatttctgtc 234660
ctaagacctg tctgagccca taaataaagt tacattaata attacggaat ggtaagggac 234720
cactcagaaa atcttggttg ataggaag tggcatctgt ggcttctaat tgagagatat 234780
tgcttcttga atcagtgcta gaccattgct ctaggggat attaagcctt ctctgtccat 234840
ggaagatgtg aaattcaaca gctgacctga ctgcttgtcg ctgttgatga tcctataaaa 234900
tttcctctaa gatacgaact ctgtgttcta gtccaaatca agtgaatatt tcctgttggt 234960
tgacctacaa cttcaagggt atgaggtcat aagtttaaaa agattccttt tctccccagt 235020
gttgtaagag ttattttagt tctatcaaat gctcccagtg agtactgcat atttcctttt 235080
tgccagatac attagctatt cactcttttt tcctatctct tctatgcttt tatttttttcc 235140 ctcatctgtt taaccaatgg taccctgaat tttagaacca gacaggtagt aggacaaggc 235200
aggtgaaaat gcacaggttg taaatttcag aatgcacatt caaattccat cgttgtctct 235260
tactaactga atgaatgtag gtaagatgct ttacctctca gagtcttact taccccatct 235320
ataaaatgag aataatacaa actgtcttct gtggttttct tgagcattaa acgtctctat 235380
ttatggaaca tagtttcaca tagtaactga ttctgtacca atgccctgcc ccccatgtag 235440
gcaaatgcat gtcccgaaag acccaaaaca agttgtccct cttttcaaga tgaagatttg 235500
taatctctcc ttaaacttat ccagttctgg tgtttaattt cctttataag ccagaagttg 235560
ttttacgtct caccaaatct tataacatga atattacact gtcttccaaa tgtgagcctc 235620
taattacctt aggccaatag cagagcctct gatcttgtct tttctccttt tccgcttacc 235680
agacagcaca ttctgcctga gagttgagac ccaaaaagat ataaatcaac taggggcaa 235740 aaatggagtt tcctaagctt gtcccagagt ttgactcagt agcctgaggt ggagttcagg 235800
ggcttgatgt taaaaacaag ctaccccagt ggttttgctg caggtggacc agactcccaa 235860
gaccacattt tgcaagcact ggcatttagg aagagcacgt acctactcta gcagagttta 235920
tgcagactat gattgcagcc tagtttgtgc agactattga ttgcagccac ttggcaaggc 235980
tctataagaa aaagcgagcc aacatgtaag taaattatca tggccttgaa actcctcatc 236040
tgaaagggtt tcctctcatc ccctcatccc cttgtgtctg cccctgaatg ccagactatc 236100
ttctccagcc ccaagtcaac ctctcatttt taagccattc ctcattctcc tatatagtcc 236160
aaaatagcga atacattttt aggaattctc ttgctttatg gacgttcatc caaaaatatt 236220
tcattatgag aataagtgct tagcttatcc tgtagtgtct ttctgctcta atatttgggc 236280
ccttcctttc cacatagttg cattttcttt gacgggcaga tgctgctcct ttaatatttt 236340 tcacacctttt gtgcttctaa cagagcaatt atttcaggat gagggcactt ggagagctgt 236400
aagaggataa ggagcccagg gctctgcctt ggatttgtgt acctaaatgt tacctaatta 236460
gataaacctg aggaagatgt ggaagcaaag tagaatggaa cagaaagtgt ttgaataata 236520
agaatttgga cattgctgct ccgtggtgac attggcagac tctaagcctc ttgcctcatt 236580
ttattcattc atgtatgacg gggttatgct cagtcataag tcactaaaat ttgtattcta 236640
catcccatta gtaaagtaat ttttgaacac atgatacata tgtttacata tttgtaagtt 236700
```

```
atatatatgt acaaggttct aatatattct gttcattgtc aaacataaaa tatatataaa    236760
tttggtttaa tataaaatat aaaattggca ttagtagaca ctgtctaccg aaatgagaca    236820
ctgtctcatt tctgaaaaaa gcacaatgta tactaagtta aaggttcatt cttaacagca    236880
gtaggagtag atctttattt caaatagtct ttgggataat ttcctatttt ggaagacagc    236940
ttatcagatt tggttagagt tgatgaaagc ttattctagg gttaagaaaa gtattagccc    237000
agccattttc ttattgttga tttgggcttg cataattagt tttaccttca gtatgaagtt    237060
tctttacatg aatcttttta actcacttat ttgttataca attattagtt aaatcaattt    237120
taaatcagta taatctatcc acaaaatcag tcatacagaa cctgcaaaaa acatgttcta    237180
acatgttaca tgaagaggta actaaagata ctacaaacaa cccctctgaa cggtaacact    237240
cccactcttc ctgcaaaatt cctctcatag caaatgcaac atgtgactca gacacaggct    237300
gactgaaggc tttatgcaac tcttacatgc tcaatattag aaaactttca tttgtttcct    237360
attttatata aacaacacat ataaataaac attttagtat cttctcatta cccagtggat    237420
tgtcttgcat ggtccatttt gaagacagta aactgtagcc tctatttta tttaatttca    237480 aatacctgtt tgccaatatt cacagccagc tcttgttaat gttcttttct gtcctgtgaa    237540
tcctgatgtc gtatcttgca acatcacctc taaagcctat ctttgcactc ctgtccatcc    237600
cccattctct attattatgc tgcctctgat ggccagagaa aaaaatcttg aaaatatata    237660
ttgtattgcc ctacctggcg aggaatcagc agttatacaa ttcaaagttg cagcaattca    237720
ccacattgtt tagcacccta ctatgtgtaa ggaggaagct tgatttaaaa aatatataca    237780
atcatgcctt cttcaagaat gttttggagc atgcaagagc ttaatgctca tggacattta    237840
ctttattcca gcaaatttag acccaatctc tgtgtagttt cattttgttt tccatttcct    237900
gattaactga ctatatatct agctacttat ttgctgccat ctagtgtaat aaagtatgtt    237960
gattatacaa ggaattttga gcccattatg tagttgaata tcagtactca aaatgattct    238020 tttttctgg tttcttataa gtttacaaaa tgcctagtca gggacctttc ttatcactgt    238080
aaccctgaac atggtcttaa tcttgtgtca tagaatctag ggctcaggat caaccttcgt    238140
tcattttcta taaatgtgac atttggaaac tgggtagggg cttagcagtt ggtggatatg    238200
aagtaaatat ataagagtaa tcattaagag atcatctcag tttagtgacc atgattttt    238260 cctcatggag gcagcaaaac acagcatgga ttcttaccag tagtgtgacc atgggcaatt    238320
tatttctctc ttggaggcat catttttctc atatctaaaa tgaaatggta ggtccaggtg    238380
actgttaagg tctcttctag ctctaagagt ctgtgtctac atataaatga ttttctctgc    238440
caaagtagtg ttttagagt ccttttaat gccagaaatg aatacggctt ctctagttct    238500
tctaagtggc catctatcct ttggtgatgg ttagaagtaa gcagagatcc tggctagaaa    238560
gagagagagg aaaatgtgga ccatgatttt attccttta ttcttgagag ttgtccaatg    238620
ggatattgtc cactagtgga taagtagata cttgccaata tgcacctgac ctcttctctt    238680
cactcataat gggaatttag aagtataata cctgttataa tcaacttcct aatctctatc    238740
ccttttttgt cactctattt cctactgtaa cttctctatg aagtactata agtctacagt    238800
aacatactgg tgtttcccct tccttatgaa gttttatata gctactccag tatatcctaa    238860
aatgttcctt tttcttgctt ttatagtgga gtcttgcttg ttggccaggc tggcctcaaa    238920
ctcctgagct caagtgatcc tcccacctaa tagtagctgg gtattcttct gagtaggtgg    238980
tcctaaaatg ttttattttc agcttatttc ataggtataa gtcttatttt cccaaccagg    239040
ctgaaaactt ttcagaatca ggacttgtct ttagtttctc attttttatg agggatgtg    239100
```

```
gcattattgc ttagggaatt cagatatttc tgataataaa gatgcttttc tgtttgttca 239160
tataaattag ggtaaaagag gaagtacaaa actatctcaa atcaagtaca ggactcttaa 239220
ttattactag ctatctaaca gctcatagaa accgataagt ttctgaacct aatgccaaaa 239280
aaaagcaacc ttaccataaa aagaaaatcc aaataaaact gaaagaggca gtgggcagtg 239340
ctacctatgg gaagaaaact ttgaagtggg aaaaatctgg attcacatcc cagctttgct 239400
acttattacc tttgtgtttt ggctaaaaat tatctaactt tcctgaagtt aagtttcctt 239460
ctctgtaaaa tgagggttat aataatatat acagcatact ccacagaaga gttgtgaaga 239520
tggaatgaga aagcaaatgg caaaaactta gcacaaagta ggagctcaat caatcatggt 239580
taaaaagaac ttttatccat tgttattttt gcttatatac agtaagaatt atccaatgca 239640
aatgtaatca gagcatctgc aattgagctt tataaagtga attataattc tcataccata 239700
gtggttctca tcaagggtga tttttttccc cccagggac attggcaat gtctagagac 239760 attttacttg tcacactgga aaagaggggg tgctactggc atctagtagg tagagagtag 239820
gaatgatgat aagcattctc taatgcacag gacagcattc cacagcaaca aatgatctga 239880
tccaaaatac caatagtgtg gaagttgaga aaccctacca taaagcctag ggagtccatt 239940
acttctgacc taaatttgtt ttatatttaa gagtggatgt ggattaaaag tagcttccat 240000
tttggtaggt tatgaagaga gttgtctaat ctgtgcttta gattctaatt ttgaggcata 240060
tttttaggct aaggcattgc aatatataag gctttctaag tttcagacat tttcttggag 240120
gtcaacaaat gaaggcttgg ggatctatta acccactaga gtagtgtaat aatggtggtg 240180
gttgtttatt gaagactaac caagtgccaa gtactctata ataatctgat ttattttca 240240 gcaactgtat aagcaggtat tttgctctca ttttacacag gggaaaactg gagcttagag 240300
aacttatgta acattactag caagttgcac agctgggatt caaactgaaa tccagctagc 240360
ttcaaagact gtgttctttc tgctgctgca tactaccct acctaccaag gctctgagat 240420
tagaaagcag gatgggtgtg ttttaaagga aataaggtag gaaagttttc aaatattaga 240480
aactctgcac aagaagatta ggtcaagttt cccactgagg ggcccttgag tatctatgaa 240540
ctcgatgaaa actctgagct tctcaggaag gtagaccaaa gggaaaggat tcatcaaaat 240600
ggatgttagc actatgccat gtgtattact ccatcctcac acggccaaaa ggacatacct 240660
gagactgggt aatttgtaag gaaaagagg tttaaaaaag ttctcttcga tggcaaaata 240720
ggaacagctc cggtctacag ctcccagcgt gagcgacaca gaagacgggt gatttctgca 240780
tttccatctg agctactgca ttcatctcac tagggagtgc cagacagtgg gcccgggaca 240840
gtgggtgcag cacactttgc aggagccgaa gcagggtgag gcattgcctc actcaggaag 240900
cgcaagggga cagggagttc cctttccgag tcaaagaaag gggtgacaga tggcacctgg 240960
aaaatcgggt cactcccacc ctaatactgc gcttttctga cgggcttaaa aaacggcgca 241020
ccaggagatt atatcccgca cctggctcgg agggtcctac gcccacgag tctcgctgat 241080 tgctagcaca gcagtctgag atcaaactgc aaggtggcag caaggctggg ggagggcgc 241140 caggcattgc ccaggtttgc ttaggtaaac aaagcaggcg ggaatctcga actgggtgga 241200
gcccacaaca gctcaaggag gcctgcctgc ctctgtagac tccacctctg ggggcaggt 241260 acagacaaac aaaaagacag cagtaacctc tgcagactta aatgtccctg tctgacagct 241320
ttgaagagag cagtggttct cccagcatgc agctgggagat ctgagaacag gcagactgcc 241380
tcctcaagtg ggtccctgac ccctgacccc tgagcagcct aactgggaga caccccctcag 241440
```

```
tagggggcaga ctgacacctc acacggccag gtactcctct gagacaaaac ttccagagga   241500
acgatcaggc agcagcattc aaggttcatg aaaatccgct gttctgcagc caccgctgct   241560
ggtacccagg aaaacagggt ctggagtgga cctctagcaa actccaacag acctgcagct   241620
gagggtcctg tctgttagaa ggaaaactaa caaacagaaa ggacatccac accaaaaacc   241680
catctgtaca tcaccatcat caaagaccaa aagtagataa aaccacaaag atggggaaaa   241740
aacagagcag aaaaactgga aactctgaaa agcagagcac ctctcctcct ccaaaggaac   241800
gcagttcctc accagcaacg gaacaaagct ggacggagaa tgactttgac gagctgagag   241860
aagacttcag acgatcaaat tactccgagc tacaggagga aattgaaacc aaaggcaaag   241920
aagttgaaaa ctctgaaaaa atttagaag aatgtataac tagaataacc aatacagaga   241980
agtgcttaaa ggagctgatg gagctgaaaa ccaaggctca agaactacat gaagaatgca   242040
gaagcctcag gagccgatgc gatcagctgg tagaaatggt atcagtgatg gaatatgaaa   242100
tgaatgaaat gaagtgagaa gggaagttta gagaaaaaag aataaaaaga aacaaagcct   242160
ccaagaaata tgggactatg tgaaaagacc aaatctatgt ctgattggtg tacctgaaat   242220
tgacggggag aatggaacca agttggaaaa cactctgcag gatattatcc aggagaactt   242280
ccccaatcta gcaaggcagg ccaacattca gattcaggaa atacaagaa cgccacaaag   242340 atattcctcg agaagagcag ctccaagaca cataattgtc agattcacca agttgaaac   242400 gaaggaaaaa atgttcaggg cagccagaga gaaaggtcgg gttacccaga aagggaagcc   242460
catcagtcta acagctaatc tcttggcaga aactctacaa gccagaagag agtgggggcc   242520
aatattcaac attcttaaag aaaagaattt tcaacccaga atttcatatc cagccaaact   242580
aagcttcata agtgaagggg aaataaaata ctttacagac aagcaaatgc tgagagattt   242640
tgtcaccacc aggcctgccc tacaagagct cctgaaggaa gcactaaaca tggaaaggaa   242700
caacaggtac cagccactgc aaaatcatgc caaattgtaa agaccatcaa ggctaggaag   242760
aaactgcatc aactaacgag taaaataacc agctaacatc ataatgacag gatcaaattc   242820
acacataaca atattaactt taaatgtaaa tggactaaat gctccaatta aagacacag   242880 actggcaaat tggataaaga gtcaagaacc atcagtgtgc tgtattcagg aaacccatct   242940
cacgtgcaga gacacacaca ggctcaaaac aaaaggatgg aggaagatct accaagcaaa   243000
tggaaaacaa aaaagtcag gggttgcaat cctcgtctct gataaaacag actttaaacc   243060
aacaaagatc aaaagagaca agaaggcca ttacataatg gtaaagggat caattcaaca   243120
agaagagcta actatcctaa atatatatgc acccaataca ggagcatcca gattcataaa   243180
gcaagtcctg agtgacctac aaacagactt agactcccac acaataataa tgggagactt   243240
taacagccca ctgtcaacat tagacagatc aacgggacag aaagttaaca aggataccca   243300
ggaattgaac tcagctctgc accaagcgga cttaatagac atctacagaa ctctccatca   243360
caaatcaaca gaatatacat tttttcagc accaccac accaccac acctattcca aaattgacca   243420
cgtggttcga agcaaagctc tcctcagcaa atggaaaaaa acagaaatta taacaaactg   243480
tctctcagac cacagtgcaa tcaaactaga actcaggatt aggaaaccca ctcaaaacca   243540
ctcaactaca tggaaactga acaacctggt cctgaatgac tactgggtac ataacaaaat   243600
gaaggcagaa ataaagatgt tctttgaaac caacaagaac aaagacacaa cataccagaa   243660
tctctgggac gcattcaaag cagtgtgtag gggaaattt atagcactaa atgcccacaa   243720
gagaaagcag gaaagatcca aaattgacac cctaacatca caattaaaag aactagaaaa   243780
gcaagagcaa acacattcaa aagctaggag aaggcaagaa ataactaaga tcagagcaga   243840
```

```
actgaaggaa atagagacac aaaaaaccct tcaaataatt aatgaatcca ggagctggtt 243900
tttggaaagg atcaacaaaa ttgatagacc actagcaaga ctaataaaga agaaaagaga 243960
gtagaaaaat aaaaaatgat aaagaggata tcaccactga tcccacagaa atgcaaacta 244020
ccatcagaga atactacaaa cacctctaca caaataaact agaaaatcta gaagaaatgg 244080
ataaattcct caacacatac accctcccaa gactaaacca ggaagagttg aatctctgaa 244140
tagaccaata acaggctctg aaattgtggc tataatcaat agcttaccaa ccaaaaagag 244200
tccaggccca gatggattca cagccgaatt ctaccagagg tacaaggagg aactggtacc 244260
attccttctg aaaccattcc aatcaataga aaaagaagga atcctctcta actcattta 244320 tgaggccagc atcatcctga taccaaagcc tggcagagac acaaccaaaa agagaattt 244380 taggccaata tccttgatga acattgatgc aaaaatcctc agtaaaatac tagcaaaccg 244440
aatccagcag cacatcaaaa agcttatcca ccatgatcaa gtgggcttca tccctgggat 244500
gcaaggctgg ttcaatattt gcaaatcaat aaatgtaatc cagcatataa acagaaccaa 244560
agacaaaaac cacatgatta tctcaataga tgcagaaaag ttctttgaca aaattcaaca 244620
acacttcatg ctaaaaactc tcaataaatt aggtattgat gggacatatc tcaaaataat 244680
aagagctata tatgacaaac ccacagccaa tatcatactg aatgggcaaa aactggaagc 244740 attcccttg aaaactggca caagacaggg atgacctctc tcaccactcc tattcaacat 244800
agtgttggaa gttctggcca gggcaattac gcaggagaag gaaataaaga gtattcaatt 244860
aggaaaagag gaagtcaact tgtccctgtt tgcagatgac atgattgtat atctagaaaa 244920
ccccattgtc tcagcccaaa atctccttaa gctgataaac aacttcagca agtctcagg 244980 atacaaaatc aatgtgcaaa aatcacaagc attcttatac accaataaca gacaaacaga 245040
gccaaatcat gagtgaactc ccattcacaa ttgcttcaaa gagaataaaa taactaggaa 245100
tccaacttac aagggacatg aaggacctct tcaaggagaa ctacaaacca ctgctcaatg 245160
aaataaaaga ggatacaaag aaatggaaga acattccatg ctcatggata ggaagaatca 245220
atattgtgaa aatggccata ctgtccaagg taattatag attcaatgcc atccccatca 245280
agctaccaat gactttcttc acagaattgg aaaaaactac cttaaagttc atatggaacc 245340
aaaaaagagc ctgcatcgcc aagtcaatcc taagccaaaa gagcaaagct ggaggcatca 245400
cactacctga cttcaaacaa tactacaagg ctacagtaac caaaacagca tggtactggt 245460
accaaagcag agatatagat caatggaaca gaacagagcc ctcagaaata acactgcatg 245520
tctacaacta tctgatcttt gacaaacctg agaaaaacaa gcaatgggaa aaggattccc 245580
tatttaataa atggtgctgg gaaaactggc tagccatatg tagaaagctg aaactggatc 245640
ccttccttac accttataca aaaattaatt caagatggag taaagactta atgttagac 245700 ctaaaaccat aaaaaccct gaagaaaacc taggcattat cattcaggac ataggcatgg 245760
gcaaggactt catgtctaaa acaccaaaag caatggcaac aaaagcaaaa attgacaaat 245820
ggggtctaat taaactaaag agcttctgca cagcaaaaga aactaccatc agagtgaaca 245880
ggcagcctac aaaatgggag aaaattttcg caacctactc atctgacaaa gggataatat 245940
ccagaatcta caatgaactc aaacaaatct acaggaaaaa acaaacaac accatcaaaa 246000 agtgggcaaa ggacatgaac agacacttct caaagaaga catttatgca gccaaaaaac 246060
acatgaaaaa atgctcacca tcactggcta tcagagaaat gcaaatcaaa accacaatga 246120
gataccatct cacaccagtt gttagaatgg cgatcattaa aaagtcagga acaacaggt 246180
```

```
gctggatagg atgtggagaa ataggaacac ttttacactg ttggtgggac tgtaaactag    246240
ttcaaccatt gtggaagtca gtgtggcgat tcctcaggga tctagaacta gaaataccat    246300
ttgacccagc catcccatta ctgggtatat acccaaatga ctgtaaatca tgctgctata    246360
aagacacatg cacactatgt ttattgcggc actattcaca atagcaaaga cttggaacca    246420
acccgaatgt ccaacaatga tagactggat taagaaaatg tggcacatat acaccacgga    246480
atactatgca gccataaaaa tgatgagttc atgtcctttg tagggacatg gatgaaattg    246540
gaaatcatca ttctgagtaa actatcgcaa gaacaaaaaa ccaaacaccg catattctca    246600
ctcataggtg ggaattgaac aatgagaaca catggacaca ggaaggggaa catcacactc    246660
tggggactgt tgtgggggtg gaggaggggg aagggatagc tttaggagat atacctaatg    246720
ctaaatgacg agttaatggg tgcagcacac cagcatgcca catgtataca catgtgacta    246780
acctgcacat tgtgcacatg taccctgaaa cttaaagtat aataataata aagaaaaaa    246840 aaagaaaaag aggtttaatg gactcacagt tccacatggc tggtgaggcc tcacagtcat    246900
ggtagagggt gaatgaggag caaaagcatg tcttgcatgg cggcagaaaa gaaagcatgt    246960 gcagggggaac tgcccttat aaaaccatca gatctcatga gacttattca ctgtcatgag    247020
aacagcacaa gaaaaacctg cccccatgat tcaattacct tccaccagct ccctctcatg    247080
acacatgcgg attatgggag gtgcaattca agatgtgatt tgtatgggga cacagccaaa    247140
ccatatcacc atgacataca atttgccgat tcagcaacag ttttcaggtc ttctattttt    247200
aagcctaatg caatatattt tatgaattct tcctatttat gttttccctt taaataagt    247260 tctactatct taactatcac tttcaaatat aatgcaagct acatatgcca ttttaaattt    247320
tttagtagtt acatttaaaa agagggtgaa attaattta acaaagtagg ttatttatcc    247380
caatatatcc aaactattat cattttgaca tgtagtgaag ctaataaaag cattcattgt    247440
taatgatcta tctcttacat tatttttttcc taataaatct tcagaatctg ggtgtgcatt    247500
ttaactttcc agcacatctc aactgggatg tgaaattttc agcaattaaa gtgaaatata    247560
gccctatcaa aactattaat gttgcattta ggaaaaagat atttttcact ctttttattt    247620
ttaaatttga gtttaaatta attaaaatgg aataaaattt aaaattcaat tctctgtcac    247680
actagccaca tttcaagtgc tcaataccta cgaaagaccc atggctacca tattggacag    247740
cacagatcta agctcttatt gctcagaatg tggtccccag agcagaatca acagcatctg    247800
tgaacttatc aaaagtgcag tatttcagtt cacacctact gaatctgcat tttaacacaa    247860
tccccaggtg atgcttgttc acatgaaagt tgtgtctctc taaatcgcag atcttttcaa    247920
caaagagccc agaaaaagca catgaatcaa taactgtgag gaataaggaa acttgccaca    247980
ggagaatggt gccagggttg gcattaatga tgtgctctgg tgaaaagtcg taggtttccc    248040
acaaaggcaa ccatggctat tctattgttt gaactgacac agagccattc tagagcttgg    248100
agttggctct gctcccagaa tctacatcaa agaatctaac actaacttcc atgactacca    248160
caattaaggc agctgcacac cccaccacta tatatatttg aaattgcaac tttagaaccc    248220
ctgtaacaca gccgtgagca tgtttctgct atacacaagt ggaatttaag gtcgaacctc    248280
cctgggagac cccaggaaga tcacccacaa gagtggcttt tgttgtctgc ctcactgtca    248340
tcctctgaga gctaacacag acacagtcaa catcctctta tatggaggtt ggcccagatg    248400
cccctgggga ttcaatgtat tctgcttcac ctcactaatc cttatttggt ttgttttttca    248460 cagaactcag tatttgatgg gccttttcaat attttccttt aaggaattca ttgtactaat    248520
ataacataga agctcattgt tctaataagt ggtccccaat gttggctgca cattagaatc    248580
```

```
acctggggca ttttgaaaaa taccaatgcc caggcatcac cccaatctaa ttaaattaaa 248640
cctgtggaag gtattttgtt aaagatcccc aagtgattac aatgtgcagc cagagttgaa 248700
atccactggt ccaattagaa ggaggcctta gctagcggtc aggtgcccaa ggaaaggcat 248760
ctcaagtttt aatgcgcata cagatagctt gggatttgtt aaaatgcaga ttctgatcca 248820
gtaggtatgg gtggaaataa acccatgttt gtgtacagat gtttctcttg tggtatgtgg 248880
ttggtaatca tcctcagtat gtttccattt ccggcaaact gggttgagtt gatgaccct a 248940 ttcttactcc tccctgaaac ctttgtctct ccctcaggct cccagttctc attaatcact 249000
actttctgtg atattctgaa gcaattatta tctttaactg cctttttttca ttagctactt 249060 ctctatctgc ttatgtacgt gagttatttc ctctactgga ttacgatctt caaggtagat 249120
ccaaatatca tgtcattttt ataattctca ctgcacctaa agagtgcctt acacacaaat 249180
gccacttgtt gattaattga acagggaat agctgatgtg atcatctcaa aaatatcca 249240 aaagacttaa aaatgcaaga tattttctct tgttggacag aaaaagaaag tttagatagg 249300
caagggggta ggagatattg aggctttcaa ttttttatttc actcggtaca tatttaaatt 249360
ttgaagaatt attttgtaat ttagtgattt taattatttg ttgggaatag ggcactattg 249420
acattttgga ctagatcatt ctttgttgtg gctgtcatcc tgtgcattgt aatatgtttc 249480
acagcatccc tggcctcaac ccactagatg ccagtatcac cctttacccc agtcttgaga 249540
accaaaaatg tctccagtca ttgcaaaatg tctcctggga aactcattca tggttgagaa 249600
cccttagttt agaaaaatgg aagtgtgaca cagctgtctt accgcactaa tatagacctg 249660 aaaaaataa aaaattaaaa acatgcacat aagagaatga caagctatgt tctgagcaat 249720
atgtgtatat ataaatatta atataaaaat gttctctgtt cctgcgtttt ggaggccatg 249780
tgcttgtaga ccatatttat ctttgtattt gtcatcttgg tcattctctt tataaaaata 249840
gaggtatatt gcatgccaat gctcctcagc ttatgaggtt acatcccaat aagcctgttg 249900
taaatttaaa aaatcataag ttagaaatgt caaaacttga aaatgcattt aatacccctga 249960 taaacacatc ataagttga aaatcctaa gtcaatccat catgagtcag gaactatttg 250020
tatatgaaac atttttaaaa tctgaacata gacttaggaa ttttaatatg tagtggtagt 250080
aattccacca agcaagagaa tacatagagc aaaaatcatt aagaaacagt gactgagatg 250140
attctcattc tcaggaaact ggtccagccc ctttacataa aatattctgt tcagtgtgct 250200
gtgatccttg gactgaatat actgttttag caagcagagt tgttaagcta aagcctgcac 250260
atcaacaggt gttcaatgtc tgctgaataa atgaagaatg aatgaatatt aactgcacct 250320
ctaaacccta aaattaaaaa gctttaatgt gctcatcaca aaagacccta ttttgttgca 250380
tttgaaattt caagcttcaa aaatgaaatt acatgcaaaa gtatattatc atcaatgaga 250440
ataaatggcc tcaacaaaat tacaagatag aaaacaaagt ttcatttgtc agttggtttc 250500
ttctggcaat agaaggctcc ccttagactt cattagcttc agatatttca gtgacagaaa 250560
tttaatgttg gcaaagcatt gctatacttt caggcttgga ttggaatgcc ccacatttac 250620
tttttcctac cattcctggc taaaaacttg aatgtgagaa ccagacacaa ggctctagtg 250680
gtagcaagca gaatgtctcc taagctccaa ggggaaaaaa tgatataagt cagtggttcc 250740
caaattaacc atcaaatgct acccattaaa atcactgggg aacttttaaa aattaaatgc 250800
ccaactaaca acaaactgta tgaaaaagaa atttagaaaa caatcctatt tttaaaagca 250860 gcaaaaagt aaaatactta ggagtaaatt taaccaagga agggaaatat ctgtttactg 250920
```

```
aaaactatga aatgttgatg aaagaaattg aagatggtaa aaataaatga aaagataaat   250980
atgtatggat tggaagaatt aatattgtta agagatctat actacccaaa gcaatctata   251040
gattcaatgc aatcctatca aaattccaaa gtcattcttt atagcagtag aaaaaaatca   251100
taaaattcat atggaaccac aaaagactct gaatagccaa agcaatcttg accaaaaaga   251160
gcaatgctgg aagcatcaca ttatcagatt tcaaaatata ttacaaagct acaatattca   251220
aaatagcatg ctactggcat taaaacagat ctatcaacta ctgaaacaga atagtgagcc   251280
cagaaataaa cccacacatc tatgatcaat tgattttcaa caaagatacc aagaacacac   251340
aatggggaaa gacagtgtct tcaataaatg gtgctgagaa aactggaaat ccacatgctg   251400
aagaatgaaa ttagatcctt atctcatccc ttatacaaga atcaactcaa aatagattaa   251460
agacttaaac ataagccctg aaactataaa actaatgcag aaaatatagg gggaaatcta   251520
catgatatta atctaggcag aagtttcatg gatatgacct caaaagcaca gacaacaaaa   251580
gcaaaaatag acaatggca ttgcatcaga ctaaaaaact tctgtacagc agatgaagca   251640
acaaatagag tgaagagaca acctacagat taggagaaaa tatttgcaaa tcatatatta   251700 gataagggt taatattcca aaaggtacaa ggaaatcaaa ctactcaata acaagaaagc   251760
caattaccct attaaaatat agggatagca ttggagata cacctaatgc tagatgacga   251820
gttagtgggt gcagtgcacc agcatggcac atgtatacat atgtaactaa cctgcacaag   251880
gtgcacatgt accctaaaac ttaaagtata ataataattt tttttaaaaa aaagcaaaaa   251940
ttaaaaaaaa aaaaaaaata tatatatata tataggcaac aaacttaaat agacatttct   252000
caaaagaagc aagtatcacc ctgatttaaa acctggcaaa gacacaatga gaaaacaaac   252060
tacaggccaa catctctgat gaacatagac acaaaaatcc ttgacaaaat actagcaaac   252120
tgaatacagc agcacatcaa aaagttaatt tgccatgata aactagtgtg ttagggtgtt   252180
ctagcatgct attaaaaaat acccaagact gagtaattta taaagaacaa aggcttaatt   252240
tgttcatggt tctgcagcct gtacaagcat ggtgccagca cctggccagc ttctggggaa   252300
gcctcatgaa attttttattc atggcagaag gtgaaacagg aacaggcaca tcacacaggg   252360
gaagcaggag taagagagag tgtgagggag gtgccacaca cttaaacaat caggtctcac   252420
aagtactcac tcactactgc aaggacagca ccaagccata agggcccacc cccatgattc   252480
aaacacctcc caccaagacc cacctccaac attgggcatt atatgtcaac atgagatttg   252540
aacagataca aatattcaaa ctatatcaag taggcttcct tcttgggatt caaggttggt   252600
tcaacataca cagatcaata aatctgactc accacataaa cagaattata acaaaaacc   252660 acatgatttc aataggtgtg ggaaaagctt ttgataaaat ccaacctccc ttcatgttaa   252720
aaaaaaaaaa aaaaccttta agaaactagg cggccgggcg cggtggctca cctgtaat    252780 cccagcactt tgggaggccg aggtgggcgg atcacgaggt caggagatcg agaccatccc   252840
ggctaaaacg gtgaaaccca gtctctacta aaaatacaaa aaattagccg ggcgtagggg   252900
cgggcgcctg tagtcccagc tacttgggag gctgaggcag gagaatggcg tgaacccggg   252960
aggcggagct tgcagtgagc cgagatcccg ccactgcact ccagcctggg cgacagagca   253020
agactccgtc tcaaaaaaaa aaaaaaaag aaactaggca ttgaaggaat atttctcaaa   253080
atagtaagag ccatctgtga caaacccaca acaacataat aataaatggg caaaactgg   253140 aagcgttccc cttgaagaca agaaaaggat gccttttctc acctgttgta ttcatgacag   253200
tacttgaagt gctagccaga gcaatcaggt aaaagaaaga aataaagac atcaaaatag   253260 aaaaagaaga aatcaaacta cctctctttta ctgactatat aattctatgc ctagaaaaac   253320
```

```
ctaaaggctc caccaaaaaa gctcttggaa ctgataaaca acttcagtaa agtttctgga 253380
tacaaaatca atgtgcaaaa atcagtagca tttctatatca gcaatagtgt tcacattgag 253440
agccaaacca agaatgtaat cccatttaca gtagccacaa aagaaataaa gtacaactag 253500
ggatacatct aaccaaggag atgaaagatc tcataatgct gcacaagtac agccatttaa 253560
tcttcaacaa agatgacaaa attagcaatg gggaaaggac tctctagtca gtaaatggta 253620
ctgggataaa tgtaaatgtc agtaaatggc tagtcagtaa gtgatactga ctagctatat 253680
gtagaagaat gaaactggac ccctaccttt caccatatac aaaaattaac tcaggatgga 253740
ttaattattc aaatgtaata tctcaaacta taagaatgta atattcaaat atatctcaaa 253800
tgatatacaa actataagat atatattata tctcaagcta tatacaaact ataagaatgt 253860
aatattcaaa tgtaatatct caaactataa gaatcctata agaaaaccta ggaaacacca 253920
ttctggacat cagccttgga aaagaattta tgactgagtt ctcaaaagca atttcaacaa 253980
aaacaaaaac tgacaagttt ttctgtgtag aagctcttag tttaagaaaa agaaaccagc 254040
aacagagtaa acagcctaca gaatgggtga aaatcttcac aaactgtgct tccaaccaag 254100
atctaatatc tggcgtctgt taggaactta aacaattgag caaacaaaaa acaaccccat 254160
ttaaaaatgg gcaagcagca tgaacagaca gttctcaaaa gaaggcatat aaacagctaa 254220
caaacatgaa aaaatgtctc acatcactaa tcatcagaga aatgcaaatc aaaaccacaa 254280
taatatgcta tatcacacca gtcagaatag ctattatcaa aaagtcaaaa acaacagacg 254340
ctggcaaggc tgcagaaaaa aaagtgaacg ctcatacacg gttgctggga atgtaagtta 254400
gttcagccac tgtgaaaagc agtttggaga tttctcaaag aacttgaaac agagttacca 254460
ttcaacccag caatcccact gggtatatat ccaaaagaaa gtacattgtt tcttttggat 254520
attgttctac ccaaaagaca catacactca catgttcatt acaacactgt tcgcaatagc 254580
aaagacatgg aatcaaccta ggtgcccaac aaaggtggat tggattaaaa aatgtggtac 254640
atgtccacca tgggatacta cacagcaata aaaaagaatg aaatcatgtc ctttgcagca 254700
acatggatgc agctggaggc cattatacta agtgaggtaa tacaggaaca gaaaaccaaa 254760
tactgcatgt ttttacttat aagtgggagc taaacattgg gtaaacatgg atataaaggt 254820
ggcaacaata gaaactgggg actaacagag tagggaggta gggagcagag agaggactaa 254880
aaaactatta ggtactatgc tcattccctg ggtgatggga tcaatcatac cccaaacctc 254940
agcatcgtgt gatatacccca ggtaacaaac ctgcacattt gttccctgaa tctaaaataa 255000
aagttgaaat tacaattttt aaaaggatag aaactagtca tcagcgtgtt ttttaatttt 255060
ccaggtgact ctaacattca ataattattt taaataatta tttctgtctg tagaccttct 255120
gccagctact aagtttcagg aattttgatg gtctcattaa agagaacctg acaacccac 255180 ttacaagtgc ttcagctaag tttcatttat aatattttca tattgccaag gatccagtag 255240
tgtctttttt acagtgagtt acaaattcct gtttttgtga cagtgacagg ccaaaattaa 255300
tgagctgtga ttttttaaact gaaaaagtga ctgtccaata gaggctaaaa agaaaactaa 255360
aattatattt tgtcaatttt agtgttaagt gtgatttttt gctttgtatg ttttagatag 255420 ttttttttatt gagataaaac ccaaatagca taaaatccac cttttttaatc tcaaagtggt 255480 ttttggtata ttcacaatgt tgtgcaacaa tcactactat ctaactctag aacattttca 255540
ttacttcctc atggaaccct gtacccatta gtagtcactc ccagtttccc attcacctca 255600
tttcctggca accactaatc tacttttctg tctctctgta tgtgactatt cttaacattt 255660
```

```
catgtaaatc agatactata atatgtggcc ttttatgtct gacttctatc acatagcaac 255720
atattttcaa ggtcattcgt gttgtagcat gtatcagtat tttattcctt tttaagacaa 255780
tactttatta taggattata ccacatcttt tttatccact catcagttga tggacctttg 255840
agttgtttct acttttctgt tattttaaat aatgctgtta tgagcattct tgcacatgtt 255900
tttgtgtgat catatgtgtt tgcttctctg gcatatacc taggagcaga attgcagggt 255960
catatggtaa ctctgtattt aacattttga ggaaccccca aattgctttc cccagtagct 256020
ataccatttt acattctgaa cagaagtgtg tgagggtttc tattacttca catcctcttg 256080
ctttctattt taattattta attatttaat ttaattatct aagatgcctt ttaccctaac 256140
caaccagaaa ataaacttga ctgaatttag tgctaattgt ttttgcatag tcattcagta 256200
taattgtctt tgacatctca aaacactgct tatgcagaat cactttttt aaaacagtga 256260
aatcatagca attctatttc ctaagtcagt tcttcttcag ggtagtaagt tataggtctt 256320
tgaggtcatg ttcctgtttc catcttccaa aaggcaacat tattaaaatc ttgttgctgt 256380
atctgccttg gcatatcccc ctctctatcc agagaaaaga tcactgacag aatagtgtcc 256440
ccacctttct atcttagagg tctcattacg agtcagtatg cttttaaaag aattaatgga 256500
taaagagcta gacatcaaga agaagagaga aatttttaaa taagacagag gagtgtatga 256560
tcactctttc taagatgatt aaatgaaata atttgaaagg caataaacta actgcaccaa 256620
gtaaatcttg tgaaagcgaa aggaaagagg agaaggaaga tttgagtgct gaaaaccagg 256680
ataaattgta ttcaaccacc agcattaagg gaagttatac aatacatttt atgaagaaag 256740
tgttccatga aaataaaaca acaaaaagaa agtttggtga aggtttaaat gataaatgcc 256800
aatagtagta tatgtgcaat tatctactga cactgctata caaatgagct atctatatag 256860
gctgtgacca cataacctca cctgccaaac cacagtacta taaataaata cttttcccag 256920
acactacaga gctcagttga cttgagattc atcttatggt aactggaaat gtagactgtg 256980
cctttatttg ggtcaatcct acaatttcct ttaatgtacc agcaattcat tatttaaagt 257040
ttactagagt ttaattaaa attataaaaaa aggaagaaat tggctgggta tggtggctca 257100
cgcctgtaat cccagcactt tgggaggcca aggcggaag atcatgaggt caggagatcg 257160
agaccctcct ggccaaaatg gtgaaaccca gtctctacta aaaatacaaa aattacctgg 257220
gcatggtggc acacgcctgt agtcccagct actcaggagg ctgaggcagg agaatcgctt 257280
gaacctggga ggcggaggtt gcagtgagcc aagatctcac cactgcactc caacttggtg 257340
acagagcgag actccatata aaaaaaaaag gaagaaatta atagttcagg tgagaacttg 257400
tgaattttta ttctcaactc taagctagta agtgcttaaa tagaagactt tacaacgagc 257460
tgtaccttct taattctaca gagaatcatg aggaaaatca aatataaatg tgaatttctt 257520
atgttcagta ttgtccaaaa agaaaatatt ttattaaatt ttttgtcagt tgccatcatt 257580
atttaaagcc ttcctgccag tagcctatac tattttgga atggagtgtt tgcagtttca 257640
taaccacttg ataacaccat aggttaaaaa aaaagtctac cagtcttttt cagatggcct 257700
ctttgacaat gcattattta tagggaagtt cagttacttt taacaataaa gacaagccaa 257760
aagaaattac agatctcttt taccatattt tgatatacta gcagcatcca ctcaggacag 257820
gacctttatt aaagggggc ttaaggtact tttaattgga ggaattactg aattcctgaa 257880
gctcttcaaa caaatagca cttgggatat gacaagagta cttggagaa ggctgcttgg 257940
tcccaaagca gagattcaag aggaggactc cagctagctg ggtaagggt tccttcctct 258000
caacctaagt gtttatgtaa gcctgctggg ggccaggaac tgcgtaaaac tcagtaagct 258060
```

```
cagtacttct cagcacagaa tccagtccca aggaagcacc cagcaaaaat ttaggttgaa   258120 tttctttaa aataaaataa agaaaaaagt aaaattaaaa aaaaaataca attcaactac    258180
tcagcccatt ccattccggg tagttttggc tcagaatgct ggaagagttg ataggctat   258240 tagtgagaga actcaaaact ccccaaactc cacttcatta ctcttccttt atatttttc    258300 tgaaaagagt attgccaata tatcaataaa gcttttgct atgacttcag agtgcccagg   258360
tcactaggga aaagtatcaa gtagcatcct gaatccacaa atcctttgag agccagccac   258420
acagtatctg cgtgagtgtg gtaattctct acccttacga gtgtcatcac agaattgcag   258480
cattctcttt tcattgtttc tcaggaaaac atagacaaag gctctgcttg gattttttta   258540
atttaacact aatatgtaat aatatagcaa catctcctag ttatctagaa ctcaggcttt   258600
gatagctgtg actgtctaga atacaaccac agaaaatcac ctctgaacag tgagggaaat   258660
agctgccaca gtatcaccac ctactccaag cttgaacctc tcaacccgca accaacagac   258720
tgcaagtagt tcagtacagc tttgaatgca gcccaagaca aactcgtaaa ccttcttaaa   258780
acattatgaa attttttttgc aacttgttca tcagctatcg ttagtgttag tatatttttt  258840
gtgttgctca agacaagtct cttcttccag tgtagcccag gaaagccaaa agattggaca   258900
cctatacttt ggatgtttca tctagtaccg atatacttat aattacatgt ttcaactagt   258960
actaatgaac ttatagttac aggatgaaat ttcaaattag caatgttcat catttgctct   259020
tcctaggtaa caacagttaa caaatcatag gttgacaatc acaactgatt gtgaggatgg   259080
aaataataac aatgagcatt tatataatgc ttactctata ccaggcactt ttctaagaac   259140
tttacataga ttagctcact taatctttac aataaccctg tgacatacca ttattatccc   259200
cattttacag gtgaggaaac tgaagaagtt aagtaatttg cccaagatta cagattgtat   259260
gtgattgagg taggatttga actcagcagt ctggcaccaa aatcagcact ctcagcctct   259320
acccagtatt atcaaaagta atttcctggt agcttcttc aattgtcatg gcaactctca     259380
agataaagaa ttattgtttt taataaataa tgtcattccc agaaatgaat tatgtgtgaa   259440
tcatactaag ctgcagtgag agaatgaata tcaccatcac agtggtgaat ctacttagtg   259500
taggggtaaa aggccagtct ctcccagcag ccctgcacat aggtacaccg taattcacta   259560
ggataatccc tgatcgccat gctgtcataa aaaaacgtta aatgatgttt aacaggtttc   259620
attaatgatt cagagaatct tataatatgt cttaggaaaa ataatttcag gagtaacttt   259680
cagttagcta gacaatacag ttctgttgag catctcataa tctatgccag acaaaggaaa   259740
cattcttgcc tttctttgag ggaattatag accaacaatt ttattaattt tcaactttca   259800
tcgaggcaag attagcttca tgaacaatgt ttctcaaact gaaagtagtg acctgtatta   259860
gtaaatcaat ttatagggtt gcaagcagca tcatttataa actgaaatca gaattcattg   259920
caggcagtaa ttttgagaca ttttatttta catgtgcgtg tgtatatcta tcatataaat   259980
aagtatgtga gaacattta aaacatttaa aatatatttt tatatctaaa gtttaaatgt   260040
aaatatatat ttatattaat aatataatta atatgaatta ataacatatt aattcatatt   260100
aacttatatt aatttatatt aacaatatgt aaacaatata ttaattagta atatattata   260160
ctaatattag tatgtattaa tatattatta taatatatta tatattaatt aatatattat   260220
atattgtata ttatatatta attaatatat tatatattgt atattatata ttaataacat   260280
actattatta atattttaaa tatattttaa tatacttaaa tttatactta aaatttacat   260340
atacatataa ataattttcc tgaaagtcac tttcaaaaac tttgaaagcc accagtgcag   260400
```

```
tggttaagaa tacaaatttt gggctgggca tggtggctca cacctgtaat cccaacactt 260460
tgggaggccg aggtgggtgg atcccgaggt caagagattg agaccatcct ggccaacatg 260520
gtgaaacatt gtctctacta aaaatataaa aattagctgg gcacggtggc acgcacctgt 260580
agtcccagct atgcaggagg ctgaggcagg agaatcactt gaacccagga ggtggaggtt 260640
gcagtgagcc gagatcatgg cactgcattc cagcctggcg acagagcgag actgcatctc 260700
aaaaaaaaaa aaagaataca aattctgaag cacagctgtt gagttggaat catggctgtg 260760
ccacttaata accaagtgac tttgggccag ttatttact  tctctatgcc tcagtgtcat 260820
ctattcagta gtgagaataa tagtacctaa ctcattctag ttttgagaat gaacactttt 260880
tatattacat ataaaatgtg taggacagag accccaaaga agccgtagtt gctgtcatat 260940
tgttattctg ttcctgctta agaagggac  ttggaaaaat aatgatgttg aatgcagtaa 261000
cttctttcac tcatggaaga attacatatt cacatcttct ttgctcatca aacctttgaa 261060
gatcatgcat gtctcattct gtaacatcgc cttaaccaaa tataaaggct aaatacaaag 261120
gtgttttaa  ataactgata catttaggcc agtcacacaa agattttacc caaagcctat 261180
gcaggcatag tccaagaagt agacttgttc tactgcaatc accatctctt gtttattatt 261240
tgtgaaagga acattatggt ttcaccacag ttggcctggc caacgtgctt atgcagtcct 261300
cagaacatat gaaagtgatt tcggctgaca ataagtattt cctcactttg gcttatgttc 261360
aataatagcc attcttttatc cagatcaggg tgactgagca tgctgtaacc attcttctct 261420
tctaaaactg acccttgttt gactgcatat gcagattgct tagcagaacc catatccacc 261480
ataacgggcc aaaagtcatt tgatccaatg tgcttttctt ttttttttctt ttttttttaa 261540
ttccatgaaa ttttattaag ataaattaat tataaacatt gcaaaacact tttttttta 261600
gacagagtct cactatgtca cccaggctgg ggtgcagtga cacgatctca gctcactgca 261660
acttccgact cccaggttca agtgattctt gtgcctcagc ctctctgagt agctgggatt 261720
acaggtatgc ccaccagac  ctggctaatt tttgtatttt tagtagagac ggagtttcac 261780
tatgttggac aggctggcct cgaactcctg gcctcaggta atccacccgc ctcagcctcc 261840
caaagtgctg gaattacagg tgtgagccac tgctcccagc cccaaacatg atttttgat  261900
tgaatgctta atgtctttct attattatta ttttttttta ttatactttg ttctggcatg 261960
catgtgcaca acgtgcagat ttgttacata ggcatacatg tgccatgttg gtttgctgca 262020
cccattaaaa attaattcaa gatggattaa agacttaaat gttaggccta aaaccataaa 262080
aaccctagaa gaaaacctag gcaataccat tcaggaaata ggcatgggca aagacttcat 262140
gactaaaaca ccaaaaacaa tggcaacaaa agccaaaatt ggcaaatggg atctaattaa 262200
actaaagagc ttctgcacag caaaagaaac taccagcaga gtgaacaggc aacctacaga 262260
atgggagaaa attttgcaa  tccgcccatc tgacaaaggg ctaatatcca gaatctacaa 262320
agaacttcaa taaatttaca agaaaaaaaa aaaaccatca aaaagtgggc aaaggatata 262380
aacagacact tctcaaaaga agacatttat gcagccaaca gacacatgaa aaaatgctca 262440
tcatcactgg tcatcagaga aatgcaaatc aaaaccacaa tgagatacca tttcacacca 262500
gttagaatgg cgatcgttaa aaagtcagga acaacagat  gctggagagg atgtggaaaa 262560
ataggaacgc ttttacactg ttggtgggag tgtaaattag ttcaaccatt gtggaagaca 262620
gtgtggcaat tcctcaagga tctagaacta gaaataccat atgacccagt gatcccatta 262680
ctgggtatat acccaaagga ttataaatca tgctactata aatacacatg cggccgggcg 262740
tggtggctca tgcctgtaat cccagcactt tgggaggctg aggcaggcag atcacaagtt 262800
```

```
caggagatcg agaccatcct ggctaacatg gtgaaacccc atctctacta aaaatacaaa  262860
aaattaggca ggcgcagtgg cgggcgcctg tagtcccagc tactcgggag gctgaggcag  262920
gagaatggca tgaacccggg aggcggagct tgcagtgagc cgagatagcg ccactgcagt  262980
ccagcctggg caaaagggca agactccgtc tcaaaaaaaa aaaaaaaaaa aaagacatat  263040
gcacacgtac gtttactgca gcactattca caatagcaaa gacttggaac caacccaaat  263100
gtccatcagt gatagactgg ataaagaaag tgtggcacat ataccacatg gaatactatg  263160
cagccataaa aaaggatgag ttcacgtcct ttgcagggac atggatgaag ctggaaacca  263220
tcattctcag caaacgatca caagagcaga aaaccaaaca ccacatgtgt gttccaactt  263280
aactcattgt tcttagtgat aattcactta ggggcaaagt taggctctct tgttaattgc  263340
aacattcctt tcagaggtgc tataaatgga tgttgaacta tactattttt agatttaatc  263400
tttaaaaatc ataagaaagc aagaaatatt actagttcag aaatgatttt ctgttcctgg  263460
ctaatcagag aagacctaag agtctatagt agtcatttgt tgtcttcgta gtaaaagtaa  263520
gattctaata ggatttttag acatagtgag aaaggtgttc attttaagat tatggtagtt  263580
cctctcagat ttagaaagcc ttaagatgac actaaggagt tggactttag gaatgctgag  263640
tgtcttcagc cacagcggca caatggtact agatgtgaca ggatgtgatt aaggagaaac  263700
taaacggcca ggcacaatat agttcttctt gcctccaaaa gaggagtcac ccactttctc  263760
acactcactg tgatacattc catttgctaa gaaaagtggc ttgtgtcatt cttgagcact  263820
acttttaagt tctgatatat taaattcatt tactctgtat taatagcatt caaatattta  263880
gtaaagttaa tatacctctc acacttttc caaagtaacc caccagctgt gtcctgtgct  263940
tcaagctatc ttataagact gcaatcaaag tgtcagccag ggctgtggtc tcatctgaag  264000
gctggatagg gaaagattgg ttcccatgct tatttacatt gttgttggca ggattcagtt  264060
cctcaaaggt tttttttatt tttatatatt ttttttgag atggagtctt gctccatcac  264120
cagactggag tgcagtggcg caatcttggc tcactgcaaa ctccgcttcc caggttcaag  264180
caattctcct gcctcagcct cccaggtagc tgggattaca ggtgcatgcc accatgccca  264240
gctaatttt ctatttttag tagagatggg atttcaccat gttggtcagg ctggtctcga  264300
tctcgtgacc tcatgatcca cctacctcag cctcccaaag tgctgggatt acaggcatga  264360
gccaccgcgc ccagccagtt cctcaagggt ttttatactg agggcctcta cttcttgctg  264420
agtgttggcc agaggccatg cttagttctc tgctgtatgg ttctcaccac acagcaacgt  264480
acttcatcaa aaccagcaaa agggtgagtc tgctagttaa aaagaagtct caatcttttg  264540
taacctaatc atagaactgc catccactcc atgctgccat attcttctga ttagaagcaa  264600
gttactcaag ggaaggaaat acataaggct gtgaatgaga gaagacagga atcattggag  264660
gctactttag gggctgtctg ccacagcact taacagcaca tacccagcca taaaatttaa  264720
aaagccgga agagagaag gagggtgcag ggtaaaataa agaaaagagg aaggtggaag  264780
ggaagaaagg aagggaaaga aagacattta aaaagacaag aacaaaacag ctctgctgca  264840
caacatctgt atcggagttc catgtgcaga cacacacgtc atcacatcag caccacaccc  264900
ataaatttcc tatttcttat ttacaatgag aaggtaataa ggactttcta tgcatctgga  264960
gttaaaagga aacaataaat ctaagaatac taagtttaag taatcaaaat gtgtttcaga  265020
ttagttattt tttctttta agtttttttt tttgttcag ctgacaaagt ttttttattc  265080
tttctgtttc aagttttgaa gttgagttta ttattcttgc tattatgtaa caggcatatt  265140
```

-continued

```
ttacagagaa tataggaacc tgattgacat ttgtatttgg tgttctattg ttgtttcaat 265200
tcaaatgcca aaattatgtt tttgttgtgt acgttattgt tcataattat atatgcctct 265260
taattgtaaa agcgaagctg taaaattgta aagtactttg tgtctcatct attccaggca 265320
ttctactaag gaaatcaaga ccaaatggct tgggaaggtc aacgttaaat agtgtcagag 265380
ccagaactag agtacacatc tctcaatttc taatctagtg catttccttt tcttatttct 265440
gtgcaaacga acagttagaa tgtgaaatag tctcctcaga tataccagca ttaaaacagt 265500
tgtggtttaa atatttagtt ttaataatta ctaactttgt agaaggacct aaaatagtgt 265560
ttgttttcag tgcttcaact aatagtaaaa aggaatattt tcagtgcttt actgtatgag 265620
aggtgcttgc ctaacgaaat acacatcttt ttcactgtac tcatttgtaa cagataatgt 265680
gggctcgtac acctcagtgt tctgagaggg gttggtaaac actgaccaca tagagagagc 265740
tgcccatctg ccctcagtac caaggcacat cccatccatg ccctaaaact cttgtaaatt 265800
tctccattca tacaggaaaa tgagtatttc ttacaacaat atgaccgtgg aatttgatta 265860
caaaaacact cctgctatcc ccaacctgtg ctcccagggc taaagacata tttgcaactc 265920
aggattttct gaagattcac ttgttttgtac tattgagggc aacagttgtt ctcaaacaag 265980
gatgcagttc ctttcttctt accctgctta ttttttcttt tattattatt attattatac 266040
tttaagttct ggggtacatg tgcagaacgt gcaggtttgt tacataggta tacatgtgcc 266100
atggtggttt gctgcaccca ccaacccgtc atctatatta ggtatttctc ctaatgttat 266160
ccctccccca gccccacagc cctcaacagg ccccagtgtg taaagttccc ctccctgtgt 266220
atgtgtgttc tcattgttca actcccactt ataagtgaga acatgtggtg tttggttttc 266280
tgttcttgtg ttagtttgct gaggatgatg gtttgcagct tcatccatgt ccctgcaaag 266340
aacatgaact catccttttt tatggctgag tagtattcca tggtgcatat atgcaacatt 266400
ttctttaacc agtctatcac tgatgggcat ttgggttggt tccaagtcct tgctattgtg 266460
aacagtgctg caataaacat acatgtgcaa gtgtctttat agtagaatga tttataatcc 266520
tttgggtata tacccagtga tgggattgct gggtcaaatg gtatttctag ttctagatcc 266580
ttgaggaatt gccacactgt cttccacaat ggttgaacta atttacactc ccaccaacag 266640
tgtaaaagcg ttcctatttc tccacatcct ctccagcatc tgttttttcc tgacttttta 266700
atgatcgcca ttctaactgg tgtgaaatgg tatctcattg tggttttgat ttgcatttct 266760
ctgatgaccg gtgatgacga gcattttttc atgtgtctgt tggctgcata aatgtcttct 266820
tttgagaagt gtctgtttat atcctttgcc cacttttga tggggttgtt ttttttcttg 266880
taaatttatt gaagttcttt gtagattctg gatattagcc ctttgtcaga tgggcagatt 266940
gcaaaaatat tcccccattc tgtaggttgc ctgttcactc tgctggtagt ttcttttgct 267000
gtgcagaagc tctttagttt aattagatcc catttgtcaa ttttggcttt tgttgctatt 267060
gcttttggtg tcttagtcat gaagtctttg ctcatgccta tttcctgaat ggtattgcct 267120
aggttttctt ctagggtttt tatggttttg ggtcttacgt ttaagtcttt aatccatctt 267180
gagttaattt ttgtataaga tgaaaggaag ggatccagct tcagctttct gcgtatggct 267240
agccagtttt cccaacacca tttattaaac agggaatcct ttccccattg cttgttttg 267300 tcaggtttgt caaagatcaa atggttgtgg atgtgtggtg ttatttctga ggcctctgtt 267360
ctgttccatt ggtctatata tcttatttgg taccagtacc atgctgtctt tgttactgta 267420
gccttgtagt atgaagtcag agacacaata aaaaagaaa attttagacc aatatccctg 267480
atgaacactg atgcaaaaat cctcaataaa atactggcaa acctaatcca gcagcacatc 267540
```

```
aaaaagctta tccaccccga tcaagtcggc ttcatccctg gaatgcaagg ctggttcaac   267600
atacacaaat caataaacgt aatccatcac agaaacagaa ccagtgacaa aaccacatga   267660
ttatctcaat agatgcagaa aaagccttcg acaaaattca acagcctttc atgctaaaaa   267720
ctctcaatta actaggtatt catggaatgt atctcaaaat aataagagct attttttgaca  267780 aacccacagc caatatcata ctgaatgggc aaaagctaga agcattccct ttgaaaaccg   267840
gcataagaaa agaatgccct ctctcaccat tccttttcaa catattattc aaaactctgg   267900
cgagggcagt caggcaagag aaagaaataa agggtattca attaggaaaa gaggaaattc   267960
aattgtctct gtttgcagat gacatgattg tatatttaga aaaccccatc gtctcagccc   268020
aaaatctcct taagctgata agcaacttca gcaaagtctc aggatacgaa atcaaagtgc   268080
aaaaatcaca agcattccta tacaccagta acagacagag agccaaatca cgagcaaact   268140
cccattcaca attgctacaa agagaataaa ataacctagga atacaactta caaaggatgt   268200
gaaggacctc ttcaaggaga actacaaacc actgctcaag gaaataagag aggacacaaa   268260
caaatggaaa aacatcctca tggataggaa gaatcaatat catgaaaatg gccatattgc   268320
ccaaagtaat ttatagattc aatgctatcc ccatcaaact accattgact ttcttcacag   268380
aattggaaaa aaactacttt agatttcata tggaaccaaa aatgagcctg catagccaag   268440
ataatcgtaa gcaaaagaaa caaagctgaa ggcatcacgc tacctgaccc agcttatttt   268500
tctacatagg atccccacat ccctgctttt gctagaatgg aaactagaca aggaccaact   268560
tttatcaact tgttcatttc tctattccta gaacacagcc tggtacaaaa tttgcgttta   268620
ataatgtttg ttgaatgaat ttgaatgatg gatttgttta aaggtttat aacatcccat    268680 gccttatgag tttgttgcca gaggaaaaaa gaagcctgtt tttggttcat aacatcaggt   268740
atgtaacctg gaatttggaa tcatgagttt ttatgcattt gcttcatatt atttatttt    268800 aagagatctt tcaaagtatt gacaaagata ctttaagatt gagagcctcc ctgataaccc   268860
aggaatgaga gttttagatt aagtttacaa tatgattgaa ggctaatcat ataaggagaa   268920
aaaaataaga aaaagaagag aaatttgaaa agaaatctcc aaaatggcca tggacatcag   268980
aacactgaga attcatacac aaaaatgtgt tttgcttcat acctgtctgt tgcacatcta   269040
tacatttcat agatgcagag gaattttggc taaattccta acacatgaga ggcattctgc   269100
acttacttct caaattagaa ttaacacatg agtatgtata agttgtttag agtgggcatc   269160
tatttaatga gtttactggc tgaatctttt aaaagaatgc aaacataagt gcctttatc    269220 aaaaatcaat gaaaagataa aaggcctgt agtgcatgct gtggttccca cactacatcc    269280
cccacatcca cctgatgtca tcacaactgt ctatggtgtc catttgccac tatgcaccct   269340
gccgggcaga ctcaggtgcc tgcctcggca aagaccctca gctcatgtgc aggtacagcc   269400
tagaagtgca tgggggtgaa catctctgag gcacccttca accagtgagt actgggagcg   269460
gtagataaat atcctagcct ctcatctttc tacacaacag tggtggtgca tattctacac   269520
agcttctcaa aggagcctca gagggattgg gccccattag ccactgtgat aaccagctca   269580
gaacacacac atattagttg ttctcccttt ccttcccacc ctccccattc cctgactgct   269640
agatccagaa gtcatcttcc agatgaacta cctatatcca aatcctaatc tctagctctg   269700
gtttcttaaa caggtcctat gaaatgcttg aaataaaagg caaatggtt tgtgtctaga    269760 atcaaaggct gacaatggca agcaacaggc actaaaacta tgacccagga aaaatgcttt   269820
tctggaagac atcggcatta cctcctagac acggaataca ctggcttcat cccagtagtt   269880
```

```
tcttcacaca ctttagatac gtgtctcatt aggatcacat atgactcacc tgatttcatg    269940
ccttgccttt tctttttatt ctgcagattc ttctaaggag cctaaattca ccaagtgccg    270000
ttcacctgag cgagagactt tttcatgcca ctggacagat gaggttcatc atggtacaaa    270060
gaacctagga cccatacagc tgttctatac cagaaggtgc caccatcatg cctttctgat    270120
tttcctctcc atggatgtac ctactaaagt acactgagtc agatgtactg tgggaatgga    270180
agtgatttgt tgtgatttat gcaatcaatg aatattcatt cactcattta ttgaaaaaaa    270240
tattaatcaa gcccatccta tgtgctgagt actattttag gccctggaga tatagcagtg    270300
attacaaaag acaaaatccc tggtctcatg gagatttcct tccaatgcag ggagacaggc    270360
aataaaaatt gaattaaatg tcagctagta atataggtta ttaagaaaaa taaagccaga    270420
aagcagcata tcagcagtgt gtgggagttt gtgtatgtgc atgagaatgt gtgagagtgt    270480
gtcaaagtgt gagtgagagc atgtatggat acacgtgggc atgtgcatgt ggatgagagt    270540
gtgtgtaaaa ggcttgaatg atgctgaaat gcgtggtcct aggaggcctc tctattgtgg    270600
tgtcctagac cagagacata agtgaaacgg gacaggccac gtgagtatct gggggaaagg    270660
ctatgcaggc agaggaaatt gcaagtacaa agtccctgag gcagtcttgg catatttgag    270720
ggatgaaaaa ggccagcact gaaggcacaa gattgaaagt gaggagagtg atatgggaag    270780
ggatcagaga gttacttagg gactgaccat gccaaacctc ataggcaagg gcaaggcttt    270840
gaattttact ttatttgtgg tggaaagctg taggtgtttt tgaaaagata tatgctttaa    270900
aagatgtagc tttgtttcta accagataat acactccttc tcttaaatat attcagtaaa    270960
agactgtagt actttttcat ttttaccagt gaccctctaa aataacagag gaagggtgaa    271020
acaaagacct ctcaatatag gtaccatcca agttgtttat ttcttcccct tcacctggca    271080
ttattttcat ttttgtttac tctcactgtg tatattttttc ccttttttac attttaggct    271140
taaacacttc attatctcct gttttccacc caacccccag agaaggccta agccaagatg    271200
cagggttagt gaggaccctt tatccttggc tcaaggtgtt cgttagtcag aggatgacat    271260
tgtctatcca accgaagagc tggaataggg aaggaagatg cagccagcag ttaagggtat    271320
gagctcaggg ctaacaaacc tgcacttcag tgtagttctg cactttctca ccaaggaata    271380
ctagggaaat tagccagttt gtgtacaact cagcctcctc atttgcagaa aggagataat    271440
ggacttgcct catgacttct tgtgaggatc atatgagata acccatgaaa atacttggc    271500
agagtacttg acacataata agtactcact aaatggtagc tggtattctt cttatcggta    271560
gtatagtgat aattttaaaa taattatgat atagaaatcc agttcctgga ctataaaatg    271620
actataaatt gtataagacc atttatacca gtaaattgtt ataattattt taattattgg    271680
tataagcaga ttttaatgca gagctgctgc ttaatttgca gataaaaaaa tacttggagt    271740
tagcaaccaa gcagaccttc cccacctttc agtataagag aggtctcttg gatgaagtga    271800
agtgaagatg aaatgtttgg gcaccaagta tactatattt ttccttaagg ctgacaccac    271860
agagaggttg gggccagtaa acagagttga tttctataaa tacattcaga catgaagtta    271920
gtatgtttga tgacactttt gaaatgtgtg gaatcattaa gttatttgta caggcacaat    271980
tagccaaact gtaaagaaaa gtagcagaat aacctcttaa gctgggccca ctttatgaaa    272040
ataattttttt gctacctcaa tatttaccaa atttgatgag caaaagaga atccaaagg    272100
aatgaagcct tgataaatat atatcccttg ccctcatcaa tcagggtcac ataactctgt    272160
ccacaggcat cttatgcaca ctccagtcat ttcagcatct ctggttcaaa tccaggatct    272220
acactaccaa ggatgctgct gaaagtgtga ctgggtaaag ggaaacgttc agacatattc    272280
```

```
agaaagatgt cttagatttt gccctggtag tgtttggaat cccaggaggg taagtacagc   272340
ttcatgatta agtgccaacc caaacttaca aaattagata tttgtgtttt ttctataaaa   272400
tataactatt ttgaatatct tagccaaact actatgagcc cacagcccag tttatccaag   272460
aaggataaaa ctgagggatt aggagtatca ggactggact ggactgatta gtgtacagtt   272520
atatttgatt tctcattgcc cacttcacag agaagacaat acaaatgcac tttctgactc   272580
ttatcactgt ttcttagaac tcagttgcca ggcaactcct gaaactatag aaacatgctt   272640
ctcatccctg acacataaat aaaactctga gatgatttta tccaaagtca gagtcagtgg   272700
gcagtgcagt tgtttcagtt tgctggcctg gcctcagtat ctaaagcaca acagaacgtg   272760
aacatgtcag gctgtcaaca ggacagttca ggcacagccc tacaggcagt tgtgtgtttt   272820
gcctggctct gctccttgcc aggtggctgg cagaaaaggc agcctccaca tgttagagca   272880
gcagattcaa aacagtgtct gccatcctgt gatgacgata gtgccaaatt cagcctctga   272940
gcttgcaggg gactcaggat gaatgcacat tacaggcatg gtaaaaagag gctctgggaa   273000
gcatgttcga gctgctctgc tctcagctcc ttgcatgtaa atgctgtgtt tttaaaggaa   273060
gtgggcatgt gaacactcag tccttaaggc tgtatccccc acctcttcca tacccattca   273120
accccacttc aaaaattacc ctggtcttaa gagaaatttc attttctata caaggttgtg   273180
tggaaaatca gtagggagaa agggcattat tactttcatt tttctttaac aaaagtatta   273240
aatttaaagc caaaaacgtg cgctttctgt catgaaaaca gctgcccttg aaaacataaa   273300
tgatgtttta tttttattac ttttatctag ttggttgtct ttagatgaaa acatttcttt   273360
ctgctctttt ttcttatttt taatgatagt ctctttctat ggttctcacc ccttccattt   273420
cacaagatag tctgggagca aacctaaagc acttaacttt tgggagtaag agcagagggg   273480
agcttccata cattgatttt ggtcatctgt agagacattc aacccagaga aggcaagtga   273540
cacagtatct gttttatgag ctaatttggg ttcttgtcta catttaatag tttaaaatat   273600
aagttataaa tatttattta aaatgaaatt caacattggt tcatgaagaa agaggttgga   273660
agtagtgttt tgaactagct gtttctgatc catcatgctt aaaatatatg ctctgtttgt   273720
cctgtggagt tcatggattt gggataatct aaacaggggtt ttttaaacag tcctcatggg   273780
gaacaaggta ctgacatgca ctgttgagaa attctgtgaa tcatgaaaga gctaatcttt   273840
tagaaatcca gacctgttaa gcactaatct acatctttgg aatatcttaa tacttttgagt   273900 tttctaactt ttatactatc acttatgcta agtacatttg atatcccttc tattatgtga   273960
aagcctcatt ttctgggcaa ttttcttaca actactctct ttaatgcact cttacttaat   274020
ttgaaagtaa atatcaaatt aagcatacta tagttcaatg aaccacccac ctattcctaa   274080 ttttttttaac atttctcttc tgactctaca tacacacata cttacacaca cacacacaaa   274140
cacaccttat cttttcttct gccttttgcc catttacttt ttgcatcaga gatgaatctc   274200
tcattcaagc atatgcaact ttttttttttt ttgagatgga gtcttgcttt ggcacccagg   274260
ctggagtgca gtggctcgat cttggcttac tgcaaacttt gcctcctgcg ttcaagcaat   274320
tctcctgcct cagcctacct accgaatagc tgggattaca gaagcatgcc atcatgccca   274380
gctaattttt gtatttttag tacagatggg gttttaccat gttagccagg ctggtctcaa   274440
tctcctaacc catgatccgc ctgcctcagc ctccgaaagt gctgggatta caggcatgaa   274500
ccaccgtacc cagccagcat atgcaacttt taagagtctc aaccaaagca gcaattcact   274560
gtctcagacc ctggagtctc tgccatttaa atcccaattt ccttccaaca gctgaggagc   274620
```

```
agctgtctca aggaccctct gatactacac aagtttctc ctagtgccaa gcagaccagc  274680
ctgagaaaca gctataagaa ggaaataggc gtcttctccc agcttggcat cctttccttc  274740
caggccctgc cttccctaca acctgcattg tcttcattgt ccactgctgc ccagcaccca  274800
tcccacagag ggatggtccc aaacctccac agtctggcct gtgagccaca ggcgcctctg  274860
cctgcacagg gccattccta cctcatcttc cacaaccaca gattacatgg ttttatgtcc  274920
ctttgactta tatattgtct tctcaattaa taggctagtg aataacatgg agatgatgaa  274980
ctacctcacc caagtagcaa ttctaattta agaaaatttt cctgtcattc cattgccttt  275040
tacttccatt accacactca tgcccatact tccttacctc aatccctttg acctctctgt  275100
ttattcccctt ccttgccgta ttgccatcta ttaaactttt acccatcctt caagaatgct  275160
aaaaacatac ctccaccttg aagccttcca tgaagagcca gagcaatcat tccctcttct  275220
gaacttttaa ggaccctaga gagcactact aatgagcact tacccacatt gctttgtaat  275280
atggttttt actctttcct tctgaggcag gaggaattcc ttagacatct atgaatccca  275340
tagtgtctgt cattatgttt tagacataac caattctcat taaatgtcaa tagaatgaat  275400
ataagaggcc caaaaaacta ctcagatggg aatttgagtc ttattttagc ctgaaattag  275460
gggaccacat cttacttatc tttatatctg cacagcgttg gtgctggata taatgcatca  275520
ctctgcctgg agcacacatc aacttgtctc ctcagtttct ttcaccatag gctggtgaaa  275580
cagccaggtc taaaccttca ctgttctctg ggaatctcta gtttgggggt gattctctgt  275640
actgttttaa tgaacatttt taaaatgtcc ctaagtctca gaaccttcat ctatacaact  275700
ggcataataa agtacctacc ataggaatcg atttatgagc aggcatagca tattcattca  275760
ataaacggaa gttttaccat aggcagaagt accaaacggc ctcgtagcag tcgtcagaca  275820
ctgatgatac tgtccactga tgtgatatgt ctcggaaatg atgttactaa aatacctctt  275880
cacaaaatat ttgtcttcca atttattgaa tcagactatc aagcaccttta cttggactta  275940
agctacaaca tgattttggg aacaattaat cttttttaa cccttcattt taggaacact  276000
caagaatgga ctcaagaatg gaagaatgc cctgattatg tttctgctgg ggaaaacagc  276060
tgttacttta attcatcgtt tacctccatc tggatacctt attgtatcaa gctaactagc  276120
aatggtggta cagtggatga aaagtgtttc tctgttgatg aaataggtaa atcacaggtt  276180
tttgtttcat ttgacatagt tttagactaa ataaatgggg aagcctgcaa ggtccaagta  276240
taatcaagta ggaagacttt gtaacagtgt tctatagata catggagatc tgttttacag  276300
gagatgggat cagctggtga acaagaggaa aagggcaggg ggaacttaag ttgactttaa  276360
cataaagtag cctggcagta aatgttgtga agaagagaat aggaaccttg tggagtcttt  276420
tcctttagga tatctttgaa gctgcgttgt gttttatgt tccactgcaa agggtgaact  276480
taatatattc ttaggatttc ttacttccta attatttgat aggatcctta tattcaaatt  276540
cactgaaata cgttggcctt tgacctctac cattgctgta atcaaagcct agattttctt  276600
tatcacaaag cataatcatt ctggaatttt acatttacaa aacagccaca gttactttaa  276660
agacatgttt attagatctc agaacaaata ctggagacaa tcagctcagt gaactaagtg  276720
aaagatccaa acagaggatc cttgcccat catatggaca caaggtggaa acaaacaaa  276780
taaaacaaac aattgtaatt agaatagtca tgtttatacc ttaatagtat aaatagcaaa  276840
atagaaagaa tcaaagaagg actttgagta gctgaaatta gtgcctcaaa atctatccac  276900
aaaagctcat ttgttgctta taggaatttc tcgttgcttc tcccaaatgt attgttcttt  276960
ttatgtggtt ttctaggcat aagctgactg gaagacatag gagtatgtgg ctagaactta  277020
```

```
cagatagaaa caaataaaat ctaataggct gactttaagg gagaagatta agagaactgt  277080
atcaagcagt aaagataacc caattgcttt gcaaagacaa tttagtatgt gtcctaacat  277140
cactgggtat agctgttgag ttgaaactaa atgggatagc agaatgggat agtagcaaga  277200
acactgggtt aaaacccatg ttctagccct gttctctgcc aatagccagt cctactcatt  277260
tacctggctg acatgcctgt catgtgtcac gcactgttct ggtggtggtg gttatagaat  277320
aagtacaata cagtcaaaga gggaagtcag gcatgttcac aaataattgc agtgcagcgt  277380
gataggtgtt agcctggaaa tacgtggaat gcagagctgc aaaggtggtg gccaaaggcg  277440
tgaatgactg acaggcctga gggatgagga agggctgcac agagatggtg acagtttagt  277500
tacctctgaa ctggaattgg actctcccta ttttttaaaaa agtgatgacc cacagtggtc  277560
aaaagcatga gtgagtattg tcaggtacca cagtggactt gcctttcagt aactactaag  277620
ttccaacagt aacttagtag ttacttagta attacaacag taacttagta gtcccaacat  277680
gttcagggac tcaggagcag ttaggaagcc ctcctagtca gctggagaaa tcatcagtag  277740
ttgtttgtgc cccaaaaagg aatttggact ttaactgtca cgaggtacct ttgaggatgt  277800
ttaaataggg aaattacttg aggatactaa tagttaacag tcacaaaagt cttaccatgt  277860
gtcaggtata aaaccatct tttgcaatca cactttacag ataatgaaac cgaggcacag  277920
agcagttaaa ggactagttc aagtcaaaca gctagtagat agagctggga tttgaacctc  277980
cagcctccat gctcttactc ttgaggcttt gcagtaccac ttgtctcttt attaatgctc  278040
agagaaatta atcttgttgc aatgtgaaac gtagattgga gtgggacgga ctagaggtag  278100
aagaggttaa aagactgaga tgatcaaggt aaaagattat gacaggtagc tacaactagc  278160
acaatagttg tggggcaagg tgctgagagt gaaagagaac aaagaactaa tgtaaccctg  278220
gtagatcttg agaaagttgt caatcattat aagcctcagc ttcctcataa aatatgtatg  278280
tatggtacta cctcacaggg ctattctttg gatttgaagt actatattag ttagacattt  278340
gtcattcatt caattcattc agcaaatatt tattatgctc ttctctcagg ccagtcaatg  278400
ttctccatgc tggggataga aactgtcttc cctggtggga tttaatccca acgaggatgg  278460
aaagcgacaa tgctatggag aaatatagga aaggagaata ggagtgttgg agaggttgca  278520
gtgttgagtt ttcaggattg gcatccctga ggcagtggca tttgaataaa gaaggattgg  278580
agaggataat tatgtgtgtg tctcagggaa gggcatttca gcaaggggc acgccagaag  278640 aaagatctca agtaggagc atgcttttcc tcactcaatg aacagcaggc cggcggtgga  278700
gtgggcacag agtgagcgag gagactggta tgagaccaaa tcgcacagac aagacagtca  278760
aatctaccca accattgcca aagactttgg cttttcacttg gagtgaggta ggcagccttt  278820
ggagggtttt agatgatgag cgatgtgatc taacgtaagt gttaggataa tcactgtgtc  278880
agttcgcttg aggattgcat ggagaataga ctggagggg acaaagacca aagggtaca  278940 gtggggagac aaatgaagca agaagaatga aaaaggataa tggccaggac caggttatta  279000
gtggtgcagg cggtgggaca tggttggatt ctgttatatc ttgaaagtac agctgacgga  279060
atgtggatta gtgaggaaaa gatgagccaa ggacaagttc attgtttta tcctgagcaa  279120 ctagaggaat tgagtcctcg ttaacagaga tggaaaagag gaaggagag caggttttgg  279180 agaggaagag caagggtttg tttggggata tattaagttt cagatatttt ttaaatatct  279240
cacaggagtt gtcaatatag catgtagatt tatgtataga gataaaggag aggtcattat  279300
tatgcctgta atggtatctc acaggaggtc attgttatgc ctgtaatggt ggtaccaaat  279360
```

```
cttttccaaa aggaccttgt ctcatatcct ctattttttca aatgcagcat aagtaatgag 279420
ttatagaaaa tcttccatta aaaacaattt tatagtttgg tcactttaaa cggttaagct 279480
ttgattatca ggattcctga atctccaaca aatccagaag ggtgaggaat tattgccatt 279540
atatcggcat atgtagtttg gccattttgc atatccttcc aatttaattt tcaaaatgta 279600
gtcatgattc atcaaatttt gactctccct gtttttaaaa aggtggtgtc gaccccacag 279660
agggcaacag catgctcctc caccataagg cctgttttca ctgtgggtgc acacaagagc 279720
ttccctcttt ggccaacaga tttgacagcc agtaagagct cctcactgtg tatatctgta 279780
aagttatctc cagtcaacgc tagggatgca cactctgcaa cactctaggt ggccttctgt 279840
atatatggca gaaaagaaa gtaaattta ctctgtatct gcaagtgatt ttcaaaaccc 279900
tcagtaatga gatccaacta gcaaaaattt accaggaact ctctagaata taaatttaga 279960
catagttcct agctttggaa tccatatttt tcttcatcag cctctgagaa attgtggtct 280020
ttgaggtcct actaagcaga atgcaacaaa ttttcgtgga actgtagagt atatcaatag 280080
aacctgagga aaacaatgtt tcaagttgtt catgtgacag tcaaaaagac agaaaacact 280140
gaattgtcac catttgtgag actagcataa tgctttcttc cttcttatgt cagaagaaaa 280200
tatcacatgt ggctaggaag atcacaaagc tagggagcat tagcagagtg tgcaggaaga 280260
ttgtatgaga agattgaaga agagtaaaaa aggataatgg ctaggaccag gttatagtgg 280320
tgcaggcggt gagatatggt tggattctgt tatatcttga aagtacagct gacggaatct 280380
gacggaatat ggattagtga ggcaaagatg agtcagggaa caacacagaa atgaggtaaa 280440
cagggtctct gcccccaggc catacatagt tgcaagaaaa aaggtttctc tacccctagt 280500
tccgaagcag ccccatgtct aaattctgta agtctttctg actctctgtt ttttcagttt 280560
caagtgaaaa taaattcctt tgccaaaatc ctgatgcatt tatgatatca gagcaaaaag 280620
aaatatacaa catggcagat cttgtaaata gtgatcagat gttttactcc aaaaggaatt 280680
tttgtaaggg cttatttaga agttaaaaac aagtcatcct tgagttaaaa aaaaaagtta 280740
ctctcttata aagtgaaagt tataataaga aaaatattgg aagaaataag agcatgaatg 280800
atcaaaaatg tagaaagtaa tttggtcttc tgagaagaat gccttccatt aatattaaat 280860
tgtgtctgtc tgtgtactaa tgctctgttg aattgcacag tgcaaccaga tccacccatt 280920
gccctcaact ggacttttact gaacgtcagt ttaactggga ttcatgcaga tatccaagtg 280980
agatgggaag caccacgcaa tgcagatatt cagaaaggat ggatggttct ggagtatgaa 281040
cttcaataca aagaagtaaa tgaaactaaa tggaaaatgg taagatgttg ctacacctta 281100
cactttgact tttctttcta tttcaacaaa ctctctctca tttatcatta gactttcctt 281160
tgacctaata ccacatgttc atgctgtatg ctccataatt tcttaattga gaaacatta 281220 tttaaccggt aaaatattgt cttgaaattc tgtaagacag gagatgctta tgtatatatg 281280
gaggcctgtg gaaggaaagg aaaactattt ctccattcat tcttgctgtc cagtttaact 281340
ttagagcaaa attatagact ggccacttag ctgtctttgg ggatgtggat aaaaatggga 281400
aagtttgtga tccagtcaac agtgactatg gccaaatatt ttcccatgat ttcagttgct 281460
gctactcaaa ggactcccac taaaacaaat tcatacgtgt ctataggaaa acagagggag 281520
ggaatttgtc tcttagaggt ttcagaagga tgttttgtta catacctcag agaagaatca 281580
agctgagatt cttatgtagg caattagaga gcatggtacc agttgacctc tgaatccctc 281640
tcttccttac caagcatatg gaactcagca ttttgataaa tttcacatgg cacataacaa 281700
gaggaaaaac aggagtatca tgctgctccc aatataacta attctaaatc tgtctaacca 281760
```

```
cagccacagc cacagccaca gccaagccaa gcagtttctg gccactcatc aggtgatgcc   281820
cagcagcctg gcacagatca ctcccagaat tttgagacac caggacattc agtgagccac   281880
tgaaaaagat gccaattttg tcattagagg aaagttaagt ttggaggaaa tttgagtagt   281940
tacaatactg ggctttgagg ctctattttc tgaatcattt taatttagat atctgttctg   282000
taacttggta caaataaaat gcctgattgg atgctaagtc aaacaagact gtctaaatcc   282060
aagctacaat caaacattat ttaacaacag gtactgaaat aactactatg cagaaggcac   282120
tgtgctaaat gcctgaggtg gcggttctca aagtgggagc cacagaccct tgagggtccc   282180
tgagacccct tcagggagtt cagtactatt ttcacaatac actaaaatat tattttatta   282240
actatgttga aatttaactt aatggcacaa aagcaatgct ggaaacactg ctggcacctt   282300
agcatgaagc aaggcagtag gatcaaattt tactaatagt catgcactcc caatgaagaa   282360
ggaagaaaaa gccagtttca cgtttgaagt tcttgatgaa gctgtaaaaa ttgttaattt   282420
tactaaacct cgacctttga gtacatagct tattaatatt ctgtgtgaca tatgggaatt   282480
acacattaag catgtctgct gcgtactgag gtattgtatt tgtcttgaag aaaagcgctt   282540
aaatgactga gttgccagct gaactagttg cttttattgc ttggagcacc atttttactt   282600
ggaagagcca ttgataaact ggcagatggt tattcatatt tgaattggca aacatttgtc   282660
aaaaaagaat gaggcaagct tgtcgcttca agaaaaacaa ctgacagtat ttttgcaat   282720 ggaaaaaatt tgacttttca aagcaattca ttttgccttt ttcgaaaatt tgtgtctcca   282780
accgtgagct tgatagtgtt ttaatatttg aagacttttc ttgaagagat tgatggtgat   282840
attaatgaaa gtgacttttt aattatattg tgtaataaaa tgtatgaaca tttagaaaaa   282900
tctacaactc agttaaccaa tattttccaa attactaata catgatgtaa tcaaatcatg   282960 catgggaaa tgatccattc aaagtactag atagaatcgt gaatttttt aatgatcaaa   283020 aattttttg tatatttatt gtgtacaaca tatttttttg aaatatggat acattgtaga   283080
atggttctat cacactaagt aacatatgca ttaccacaca taccttttttt tgtgtgttga   283140 gaacacttaa aatctactca gagattttca aaatacaata cataagcatt aactatagtc   283200
accattttgc acaatagatt tcttaaactc attcctacta actgaaaatt ttaattcttt   283260
catcaatatc tccttaactc tgcaccctgc ccacaacccc tgataaccac cattcaactc   283320
tctgcttctg agttcaactt ttttagattc tgcatataag tgagattatg tggtatttgt   283380
ttttctgtct ctggatcatt tttcttaata taatatcctc caggttcatc cacattgtca   283440
caagtgacag gatatccttc tttttttaag gctgatagca ttccattgta tatacctacc   283500 acatttttctt tatccactta tccattaatg gaacataggt cgattctatt tcttggctgt   283560
tataagtaat gaacatggga gcccagatat tctggctcaa catactgatt tcatttttcct   283620 tggatatata cttagtagtg gaataatata atggatcaca tggtagttct attttttaatc   283680 ttttgaggaa gcttcatatt attttccata gagggtatac taattacac tcccaccaat   283740 agtgtgcaag ggttccctttt tgtccacatt ctcaccaaca cttgttatct cttcttttttt   283800 tgaaaatagc catcctaaca tctttgtgca ctctatgcct tctgtgagct gatagctcat   283860
tgtggtttaa atttacattt ccctgatgat taaagatgtc aagcattttt catatacctg   283920 ttggccatttt ctatatcttc tttttaaaaa tttatattca ggtcctttgc ccatttttta   283980
attgggttat tttcttgtta ttgaattgtt ttagttcctt atatatttca gatagtaact   284040
tcttatcaga tgtatgcaaa tattgtctcc cattccatag agtgtcttttt tactctgttg   284100
```

```
attgtttcct tggcagtgca gaagcttttt agtttcatgt aatcccgttt atctatttcc   284160
acttttgttg cctgttccca atggagtcat atccaaaaaa tcattgccca aaccaatgtc   284220
atggagcttt ttcctatatt ttcttccagt agttgtacag tttcaggttt tacatttaag   284280
tctttaatcg atttttgagtt tattttgta tatgaggtaa aataagggta taatttcatt   284340
cttctgcata tggatgtcca atttttcccaa caacatttaa agacagagtc ctttccttac   284400
tgtgtattct tagcaccttt gtgataaatc aatttactgt aaatgtgtgg attttatttcc  284460
gaacactta ttcttttaca ttggtttatg tcatttttat gccagtacca tgctgttttg    284520
atgactatag cttgtatta tgttttgagg ttggtagagt gatgattca tccttgttct     284580
tcttgttcaa gattgctttg gctattcata gtctattgca gttgcataca aattttagaa   284640
ttgcttttcc tatttctgtg aaaaatgaca ttggaatttt gataaggatt gcattgaatc   284700
tgtagattgc tttaggtagc agggacattc gaacaatat aattcttcta atccatgaac    284760
atgggctatc tgttcattta tttgtgttgt cttcatgttt tacagttttc agtgttcaga   284820
tctttcacct ttttgtttaa atttatttct aggtcttta ttttatttt atttttatag     284880
atattgtgaa agggatttct ttatttcttt ctcagattgt tccttattag tgtatagaaa   284940
tgttactgat ttttgtatgt tgactttgta tcctgcagct ttactgaatt tgtttatctg   285000
ttctagcaat tttttgttga agtctttagg gttttctata tataaaatca tgtcatctgt   285060
aagcaaggac aatttaactt tttccttctc aatttgggat gccttttat tctctctttt    285120
gcttaattgc tctgactagg attttgaatc gagtagaata gagtagagga gttacattga   285180
ataaaaatgg caagagtagg catctttgtc ttgttcctca tcttagaaga aaagctttcc   285240
acatttcact gtttattatg atgtgagttt gttatatatg gcctttattg tgttgaaata   285300
cattccttct atatctaatt gttaagggtt tttatcatga aaggatattg aatttttgaca  285360
agtgcttctt ctgtatctgt tgagatggtt ccatggtttt cgtctcggtt ctgttaaagt   285420
gatgtattat gtttatgtat ttgtgtgtga tgaaccatcc ttgcatccct ggaataaatc   285480
ctacttgatc atggagaatg ttcctttag tgtgcttttg agttagtttc ctagtatttt    285540
gtttaagatt tttacatctg tatttatcag agatattagc ccataatttt cttttcttgt   285600
agtgtccttt catggtttgg gtataagggt aatgctagca tcaagaaata gtttggtagt   285660
atccccttt cttccacttt ttggaaaagt ttgagaagga ttggtgttcc ggtgaagctt    285720
ccagtgaaac tgtcaggtcc tggacttctc tttgatgaca gactttttat tactgattca   285780
atctccttac ttattattgg tttattagat tttctatttc ttcaagaaag tcttagtagg   285840
ttgttgtgtg taggaattta ttcatttctc atgcatataa ttttcagaa tggtctctta    285900
tgaacatttg tatttctatg gtattggttg taatgtctcc tccttcattt ctgattttgt   285960
ttttaatttg ggctttctct ttttttatta tttagtctag ctaaagattg gttgattttg   286020
tttatcttt caaaaaact tgtttcatta atctttcta ctgttttaat gtgctaactg      286080
aaaagcacat taaaaggatc attctccatg atcaagtagg atttatccca gggatgcaag   286140
gatggttcat cacacgcaaa tacataaaca taatacatca cattactaga accaaaaaca   286200
aaattatgga accatctcaa tatttctat tctctatttc atttatttct gttctgatct    286260
ttattatttc cttccttcta tgaactttat gcttagttta ttcttttttct ggtttcttca   286320
ggtaaaatgt taggttattc atttgagatc tttgttttct gatggaggca tttattgcca   286380
tgaacttcca ttgctcttag aacgactttt actgcattcc ttaaggtttg ctatgttgtt   286440
tccattttg tctcaagata ttttgattt tatttttac tttttaacta ttttttagg      286500
```

```
ttcagagata catgtgcacg tttgttatat aggtaaattg catgtcacag gggtttacca   286560
tacagattat ttcatcacca ggtaataagc atagtaccca gaaggtagtt ttttgatctt   286620
caccttcctt ccacccacta ccctccagta ggccccaata tctgtggttt cagtcttcgt   286680
gtccatgtgt tctcaatgtt tagctcctac taataagtga gaatatgtgg tatttgtttt   286740
cctgttcatg cattagtgtg cttagcataa tggcctccag ctccatccat gtgactgcag   286800
aggacatgat cttgttcctt tttacgcctg agcagtattc catggtgtac atataccaca   286860
tttcctttat ccagtgtacc attttcttta ttccatgtct ttgctattgt gaatagtgct   286920
atgatgaaca cacgcatgca tgtgtcttta tggtaaaatg gtttatattc cttcaggtat   286980
atacccaata acgggactgc tgggtcaaat gacaattctc ttttaagttc tttgagaagt   287040
tgctaaactg cttgccacaa tggctgaact aatttgaatt attaccagca ggatataagt   287100
gttcccttt ctttgcaacc tcaccagcat ctgttatttt ttgacttttt gataatagcc   287160
tttctgactg ctgtgatgta gtatctcatt atggttttga tatgcctttc tctctaatta   287220
ttagtaatgt tgagcatttt ttcttacact tgttggctca tgtttgtgtt cttttgaaaa   287280
gtgtctgttt atgccttttg tccattttt aatgggactg tttgttttg gcttgttgat    287340
ttaaagttcc ttatagattc tggatattag acatttgtca gatgtatagt ttgcaaatat   287400
tttcagccat tctgtagatt atctgttttt tcagttgttt cttttgctgt gcagaagctc   287460
tttggtttaa ttagatccca tttgtcaatt tttgttttg ttgcaattgt ttttggcatc    287520
tttgtcatga aacctttgct aaggcctatg tccagaatgg tatttcctag gttttcttct   287580
agggttttta tagtttgggg ttttgcattt aaacctttaa tccatcttga gttgatagtc   287640
gtacatgttg aaaggaaggg gtccagtttc aatcttctgc atataactag ccagttaccc   287700
agcaccattt attaaacagt gttttcctca tttcctgttt ttgtcaactt tgtcaaatat   287760
tagttggttg caggtatgag gctttatttt ggggttctct gttctgttcc attgatctat   287820
gtgtcttctt ttttaaccag taccatactg ttttgattcc tgtagccttg tagtataatt   287880
tgaagtcagg taatgtgatg cccctgggtt tattctttt agttaggatt gctttgacta   287940
tttgggctgt tttttgcttc catatgaatt ttacaattgt ttttctaaa tctgtgaaaa    288000
attacattga taatttgata ggcattgcat tgaatgtgta gattggcttg ggcagtatgg   288060
tcatcttaac gatattgatt cttctaatcc ataagcatgg aatgttttc catttgcgtt    288120
atctgtcatt ttctttcatc agtgttttat agttctactt ataaagatat ttcacctcct   288180
ttgttaaatg tattcctagg tttctgtgtg tgtgtgtggc tataataggc tatgttaacc   288240
tgataacaat ttaactttct tgcataaaaa actctacact tttactccac ataccgcccc   288300
cccaaacaca ttttaaattt ttgatgtcac acttacatct ttttatattg catatttctt   288360
aacaaattat tgtacctagt attattttta ataatttat cttttaacct tcattctaaa    288420
ataaagtga tttgcatatt accatgaaaa tattagacag gtaatgtgat gcccctgggt    288480
ttattcattt tagttaggat tgctttgcca attgggctgt ttttgcttc catatgaatt    288540
ttacaattgt ttttctaat tctctgaaaa attacattga taatttgata ggtattgcac    288600
tgaatgtgta gattggcttg ggcagtatgg tcatcttaac aatattgatt cttctaatcc   288660
ataagcatgg aatgttttc catttgcgtt atctgtcatt ttctttcatc agtgttttat    288720
agttctactt ataaagatat ttcacctcct ttgttaaatg tattcctagg tttctgtgtg   288780
tgtgtgtggc tataataggc tatttaacc tgataacaat ttagtttct tgcataaaaa     288840
```

```
actctacact tttactccac atactccaca cacacacacg ttttaaattt tcgatgtcac   288900
acttacatct tttttatattg catatttctt aacaaattat tgtacctagt attattttta   288960
ataattttgt cttttaacct tcattctaaa aagtgatttg catattacca tgaaaatatt   289020
agactacttt aaattggact gtgtacttac ttttactagt gagttttata ctttcatatg   289080
tttttatgtt actcattagc ctccttttct ttcagctaaa gacctccctt tagcagttct   289140
tgtaagatag gtctgttggt gaggaatggt taatttaaat ataacaaagt acaaaaagtt   289200
catcagtaga gtttcaggtt tcattttttcc actaacctgt aagaatttat catttgagtt   289260
ttagtctatt gttaaacaga aatgttcaca attatgtgaa aagtttatta aaatattcct   289320
cattttcctc attatttatc tgtgtgaggc caggttttat tcatttacga aaatagcaca   289380
ttctaataga tttaattcag aagcagttat aaaaatacag tcatcttcct ttaagtctga   289440
cattaaataa atttgcaaaa atgtaaaaca gtatcactct tctcactctc ttttttgttg   289500
tttgggaaag tacaataatt tttatgaaaa tatattattt aacaaaatca atttattatt   289560
ttcagtttaa aaataaggat tttaaaattt tttcatttca atttctaata ctgtaaatag   289620
tgataggtat aacccaacta aaccaaactc tttaagattc tcaaattttt aagagtgtaa   289680
aggagtcctg aaataaaaaa gttaaacaac ctagaaaaaa acaagatat aaatcagcat   289740 gttagcattc atcaattcag ttaccatcat ttcatcccta aaagccatgg catatagtta   289800
cgtctcactg agccaccact ttgaaactcc caccctgtgc caggtacttg tgagcatgta   289860
actttgttaa tcaactgttc agggctatat cccaacatgg ctttgttgca cttttcgtgg   289920
cacctctgct aaatctcgtt aggtagacca aaggggtcag ttaacttttt ctttataacct   289980 tttattcatg atatttataa gtttggtaat ttacaaaggt cttggacaaa gaccagggc   290040 ttatatataa taatttattt atctcttgaa gaaacaaaca atataattgg ttatgaagca   290100
caggcgtcat aagcagaaaa caggtttata ggtaaagggg gaagacctag tgtgtgtcgc   290160
ttgcatcagg aattcatgtt accatttggc aatatgaatt tgcttagcag gtgcttttt   290220 tttctccccc ccacaggatc ttgctctgtc cccaggctag agtacagtgg cccaatctcg   290280
gctcactgca acctccacct ccagagttca agtgattctc gtgcctcaga ctcctgagta   290340
gctaggatta caggcgcaag ccaccacacc cagctaatac agctaatttt tgtattttta   290400
gtagagacag ggtttcatca tgttggccag actggtctcg aactcctgac ctcaggtcat   290460
ctgccaacct cggcctccca aagtgctggg attataggca tgagccactg tgcctggctg   290520
ccctttttag taaatacatt ttgcatgacc atgtggttgt ttacagctat ttatctagta   290580
aaccaataac ttacagcttt ttaaaggctt aatgaatagc atggaattat tcatgatatc   290640
tgtgccatat cttgaggacc cactgtatac ctgatattgc actggacttt ggaaatgaaa   290700
aataatgagt gatcttgggg aatttacaat gtaacataga aaggtgtgta tcactaaatt   290760
tgcacaatga aacataatta ataatagaag aagtatatta tctggcagaa tagagtgggg   290820
aaaagtacca gcaaagactt agaataccag ctctcctcaa tacttgcact tagacttgga   290880
tgagaaacag ttccccgcac aggcagatga cagggttagg tatgatagga gccacgtaag   290940
taggagccac tcgaaatctg agtttggtgt ggctggtgtg gagggttgag ggaatatgaa   291000
gagaggacca caacttgaat cactgagggc ccttttttga tcctattagt gaaatcttta   291060
aagaaattgt attggtgaca ataacagaga aataagggct ttgaggatga aaacataggc   291120
tttaaaaaaa aaacttaaga aaaaaataat aaagtaagtt cagtattcag tgtcctgcct   291180
taaagaaagc attttaggca tgcaaatatc ccatatattc agaggcttct ataaaaaata   291240
```

```
caaacaaacc ctgtcatata cacatgaggc aaaaaaagat actttgtgag tagaaactat    291300
tgaggtaaaa gaaaaacttg ttttagaagc tgaaggccca gctgctgact taataaaaca    291360
aattatgaga attttgttta tgcgaaaatc catgctgttg aaaacgcgag tgtttaaagt    291420
tttctataaa caggaacaag gtgttctacc aaaaaaaagt ataaaagcac attgaataac    291480
tgctttgagt atttgacttg gaggaaacta ccatcactag ttgagtatac ctctttgata    291540
gcaatatgtg ttaaaagtct aacagtctca ctctacccct ccccgagaag gtaaaggaat    291600
atcctgacct taagggttgt gagacctaga tgtttcttac caagaactc cggtgacttt     291660 tctttgcaga ttttaaatag caaactattt tatggtggct ttaagccttc cagagcaagc    291720
agattaggta tgtagttcct tttaataaaa gtatttggaa gttcaataaa ggcaattatg    291780 attttttctag gaccttttcc aattctgtga ttatgtgaat gactacccgg aatttccatc    291840
aaacactgat atacaacttg ctatggctac aatttatttt ggtgtgaaaa catgtttgct    291900
tttctgttct tatgtctccc ttcatacaaa agtataatat cccagatatg taggcatata    291960
gttctgccat tcagagtaat tctaatatac tttaatctta ttaactatct ggaagactaa    292020
tgcacagtta tagctgcatt tctttaagca agtctatcat atctttgggt ttatgccaaa    292080
ctaaatttgt gaactattat ccatttacaa aatgattatt tacatcaatc ttcctttaaa    292140
taacaaatgc tcacaatgca ttttaaaata ttacctactt tataaaaatc cattctgaat    292200
aaaaatggga gaatacctgt agtgttcatt gcattgagtt gttgactctt tggccaatat    292260
gcgtttatat tttgtcttga aagatggacc ctatattgac aacatcagtt ccagtgtact    292320
cattgaaagt ggataaggaa tatgaagtgc gtgtgagatc caaacaacga aactctggaa    292380
attatgcgga gttcagtgag gtgctctatg taacacttcc tcagatgagc caatttacat    292440
gtgaagaagg taaagaaat aaaagattaa aatagtagct aacctggctt ttgtcaatat     292500
aacagttgat tcaccccctgc actggtagtg tgttgtccaa atcaaaatat attaacatca    292560
gatatcagga tgagagacct tgagctcact atctgtaaca gatattgttc attgcaaaag    292620
cagaaggaag atttagtttc caaatttttc attcaggaga agtccggggg gcaggtggaa    292680
gtttagagac aggaatttgg tggcaatctc cggatggtag aattcagatg attctttct      292740 ttatatattt ttatattct gaaatttttct atagtaagtt tgttttgaat ttataatcag     292800
gaaaaaaagc tgtactgatg gttagggaag aaagtatgta tctatatgga tggatagata    292860
tgtgacatct aagaggaaac ccaatattga gtcagcatag gtagtcaaca gcaggtgcat    292920
acggttttag aaagcggagg tgtggctttt acctagagga atgcctaata agtagtgtgg    292980
cagtcatact taaggagac gtggaacatt tgaaaaccct atgtaggaga atcacaacaa     293040
tgattaaagt ttttaaaaat gggacctatg aatttagaat aaaagaatta aaactttag     293100 atacagaaat aaagaaaact gattaatgat gagcagaaag tatagagtat tattattctc    293160 aaaatgggaaa tggctctatt ccatcttcat tgaaaacaga agtttacagg gctatatgtt    293220
tgttaatgaa acaaccacaa gctacataga aaataaattt atatttctgt atttactata    293280
caggtagaat ctcatgatac taaatagcat taggatgaaa attttctatag caccatttc     293340 tctatactct agttaactga attcttgttt ccaaactatt tgatattatg caattctggc    293400
cttaaaagta caatagctat acacccttaa gcttagtgta gtggcattta attcacttaa    293460
catatatttt ttaaactgcc ttttccttct gttactaaca aaaagaagc tctaacttta     293520 tgttattttc ctgaatatgt cattgatatg aaattataga cactacaaga caaaaaatga   293580
```

```
tttttttctcc cccaccaatt ctttaaaatg cttataatat ctccctaggg gattttaata  293640 acttttttaaa taagaaaaga ctatttcagc ataaagacct acattttaaa tggcaatgtt  293700
aaggtaaatt tcatctgtca ttttttataaa aaagtggtta gcctctgcct ctgtggtaag  293760
aatactgggt accaactgca aagtagctgg caggtactca atcttaagga atgaaataga  293820
agttttacaa acaggttccc ccaagtctca tacaaagtat actaaaacct gaagatggga  293880
gcctcagtag tgatctttct gtcaatttta tgtatataat atacatgaga tatatttatt  293940 atatttttaat aatttaatttt attgatataa atacgtatat ttatagctgt aaaatatatg  294000
ttatttgtgt ctaagaagtt tctgtcatga tttatcaata aaaactctgc cttcatcttt  294060
ttgataaatc ttcaatctgg aaactaagaa aatcaccaca cttaaaaaaa aatagaaaag  294120
aaaccgagtg ggcattattt aggtagtgtg ttaataagca cactttttt actgaagctg  294180 aaaccttttat gatactccct ggacacatag tatgcttaaa gcagattgtt tgttttcata  294240
aaacacacat tgattttgaa ctatatgctg tttctttatt ttgaagttttt tttttaatgt  294300 gaggagattt gaaaagtgga cagagatgtt cataaaacag aaaaaaacta agtcgttgca  294360
ttctgtttca gtggttatca agagaaatca ctgactttat tagatgaata caaattatga  294420 atttttttgtg aaaagggaaa gggaaatgta aactgtgctt caactattcg taattctgaa  294480
agcgaaatat tcttgtgtgt ttcagatttc tactttccat ggctcttaat tattatctttt  294540 ggaatatttg ggctaacagt gatgctattt gtattcttat tttctaaaca gcaaaggtag  294600
gtgtggagta gtattctttg gtattttgta ccagttgttt agatttccat atgtgtttct  294660
atttgttatt tgatattttc tttgtcaaat tatgagtgga aattttagtt aacctagtac  294720
acttttatct ccagttatat atttaccatt catataaaac tcaatttgtt gtatttatct  294780
tagacaattt agaggtttag attctatctg gagacttgta caggacatta agaggcttag  294840
gctggtgact atgcatacct tgtgatatgt acctctttat ccaagagcta gctctttccc  294900
tcaagtcctc aacaagttga cccattcatt ccaggacttc aaagtatcac tgagcctttg  294960
gctgagtctg atacagtcct tatatacaga caattttttt ttttccttga gacggagtct  295020
tactctgttg cccaggctgg agtgcaatgg cgcaatcttg gctcactgca accgccgccc  295080
cccaggttca agcaattctc ctgcctcagc ctccagagta gctgggatta caggcatgcg  295140
ccaccaagcc cagctaattt tgtatttttta gatacagttt caccatgttg gtcagactgg  295200
tctcgaactc ctgacctcag gtgatctgcc cacctcagcc tcccaaagcg ctgggattac  295260
aggcgtgagc taccgcgcct ggccccattt aaggtatttt taaagtccca atggttaatc  295320
ttgttgcttc tcctagaatt aaggtgacta acactcccag gttgcctaga actctcctgg  295380
tttttagcaa tgcaagtccg gtgtgccagg aaatccctca gttccaggta accaagacag  295440
ttgatcccct tacctagaat tgaaaatacg ttctccagct gaagccaaga ggcatctata  295500
aatcaaaatg agatctatgt taatatattt taaaagattt tactttgttt tgtaaggtag  295560
tatagcactt gtaaacttca aaacagaatt ttgttaggaa gaagaattat tgggacgcta  295620
gatttctata gtgtcaagca tgctaaaagt ctaactgaat gcagaaaggg ttattttcag  295680
tagagcttca tgtccaattt tataatataa accaattgga agtaaaaatt cattctgaat  295740 tccatttttgc acctaacttt ctggcaacat tcctgttttc caaaaaagca gctatcataa  295800
atcacaacac aattttctat tgtttcagga aaataaataa atatattttt agaatttaa  295860 tttgtgtatt taagtaatgc caacaacaaa aaagccaaat tattctgttg attaatttca  295920
gtttattaat ctatatattt ggtgggaaaa tttatacata acttcagtag ataaactcac  295980
```

```
gaggtatgta aagtaattag ctcttagtat tagctgtgaa tttctagcca ttgtgaaggc 296040
caagtcaatt tgttatgttg tttagttata ttagttaaca atattaggaa gaaaaaatta 296100
tcctctcaaa aagtaggatt tccaagaaaa catattactt ctaatacagt gcttttata 296160 aataatgaaa tgcttaacta taatgtttag tcaaaatcac caaattctac aattgatttg 296220
aaatctttat tgttctccca aatttcctgc actaaattga attttctgta ggaaagaatt 296280
aactttattt tttatttgcc cattaaaaac gcttatcatt gtctaaattt gcatgttcta 296340
ctgaaagtgg gaaatagtag caaatatttg tcagcaagta tggacagaac atgtagttcc 296400
aacaattaaa ttgatactgc aaagaacgag atttttccta gaactgtagg gctgtaaagt 296460
ggcgtcaggt cctacatgcc tttgaaattt tctgagtcca caattcatta tccaacccac 296520
ttcaccctgc tttaatccag ttaattgagt caactctagc aaaatttata attttatttg 296580
tatctgatac aaaaccacaa acatagtttc aagtcaggct attattatac tggttcctac 296640
cacacaaccc tcccagcctt tgagctgtta ccaattgagg aaagaaataa ctgaatcagc 296700
ctaaaataga atttccaaac cagtagcgaa attcagccta cagattcata ttttgttatt 296760
ttattttaat tagttttgat ttcagagtga agattttcct acaaagtgtt tgtaaaatag 296820
agaattttca cacaaaaatc cagatttggg gattatcttt taaaaaatga aagatgtagt 296880
gaaactaaac aaggcagcat atgctgcagc agacaaccag ctatcctatt tgggattggc 296940
tcacattctt taatttgcca ccatcctcat tcctcctaat gactttgcaa ctggcttgct 297000
ttattcctct gcatgacctg cttgggcctc ttagatttat gctctgccac tgtggcataa 297060
ggtcactaca accactagaa aaccactagc gcatgcctga atgcatcatc ctatttaaaa 297120
aggaaaagca cacgtcacaa agtcaaacat cagccatttg gaaacctttg cttcctgtaa 297180
ttagaattat gttccatctt tttatgtttt tgggaatttg aaataccaat ttcgagatgc 297240
agaatcaaaa aaaaaaaaac aaaacagcga acagcagca tgacacaaag aacctgggtt 297300
ttgatttgga gtcaggttct ctgggtttga gccccaactg tgccaactat gaatgcatga 297360
tttgaacatg ttgcttaatt ttccaagttt ttgcacagat atatcatctg cctccctggg 297420
agtcataagg attaagtgaa atgtttagtg caggggtcac aaacttattt catagagtta 297480
gagtacattt ttaggctttt caagccatac agtctctatc acagctactc aactctgcca 297540
ctgtagcacg aaagtggcca taaacaaaat ggaaatgaat gaagatgctt gtgttctcat 297600
aaaattttat ctacacaaac atgtgacagg ccagatttgg cccacagacc ttaatttagt 297660
gacccatagt ttagtgcaaa gtatatccca cagtgtctga tttatcagaa gcactaaaaa 297720
atgatagtag ttattattaa taatttgtat tacttatttc tatatctgta attcatcagt 297780
aacaatatgc tttaacattt gccccactga gtagtagagg ctacttaatg caatttataa 297840
aatggatttt tgcttattac ttggattagg taaaatagca agtggaaata ctgagaaaat 297900
gtactcctta tggaatggac tggactgacc attcacactg agtggaatag taactgatat 297960
ccaaaaatct ggttaccacc tcttcatgac agtgtcatct ctgaatagtc aggagttttt 298020
taaaaaatta aatgaattgt ttggaataat ctctgagcct ttttccagtg ctataatttg 298080
attttaaaaa ataaactcca ggccagatac aatggcttat agcatataaa tccagcactt 298140
tgggaggatg gggcgggagt attgccctga ggccaggagt tccagacagc tcgggcaatg 298200
actagagcaa gactccatta caaaaaatga aacaacaaaa attagcacac cctgtagtcc 298260
tagctactta ggaggctgag gcaagaatat cgcttggccc aggagtttga ggctgcagtg 298320
```

```
aattatgatt gcaccactgg actccagtgt gggcaatgaa gtaagaccct gtctcaaaaa    298380
gttttaaaaa aaattaaaaa caccataaat tccaattaca ctattaattg tacaaaatag    298440
atacatgatt tattcatttt tatgaccaaa aaataattta aagatttgga acaaaaaatg    298500
taagtgcatc ctagaattgt atatataaac ccatactgat tagttagaga tagttaaaat    298560
ttaatctgtc ccatctgaaa tgaaccctgt agtaaaaccc tggttaataa gatcatctta    298620
gataatttca taattaatat gaactatatg gctaacctac ccaagtctac cctttttcaa    298680
gggtgtaagt aatcttggct ccatgtggat tgactctttt ttctttcttt cctgtacaaa    298740
ttactgatga gatgtacact agaattgcct tatagctgaa atggaaatca gctttagatg    298800
aaattaaatt tctttctttc aaatactaaa tctggctgaa aataaaaagc attaagaaaa    298860
aaacaattgt gggaaaacca cattttcttt taatagactt cagatgaggc tttttgggtt    298920
ttttagttgt tctttttttt ccttctacag tttttctttc tcatttactg tctaatattt    298980
tcttctgttt ctcacactcc aattatataa agtaccagaa tatttggaaa aagtaatagt    299040
attgccaata ttttatttct atcttttgct ataattgaga atatgtagct tttaagatgt    299100
caaaaccaaa atttttatatg ttttcaagga ttaaaatgct gattctgccc ccagttccag   299160
ttccaaagat taaaggaatc gatccagatc tcctcaaggt aactaataat tttatctaaa    299220
ttgtagctag tactaattaa cacctgaaga ctcctgtcat atgttgaagg ttttctgtaa    299280
gctatatata tcacattcaa ttttcttgtg tctcttctcc tggagaaaat tttttttaaat   299340 attctatttc ttaaaaataa gaaaacgtca tatgtattta aaagttaca cactaattta     299400 tgttttttta tatgttttgt tactgttgtt cttattgtaa ccataattaa tctctgaaca    299460
ttatttgcta attcatttaa ttattatgag tttctttcca tagatcttca ttttctttct    299520
attttctagg aaggaaaatt agaggaggtg aacacaatct tagccattca tgatagctat    299580
aaacccgaat tccacagtga tgactcttgg gttgaattta ttgagctaga tattgatgag    299640
ccagatgaaa agactgagga atcagacaca gacagacttc taagcagtga ccatgagaaa    299700
tcacatagta acctaggggt gaaggatggc gactctggac gtaccagctg ttgtgaacct    299760
gacattctgg agactgattt caatgccaat gacatacatg agggtacctc agaggttgct    299820
cagccacaga ggttaaaagg ggaagcagat ctcttatgcc ttgaccagaa gaatcaaaat    299880
aactcacctt atcatgatgc ttgccctgct actcagcagc ccagtgttat ccaagcagag    299940
aaaaacaaac cacaaccact tcctactgaa ggagctgagt caactcacca agctgcccat    300000
attcagctaa gcaatccaag ttcactgtca aacatcgact tttatgccca ggtgagcgac    300060
attacaccag caggtagtgt ggtcctttcc ccgggccaaa agaataaggc agggatgtcc    300120
caatgtgaca tgcacccgga aatggtctca ctctgccaag aaaacttcct tatgacaat     300180 gcctacttct gtgaggcaga tgccaaaaag tgcatccctg tggctcctca catcaaggtt    300240
gaatcacaca tacagccaag cttaaaccaa gaggacattt acatcaccac agaaagcctt    300300
accactgctg ctgggaggcc tgggacagga gaacatgttc caggtctga gatgcctgtc      300360 ccagactata cctccattca tatagtacag tccccacagg gcctcatact caatgcgact    300420
gccttgccct tgcctgacaa agagtttctc tcatcatgtg gctatgtgag cacagaccaa    300480
ctgaacaaaa tcatgcctta gcctttcttt ggtttcccaa gagctacgta tttaatagca    300540
aagaattgac tggggcaata acgtttaagc caaaacaatg tttaaacctt tttggggga    300600 gtgacaggat ggggtatgga ttctaaaatg ccttttccca aaatgttgaa atatgatgtt    300660
aaaaaaataa gaagaatgct taatcagata gatattccta ttgtgcaatg taaatatttt    300720
```

```
aaagaattgt gtcagactgt ttagtagcag tgattgtctt aatattgtgg gtgttaatttt 300780 ttgatactaa gcattgaatg gctatgtttt taatgtatag taaatcacgc tttttgaaaa 300840
agcgaaaaaa tcaggtggct tttgcggttc aggaaaattg aatgcaaacc atagcacagg 300900
ctaatttttt gttgtttctt aaataagaaa ctttttatt taaaaaacta aaaactagag 300960
gtgagaaatt taaactataa gcaagaaggc aaaaatagtt tggatatgta aaacatttat 301020
tttgacataa agttgataaa gatttttaa taatttagac ttcaagcatg gctattttat 301080
attacactac acactgtgta ctgcagttgg tatgacccct ctaaggagtg tagcaactac 301140
agtctaaagc tggtttaatg ttttggccaa tgcacctaaa gaaaaacaaa ctcgtttttt 301200
acaaagccct tttatacctc cccagactcc ttcaacaatt ctaaaatgat tgtagtaatc 301260
tgcattattg gaatataatt gttttatctg aattttaaa caagtatttg ttaatttaga 301320
aaactttaaa gcgtttgcac agatcaactt accaggcacc aaaagaagta aagcaaaaa 301380 agaaaacctt tcttcaccaa atcttggttg atgccaaaaa aaatacatg ctaagagaag 301440 tagaaatcat agctggttca cactgaccaa gatacttaag tgctgcaatt gcacgcggag 301500
tgagtttttt agtgcgtgca gatggtgaga gataagatct atagcctctg cagcggaatc 301560
tgttcacacc caacttggtt ttgctacata attatccagg aagggaataa ggtacaagaa 301620
gcattttgta agttgaagca aatcgaatga aattaactgg gtaatgaaac aaagagttca 301680
agaaataagt ttttgtttca cagcctataa ccagacacat actcattttt catgataatg 301740
aacagaacat agacagaaga aacaaggttt tcagtcccca cagataactg aaaattattt 301800
aaaccgctaa aagaaacttt ctttctcact aaatctttta taggatttat ttaaaatagc 301860
aaaagaagaa gtttcatcat ttttttacttc ctctctgagt ggactggcct caaagcaagc 301920
attcagaaga aaaagaagca acctcagtaa tttagaaatc attttgcaat cccttaatat 301980
cctaaacatc attcattttt gttgttgttg ttgttgttga cagagtct cgctctgtcg 302040 ccaggctaga gtgcggtggc gcgatcttga ctcactgcaa tctccacctc ccacaggttc 302100
aggcgattcc cgtgcctcag cctcctgagt agctgggact acaggcacgc accaccatgc 302160
caggctaatt ttttttgtatt ttagcagaga cggggtttca ccatgttggc caggatggtc 302220
tcgatctcct gacctcgtga tccacccgac tcggcctccc aaagtgctgg gattacaggt 302280
gtaagccacc gtgcccagcc ctaaacatca ttcttgagag cattgggata tctcctgaaa 302340
aggtttatga aaaagaagaa tctcatctca gtgaagaata cttctcattt tttaaaaaag 302400
cttaaaactt tgaagttagc tttaacttaa atagtatttc ccatttatcg cagacctttt 302460
ttaggaagca agcttaatgg ctgataattt taaattctct ctcttgcagg aaggactatg 302520
aaaagctaga attgagtgtt taaagttcaa catgttattt gtaatagatg tttgatagat 302580
tttctgctac tttgctgcta tggttttctc caagagctac ataatttagt ttcatataaa 302640
gtatcatcag tgtagaacct aattcaattc aaagctgtgt gtttggaaga ctatcttact 302700
atttcacaac agcctgacaa catttctata gccaaaaata gctaaatacc tcaatcagtc 302760
tcagaatgtc attttggtac tttggtggcc acataagcca ttattcacta gtatgactag 302820
ttgtgtctgg cagtttatat ttaactctct ttatgtctgt ggattttttc cttcaaagtt 302880
taataaattt attttcttgg attcctgata gtgtgcttct gttatcaaac accaacataa 302940
aaatgatcta aaccactctg tatactgtga attatcattg taaggagagc ttagcaccac 303000
tggatcaaat acatcagcat tgggtatgga gatttttatg tgctgagata tagagaggga 303060
```

```
aacatatccc ccttcccttа tttttгаgа агасааагс ссаастcagа аататcccас 303120 tggcttggcc ctccccttag gctgtgactc cccataggca aaggttcata gagctgtgta 303180
tttgatgcat catggaaaat aaatgacatg ggtgttggat gagggagagt gatatgtgag 303240
cattatcttt acatttccag cttgagcatg ttgtctggaa ggaaggaaag cagctcttcc 303300
tctgccattc acccattggc ctaagtcagt ttattggact agctgcttgt tatcatggga 303360
atcagctaat aagtcaggct tgggaggaag gctgattagg taagttgtgt aggagcctga 303420
gagagccatg aagtttagat tcctacagca ggaggcagga tgcaggtgag gtagctgctg 303480
aaccctaggc tcctgagcag gcactggatt ctgagatgta ggaatctggt gaggacattg 303540
ataaacctac taaacaatga cgtattgctt cagcaagtca aatgcaaagt gccacaactt 303600
tttataatac tcaagtgtta tgttaaaaaa aaaaaatgtc ttcacctgct gccctctgcc 303660
ctgtgagcag ccattacctg aaagaaccat ggagtgaagc ctcagggctt cttcatatag 303720
atgctttaag atatgaggag tacagggaaa agaaagcctg cctacttcca tggattgaaa 303780
taacacaatt ctatttcaga agattaatgg tgtgttgaaa atggctacac acatctttca 303840
gcatttcaat ttctcaaagt ttctactaac actttattca agtgctataa tatttacata 303900
tttacatatt tgtataccaa aatatgtctt gttatgtgct tgttttaggg taagaaatag 303960
tgaccagaaa aaccagaagt tacttaaatc taaacttttt agtttggaat ccaagatccc 304020
acataatttg ccccagtctc ctttgagagt ttaaaattta agacctagat gtaaagggca 304080
cagcttctga ataagaattt gatgtttggt taacattcaa actctattgc tgtggaaatc 304140
taatgagcat atgatgtcag ctatgttaca cgggaaacat tgctcatagt ttaaatgatc 304200
tctgactgat aaatgacatc tggataggga gaaactataa ccacctggag ataagttata 304260 cttttggactt gagtgtagtg acttgtaatt aagcatttcc cctatagaaa ctctggaagc 304320
tatgtttctg gagatgtaac aagagtaact ggctccagtg aggcatagag cttctaagcc 304380
tgggagactc ctttacctgc ccaatacctt ctctgaatct gagctgccag ttgtaggagg 304440
agaggaagga aaagaccttc tggatagcta tataaacagc tgtttagatt gcttcatgca 304500
ctgttatcat tactgtgact ctaaagcaga agcctgatg ctgtatccct tctgtcctac 304560
atccctctga gtagactgga accaagtatg gtgaatctgg ggaatgtgtg gttgagccta 304620
agaagatccc cttgcatatg tagcaaaaga cacttgccat ttcttgaaca agtttgtgc 304680

ттттccccатст ctatgttctt ggtcatgcct cctccttcaa ctaaaaagct cccacttacc 304740
aaccctgcct gtcaagattc ccttcatcct tcatggccca gctctaatgc ctccttcatg 304800

aactctcctc tgattcccac catccaatca gtgatttttt cttctgaacc atgtttaatg 304860
gtgtttatca cattactttg gtagctcacc tgacaaacgg c                  304901

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
tcagggcatt ctttccattc                                               20

<210> SEQ ID NO 7
<211> LENGTH: 20
<212> TYPE: DNA
<213> ORGANISM: Artificial Sequence
```

-continued

```
<220> FEATURE:
<223> OTHER INFORMATION: oligonucleotide

<400> SEQUENCE: 7
cataatcagg gcattctttc                                              20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
cctttaatct ttggaactgg                                              20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
tcatcaatat ctagctcaat                                              20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
cttagaagtc tgtctgtgtc                                              20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
cctgctggtg taatgtcgct                                              20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
atgtaaatgt cctcttggtt                                              20

<210> SEQ ID NO 13
<211> LENGTH: 20
<212> TYPE: DNA
<213> ORGANISM: Artificial Sequence
<220> FEATURE:
<223> OTHER INFORMATION: oligonucleotide

<400> SEQUENCE: 13
tggtgatgta aatgtcctct                                              20
```

```
<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
ttctgtggtg atgtaaatgt                                                    20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
aggctttctg tggtgatgta                                                    20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
tggtaaggct ttctgtggtg                                                    20

<210> SEQ ID NO 17
<211> LENGTH: 20
<212> TYPE: DNA
<213> ORGANISM: Artificial Sequence
<220> FEATURE:
<223> OTHER INFORMATION: oligonucleotide

<400> SEQUENCE: 17
agttggtctg tgctcacata                                                    20

<210> SEQ ID NO 18
<211> LENGTH: 20
<212> TYPE: DNA
<213> ORGANISM: Artificial Sequence
<220> FEATURE:
<223> OTHER INFORMATION: oligonucleotide

<400> SEQUENCE: 18
tgttcagttg gtctgtgctc                                                    20

<210> SEQ ID NO 19
<211> LENGTH: 20
<212> TYPE: DNA
<213> ORGANISM: Artificial Sequence
<220> FEATURE:
<223> OTHER INFORMATION: oliognucleotide

<400> SEQUENCE: 19
gcatgatttt gttcagttgg                                                    20

<210> SEQ ID NO 20
<211> LENGTH: 20
<212> TYPE: DNA
<213> ORGANISM: Artificial Sequence
<220> FEATURE:
<223> OTHER INFORMATION: oligonucleotide
```

-continued

<400> SEQUENCE: 20
tataaagggg ctttgtaaaa                                              20

<210> SEQ ID NO 21
<211> LENGTH: 20
<212> TYPE: DNA
<213> ORGANISM: Artificial Sequence
<220> FEATURE:
<223> OTHER INFORMATION: oligonucleotide

<400> SEQUENCE: 21
catagcagca aagtagcaga                                              20

<210> SEQ ID NO 22
<211> LENGTH: 20
<212> TYPE: DNA
<213> ORGANISM: Artificial Sequence
<220> FEATURE:
<223> OTHER INFORMATION: oligonucleotide

<400> SEQUENCE: 22
gctatttttg gctatagaaa                                              20

<210> SEQ ID NO 23
<211> LENGTH: 20
<212> TYPE: DNA
<213> ORGANISM: Artificial Sequence
<220> FEATURE:
<223> OTHER INFORMATION: oligonucleotide

<400> SEQUENCE: 23
gattgaggta tttagctatt                                              20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide

<400> SEQUENCE: 24
gatccatacc tgtaggacct                                              20

<210> SEQ ID NO 25
<211> LENGTH: 20
<212> TYPE: DNA
<213> ORGANISM: Artificial Sequence
<220> FEATURE:
<223> OTHER INFORMATION: oligonucleotide

<400> SEQUENCE: 25
ccagagatcc atacctgtag                                              20

<210> SEQ ID NO 26
<211> LENGTH: 20
<212> TYPE: DNA
<213> ORGANISM: Artificial Sequence
<220> FEATURE:
<223> OTHER INFORMATION: oligonucleotide

<400> SEQUENCE: 26
tgctaaggat agctgctgtg                                              20

<210> SEQ ID NO 27

```
<211> LENGTH: 20
<212> TYPE: DNA
<213> ORGANISM: Artificial Sequence
<220> FEATURE:
<223> OTHER INFORMATION: oligonucleotide

<400> SEQUENCE: 27
ttgtctttag gcctggatta                                              20

<210> SEQ ID NO 28
<211> LENGTH: 20
<212> TYPE: DNA
<213> ORGANISM: Artificial Sequence
<220> FEATURE:
<223> OTHER INFORMATION: oligonucleotide

<400> SEQUENCE: 28
ttagaagaat ttgtctttag                                              20

<210> SEQ ID NO 29
<211> LENGTH: 20
<212> TYPE: DNA
<213> ORGANISM: Artificial Sequence
<220> FEATURE:
<223> OTHER INFORMATION: oligonucleotide

<400> SEQUENCE: 29
gtgaatttag gctccttaga                                              20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide

<400> SEQUENCE: 30
gctgtatggg tcctaggttc                                              20

<210> SEQ ID NO 31
<211> LENGTH: 20
<212> TYPE: DNA
<213> ORGANISM: Artificial Sequence
<220> FEATURE:
<223> OTHER INFORMATION: oligonucleotide

<400> SEQUENCE: 31
taacagctgt tttccccagc                                              20

<210> SEQ ID NO 32
<211> LENGTH: 20
<212> TYPE: DNA
<213> ORGANISM: Artificial Sequence
<220> FEATURE:
<223> OTHER INFORMATION: oligonucleotide

<400> SEQUENCE: 32
tttcatccac tgtaccacca                                              20

<210> SEQ ID NO 33
<211> LENGTH: 20
<212> TYPE: DNA
<213> ORGANISM: Artificial Sequence
<220> FEATURE:
<223> OTHER INFORMATION: oligonucleotide

<400> SEQUENCE: 33
```
ttgcactatt tcatcaacag                                               20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide

<400> SEQUENCE: 34
gggtggatct ggttgcacta                                               20

<210> SEQ ID NO 35
<211> LENGTH: 20
<212> TYPE: DNA
<213> ORGANISM: Artificial Sequence
<220> FEATURE:
<223> OTHER INFORMATION: oligonucleotide

<400> SEQUENCE: 35
attgcgtggt gcttcccatc                                               20

<210> SEQ ID NO 36
<211> LENGTH: 20
<212> TYPE: DNA
<213> ORGANISM: Artificial Sequence
<220> FEATURE:
<223> OTHER INFORMATION: oligonucleotide

<400> SEQUENCE: 36
tagggtccat cattttccat                                               20

<210> SEQ ID NO 37
<211> LENGTH: 20
<212> TYPE: DNA
<213> ORGANISM: Artificial Sequence
<220> FEATURE:
<223> OTHER INFORMATION: oligonucleotide

<400> SEQUENCE: 37
caatgagtac actggaactg                                               20

<210> SEQ ID NO 38
<211> LENGTH: 20
<212> TYPE: DNA
<213> ORGANISM: Artificial Sequence
<220> FEATURE:
<223> OTHER INFORMATION: oligonucleotide

<400> SEQUENCE: 38
aactcgccat aatttccaga                                               20

<210> SEQ ID NO 39
<211> LENGTH: 20
<212> TYPE: DNA
<213> ORGANISM: Artificial Sequence
<220> FEATURE:
<223> OTHER INFORMATION: oligonucleotide

<400> SEQUENCE: 39
agcccaaata ttccaaagat                                               20

<210> SEQ ID NO 40
<211> LENGTH: 20
<212> TYPE: DNA

```
<213> ORGANISM: Artificial Sequence
<220> FEATURE:
<223> OTHER INFORMATION: oligonucleotide

<400> SEQUENCE: 40
tcagcatttt aatcctttgc                                              20

<210> SEQ ID NO 41
<211> LENGTH: 20
<212> TYPE: DNA
<213> ORGANISM: Artificial Sequence
<220> FEATURE:
<223> OTHER INFORMATION: oligonucleotide

<400> SEQUENCE: 41
attttccttc cttgaggaga                                              20

<210> SEQ ID NO 42
<211> LENGTH: 20
<212> TYPE: DNA
<213> ORGANISM: Artificial Sequence
<220> FEATURE:
<223> OTHER INFORMATION: oligonucleotide

<400> SEQUENCE: 42
agattgtgtt cacctcctct                                              20

<210> SEQ ID NO 43
<211> LENGTH: 20
<212> TYPE: DNA
<213> ORGANISM: Artificial Sequence
<220> FEATURE:
<223> OTHER INFORMATION: oligonucleotide

<400> SEQUENCE: 43
aacccaagag tcatcactgt                                              20

<210> SEQ ID NO 44
<211> LENGTH: 20
<212> TYPE: DNA
<213> ORGANISM: Artificial Sequence
<220> FEATURE:
<223> OTHER INFORMATION: oligonucleotide

<400> SEQUENCE: 44
ctggctcatc aatatctagc                                              20

<210> SEQ ID NO 45
<211> LENGTH: 20
<212> TYPE: DNA
<213> ORGANISM: Artificial Sequence
<220> FEATURE:
<223> OTHER INFORMATION: oligonucleotide

<400> SEQUENCE: 45
tgtgtctgat tcctcagtct                                              20

<210> SEQ ID NO 46
<211> LENGTH: 20
<212> TYPE: DNA
<213> ORGANISM: Artificial Sequence
<220> FEATURE:
<223> OTHER INFORMATION: oligonucleotide

<400> SEQUENCE: 46
tatgtcattg gcattgaaat                                              20
```

```
<210> SEQ ID NO 47
<211> LENGTH: 20
<212> TYPE: DNA
<213> ORGANISM: Artificial Sequence
<220> FEATURE:
<223> OTHER INFORMATION: oligonucleotide

<400> SEQUENCE: 47
aaggcataag agatctgctt                                           20

<210> SEQ ID NO 48
<211> LENGTH: 20
<212> TYPE: DNA
<213> ORGANISM: Artificial Sequence
<220> FEATURE:
<223> OTHER INFORMATION: oligonucleotide

<400> SEQUENCE: 48
actcagctcc ttcagtagga                                           20

<210> SEQ ID NO 49
<211> LENGTH: 20
<212> TYPE: DNA
<213> ORGANISM: Artificial Sequence
<220> FEATURE:
<223> OTHER INFORMATION: oligonucleotide

<400> SEQUENCE: 49
ggacatccct gccttattct                                           20

<210> SEQ ID NO 50
<211> LENGTH: 20
<212> TYPE: DNA
<213> ORGANISM: Artificial Sequence
<220> FEATURE:
<223> OTHER INFORMATION: oligonucleotide

<400> SEQUENCE: 50
ggcattgtcc ataaggaagt                                           20

<210> SEQ ID NO 51
<211> LENGTH: 20
<212> TYPE: DNA
<213> ORGANISM: Artificial Sequence
<220> FEATURE:
<223> OTHER INFORMATION: oligonucleotide

<400> SEQUENCE: 51
actttttggc atctgcctca                                           20

<210> SEQ ID NO 52
<211> LENGTH: 20
<212> TYPE: DNA
<213> ORGANISM: Artificial Sequence
<220> FEATURE:
<223> OTHER INFORMATION: oligonucleotide

<400> SEQUENCE: 52
gatgcacttt ttggcatctg                                           20

<210> SEQ ID NO 53
<211> LENGTH: 20
<212> TYPE: DNA
<213> ORGANISM: Artificial Sequence
<220> FEATURE:
```

<223> OTHER INFORMATION: oligonucleotide

<400> SEQUENCE: 53
cagtcgcatt gagtatgagg                                              20

<210> SEQ ID NO 54
<211> LENGTH: 20
<212> TYPE: DNA
<213> ORGANISM: Artificial Sequence
<220> FEATURE:
<223> OTHER INFORMATION: oligonucleotide

<400> SEQUENCE: 54
ctctttgtca ggcaagggca                                              20

<210> SEQ ID NO 55
<211> LENGTH: 20
<212> TYPE: DNA
<213> ORGANISM: Artificial Sequence
<220> FEATURE:
<223> OTHER INFORMATION: oligonucleotide

<400> SEQUENCE: 55
gtgctcacat agccacatga                                              20

<210> SEQ ID NO 56
<211> LENGTH: 20
<212> TYPE: DNA
<213> ORGANISM: Artificial Sequence
<220> FEATURE:
<223> OTHER INFORMATION: oligonucleotide

<400> SEQUENCE: 56
aagaaaggct aaggcatgat                                              20

<210> SEQ ID NO 57
<211> LENGTH: 20
<212> TYPE: DNA
<213> ORGANISM: Artificial Sequence
<220> FEATURE:
<223> OTHER INFORMATION: oligonucleotide

<400> SEQUENCE: 57
aaatacgtag ctcttgggaa                                              20

<210> SEQ ID NO 58
<211> LENGTH: 20
<212> TYPE: DNA
<213> ORGANISM: Artificial Sequence
<220> FEATURE:
<223> OTHER INFORMATION: oligonucleotide

<400> SEQUENCE: 58
caatcactgc tactaaacag                                              20

<210> SEQ ID NO 59
<211> LENGTH: 20
<212> TYPE: DNA
<213> ORGANISM: Artificial Sequence
<220> FEATURE:
<223> OTHER INFORMATION: oligonucleotide

<400> SEQUENCE: 59
aaacatagcc attcaatgct                                              20

<210> SEQ ID NO 60
<211> LENGTH: 20
<212> TYPE: DNA
<213> ORGANISM: Artificial Sequence
<220> FEATURE:
<223> OTHER INFORMATION: oligonucleotide

<400> SEQUENCE: 60
gtgctatggt ttgcattcaa                                           20

<210> SEQ ID NO 61
<211> LENGTH: 20
<212> TYPE: DNA
<213> ORGANISM: Artificial Sequence
<220> FEATURE:
<223> OTHER INFORMATION: oligonucleotide

<400> SEQUENCE: 61
gttttacata tccaaactat                                           20

<210> SEQ ID NO 62
<211> LENGTH: 20
<212> TYPE: DNA
<213> ORGANISM: Artificial Sequence
<220> FEATURE:
<223> OTHER INFORMATION: oligonucleotide

<400> SEQUENCE: 62
catcaaccaa gatttggtga                                           20

<210> SEQ ID NO 63
<211> LENGTH: 20
<212> TYPE: DNA
<213> ORGANISM: Artificial Sequence
<220> FEATURE:
<223> OTHER INFORMATION: oligonucleotide

<400> SEQUENCE: 63
gaggctatag atcttatctc                                           20

<210> SEQ ID NO 64
<211> LENGTH: 20
<212> TYPE: DNA
<213> ORGANISM: Artificial Sequence
<220> FEATURE:
<223> OTHER INFORMATION: oligonucleotide

<400> SEQUENCE: 64
tagtgagaaa gaaagtttct                                           20

<210> SEQ ID NO 65
<211> LENGTH: 20
<212> TYPE: DNA
<213> ORGANISM: Artificial Sequence
<220> FEATURE:
<223> OTHER INFORMATION: oligonucleotide

<400> SEQUENCE: 65
aatgctctca agaatgatgt                                           20

<210> SEQ ID NO 66
<211> LENGTH: 20
<212> TYPE: DNA
<213> ORGANISM: Artificial Sequence
<220> FEATURE:
<223> OTHER INFORMATION: oligonucleotide

<400> SEQUENCE: 66
acactcaatt ctagcttttc                                               20

<210> SEQ ID NO 67
<211> LENGTH: 20
<212> TYPE: DNA
<213> ORGANISM: Artificial Sequence
<220> FEATURE:
<223> OTHER INFORMATION: oligonucleotide

<400> SEQUENCE: 67
catctattac aaataacatg                                               20

<210> SEQ ID NO 68
<211> LENGTH: 20
<212> TYPE: DNA
<213> ORGANISM: Artificial Sequence
<220> FEATURE:
<223> OTHER INFORMATION: oligonucleotide

<400> SEQUENCE: 68
ctcttggaga aaaccatagc                                               20

<210> SEQ ID NO 69
<211> LENGTH: 20
<212> TYPE: DNA
<213> ORGANISM: Artificial Sequence
<220> FEATURE:
<223> OTHER INFORMATION: oligonucleotide

<400> SEQUENCE: 69
tctacactga tgatactta                                                20

<210> SEQ ID NO 70
<211> LENGTH: 20
<212> TYPE: DNA
<213> ORGANISM: Artificial Sequence
<220> FEATURE:
<223> OTHER INFORMATION: oligonucleotide

<400> SEQUENCE: 70
cacagctttg aattgaatta                                               20

<210> SEQ ID NO 71
<211> LENGTH: 20
<212> TYPE: DNA
<213> ORGANISM: Artificial Sequence
<220> FEATURE:
<223> OTHER INFORMATION: oligonucleotide

<400> SEQUENCE: 71
agtcttccaa acacacagct                                               20

<210> SEQ ID NO 72
<211> LENGTH: 20
<212> TYPE: DNA
<213> ORGANISM: Artificial Sequence
<220> FEATURE:
<223> OTHER INFORMATION: oligonucleotide

<400> SEQUENCE: 72
aggctgttgt gaaatagtaa                                               20

<210> SEQ ID NO 73
<211> LENGTH: 20

```
<212> TYPE: DNA
<213> ORGANISM: Artificial Sequence
<220> FEATURE:
<223> OTHER INFORMATION: oligonucleotide

<400> SEQUENCE: 73
atagaaatgt tgtcaggctg                                                   20

<210> SEQ ID NO 74
<211> LENGTH: 20
<212> TYPE: DNA
<213> ORGANISM: Artificial Sequence
<220> FEATURE:
<223> OTHER INFORMATION: oligonucleotide

<400> SEQUENCE: 74
ccaaaatgac attctgagac                                                   20

<210> SEQ ID NO 75
<211> LENGTH: 20
<212> TYPE: DNA
<213> ORGANISM: Artificial Sequence
<220> FEATURE:
<223> OTHER INFORMATION: oligonucleotide

<400> SEQUENCE: 75
ataatggctt atgtggccac                                                   20

<210> SEQ ID NO 76
<211> LENGTH: 20
<212> TYPE: DNA
<213> ORGANISM: Artificial Sequence
<220> FEATURE:
<223> OTHER INFORMATION: oligonucleotide

<400> SEQUENCE: 76
agttatgtga ccctgattga                                                   20

<210> SEQ ID NO 77
<211> LENGTH: 20
<212> TYPE: DNA
<213> ORGANISM: Artificial Sequence
<220> FEATURE:
<223> OTHER INFORMATION: oligonucleotide

<400> SEQUENCE: 77
ttgagtgttc ctaaaatgaa                                                   20

<210> SEQ ID NO 78
<211> LENGTH: 20
<212> TYPE: DNA
<213> ORGANISM: Artificial Sequence
<220> FEATURE:
<223> OTHER INFORMATION: oligonucleotide

<400> SEQUENCE: 78
atggaggctg gaggttcaaa                                                   20

<210> SEQ ID NO 79
<211> LENGTH: 20
<212> TYPE: DNA
<213> ORGANISM: Artificial Sequence
<220> FEATURE:
<223> OTHER INFORMATION: oligonucleotide

<400> SEQUENCE: 79
```
tagggtccat ctttcaagac                                           20

<210> SEQ ID NO 80
<211> LENGTH: 20
<212> TYPE: DNA
<213> ORGANISM: Artificial Sequence
<220> FEATURE:
<223> OTHER INFORMATION: oligonucleotide

<400> SEQUENCE: 80
tctccagata gaatctaaac                                           20

<210> SEQ ID NO 81
<211> LENGTH: 20
<212> TYPE: DNA
<213> ORGANISM: Artificial Sequence
<220> FEATURE:
<223> OTHER INFORMATION: oligonucleotide

<400> SEQUENCE: 81
tccaaatatt ctggtacttt                                           20

<210> SEQ ID NO 82
<211> LENGTH: 20
<212> TYPE: DNA
<213> ORGANISM: Artificial Sequence
<220> FEATURE:
<223> OTHER INFORMATION: oligonucleotide

<400> SEQUENCE: 82
tattagttac cttgaggaga                                           20

<210> SEQ ID NO 83
<211> LENGTH: 20
<212> TYPE: DNA
<213> ORGANISM: Artificial Sequence
<220> FEATURE:
<223> OTHER INFORMATION: oligonucleotide

<400> SEQUENCE: 83
attttccttc ctagaaaata                                           20

<210> SEQ ID NO 84
<211> LENGTH: 20
<212> TYPE: DNA
<213> ORGANISM: Artificial Sequence
<220> FEATURE:
<223> OTHER INFORMATION: target sequence

<400> SEQUENCE: 84
gaatggaaag aatgccctga                                           20

<210> SEQ ID NO 85
<211> LENGTH: 20
<212> TYPE: DNA
<213> ORGANISM: Artificial Sequence
<220> FEATURE:
<223> OTHER INFORMATION: target sequence

<400> SEQUENCE: 85
gaaagaatgc cctgattatg                                           20

<210> SEQ ID NO 86
<211> LENGTH: 20
<212> TYPE: DNA
<213> ORGANISM: Artificial Sequence

```
<220> FEATURE:
<223> OTHER INFORMATION: target sequence

<400> SEQUENCE: 86
ccagttccaa agattaaagg                                              20

<210> SEQ ID NO 87
<211> LENGTH: 20
<212> TYPE: DNA
<213> ORGANISM: Artificial Sequence
<220> FEATURE:
<223> OTHER INFORMATION: target sequence

<400> SEQUENCE: 87
attgagctag atattgatga                                              20

<210> SEQ ID NO 88
<211> LENGTH: 20
<212> TYPE: DNA
<213> ORGANISM: Artificial Sequence
<220> FEATURE:
<223> OTHER INFORMATION: target sequence

<400> SEQUENCE: 88
gacacagaca gacttctaag                                              20

<210> SEQ ID NO 89
<211> LENGTH: 20
<212> TYPE: DNA
<213> ORGANISM: Artificial Sequence
<220> FEATURE:
<223> OTHER INFORMATION: target sequence

<400> SEQUENCE: 89
agcgacatta caccagcagg                                              20

<210> SEQ ID NO 90
<211> LENGTH: 20
<212> TYPE: DNA
<213> ORGANISM: Artificial Sequence
<220> FEATURE:
<223> OTHER INFORMATION: target sequence

<400> SEQUENCE: 90
aaccaagagg acatttacat                                              20

<210> SEQ ID NO 91
<211> LENGTH: 20
<212> TYPE: DNA
<213> ORGANISM: Artificial Sequence
<220> FEATURE:
<223> OTHER INFORMATION: target sequence

<400> SEQUENCE: 91
agaggacatt tacatcacca                                              20

<210> SEQ ID NO 92
<211> LENGTH: 20
<212> TYPE: DNA
<213> ORGANISM: Artificial Sequence
<220> FEATURE:
<223> OTHER INFORMATION: target sequence

<400> SEQUENCE: 92
acatttacat caccacagaa                                              20
```

<210> SEQ ID NO 93
<211> LENGTH: 20
<212> TYPE: DNA
<213> ORGANISM: Artificial Sequence
<220> FEATURE:
<223> OTHER INFORMATION: target sequence

<400> SEQUENCE: 93
tacatcacca cagaaagcct                                                   20

<210> SEQ ID NO 94
<211> LENGTH: 20
<212> TYPE: DNA
<213> ORGANISM: Artificial Sequence
<220> FEATURE:
<223> OTHER INFORMATION: target sequence

<400> SEQUENCE: 94
caccacagaa agccttacca                                                   20

<210> SEQ ID NO 95
<211> LENGTH: 20
<212> TYPE: DNA
<213> ORGANISM: Artificial Sequence
<220> FEATURE:
<223> OTHER INFORMATION: target sequence

<400> SEQUENCE: 95
tatgtgagca cagaccaact                                                   20

<210> SEQ ID NO 96
<211> LENGTH: 20
<212> TYPE: DNA
<213> ORGANISM: Artificial Sequence
<220> FEATURE:
<223> OTHER INFORMATION: target sequence

<400> SEQUENCE: 96
gagcacagac caactgaaca                                                   20

<210> SEQ ID NO 97
<211> LENGTH: 20
<212> TYPE: DNA
<213> ORGANISM: Artificial Sequence
<220> FEATURE:
<223> OTHER INFORMATION: target sequence

<400> SEQUENCE: 97
ccaactgaac aaaatcatgc                                                   20

<210> SEQ ID NO 98
<211> LENGTH: 20
<212> TYPE: DNA
<213> ORGANISM: Artificial Sequence
<220> FEATURE:
<223> OTHER INFORMATION: target sequence

<400> SEQUENCE: 98
tctgctactt tgctgctatg                                                   20

<210> SEQ ID NO 99
<211> LENGTH: 20
<212> TYPE: DNA
<213> ORGANISM: Artificial Sequence
<220> FEATURE:
<223> OTHER INFORMATION: target sequence

<400> SEQUENCE: 99
tttctatagc caaaaatagc                                        20

<210> SEQ ID NO 100
<211> LENGTH: 20
<212> TYPE: DNA
<213> ORGANISM: Artificial Sequence
<220> FEATURE:
<223> OTHER INFORMATION: target sequence

<400> SEQUENCE: 100
aatagctaaa tacctcaatc                                        20

<210> SEQ ID NO 101
<211> LENGTH: 20
<212> TYPE: DNA
<213> ORGANISM: Artificial Sequence
<220> FEATURE:
<223> OTHER INFORMATION: target sequence

<400> SEQUENCE: 101
aggtcctaca ggtatggatc                                        20

<210> SEQ ID NO 102
<211> LENGTH: 20
<212> TYPE: DNA
<213> ORGANISM: Artificial Sequence
<220> FEATURE:
<223> OTHER INFORMATION: target sequence

<400> SEQUENCE: 102
ctacaggtat ggatctctgg                                        20

<210> SEQ ID NO 103
<211> LENGTH: 20
<212> TYPE: DNA
<213> ORGANISM: Artificial Sequence
<220> FEATURE:
<223> OTHER INFORMATION: target sequence

<400> SEQUENCE: 103
cacagcagct atccttagca                                        20

<210> SEQ ID NO 104
<211> LENGTH: 20
<212> TYPE: DNA
<213> ORGANISM: Artificial Sequence
<220> FEATURE:
<223> OTHER INFORMATION: target sequence

<400> SEQUENCE: 104
taatccaggc ctaaagacaa                                        20

<210> SEQ ID NO 105
<211> LENGTH: 20
<212> TYPE: DNA
<213> ORGANISM: Artificial Sequence
<220> FEATURE:
<223> OTHER INFORMATION: target sequence

<400> SEQUENCE: 105
tctaaggagc ctaaattcac                                        20

<210> SEQ ID NO 106

```
<211> LENGTH: 20
<212> TYPE: DNA
<213> ORGANISM: Artificial Sequence
<220> FEATURE:
<223> OTHER INFORMATION: target sequence

<400> SEQUENCE: 106
gaacctagga cccatacagc                                               20

<210> SEQ ID NO 107
<211> LENGTH: 20
<212> TYPE: DNA
<213> ORGANISM: Artificial Sequence
<220> FEATURE:
<223> OTHER INFORMATION: target sequence

<400> SEQUENCE: 107
gctggggaaa acagctgtta                                               20

<210> SEQ ID NO 108
<211> LENGTH: 20
<212> TYPE: DNA
<213> ORGANISM: Artificial Sequence
<220> FEATURE:
<223> OTHER INFORMATION: target sequence

<400> SEQUENCE: 108
tggtggtaca gtggatgaaa                                               20

<210> SEQ ID NO 109
<211> LENGTH: 20
<212> TYPE: DNA
<213> ORGANISM: Artificial Sequence
<220> FEATURE:
<223> OTHER INFORMATION: target sequence

<400> SEQUENCE: 109
ctgttgatga aatagtgcaa                                               20

<210> SEQ ID NO 110
<211> LENGTH: 20
<212> TYPE: DNA
<213> ORGANISM: Artificial Sequence
<220> FEATURE:
<223> OTHER INFORMATION: target sequence

<400> SEQUENCE: 110
tagtgcaacc agatccaccc                                               20

<210> SEQ ID NO 111
<211> LENGTH: 20
<212> TYPE: DNA
<213> ORGANISM: Artificial Sequence
<220> FEATURE:
<223> OTHER INFORMATION: target sequence

<400> SEQUENCE: 111
gatgggaagc accacgcaat                                               20

<210> SEQ ID NO 112
<211> LENGTH: 20
<212> TYPE: DNA
<213> ORGANISM: Artificial Sequence
<220> FEATURE:
<223> OTHER INFORMATION: target sequence

<400> SEQUENCE: 112
```

-continued atggaaaatg atggacccta                                              20

<210> SEQ ID NO 113
<211> LENGTH: 20
<212> TYPE: DNA
<213> ORGANISM: Artificial Sequence
<220> FEATURE:
<223> OTHER INFORMATION: target sequence

<400> SEQUENCE: 113
cagttccagt gtactcattg                                              20

<210> SEQ ID NO 114
<211> LENGTH: 20
<212> TYPE: DNA
<213> ORGANISM: Artificial Sequence
<220> FEATURE:
<223> OTHER INFORMATION: target sequence

<400> SEQUENCE: 114
tctggaaatt atggcgagtt                                              20

<210> SEQ ID NO 115
<211> LENGTH: 20
<212> TYPE: DNA
<213> ORGANISM: Artificial Sequence
<220> FEATURE:
<223> OTHER INFORMATION: target sequence

<400> SEQUENCE: 115
atctttggaa tatttgggct                                              20

<210> SEQ ID NO 116
<211> LENGTH: 20
<212> TYPE: DNA
<213> ORGANISM: Artificial Sequence
<220> FEATURE:
<223> OTHER INFORMATION: target sequence

<400> SEQUENCE: 116
gcaaaggatt aaaatgctga                                              20

<210> SEQ ID NO 117
<211> LENGTH: 20
<212> TYPE: DNA
<213> ORGANISM: Artificial Sequence
<220> FEATURE:
<223> OTHER INFORMATION: target sequence

<400> SEQUENCE: 117
tctcctcaag gaaggaaaat                                              20

<210> SEQ ID NO 118
<211> LENGTH: 20
<212> TYPE: DNA
<213> ORGANISM: Artificial Sequence
<220> FEATURE:
<223> OTHER INFORMATION: target sequence

<400> SEQUENCE: 118
agaggaggtg aacacaatct                                              20

<210> SEQ ID NO 119
<211> LENGTH: 20
<212> TYPE: DNA

```
<213> ORGANISM: Artificial Sequence
<220> FEATURE:
<223> OTHER INFORMATION: target sequence

<400> SEQUENCE: 119
acagtgatga ctcttgggtt                                               20

<210> SEQ ID NO 120
<211> LENGTH: 20
<212> TYPE: DNA
<213> ORGANISM: Artificial Sequence
<220> FEATURE:
<223> OTHER INFORMATION: target sequence

<400> SEQUENCE: 120
gctagatatt gatgagccag                                               20

<210> SEQ ID NO 121

<400> SEQUENCE: 121

000

<210> SEQ ID NO 122
<211> LENGTH: 20
<212> TYPE: DNA
<213> ORGANISM: Artificial Sequence
<220> FEATURE:
<223> OTHER INFORMATION: target sequence

<400> SEQUENCE: 122
atttcaatgc caatgacata                                               20

<210> SEQ ID NO 123
<211> LENGTH: 20
<212> TYPE: DNA
<213> ORGANISM: Artificial Sequence
<220> FEATURE:
<223> OTHER INFORMATION: target sequence

<400> SEQUENCE: 123
aagcagatct cttatgcctt                                               20

<210> SEQ ID NO 124
<211> LENGTH: 20
<212> TYPE: DNA
<213> ORGANISM: Artificial Sequence
<220> FEATURE:
<223> OTHER INFORMATION: target sequence

<400> SEQUENCE: 124
tcctactgaa ggagctgagt                                               20

<210> SEQ ID NO 125
<211> LENGTH: 20
<212> TYPE: DNA
<213> ORGANISM: Artificial Sequence
<220> FEATURE:
<223> OTHER INFORMATION: target sequence

<400> SEQUENCE: 125
agaataaggc agggatgtcc                                               20

<210> SEQ ID NO 126
<211> LENGTH: 20
<212> TYPE: DNA
```

```
<213> ORGANISM: Artificial Sequence
<220> FEATURE:
<223> OTHER INFORMATION: target sequence

<400> SEQUENCE: 126
acttccttat ggacaatgcc                                               20

<210> SEQ ID NO 127
<211> LENGTH: 20
<212> TYPE: DNA
<213> ORGANISM: Artificial Sequence
<220> FEATURE:
<223> OTHER INFORMATION: target sequence

<400> SEQUENCE: 127
tgaggcagat gccaaaaagt                                               20

<210> SEQ ID NO 128
<211> LENGTH: 20
<212> TYPE: DNA
<213> ORGANISM: Artificial Sequence
<220> FEATURE:
<223> OTHER INFORMATION: target sequence

<400> SEQUENCE: 128
cagatgccaa aaagtgcatc                                               20

<210> SEQ ID NO 129
<211> LENGTH: 20
<212> TYPE: DNA
<213> ORGANISM: Artificial Sequence
<220> FEATURE:
<223> OTHER INFORMATION: target sequence

<400> SEQUENCE: 129
cctcatactc aatgcgactg                                               20

<210> SEQ ID NO 130
<211> LENGTH: 20
<212> TYPE: DNA
<213> ORGANISM: Artificial Sequence
<220> FEATURE:
<223> OTHER INFORMATION: target sequence

<400> SEQUENCE: 130
tgcccttgcc tgacaaagag                                               20

<210> SEQ ID NO 131
<211> LENGTH: 20
<212> TYPE: DNA
<213> ORGANISM: Artificial Sequence
<220> FEATURE:
<223> OTHER INFORMATION: target sequence

<400> SEQUENCE: 131
tcatgtggct atgtgagcac                                               20

<210> SEQ ID NO 132

<400> SEQUENCE: 132

000

<210> SEQ ID NO 133
<211> LENGTH: 20
<212> TYPE: DNA
```

```
<213> ORGANISM: Artificial Sequence
<220> FEATURE:
<223> OTHER INFORMATION: target sequence

<400> SEQUENCE: 133
ttcccaagag ctacgtattt                                          20

<210> SEQ ID NO 134
<211> LENGTH: 20
<212> TYPE: DNA
<213> ORGANISM: Artificial Sequence
<220> FEATURE:
<223> OTHER INFORMATION: target sequence

<400> SEQUENCE: 134
ctgtttagta gcagtgattg                                          20

<210> SEQ ID NO 135
<211> LENGTH: 20
<212> TYPE: DNA
<213> ORGANISM: Artificial Sequence
<220> FEATURE:
<223> OTHER INFORMATION: target sequence

<400> SEQUENCE: 135
ttgaatgcaa accatagcac                                          20

<210> SEQ ID NO 136
<211> LENGTH: 20
<212> TYPE: DNA
<213> ORGANISM: Artificial Sequence
<220> FEATURE:
<223> OTHER INFORMATION: target sequence

<400> SEQUENCE: 136
atagtttgga tatgtaaaac                                          20

<210> SEQ ID NO 137
<211> LENGTH: 20
<212> TYPE: DNA
<213> ORGANISM: Artificial Sequence
<220> FEATURE:
<223> OTHER INFORMATION: target sequence

<400> SEQUENCE: 137
tcaccaaatc ttggttgatg                                          20

<210> SEQ ID NO 138
<211> LENGTH: 20
<212> TYPE: DNA
<213> ORGANISM: Artificial Sequence
<220> FEATURE:
<223> OTHER INFORMATION: target sequence

<400> SEQUENCE: 138
gagataagat ctatagcctc                                          20

<210> SEQ ID NO 139
<211> LENGTH: 20
<212> TYPE: DNA
<213> ORGANISM: Artificial Sequence
<220> FEATURE:
<223> OTHER INFORMATION: target sequence

<400> SEQUENCE: 139
agaaactttc tttctcacta                                          20
```

<210> SEQ ID NO 140
<211> LENGTH: 20
<212> TYPE: DNA
<213> ORGANISM: Artificial Sequence
<220> FEATURE:
<223> OTHER INFORMATION: target sequence

<400> SEQUENCE: 140
acatcattct tgagagcatt                                               20

<210> SEQ ID NO 141
<211> LENGTH: 20
<212> TYPE: DNA
<213> ORGANISM: Artificial Sequence
<220> FEATURE:
<223> OTHER INFORMATION: target sequence

<400> SEQUENCE: 141
gaaaagctag aattgagtgt                                               20

<210> SEQ ID NO 142
<211> LENGTH: 20
<212> TYPE: DNA
<213> ORGANISM: Artificial Sequence
<220> FEATURE:
<223> OTHER INFORMATION: target sequence

<400> SEQUENCE: 142
gctatggttt tctccaagag                                               20

<210> SEQ ID NO 143
<211> LENGTH: 20
<212> TYPE: DNA
<213> ORGANISM: Artificial Sequence
<220> FEATURE:
<223> OTHER INFORMATION: target sequence

<400> SEQUENCE: 143
taaagtatca tcagtgtaga                                               20

<210> SEQ ID NO 144
<211> LENGTH: 20
<212> TYPE: DNA
<213> ORGANISM: Artificial Sequence
<220> FEATURE:
<223> OTHER INFORMATION: target sequence

<400> SEQUENCE: 144
taattcaatt caaagctgtg                                               20

<210> SEQ ID NO 145
<211> LENGTH: 20
<212> TYPE: DNA
<213> ORGANISM: Artificial Sequence
<220> FEATURE:
<223> OTHER INFORMATION: target sequence

<400> SEQUENCE: 145
agctgtgtgt ttggaagact                                               20

<210> SEQ ID NO 146
<211> LENGTH: 20
<212> TYPE: DNA
<213> ORGANISM: Artificial Sequence
<220> FEATURE:

<223> OTHER INFORMATION: target sequence

<400> SEQUENCE: 146
ttactatttc acaacagcct                                              20

<210> SEQ ID NO 147
<211> LENGTH: 20
<212> TYPE: DNA
<213> ORGANISM: Artificial Sequence
<220> FEATURE:
<223> OTHER INFORMATION: target sequence

<400> SEQUENCE: 147
cagcctgaca acatttctat                                              20

<210> SEQ ID NO 148
<211> LENGTH: 20
<212> TYPE: DNA
<213> ORGANISM: Artificial Sequence
<220> FEATURE:
<223> OTHER INFORMATION: target sequence

<400> SEQUENCE: 148
gtctcagaat gtcattttgg                                              20

<210> SEQ ID NO 149
<211> LENGTH: 20
<212> TYPE: DNA
<213> ORGANISM: Artificial Sequence
<220> FEATURE:
<223> OTHER INFORMATION: target sequence

<400> SEQUENCE: 149
gtggccacat aagccattat                                              20

<210> SEQ ID NO 150
<211> LENGTH: 20
<212> TYPE: DNA
<213> ORGANISM: Artificial Sequence
<220> FEATURE:
<223> OTHER INFORMATION: target sequence

<400> SEQUENCE: 150
tcaatcaggg tcacataact                                              20

<210> SEQ ID NO 151
<211> LENGTH: 20
<212> TYPE: DNA
<213> ORGANISM: Artificial Sequence
<220> FEATURE:
<223> OTHER INFORMATION: target sequence

<400> SEQUENCE: 151
tttgaacctc cagcctccat                                              20

<210> SEQ ID NO 152
<211> LENGTH: 20
<212> TYPE: DNA
<213> ORGANISM: Artificial Sequence
<220> FEATURE:
<223> OTHER INFORMATION: target sequence

<400> SEQUENCE: 152
gtcttgaaag atggacccta                                              20

```
<210> SEQ ID NO 153
<211> LENGTH: 20
<212> TYPE: DNA
<213> ORGANISM: Artificial Sequence
<220> FEATURE:
<223> OTHER INFORMATION: target sequence

<400> SEQUENCE: 153
gtttagattc tatctggaga                                               20

<210> SEQ ID NO 154
<211> LENGTH: 20
<212> TYPE: DNA
<213> ORGANISM: Artificial Sequence
<220> FEATURE:
<223> OTHER INFORMATION: target sequence

<400> SEQUENCE: 154
aaagtaccag aatatttgga                                               20
```

COMBINATION THERAPY

CROSS-REFERENCE TO RELATED APPLICATIONS

This application is a divisional of U.S. patent application Ser. No. 14/376390, filed Aug. 1, 2014, which is a U.S. National Phase under 35 U.S.C. §371 of International Application No. PCT/AU2013/000095, filed Feb. 4, 2013, which claims priority to the U.S. Patent Application No. 61/594532, filed Feb. 3, 2012, each of which is hereby incorporated by reference in its entirety into this application.

SEQUENCE LISTING

A Sequence Listing is provided herewith as a text file, FBRIC67 003D1.txt created on Jan. 26, 2016 and having a size of 425 KB. The contents of the text file are incorporated by reference herein in their entirety.

FIELD OF THE INVENTION

The present disclosure relates to a method for treatment or prevention of diseases caused by and/or associated with an increased level of insulin-like growth factor I (IGF-I) that relies on administration of a growth hormone (GH) variant having antagonistic activity in combination with an antisense oligonucleotide targeted to the growth hormone receptor (GHR).

BACKGROUND OF THE INVENTION

Growth hormone (GH), released by the pituitary, is a member of a cascade of hormones that regulate growth of the body and its organs. Secretion of GH into the bloodstream is followed by binding to growth hormone receptor (GHR) on many cell and organ types. Growth hormone signaling is mediated by this interaction. Growth hormone signaling causes the production of another hormone, insulin-like growth factor I (IGF-I), which is produced in the liver, adipose tissue, kidney and other organs and secreted into the bloodstream. About 75% of serum IGF-I is produced in the liver in response to GH stimulation. Many disorders are caused by and/or associated with increased GH levels and/or increased IGF-I levels in plasma and/or tissues including acromegaly, gigantism, retinopathy, macular degeneration, nephropathy, diabetes and cancers. The role of GH and IGF-I in these and other disorders is well recognized. The role of IGF-I in mediating many GH effects is well recognized and this interrelationship is referred to as the GH/IGF-I axis. In a normal feedback loop, IGF-I also causes the production of GH by the pituitary to be reduced. There is a need for treatments that reduce IGF-I levels in a subject, for example, more effectively, safely, conveniently and/or at reduced cost.

Somavert, a GH variant having antagonistic activity is approved in the treatment of acromegaly for its ability to reduce serum IGF-I levels in a patient. For a review of current practices for the treatment of acromegaly see Guistina et al., 2011. Briefly, in acromegaly, surgery is first used in treatment to debulk the tumor and reduce the pituitary tumor's GH secretion and reduce production of IGF-I in the serum. Medicinal treatments are also used to reduce serum IGF-I and in some cases also reduce GH release. All treatments use a medicinal monotherapy or a combination therapy where the combination is directed to two different biological targets. First line medicinal treatment is with a somatostatin (SST) agonist, and this treatment is started initially at low doses and escalated to doses that reduce GH and normalize the patients serum IGF-I. When an SST agonist treatment fails, a dopamine agonist is used in combination with a SST agonist, or Somavert is used in combination with a SST agonist or Somavert is used as a monotherapy. Somavert doses typically start with a loading dose of 40 mg on the first day, and 10 mg daily doses, and these daily doses are escalated until normalization of serum IGF-I, with up to 30 mg daily doses approved. There are failures with the highest approved daily doses of Somavert, and clinicians have escalated beyond approved doses. Somavert is however, prohibitively expensive, requires inconvenient daily (once or twice daily) injection, is a lyophilized powder and needs reconstitution, has safety issues causing injection site reactions and an increase in liver enzymes, and produces undesirable increases in GH. Thus, clinicians typically do not seek to use Somavert in different combination therapies to those outlined above. In patients where first line therapy using SST has failed or in patients where Somavert monotherapy or combination with SST has failed, clinicians are seeking new more effective monotherapies. Combination therapies using, for example, Somavert are only considered with a drug directed to a different biological target and typically an SST agonist, as SST agonists have potential to reduce tumor size.

SUMMARY OF THE INVENTION

The present inventors have now made the surprising finding that a growth hormone (GH) variant having antagonistic activity and an antisense oligonucleotide targeted to GHR act synergistically to reduce insulin-like growth factor I (IGF-I) levels in a subject. In other words, the combined administration of the GH variant and the oligonucelotide to GHR exhibits greater than additive effect. This is surprising, particularly considering that there are no expected synergies with using drugs to the same target, and one can just escalate the dose of the drug to the target. Accordingly, the present disclosure provides a method for treatment or prevention of a disease caused by and/or associated with an increased level of IGF-I, the method comprising administering to a subject in need thereof, a GH variant having GH antagonistic activity in combination with an oligonucleotide 8 to 80 nucleobases in length targeted to a nucleic acid encoding GHR so as to inhibit expression of the GHR, thereby reducing the level of IGF-I in the subject. In one embodiment, the level of serum/plasma IGF-I is reduced.

In one embodiment, the method further comprises identifying a subject in need of a reduction in said subject's GHR and/or IGF-I levels, for example serum/plasma IGF-I levels.

In one embodiment, the disease is acromegaly, diabetic retinopathy, diabetic nephropathy, or an IGF-I positive and/or IGF-I and/or GH responsive cancer such as prostate, myeloma, lung, breast, or colon cancer.

In one embodiment, the GH variant is a human GH variant in which amino acid Gly120 is deleted or substituted with an amino acid, for example, Arg, Trp, Pro, Lys or Leu. In one embodiment, the Gly120 is substituted with Lys.

In a further embodiment, the human GH variant comprises the following set of amino acid substitutions: H18D, H21N, R167N, K168A, D171S, K172R, E174S, I179T.

In one embodiment, the nucleic acid encodes human GHR. The nucleic acid may have a nucleotide sequence as shown in SEQ ID NO:4 or SEQ ID NO:5.

In one embodiment, the oligonucleotide is from 12 to 50 nucleobases in length. In another embodiment, the oligonucleotide is from 15 to 30 nucleobases in length.

In one embodiment, the oligonucleotide is a DNA oligonucleotide. In another embodiment, the oligonucleotide is a RNA oligonucleotide, for example, a short interfering RNA (siRNA). In another embodiment, the oligonucleotide is a chimeric oligonucleotide.

In one embodiment, the oligonucelotide has at least 70% complementarity with the nucleic acid encoding GHR. In another embodiment, the oligonucelotide has at least 80% complementarity with the nucleic acid encoding GHR. In another embodiment, the oligonucelotide has at least 90% complementarity with the nucleic acid encoding GHR. In another embodiment, the oligonucelotide has at least 95% complementarity, for example, 96%, 97%, 98%, or 99% complementarity with the nucleic acid encoding GHR.

In one embodiment, the oligonucelotide comprises at least an 8 consecutive nucleobase portion of SEQ ID NO: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 78, 79, 80, or 81.

In another embodiment, the oligonucelotide consists of the nucleobase sequence of SEQ ID NOs: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 78, 79, 80, or 81.

In one embodiment, the oligonucleotide consists of the nucleobase sequence of SEQ ID NO:6.

In one embodiment, the oligonucleotide specifically hybridises with a region encoding GHR, wherein the region comprises a translation initiation codon, a termination codon, a coding region, a 5' untranslated region, a 3' untranslated region, an intron:exon junction or an exon:intron junction. In one embodiment, the region comprises at least an 8 consecutive nucleobase portion of a sequence selected from SEQ ID NOs: 84-154.

In one embodiment, the oligonucleotide comprises at least an 8 consecutive nucleobase portion complementary to a region of SEQ ID NO:4 selected from the group consisting of nucleotides 260-339, 332-351 and 344-423 of SEQ ID NO:4.

In one embodiment, the oligonucleotide inhibits the expression of GHR and/or growth hormone binding protein (GHBP) by at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45%.

In one embodiment, the oligonucleotide comprises at least one modified internucleoside linkage, sugar moiety, or nucleobase. The oligonucleotide may, for example, comprise at least one 2'-O-methoxyethyl sugar moiety and/or at least one phosphorothioate internucleoside linkage and/or at least one 5-methylcytosine.

In one embodiment, the oligonucleotide consists of 20 linked nucleosides, wherein the oligonucleotide consists of a nucleobase of SEQ ID NO:6; and wherein the oligonucleotide consists of a ten deoxynucleotide region flanked on both the 5' end and the 3' end of said ten deoxynucleotide region with five 2'-O-(2-methoxyethyl) nucleotides, and wherein each internucleoside linkage in the oligonucleotide is a phosphorothioate linkage, and wherein each cytosine in said oligonucleotide is a 5-methylcytosine.

The present disclosure also provides a method of reducing the level of IGF-I in a subject, the method comprising administering a GH variant having GH antagonistic activity in combination with an oligonucleotide 8 to 80 nucleobases in length targeted to a nucleic acid encoding GHR so as to inhibit expression of the GHR, thereby reducing the level of IGF-I in the subject. In one embodiment, the level of serum/plasma IGF-I is reduced.

In one embodiment, the method further comprises identifying a subject in need of a reduction in said subject's GHR and/or IGF-I levels, for example serum/plasma IGF-I levels.

The GH variant, the GHR and the oligonucleotide may be further characterized by any one of the above features.

The present disclosure also provides for use of a GH variant and an oligonucleotide 8 to 80 nucleobases in length targeted to a nucleic acid encoding GHR in the manufacture of a medicament for the treatment or prevention of a disease caused by and/or associated with an increased level of IGF-I. In one embodiment, the level of serum/plasma IGF-I is reduced.

In one embodiment, the disease is acromegaly, diabetic retinopathy, diabetic nephropathy, or an IGF-I positive cancer such as prostate, myeloma, lung, breast, or colon cancer.

The GH variant, the GHR and the oligonucleotide may be further characterized by any one of the above features.

The present disclosure also provides for use of a GH variant and an oligonucleotide 8 to 80 nucleobases in length targeted to a nucleic acid encoding GHR in the manufacture of a medicament for reducing the level of IGF-I in a subject.

The GH variant, the GHR and the oligonucleotide may be further characterized by any one of the above features.

The present disclosure also provides for a composition comprising a GH variant and an oligonucleotide 8 to 80 nucleobases in length targeted to a nucleic acid encoding GHR for the treatment or prevention of a disease caused by and/or associated with an increased level of IGF-I.

The GH variant, the GHR and the oligonucleotide may be further characterized by any one of the above features.

The present disclosure also provides for a composition comprising a GH variant and an oligonucleotide 8 to 80 nucleobases in length targeted to a nucleic acid encoding GHR for reducing the level of IGF-I in a subject.

The GH variant, the GHR and the oligonucleotide may be further characterized by any one of the above features.

Any embodiment herein shall be taken to apply mutatis mutandis to any other embodiment unless specifically stated otherwise.

The invention is hereinafter described by way of the following non-limiting Examples and with reference to the accompanying Figures.

KEY TO THE SEQUENCE LISTING

SEQ ID NO:1 Wild-type human growth hormone (hGH) nucleotide sequence

SEQ ID NO:2 Wild-type hGH polypeptide sequence

SEQ ID NO;3 Somavert polypeptide sequence

SEQ ID NO:4 Human growth hormone receptor (hGHR) cDNA sequence

SEQ ID NO:5 hGHR gene sequence

SEQ ID NO:6-83 Oligonucleotides targeted to hGHR

SEQ ID NO:84-154 Target sequences of hGHR

DETAILED DESCRIPTION OF THE INVENTION

General Techniques and Selected Definitions

Unless specifically defined otherwise, all technical and scientific terms used herein shall be taken to have the same meaning as commonly understood by one of ordinary skill in the art (e.g., in antisense technology, recombinant technology, cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), F. M. Ausubel et al. (editors), Current Protocols in Molecular Biology, Greene Pub. Associates and Wiley-Interscience (1988, including all updates until present), E. Harlow and D. Lane (editors), Antibodies: A Laboratory Manual, Cold Spring Harbour Laboratory (1988), and J. E. Coligan et al. (editors), Current Protocols in Immunology, John Wiley and Sons (including all updates until present).

The term "and/or", for example, "X and/or Y" shall be understood to mean either "X and Y" or "X or Y" and shall be taken to provide explicit support for both meanings or for either meaning.

As used herein, "about" or "approximately" shall generally mean within 20%, more preferably within 10%, and even more preferably within 5%, of a given value or range.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, group of steps or group of compositions of matter.

Treatment and Prevention of IGF-I Positive Diseases

The present invention provides methods useful in the prevention and/or treatment of a disease, disorder, or condition caused by and/or associated with an increased level of insulin-like growth factor I (IGF-I). As used herein, the term "treatment" refers to administering a pharmaceutical composition to effect an alteration or improvement of a disease, disorder, or condition. As used herein, the term "prevention" refers to administering a pharmaceutical composition to stop or hinder the development of at least one symptom of a disease, disorder, or condition. The subject targeted for treatment is a mammal, preferably a human. As used herein, "an increased level of insulin-like growth factor I (IGF-I)" includes a level above the normal range or in the normal range, for example, at the high end of the normal range, adjusted for age and sex.

The methods involve administration of a growth hormone (GH) variant having GH antagonistic activity and an oligonucelotide targeted to growth hormone receptor (GHR) to a subject. The "subject" can be any mammal, preferably a human. Although not wishing to be limited to the theory, the oligonucleotide acts to inhibit GHR expression in said subject, whilst the GH variant acts to prevent GH binding to the GHR, thereby reducing the level of IGF-I (which is produced in response to GH signalling) in the subject. Insulin-like growth factor I is a ubiquitous polypeptide important in proliferation, having potent mitogenic effects on a broad range of cells, and important in cell survival, regulating apoptosis on a broad range of cells.

Although not wishing to be limited to theory, the antisense oligonucleotide inhibits GHR expression at the RNA level whilst the GH variant may increase GHR RNA by feedback inhibition. In one embodiment, the oligonucleotide also acts to reduce growth hormone binding protein (GHBP) expression. The GHBP is the soluble extracellular portion of the GH receptor, derived by alternative mRNA splicing of the mRNA transcript (in for example, mice and rats) or proteolytic cleavage of the GHR (in for example, humans, cows and pigs).

In one embodiment, the treatment reduces or prevents occurrence of one or more symptoms of acromegaly, for example, reducing the increased serum IGF-I levels in acromegaly to normal levels, or reducing soft tissue swelling, enlargement of internal organs, extremities like overgrowth of the jaw, enlargement of hands and feet, deepening of the voice, thickening of skin, offensive body odor, articular cartilage problems, hyperphosphatemia, peripheral neuropathies, higher blood pressure, diabetes, heart disease, and cancer.

In another embodiment, the treatment reduces or prevents occurrence of one or more symptoms of retinopathy, for example, reducing new blood vessel formation and/or edema, blurred, double, or distorted vision, or difficulty reading, floaters or spots in vision, loss of vision or a shadow or veil across field of vision, pain, pressure, or constant redness of the eye.

In another embodiment, the treatment reduces or prevents occurrence of one or more symptoms of diabetic nephropathy, for example glomerula filtration, microalbuminuria, proteinuria, renal damage, swelling in the legs, nausea and vomiting, malaise, fatigue, headache, itching, frequent hiccups, unintended weight loss, swelling of the face, unintended weight gain due to fluid buildup, and high blood pressure.

In another embodiment, the treatment reduces the size and/or growth of a tumor or cancer (such as prostate, myeloma, lung, breast, or colon cancer) and/or delays progression of the tumor or cancer (such as prostate cancer) from androgen responsive/dependent to androgen unresponsive/independent. Tumor or cancer size and/or growth may be reduced, for example, by reducing the proliferation rate of the tumor/cancer cells, increasing the apoptotic rate of the tumor/cancer cells, modulating tumor/cancer cell signaling, chemosensitization, and/or inhibiting adhesion, anchorage, metastasis of the tumor/caner cells and/or transformation of cells, for example, prostate cells. The treatment may, for example, reduce IGF-I levels at the high end of the normal range to lower levels, and/or from the top quartile to the $2^{nd}$ quartile, $3^{rd}$ or $4^{th}$ quartile, and/or from the $2^{nd}$ quartile to the $3^{rd}$ or $4^{th}$ quartile as adjusted for age and sex. The treatment may reduce endocrine, autocrine or paracrine levels of IGF-I as antisense oligonucleotides and the GH variant may work in the tissues.

Growth Hormone Variant Having Growth Hormone Antagonistic Activity

The methods of the present disclosure rely on the use of growth hormone (GH) variants having GH antagonistic activity. In one example, the GH variant is a peptide or protein having a similarity in sequence and/or secondary structure to a vertebrate GH, including but not limited to, mammalian growth hormones such as human and bovine growth hormones.

GH is synthesized and secreted by the somatotroph cells of the anterior pituitary gland. The GH gene consists of 5 exons and 4 introns encoding a 217-amino acid precursor protein. The amino-terminal signal peptide is removed by proteolysis, yielding the mature single chain 191-amino acid polypeptide, with a molecular mass of 22 kDa. The 3-dimensional structure of human (h) GH and of GH from other mammalian species was established by X-ray crystallography (Ultsch et al., 1991; Ultsch et al., 1993; de Vos et al., 1992). The protein consists of four α-helices, with 20-30 amino acid residues bound together by stretches of non-helical chains which are packed together in an antiparallel bundle (Ultsch et al., 1994). It has been demonstrated that the 4 alpha helix bundle GH possesses two non-identical binding surfaces, but binds to similar receptor binding sites in an ordered sequence, with the initial binding site possessing a higher affinity (Site 1) (WO 92/21029). Site 2 binding is stabilized by a further inter-receptor interaction involving the "dimerization domain" in the lower of the two cytokine homology modules (Cunningham et al., 1991; de Vos et al., 1992; Chen et al., 1997).

In one embodiment, the GH variant comprises an alpha helix having an amino acid sequence homology of at least about 50% with the third alpha helix of a vertebrate GH. The other alpha helices of the wild-type GH may be omitted if this can be done without loss of GH antagonist activity. The use of the term "antagonist" is in a functional sense and is not intended to limit the disclosure to compounds having a particular mechanism of action. Suitable GH variants are described in U.S. Pat. Nos. 5,350,836 and 5,849,535.

Variant GH sequence notation defines the actual amino acid substitutions in the GH variant. For a variant, substitutions are indicated by a letter representing the wild-type residue (in single-letter code), a number indicating the amino acid position in the wild-type sequence, and a second letter indicating the substituted amino acid residue. For example, G120K indicates a mutation in which glycine at position 120 is substituted with lysine. Multiple mutants are indicated by a series of single mutants separated by commas.

In one embodiment, the growth hormone variant is an hGH variant. The DNA (SEQ ID NO:1) and amino acid (SEQ ID NO:2) sequences of wild-type hGH have been reported (Goeddel et al., 1979; Gray et al., 1985).

In one embodiment, the hGH variant comprises a mutation at amino acid Gly120. Gly120 may be deleted or substituted with an amino acid. In one example, the amino acid is selected from the group consisting of Arg, Trp, Pro, Lys and Leu. In a preferred example, the amino acid is Lys. This mutation disrupts Site 2 binding. An hGH variant comprising this mutation acts as an hGH antagonist.

In a further embodiment, the hGH variant comprises the following set of amino acid substitutions: H18D, H21N, R167N, K168A, D171S, K172R, E174S, I179T. These substitutions increase binding affinity for the hGH receptor at Site 1. An hGH variant including this set of amino acid substitutions acts as an hGH agonist in the absence of an additional modification that disrupts binding to the hGHR at Site 2.

In one embodiment, the hGH variant comprises a G120 amino acid deletion or substitution and amino acid substitutions H18D, H21N, R167N, K168A, D171S, K172R, E174S, I179T. In one embodiment, the hGH variant includes the following set of amino acid substitutions: H18D, H21N, G120K, R167N, K168A, D171S, K172R, E174S, I179T. In one embodiment, the hGH variant is Somavert® (Pegvisomant for injection) (SEQ ID NO:3) which is a protein with 191 amino acid residues to which several polyethylene glycol (PEG) polymers are covalently bound (van der Lely et al., 2001).

Mutagenesis

The DNA sequence encoding GH can be mutated at one or more selected codons. A mutation is defined as a substitution, deletion, or insertion of one or more nucleotides in the DNA encoding the GH that results in a change in the amino acid sequence of the GH as compared with the wild-type sequence of the GH. Preferably, at least one amino acid is substituted with any other amino acid in one or more regions of the protein.

Site-specific mutagenesis (Carter et al., 1986; Zoller et al., 1987), cassette mutagenesis (Wells et al., 1985), restriction selection mutagenesis (Wells et al., 1986), or other known techniques can be performed on GH DNA to produce the variant DNA that encodes for the changes in the amino acid sequence.

Oligonucleotide-mediated mutagenesis is the preferred method for preparing substitution, deletion, or insertion variants of GH. The technique is well known in the art as described by Zoller et al., 1987. Briefly, an oligonucleotide encoding the desired mutation is hybridized to a DNA template which comprises the single-stranded form of the wild-type DNA sequence for GH. After hybridization, a DNA polymerase is used to synthesize an entire second complementary strand of the template, and thus incorporates the oligonucleotide primer and codes for the selected alteration in the GH DNA.

Generally, oligonucleotides of at least 25 nucleotides in length are used. Although smaller oligonucleotides can be employed, an optimal oligonucleotide has 12 to 15 nucleotides that are complementary to the template on either side of the nucleotide(s) coding for the mutation(s). This ensures that the oligonucleotide hybridizes properly to the single-stranded DNA template molecule. The oligonucleotides are readily synthesized using techniques known in the art such as that described by Crea et al., 1978.

The DNA template can only be generated by those vectors that are either derived from bacteriophage M13 vectors (the commercially available M13mp18 and M13mp19 vectors are suitable), or those vectors that contain a single-stranded phage origin of replication as described by Vieira and Messing, 1987. Thus, the DNA that is to be mutated must be inserted into one of these vectors in order to generate single-stranded template. Production of the single-stranded template is described in sections 4.21-4.41 of Sambrook et al., supra.

To alter the wild-type DNA sequence, the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form, and the other strand (the original template) encodes the wild-type GH. This heteroduplex molecule is then transformed into a suitable host cell, usually a prokaryote such as *Escherichia coli* JM101. After the cells are grown, they are plated onto agarose plates and screened using the oligonucleotide primer radiolabeled with 32-phosphate to identify the bacterial colonies that contain the mutated DNA.

The method described immediately above can be modified such that a homoduplex molecule is created wherein both strands of the DNA contain the mutation(s). The modifications are as follows: The single-stranded oligonucleotide is annealed to the single-stranded DNA template as described above. A mixture of three deoxyribonucleotides, deoxyriboadenosine (dATP), deoxyriboguanosine (dGTP), and deoxyribothymidine (dTTP) is combined with a modified thio-deoxyribocytosine called dCTP-(aS). This mixture is added to the template-oligonucleotide complex. Upon addition of DNA polymerase to this mixture, a strand of DNA identical to the template except for the mutated base(s) is generated. In addition, this new strand of DNA contains dCTP-(AS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

Mutants with more than one amino acids to be substituted can be generated in one of several ways. If the amino acids are located close together in the polypeptide chain, they can be mutated simultaneously using one oligonucleotide that codes for all of the desired amino acid substitutions. If however, the amino acids are located some distance from each other (separated by more than about ten amino acids), it is more difficult to generate a single oligonucleotide that encodes all of the desired changes. Instead, one of two alternative methods can be employed.

In the first method, a separate oligonucleotide is generated for each amino acid to be substituted. The oligonucleotides are then annealed to the single-stranded template DNA simultaneously, and the second strand of DNA that is synthesized from the template encodes all of the desired amino acid substitutions. The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Cassette mutagenesis is also a preferred method for preparing substitution, deletion, and insertion variants of DNA encoding GH. The method is based on that described by Wells et al., 1985. The starting material is a plasmid (or other vector) comprising the GH DNA to be mutated. The nucleotide(s) in the GH DNA to be mutated are identified, optimally, there is a unique restriction endonuclease site on each side of the identified mutation site(s); however, this is not a requirement. If no such restriction sites exist, they can be generated using the above-described oligonucleotide-mediated mutagenesis method to introduce them at appropriate locations in the GH DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated DNA sequence of GH.

Of course, other methods can be employed to produce GH variants such as the in vitro chemical synthesis of the desired GH variant (Barany et al., The Peptides, E. Gross and J. Meienhofer (editors), Academic Press, New York (1979) Volume 2, pp. 3-254).

Production of GH Variants

The GH variants can be conveniently produced by standard recombinant techniques. More specifically, a GH variant can be expressed using a vector-host cell system.

The GH DNA can be inserted into an appropriate plasmid or vector that can subsequently be used to transform a host cell. Prokaryotes are preferred for expressing DNA sequences to produce the GH variants. For example, *E. coli* K12 strain 294 (ATCC No. 31446) can be used, as well as *E. coli* B, *E. coli* X1776 (ATCC No. 31537), *E. coli* c600 and c600hfl, and *E. coli* W3110 (F⁻, γ⁻, prototrophic, ATCC No. 27325), Bacilli such as *Bacillus subtilis*, and other Enterobacteriaceae such as *Salmonella typhimurium* or *Serratia marcescens*, and various *Pseudomonas* species. A preferred prokaryote is *E. coli* W3110 (ATCC 27325). When expressed intracellularly in prokaryotes, the GH typically contains an N-terminal methionine or a formyl methionine and is not glycosylated. When expressed extracellularly into the medium or the periplasm, the GH does not contain a N-terminal methionine. These examples are, of course, intended to be illustrative rather than limiting.

In addition to prokaryotes, eukaryotic organisms, such as yeast cultures, or cells derived from multicellular organisms, can be used. In principle, any such cell culture is workable. However, interest has been greatest in vertebrate cells, and propagation of vertebrate cells in culture has become a repeatable procedure. Examples of such useful host cell lines are VERO, HeLa, Chinese hamster ovary (CHO), W138, BHK, COS-7, and MDCK cell lines.

In general, plasmid vectors containing replication and control sequences that are derived from species compatible with the host cell are used. The vector ordinarily carries a replication site, as well as sequences that encode proteins that are capable of providing phenotypic selection in transformed cells. For example, *E. coli* can be transformed using pBR322, a plasmid derived from an *E. coli* species (Mandel et al., 1970). Plasmid pBR322 contains genes for ampicillin and tetracycline resistance and thus provides easy means for selection. One preferred vector is pBO475. This vector contains origins of replication for phage and *E. coli* that allow it to be shuttled between such hosts, thereby facilitating mutagenesis and expression. "Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector can be a plasmid, a phage particle, or simply a potential genomic insert. Once transformed into a suitable host, the vector can replicate and function independently of the host genome, or can, in some instances, integrate into the genome itself. In the present specification, "plasmid" and "vector" are sometimes used interchangeably as the plasmid is the most commonly used form of vector at present. However, use of other forms of expression vectors which serve equivalent functions and which are, or become, known in the art fall within the scope of the present disclosure.

"Operably linked" when describing the relationship between two DNA or polypeptide regions simply means that they are functionally related to each other. For example, a presequence is operably linked to a peptide if it functions as a signal sequence, participating in the secretion of the mature form of the protein, most probably involving cleavage of the signal sequence. A promoter is operably linked to a coding sequence if it controls the transcription of the sequence; a ribosome binding site is operably linked to a coding sequence if it is positioned so as to permit translation.

Host cells containing a GH variant expression vector are cultured under conditions suitable for cell growth and for expression of the GH variant. In particular, the culture medium contains appropriate nutrients and growth factors for the host cell employed. The nutrients and growth factors required for growth of a selected host cell are, in many instances, well known or can be readily determined empirically by those skilled in the art. Suitable culture conditions for mammalian host cells, for instance, are described in Mammalian Cell Culture, J. P. Mather (editor), Plenum Press (1984) and Barnes and Sato, 1980.

In addition, the culture conditions should allow transcription, translation, and protein transport between cellular compartments. Factors that affect these processes are well-known and include, for example, DNA/RNA copy number; factors that stabilize RNA; nutrients, supplements, and transcriptional inducers or repressors present in the culture medium; temperature, pH, and osmolality of the culture; and cell density. The adjustment of these factors to promote expression in a particular vector-host cell system is within the level of skill in the art.

The cell culture procedure employed in the production of a GH variant can be any of a number of well-known procedures for large- or small-scale production of proteins. These include, but are not limited to, the use of: a fluidized bed bioreactor, a hollow fiber bioreactor, a roller bottle culture system, and a stirred tank bioreactor system. A GH variant can be produced, for instance, in a batch, fed-batch, or continuous mode process.

Methods for recovery of recombinant proteins produced as described above are well-known and vary depending on the expression system employed. For example, if, as is typical, the expression vector contains a signal sequence, the GH variant is recovered from the culture medium or the periplasm. Conveniently, the variant is secreted into the periplasmic space as a fully processed protein (i.e., lacking the secretion signal sequence). However, the GH variant can also be expressed intracellularly and recovered from cell lysates.

The GH variant can be purified from culture medium or a cell lysate by any method capable of separating the variant from components of the host cell or culture medium. Typically the GH variant is separated from host cell and/or culture medium components that would interfere with pegylation, if desired, or with diagnostic or therapeutic use of the GH variant.

As a first step, the culture medium or cell lysate is usually centrifuged or filtered to remove cellular debris. The supernatant is then typically concentrated or diluted to a desired volume or diafiltered into a suitable buffer to condition the preparation for further purification. Further purification of the GH variant typically includes separating deamidated and clipped forms of the GH variant from the intact form.

In one variation of this embodiment, the GH variant is purified (1) to a degree sufficient to obtain at least 15 residues of N-terminal or internal amino acid sequence, using a spinning cup sequenator, or (2) to homogeneity by SDS-PAGE under non-reducing or reducing conditions using Coomassie blue stain.

Any of the following exemplary procedures can be employed for purification of a GH variant: affinity chromatography; anion- or cation-exchange chromatography (using, e.g., DEAE SEPHAROSE); chromatography on silica; reverse phase HPLC; gel filtration (using, e.g., SEPHADEX G-75); hydrophobic interaction chromatography; metal-chelate chromatography; ultrafiltration/diafiltration; ethanol precipitation; ammonium sulfate precipitation; chromatofocusing; and displacement chromatography.

Conjugates

GH variants useful in the methods of the present disclosure may be covalently attached (hereinafter "conjugated") to one or more chemical groups. Such conjugation produces a GH variant conjugate having a greater actual molecular weight than the unmodified GH variant. As used herein, the term "actual molecular weight" refers to the molecular weight, as measured by mass spectrometry (e.g., matrix-assisted laser desorption ionization mass spectrometry). The actual molecular weight of the hGH variant conjugate is usually at least about 30 kDa; preferably, in the range of about 35 kDa to about 55 kDa; and more preferably, in the range of about 40 kDa to about 50 kDa. Generally, the actual molecular weight of the hGH variant conjugate does not exceed 100 kDa.

Chemical groups suitable for use in a GH variant conjugate are preferably not significantly toxic or immunogenic, i.e., any toxicity or immunogenicity observed with a GH variant conjugate is not significantly greater (i.e., less than 50%) than any toxicity or immunogenicity observed with the corresponding unmodified GH variant. Typically, a chemical group is selected that reduces toxicity and/or immunogenicity associated with the unmodified GH variant. In addition, the chemical group is conveniently selected to produce a GH variant conjugate that can be stored and used under conditions suitable for storage and use of the unmodified GH variant. Exemplary chemical groups include carbohydrates, such as, for example, those carbohydrates that occur naturally on glycoproteins, and non-proteinaceous polymers, such as polyols.

A polyol, for example, can be conjugated to a GH variant molecule at one or more amino acid residues, including lysine residues, as disclosed in WO 93/00109. The polyol employed can be any water-soluble poly(alkylene oxide) polymer and can have a linear or branched chain. Suitable polyols include those substituted at one or more hydroxyl positions with a chemical group, such as an alkyl group having between one and four carbons. Typically, the polyol is a poly(alkylene glycol), such as poly(ethylene glycol) (PEG), and thus, for ease of description, the remainder of the discussion relates to an exemplary embodiment wherein the polyol employed is PEG and the process of conjugating the polyol to a GH variant is termed "pegylation." However, those skilled in the art recognize that other polyols, such as, for example, poly(propylene glycol) and polyethylene-polypropylene glycol copolymers, can be employed using the techniques for conjugation described herein for PEG.

The average molecular weight of the PEG can range from about 500 to about 30,000 Da; preferably, from about 1,000 to about 25,000 Da; and more preferably, from about 4,000 to about 20,000 Da. In one embodiment, pegylation is carried out with PEG having an average molecular weight of about 5,000 Da (hereinafter "PEG(5000)"). The reaction conditions are adjusted to maximize production of GH variant molecules conjugated to between about four and about six molecules of PEG(5000). In another embodiment, pegylation is carried out with PEG having an average molecular weight of about 20,000 Da (hereinafter "PEG(20,000)") under conditions adjusted to maximize production of GH molecules conjugated to one molecule of PEG(20,000). In a variation of this embodiment, a branched-chain PEG having two chains of about 10,000 Da each is employed.

PEG preparations that are commercially available, and suitable for use in the present methods, are nonhomogeneous preparations that are sold according to average molecular weight. For example, PEG(5000) preparations typically contain molecules that vary slightly in molecular weight, usually ±500 Da.

A variety of methods for pegylating proteins have been described (see, for example, U.S. Pat. No. 4,179,337), disclosing the conjugation of a number of hormones and enzymes to PEG and polypropylene glycol to produce physiologically active non-immunogenic compositions. Generally, a PEG having at least one terminal hydroxy group is reacted with a coupling agent to form an activated PEG having a terminal reactive group. This reactive group can then react with the α- and ε-amines of proteins to form a covalent bond. Conveniently, the other end of the PEG molecule can be "blocked" with a non-reactive chemical group, such as a methoxy group, to reduce the formation of PEG-crosslinked complexes of protein molecules.

For pegylation of a GH variant, the activated PEG is one that can react with the variant under conditions that do not destroy Site 1 binding activity. Furthermore, activated PEGs that introduce a toxic linking group into the conjugate are usually avoided.

Suitable activated PEGs can be produced by a number of conventional reactions. For example, an N-hydroxysuccinimide ester of a PEG (M-NHS-PEG) can be prepared from PEG-monomethyl ether by reaction with N,N'-dicyclohexylcarbodiimide (DCC) and N-hydroxysuccinimide (NHS), according to the method of Buckmann and Merr, 1981.

In addition, a PEG terminal hydroxy group can be converted to an amino group, for example, by reaction with thionyl bromide to form PEG-Br, followed by aminolysis with excess ammonia to form PEG-NH$_2$. The PEG-NH$_2$ is then conjugated to the protein of interest using standard coupling reagents, such as Woodward's Reagent K. Furthermore, a PEG terminal —CH$_2$OH group can be converted to an aldehyde group, for example, by oxidation with MnO$_2$. The aldehyde group is conjugated to the protein by reductive alkylation with a reagent such as cyanoborohydride.

Alternatively, activated PEGs suitable for use in the present methods can be purchased.

The degree of pegylation of a GH variant can be adjusted to provide a desirably increased in vivo half-life, compared to the corresponding non-pegylated GH variant. It is believed that the half-life of a pegylated GH variant typically increases incrementally with increasing degree of pegylation. At higher degrees of pegylation, the increase in half-life of a pegylated GH variant is believed to be partially offset by an increase in the dissociation constant (Kd) for Site 1 binding, indicating a decrease in Site 1 affinity. It is believed that this decrease in affinity is accompanied by a corresponding decrease in potency, which is reflected in an increase in the concentration of conjugate required for 50% maximal effect (EC50). As Site 1 binding is essential for GH antagonist activity of the GH variant, increased pegylation reduces the potency of the GH variants. However, the increase in half-life generally compensates for the reduction in potency, so that the in vivo efficacy of pegylated GH variants is believed to be comparable to, or better than, that observed with the corresponding non-pegylated GH variants. Accordingly, one skilled in the art can readily determine a suitable degree of pegylation for a GH variant to produce a conjugate having a desirably increased half-life, compared to the non-pegylated protein, yet retaining sufficient potency to be efficacious in vivo.

Usually, the half-life is increased at least about five-fold; preferably, at least about 10-fold; more preferably, at least about 50-fold; and most preferably, at least about 100-fold. In addition, the degree and sites of pegylation are such that the PEG-GH variant conjugate is capable of binding GHR at Site 1, typically with a Kd of about 400 nM or lower; preferably, with a Kd of 150 nM or lower; and more preferably, with a Kd of 100 nM or lower, as measured by an equilibrium binding assay, such as that described in Spencer et al., 1988.

The degree and sites of pegylation of a protein are determined by (1) the number and reactivities of pegylation sites (i.e., primary amines) and (2) pegylation reaction conditions. For example, wild-type hGH contains ten primary amines that are theoretically available to react with an activated PEG: the α-amino group of the N-terminal phenylalanine and the ε-amino groups of nine lysines. However, because some of the primary amines in hGH and the hGH variants are relatively unreactive, standard pegylation reactions typically result in less than complete pegylation (e.g., seven or eight PEGs per molecule for wild-type hGH).

The sites of pegylation of a protein are also somewhat constrained by the reactivities of the various primary amines. For example, a potential lysine in the Site 1 hormone-receptor binding interface of a given hGH variant may be relatively unreactive with a PEG. Thus, such moderately pegylated hGH variants, having of the order of four to six PEGs per variant molecule, may retain the ability to bind GH receptor at Site 1, despite the presence of a potential pegylation site at this binding interface. In one embodiment, the hGH variant comprises a phenylalanine at position 1 and lysines at positions 38, 120, 140 and 158 conjugated to PEG.

Standard mutagenesis techniques can be used to alter the number of lysines in the protein. Thus, to the extent that amino acid substitutions introduce or replace lysines, GH variants of the present disclosure can contain a greater or lesser number of potential pegylation sites than wild-type GH. In one embodiment, the hGH variant comprises nine potential pegylation sites (Phel, Lys38, Lys41, Lys70, Lys115, Lys120, Lys140, Lys145, Lys158).

Furthermore, amino acid substitutions introducing or replacing lysines alter the locations of potential pegylation sites. For example, the replacement of G120 with lysine provides an additional potential pegylation site in Site 2, which if pegylated is expected to impair any residual binding at this site.

The degree and sites of pegylation can also be manipulated by adjusting reaction conditions, such as the relative concentrations of the activated PEG and the protein as well as the pH. Suitable conditions for a desired degree of pegylation can be determined empirically.

A composition containing a pegylated GH variant for use in a therapeutic formulation can be heterogeneous or homogeneous, i.e., containing multiple or single pegylated GH variants. Typically, the composition contains at least 70% one or two forms of pegylated GH variants; preferably, at least 80% one or two forms; and more preferably, at least 90% one or two forms.

Antisense Compounds to Growth Hormone Receptor

The methods of the present disclosure rely on the use of an antisense compound to growth hormone receptor (GHR) to modulate growth hormone (GH) signalling or the GH/insulin-like growth factor-I (IGF-I) axis, particularly the expression of GHR and/or IGF-I. Preferably, the antisense compound is an oligonucleotide. However, other oligomeric antisense compounds, including but not limited to oligonucleotide mimetics are contemplated.

Hybridization of an antisense compound with its target nucleic acid is generally referred to as "antisense". Hybridization of the antisense compound with its target nucleic acid inhibits the function of the target nucleic acid. Such "antisense inhibition" is typically based upon hydrogen bonding-based hybridization of the antisense compound to the target nucleic acid such that the target nucleic acid is cleaved, degraded, or otherwise rendered inoperable. The functions of target DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA.

"Hybridization" as used herein means pairing of complementary bases of the oligonucleotide and target nucleic acid. Base pairing typically involves hydrogen bonding, which may be Watson-Crick, Hoogsteen or reversed Hoogsteen hydrogen bonding, between complementary nucleoside or nucleotide bases (nucleobases). Guanine (G) and cytosine (C) are examples of complementary nucleobases which pair through the formation of 3 hydrogen bonds. Adenine (A) and thymine (T) are examples of complementary nucleobases which pair through the formation of 2 hydrogen bonds. Hybridization can occur under varying circumstances.

A "nucleoside" is a base-sugar combination. The base portion of the nucleoside is normally a heterocyclic base. The two most common classes of such heterocyclic bases are the purines and the pyrimidines. "Nucleotides" are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar.

"Specifically hybridizable" and "complementary" are terms which are used to indicate a sufficient degree of complementarity such that stable and specific binding occurs between the antisense compound and target nucleic acid. It is understood that the antisense compound need not be 100% complementary to its target nucleic acid sequence to be specifically hybridizable. An antisense compound is specifically hybridizable when binding of the antisense compound to the target nucleic acid interferes with the expression of the target nucleic acid and there is a sufficient degree of complementarity to avoid non-specific binding of the antisense compound to non-target sequences under conditions in which specific binding is desired, for example, under physiological conditions in the case of therapeutic treatment.

The term "stringent hybridization conditions" or "stringent conditions" as used herein refers to conditions under which the antisense compound will hybridize to its target sequence, but to a minimal number of other sequences. Stringent conditions are sequence-dependent and will be different in different circumstances. Stringent condition under which the antisense compound hybridizes to a target sequence is determined by the nature and composition of the antisense compound and the assays in which it is being investigated.

"Complementary" as used herein, refers to the capacity for precise pairing between a nucleobase of the antisense compound and the target nucleic acid. For example, if a nucleobase at a certain position of the antisense compound is capable of hydrogen bonding with a nucleobase at a certain position of the target nucleic acid, then the position of hydrogen bonding between the antisense compound and the target nucleic acid is considered to be a complementary position. The antisense compound may hybridize over one or more segments, such that intervening or adjacent segments are not involved in the hybridization event (e.g., a loop structure or hairpin structure). In one embodiment, the antisense compound comprises at least 70% sequence complementarity to a target region within the target nucleic acid. For example, an antisense compound in which 18 of 20 nucleobases are complementary to a target region within the target nucleic acid, and would therefore specifically hybridize, would represent 90% complementarity. In this example, the remaining noncomplementary nucleobases may be clustered or interspersed with complementary nucleobases and need not be contiguous to each other, or to complementary nucleobases. As such, an antisense compound which is 18 nucleobases in length having 4 non-complementary nucleobases which are flanked by 2 regions of complete complementarity with the target nucleic acid would have 77.8% overall complementarity with the target nucleic acid and would thus, fall within the scope of the present disclosure. Percent complementarity of an antisense compound with a region of a target nucleic acid can be determined routinely using BLAST programs (basic local alignment search tools) and PowerBLAST programs known in the art (Altschul et al., 1990; Zhang and Madden, 1997).

Antisense Oligonucleotides

The present disclosure provides for use of an antisense oligonucleotide for inhibiting expression of a growth hormone receptor (GHR).

The term "inhibits" as used herein means any measurable decrease (e.g., 10%, 20%, 50%, 90%, or 100%) in GHR expression.

As used herein, the term "oligonucleotide" refers to an oligomer or polymer of RNA or DNA or mimetics, chimeras, analogs and homologs thereof. This term includes oligonucleotides composed of naturally occurring nucleobases, sugars and covalent internucleoside (backbone) linkages, as well as oligonucleotides having non-naturally occurring portions which function similarly. Such modified or substituted oligonucleotides are often preferred over native forms because of desirable properties such as, for example, enhanced cellular uptake, enhanced affinity for the target nucleic acid and increased stability in the presence of nucleases.

In forming oligonucleotides, phosphate groups covalently link adjacent nucleosides to one another to form a linear polymeric compound. In turn, the respective ends of this linear polymeric compound can be further joined to form a circular compound; however, linear compounds are generally preferred. In addition, linear compounds may have internal nucleobase complementarity and may therefore fold in a manner so as to produce a fully or partially double-stranded compound. With regard to oligonucleotides, the phosphate groups are commonly referred to as forming the internucleoside backbone of the oligonucleotide. The normal linkage or backbone of RNA and DNA is a 3' to 5' phosphodiester linkage.

Antisense oligonucleotides useful in the methods of the present disclosure include, for example, ribozymes, siRNA, external guide sequence (EGS) oligonucleotides, alternate splicers, primers, probes, and other oligonucleotides which hybridize to at least a portion of the target nucleic acid.

Antisense oligonucleotides may be administered in the form of single-stranded, double-stranded, circular or hairpin and may contain structural elements such as internal or terminal bulges or loops. Once administered, the antisense oligonucleotides may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H therefore results in cleavage of the RNA target, thereby greatly enhancing the efficiency of oligonucleotide-mediated inhibition of gene expression. Similar roles have been postulated for other ribonucleases, such as those in the RNase III and ribonuclease L family of enzymes.

The introduction of double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, 1995). Montgomery et al. (1998) have shown that the primary interference effects of dsRNA are posttranscriptional. The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., 1998). It has been shown that it is, in fact, the single-stranded RNA oligomers of antisense polarity of the dsRNAs which are the potent inducers of RNAi (Tijsterman et al., 2002).

A person having ordinary skill in the art could, without undue experimentation, identify antisense oligonucleotides useful in the methods of the present disclosure.

Modified Internucleoside Linkages (Backbones)

Antisense compounds useful in the methods of the present disclosure include oligonucleotides having modified backbones or non-natural internucleoside linkages. Oligonucleotides having modified backbones include those that retain a phosphorus atom in the backbone and those that do not have a phosphorus atom in the backbone.

Modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

Oligonucleotides having inverted polarity comprise a single 3' to 3' linkage at the 3'-most internucleotide linkage, that is, a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808, 4,469,863, 4,476,301, 5,023,243, 5,177,196, 5,188,897,5,264,423, 5,276,019, 5,278,302, 5,286,717, 5,321,131, 5,399,676, 5,405,939, 5,453,496, 5,455,233, 5,466,677, 5,476,925, 5,519,126, 5,536,821, 5,541,306, 5,550,111, 5,563,253, 5,571,799, 5,587,361, 5,194,599, 5,565,555, 5,527,899, 5,721,218, 5,672,697 and 5,625,050.

Modified oligonucleotide backbones that do not include a phosphorus atom therein include, for example, backbones formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleotides include, but are not limited to, U.S. Pat. Nos. 5,034,506, 5,166,315, 5,185,444, 5,214,134, 5,216,141, 5,235,033, 5,264,562, 5,264,564, 5,405,938, 5,434,257, 5,466,677, 5,470,967, 5,489,677, 5,541,307, 5,561,225, 5,596,086, 5,602,240, 5,610,289, 5,602,240, 5,608,046, 5,610,289, 5,618,704, 5,623,070, 5,663,312, 5,633,360, 5,677,437, 5,792,608, 5,646,269 and 5,677,439.

Modified Sugar and Internucleoside Linkages

Antisense compounds useful in the methods of the present disclosure include oligonucleotide mimetics where both the sugar and the internucleoside linkage (i.e. the backbone) of the nucleotide units are replaced with novel groups. The nucleobase units are maintained for hybridization with the target nucleic acid.

An oligonucleotide mimetic that has been shown to have excellent hybridization properties is referred to as a peptide nucleic acid (PNA). In PNA compounds, the sugar-backbone of an oligonucleotide is replaced with an amide containing backbone, in particular, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082, 5,714,331, and 5,719,262. Further teaching of PNA compounds can be found in Nielsen et al., 1991.

The antisense compounds useful in the methods of the present disclosure also include oligonucleotides with phosphorothioate backbones and oligonucleotides with heteroatom backbones, for example, —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$-] of U.S. Pat. No. 5,489,677, and the amide backbones of U.S. Pat. No. 5,602,240.

The antisense compounds useful in the methods of the present disclosure also include oligonucleotides having morpholino backbone structures of U.S. Pat. No. 5,034,506.

Modified Sugars

Antisense compounds useful in the methods of the present disclosure include oligonucleotides having one or more substituted sugar moieties.

Examples include oligonucleotides comprising one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl.

In one embodiment, the oligonucleotide comprises one of the following at the 2' position: O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$]$_2$, where n and m are from 1 to about 10.

Further examples include of modified oligonucleotides include oligonucleotides comprising one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties.

In one embodiment, the modification includes 2'-methoxyethoxy (2'-O—$CH_2CH_2OCH_3$ (also known as 2'-O-(2-methoxyethyl) or 2'-MOE) (Martin et al., 1995), that is, an alkoxyalkoxy group. In a further embodiment, the modification includes 2'-dimethylaminooxyethoxy, that is, a O($CH_2$)$_2$ON($CH_3$)$_2$ group (also known as 2'-DMAOE), or 2'-dimethylaminoethoxyethoxy (also known in the art as 2'-O-dimethyl-amino-ethoxy-ethyl or 2'-DMAEOE), that is, 2'-O—$CH_2$—O—$CH_2$—N($CH_3$)$_2$.

Other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. In one embodiment a 2'-arabino modification is 2'-F.

Similar modifications may also be made at other positions on the oligonucleotide, particularly the 3' position of the sugar on the 3' terminal nucleotide or in 2'-5' linked oligonucleotides and the 5' position of the 5' terminal nucleotide.

Oligonucleotides may also have sugar mimetics, such as cyclobutyl moieties in place of the pentofuranosyl sugar.

Representative United States patents that teach the preparation of such modified sugar structures include, but are not limited to, U.S. Pat. Nos. 4,981,957, 5,118,800, 5,319,080, 5,359,044, 5,393,878, 5,446,137, 5,466,786, 5,514,785, 5,519,134, 5,567,811, 5,576,427, 5,591,722, 5,597,909, 5,610,300, 5,627,053, 5,639,873, 5,646,265, 5,658,873, 5,670,633, 5,792,747, and 5,700,920.

A further modification of the sugar includes Locked Nucleic Acids (LNAs) in which the 2'-hydroxyl group is linked to the 3' or 4' carbon atom of the sugar ring, thereby forming a bicyclic sugar moiety. In one embodiment, the linkage is a methylene (—$CH_2$—)$_n$ group bridging the 2' oxygen atom and the 4' carbon atom, wherein n is 1 or 2. LNAs and preparation thereof are described in WO 98/39352 and WO 99/14226.

Natural and Modified Nucleobases

Antisense compounds useful in the methods of the present disclosure include oligonucleotides having nucleobase modifications or substitutions. As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as, for example, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Further modified nucleobases include tricyclic pyrimidines, such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as, for example, a substituted phenoxazine cytidine (e.g., 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one).

Modified nucleobases may also include those in which the purine or pyrimidine base is replaced with other heterocycles, for example, 7-deaza-adenine, 7-deazaguanosine, 2-aminopyridine and 2-pyridone. Further nucleobases include those disclosed in U.S. Pat. No. 3,687,808, those disclosed in J. I. Kroschwitz (editor), The Concise Encyclopedia of Polymer Science and Engineering, pages 858-859, John Wiley and Sons (1990), those disclosed by Englisch et al. (1991), and those disclosed by Y. S. Sanghvi, Chapter 15: Antisense Research and Applications, pages 289-302, S. T. Crooke, B. Lebleu (editors), CRC Press, 1993.

Certain of these nucleobases are particularly useful for increasing the binding affinity of the oligonucleotide. These include 5-substituted pyrimidines, 6-azapyrimidines and N-2, N-6 and O-6 substituted purines, including 2-aminopropyladenine, 5-propynyluracil and 5-propynylcyto sine. 5-methylcytosine substitutions have been shown to increase nucleic acid duplex stability by 0.6-1.2° C. In one embodiment, these nucleobase substitutions are combined with 2'-O-methoxyethyl sugar modifications.

Representative United States patents that teach the preparation of certain of the above noted modified nucleobases as well as other modified nucleobases include, but are not limited to, U.S. Pat. Nos. 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091. 5,614,617, 5,645,985, 5,830,653, 5,763,588, 6,005,096, , 5,681,941 and 5,750,692.

Conjugates

Antisense compounds useful in the methods of the present disclosure may be conjugated to one or more moieties or groups which enhance the activity, cellular distribution or cellular uptake of the antisense compound.

These moieties or groups may be covalently bound to functional groups such as primary or secondary hydroxyl groups.

Exemplary moieties or groups include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins and dyes.

Moieties or groups that enhance the pharmacodynamic properties include those that improve uptake, enhance resistance to degradation, and/or strengthen sequence-specific hybridization with the target nucleic acid.

Moieties or groups that enhance the pharmacokinetic properties include those that improve uptake, distribution, metabolism or excretion of the antisense compounds.

Representative moieties or groups are disclosed in PCT/US92/09196 and U.S. Pat. No. 6,287,860.

Moieties or groups include but are not limited to lipid moieties such as a cholesterol moiety, cholic acid, a thioether, for example, hexyl-S-tritylthiol, a thiocholesterol, an aliphatic chain, for example, dodecandiol or undecyl residues, a phospholipid, for example, di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

Antisense compounds useful in the methods of the present disclosure may also be conjugated to active drug substances.

Oligonucleotide-drug conjugates and their preparation are described in U.S. Ser. No. 09/334,130.

Representative United States patents that teach the preparation of such conjugates include, but are not limited to, U.S. Pat. Nos. 4,828,979, 4,948,882, 5,218,105, 5,525,465, 5,541,313, 5,545,730, 5,552,538, 5,578,717, 5,580,731, 5,580,731, 5,591,584, 5,109,124, 5,118,802, 5,138,045, 5,414,077, 5,486,603, 5,512,439, 5,578,718, 5,608,046, 4,587,044, 4,605,735, 4,667,025, 4,762,779, 4,789,737, 4,824,941, 4,835,263, 4,876,335, 4,904,582, 4,958,013, 5,082,830, 5,112,963, 5,214,136, 5,082,830, 5,112,963, 5,214,136, 5,245,022, 5,254,469, 5,258,506, 5,262,536, 5,272,250, 5,292,873, 5,317,098, 5,371,241, 5,391,723, 5,416,203, 5,451,463, 5,510,475, 5,512,667, 5,514,785, 5,565,552, 5,567,810, 5,574,142 5,585,481, 5,587,371, 5,595,726, 5,597,696, 5,599,923, 5,599,928 and 5,688,941.

Chimeric Compounds

As would be appreciated by those skilled in the art, it is not necessary for all positions in a given compound to be uniformly modified and in fact, more than one of the aforementioned modifications may be incorporated in a single oligonucleotide or even at a single nucleoside within an oligonucleotide.

Antisense compounds useful in the methods of the present disclosure include chimeric oligonucleotides. "Chimeric oligonucleotides" contain two or more chemically distinct regions, each made up of at least one monomer unit, that is, a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and if necessary, associated nucleic acid hybridization techniques known in the art.

Chimeric antisense compounds useful in the methods of the present disclosure may be formed as composite structures of two or more oligonucleotides, modified oligonucleotides, and/or oligonucleotide mimetics. Such compounds have also been referred to in the art as hybrids or gapmers.

Representative United States patents that teach the preparation of such hybrid structures include, but are not limited to, U.S. Pat. Nos. 5,013,830, 5,149,797, 5,220,007, 5,256, 775, 5,366,878, 5,403,711, 5,491,133, 5,565,350, 5,623,065, 5,652,355, 5,652,356, and 5,700,922.

Exemplary Oligonucleotides

In one embodiment, the antisense compound is a second generation phosphorothioate backbone 2'-MOE-modified chimeric oligonucleotide gapmer designed to hybridize to GHR mRNA.

Exemplary oligonucleotides are shown in Table 1. "Target site" indicates the first (5'-most) nucleotide number on the particular target sequence to which the oligonucleotide binds. "% Inhib" indicates the inhibitory effect on hGHR mRNA levels by quantitative real-time PCR. Data are averages from three experiments in which MCF7 cells were treated with the antisense oligonucleotides.

TABLE 1

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 227452 | Coding | 4 | 332 | tcagggcattctttccattc | 79 | 6 |
| 227453 | Coding | 4 | 337 | cataatcagggcattctttc | 52 | 7 |
| 227464 | Coding | 4 | 947 | cctttaatctttggaactgg | 58 | 8 |
| 227468 | Coding | 4 | 1079 | tcatcaatatctagctcaat | 62 | 9 |
| 227469 | Coding | 4 | 1124 | cttagaagtctgtctgtgtc | 63 | 10 |
| 227475 | Coding | 4 | 1514 | cctgctggtgtaatgtcgct | 68 | 11 |
| 227480 | Coding | 4 | 1724 | atgtaaatgtcctcttggtt | 66 | 12 |
| 227481 | Coding | 4 | 1729 | tggtgatgtaaatgtcctct | 45 | 13 |
| 227482 | Coding | 4 | 1734 | ttctgtggtgatgtaaatgt | 53 | 14 |
| 227483 | Coding | 4 | 1739 | aggctttctgtggtgatgta | 75 | 15 |
| 227484 | Coding | 4 | 1744 | tggtaaggctttctgtggtg | 63 | 16 |
| 227488 | Coding | 4 | 1922 | agttggtctgtgctcacata | 86 | 17 |
| 227489 | Coding | 4 | 1927 | tttcagttggtctgtgctc | 75 | 18 |
| 227490 | Coding | 4 | 1936 | gcatgattttttcagttgg | 67 | 19 |
| 227499 | 3'UTR | 4 | 2656 | tataaagggctttgtaaaa | 14 | 20 |
| 227500 | 3'UTR | 4 | 4043 | catagcagcaaagtagcaga | 69 | 21 |
| 227501 | 3'UTR | 4 | 4183 | gctattttggctatagaaa | 64 | 22 |
| 227502 | 3'UTR | 4 | 4197 | gattgaggtatttagctatt | 56 | 23 |
| 272302 | Start Codon | 4 | 31 | gatccatacctgtaggacct | 60 | 24 |
| 272303 | Start Codon | 4 | 36 | ccagagatccatacctgtag | 55 | 25 |
| 272304 | Coding | 4 | 115 | tgctaaggatagctgctgtg | 48 | 26 |
| 272305 | Coding | 4 | 160 | ttgtctttaggcctggatta | 68 | 27 |
| 272306 | Coding | 4 | 170 | ttagaagaatttgtctttag | 13 | 28 |
| 272307 | Coding | 4 | 185 | gtgaatttaggctccttaga | 55 | 29 |
| 272308 | Coding | 4 | 274 | gctgtatgggtcctaggttc | 57 | 30 |
| 272309 | Coding | 4 | 362 | taacagctgttttccccagc | 85 | 31 |
| 272310 | Coding | 4 | 439 | tttcatccactgtaccacca | 76 | 32 |
| 272311 | Coding | 4 | 468 | ttgcactatttcatcaacag | 47 | 33 |
| 272312 | Coding | 4 | 480 | gggtggatctggttgcacta | 57 | 34 |
| 272313 | Coding | 4 | 564 | attgcgtggtgcttcccatc | 77 | 35 |
| 272314 | Coding | 4 | 652 | tagggtccatcattttccat | 56 | 36 |
| 272315 | Coding | 4 | 684 | caatgagtacactggaactg | 53 | 37 |
| 272316 | Coding | 4 | 752 | aactcgccataatttccaga | 64 | 38 |
| 272317 | Coding | 4 | 857 | agcccaaatattccaaagat | 65 | 39 |
| 272318 | Coding | 4 | 913 | tcagcattttaatcctttgc | 55 | 40 |

TABLE 1-continued

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 272319 | Coding | 4 | 979 | attttccttccttgaggaga | 67 | 41 |
| 272320 | Coding | 4 | 1000 | agattgtgttcacctcctct | 70 | 42 |
| 272321 | Coding | 4 | 1053 | aacccaagagtcatcactgt | 64 | 43 |
| 272322 | Coding | 4 | 1084 | ctggctcatcaatatctagc | 84 | 44 |
| 272323 | Coding | 4 | 1110 | tgtgtctgattcctcagtct | 67 | 45 |
| 272324 | Coding | 4 | 1236 | tatgtcattggcattgaaat | 53 | 46 |
| 272325 | Coding | 4 | 1302 | aaggcataagagatctgctt | 66 | 47 |
| 272326 | Coding | 4 | 1420 | actcagctccttcagtagga | 77 | 48 |
| 272327 | Coding | 4 | 1560 | ggacatccctgccttattct | 60 | 49 |
| 272328 | Coding | 4 | 1623 | ggcattgtccataaggaagt | 85 | 50 |
| 272329 | Coding | 4 | 1651 | acttttggcatctgcctca | 63 | 51 |
| 272330 | Coding | 4 | 1656 | gatgcacttttggcatctg | 47 | 52 |
| 272331 | Coding | 4 | 1861 | cagtcgcattgagtatgagg | 67 | 53 |
| 272332 | Coding | 4 | 1884 | ctctttgtcaggcaagggca | 75 | 54 |
| 272333 | Coding | 4 | 1913 | gtgctcacatagccacatga | 72 | 55 |
| 272334 | Stop Codon | 4 | 1949 | aagaaaggctaaggcatgat | 61 | 56 |
| 272335 | 3'UTR | 4 | 1973 | aaatacgtagctcttgggaa | 47 | 57 |
| 272336 | 3'UTR | 4 | 2196 | caatcactgctactaaacag | 69 | 58 |
| 272337 | 3'UTR | 4 | 2249 | aaacatagccattcaatgct | 39 | 59 |
| 272338 | 3'UTR | 4 | 2337 | gtgctatggtttgcattcaa | 78 | 60 |
| 272339 | 3'UTR | 4 | 2454 | gttttacatatccaaactat | 72 | 61 |
| 272340 | 3'UTR | 4 | 2853 | catcaaccaagatttggtga | 69 | 62 |
| 272341 | 3'UTR | 4 | 2988 | gaggctatagatcttatctc | 65 | 63 |
| 272342 | 3'UTR | 4 | 3271 | tagtgagaaagaaagtttct | 45 | 64 |
| 272343 | 3'UTR | 4 | 3765 | aatgctctcaagaatgatgt | 48 | 65 |
| 272344 | 3'UTR | 4 | 3980 | acactcaattctagcttttc | 60 | 66 |
| 272345 | 3'UTR | 4 | 4011 | catctattacaaataacatg | 24 | 67 |
| 272346 | 3'UTR | 4 | 4057 | ctcttggagaaaaccatagc | 67 | 68 |
| 272347 | 3'UTR | 4 | 4097 | tctacactgatgatacttta | 62 | 69 |
| 272348 | 3'UTR | 4 | 4120 | cacagctttgaattgaatta | 57 | 70 |
| 272349 | 3'UTR | 4 | 4133 | agtcttccaaacacacagct | 68 | 71 |
| 272350 | 3'UTR | 4 | 4156 | aggctgttgtgaaatagtaa | 67 | 72 |
| 272351 | 3'UTR | 4 | 4170 | atagaaatgttgtcaggctg | 57 | 73 |
| 272352 | 3'UTR | 4 | 4218 | ccaaaatgacattctgagac | 77 | 74 |
| 272353 | 3'UTR | 4 | 4245 | ataatggcttatgtggccac | 72 | 75 |
| 272354 | intron | 5 | 2571 | agttatgtgaccctgattga | 65 | 76 |

TABLE 1-continued

Inhibition of human growth hormone receptor mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 272355 | intron: exon junction | 5 | 6418 | ttgagtgttcctaaaatgaa | 24 | 77 |
| 272356 | intron | 5 | 8405 | atggaggctggaggttcaaa | 63 | 78 |
| 272357 | intron: exon junction | 5 | 22712 | tagggtccatctttcaagac | 62 | 79 |
| 272358 | intron | 5 | 25543 | tctccagatagaatctaaac | 53 | 80 |
| 272359 | intron | 5 | 29755 | tccaaatattctggtactttt | 72 | 81 |
| 272360 | exon: intron junction | 5 | 29935 | tattagttaccttgaggaga | 0 | 82 |
| 272361 | intron: exon junction | 5 | 30267 | attttccttcctagaaaata | 10 | 83 |

All oligonucelotides in Table 1 are chimeric oligonucleotides ("gapmers"), 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All uracils are 5-methyluracils ($^{Me}$U). Typically, the oligonucleotide is synthesized using 2-methoxyethyl modified thymidines not 5-methyluracils. All pyrimidines are C5 methylated (i.e., U, T, C are C5 methylated).

The oligonucleotide may be synthesized by a multi-step process that may be divided into two distinct operations: solid-phase synthesis and downstream processing. In the first operation, the nucleotide sequence of the oligonucleotide is assembled through a computer-controlled solid-phase synthesizer. Subsequent downstream processing includes deprotection steps, preparative reversed-phase chromatographic purification, isolation and drying to yield the oligonucleotide drug substance. The chemical synthesis of the oligonucelotide utilizes phosphoramidite coupling chemistry followed by oxidative sulfurization and involves sequential coupling of activated monomers to an elongating oligomer, the 3'-terminus of which is covalently attached to the solid support.

Detritylation (reaction a).

Each cycle of the solid-phase synthesis commences with removal of the acid-labile 5'-O-4, 4'-dimethoxytrityl (DMT) protecting group of the 5' terminal nucleoside of the support bound oligonucleotide. This is accomplished by treatment with an acid solution (e.g., dichloroacetic acid (DCA) in toluene). Following detritylation, excess reagent is removed from the support by washing with acetonitrile in preparation for the next reaction.

Coupling (Reaction b)

Chain elongation is achieved by reaction of the 5'-hydroxyl group of the support-bound oligonucleotide with a solution of the phosphoramidite corresponding to that particular base position (e.g., for base2: MOE-$^{Me}$C amidite) in the presence of an activator (e.g., 1H-tetrazole). This results in the formation of a phosphite triester linkage between the incoming nucleotide synthon and the support-bound oligonucleotide chain. After the coupling reaction, excess reagent is removed from the support by washing with acetonitrile in preparation for the next reaction.

Sulfurization (Reaction c)

The newly formed phosphite triester linkage is converted to the corresponding [O, O, O)-trialkyl phosphorothioate triester by treatment with a solution of a sulfur transfer reagent (e.g., phenylacetyl disulfide). Following sulfurization, excess reagent is removed from the support by washing with acetonitrile in preparation for the next reaction.

Capping (Reaction d)

A small proportion of the 5'-hydroxy groups available in any given cycle fail to extend. Coupling of these groups in any of the subsequent cycles would result in formation of process-related impurities ("DMT-on (n-1)-mers") which are difficult to separate from the desired product. To prevent formation of these impurities and to facilitate purification, a "capping reagent" (e.g., acetic anhydride and N-methylimidazole/acetonitrile/pyridine) is introduced into the reactor vessel to give capped sequences. The resulting failure sequences ("DMT-off shortmers") are separated from the desired product by reversed phase HPLC purification. After the capping reaction, excess reagent is removed from the support by washing with acetonitrile in preparation of the next reaction.

Reiteration of this basic four-step cycle using the appropriate protected nucleoside phosphoramidite allows assembly of the entire protected oligonucleotide sequence.

Backbone Deprotection (Reaction e)

Following completion of the assembly portion of the process the cyanoethyl groups protecting the (O, O, O)-trialkyl phosphorothioate triester internucleotide linkages are removed by treatment with a solution of triethylamine (TEA) in acetonitrile. The reagent and acrylonitrile generated during this step are removed by washing the column with acetonitrile.

Cleavage from Support and Base Deprotection (Reaction f)

Deprotection of the exocyclic amino groups and cleavage of the crude product from the support is achieved by incubation with aqueous ammonium hydroxide (reaction f). Purification of the crude, 5'-O-DMT-protected product is accomplished by reversed phase HPLC. The reversed phase HPLC step removes DMT-off failure sequences. The elution profile is monitored by UV absorption spectroscopy. Fractions containing DMT-on oligonucleotide product are collected and analyzed.

Acidic Deprotection (Reaction g)

Reversed phase HPLC fractions containing 5'-O-DMT-protected oligonucleotide are pooled and transferred to a precipitation tank. The products obtained from the purification of several syntheses are combined at this stage of the process. Purified DMT-on oligonucleotide is treated with acid (e.g., acetic acid) to remove the DMT group attached to the 5' terminus. After acid exposure for the prescribed time and neutralization, the oligonucleotide drug substance is isolated and dried.

Following the final acidic deprotection step, the solution is neutralized by addition of aqueous sodium hydroxide and the oligonucleotide drug substance is precipitated from solution by adding ethanol. The precipitated material is allowed to settle at the bottom of the reaction vessel and the ethanolic supernatant decanted. The precipitated material is redissolved in purified water and the solution pH adjusted to between pH 7.2 and 7.3. The precipitation step is repeated. The precipitated material is dissolved in water and the solution filtered through a 0.45 micron filter and transferred into disposable polypropylene trays that are then loaded into a lyophilizer. The solution is cooled to −50° C. Primary drying is carried out at 25° C. for 37 hours. The temperature is increased to 300° C. and a secondary drying step performed for 5.5 hours. Following completion of the lyophilization process, the drug substance is transferred to high density polyethylene bottles and stored at −200° C.

Target Nucleic Acid

"Targeting" an antisense compound to a particular nucleic acid can be a multistep process. The process usually begins with the identification of a target nucleic acid whose function is to be modulated. In the present disclosure, the target nucleic acid encodes growth hormone receptor (GHR). The term "target nucleic acid" encompasses DNA encoding GHR, RNA (including pre-mRNA and mRNA or portions thereof) transcribed from such DNA, and further, cDNA derived from such RNA.

The cDNA encoding the growth hormone receptor has been cloned from many species. The receptor consists of an extracellular hormone-binding region (exons 2-7), a single membrane spanning region (exon 8), and an intracellular region (exons 9-10). There are also multiple alternative 5' untranslated regions which are alternative first exons of the gene, in both the human and mouse transcripts. Growth hormone receptor has no intrinsic kinase domain, but the intracellular region plays a major role in the signal transduction process. A truncated form of the receptor, known as growth hormone binding protein (GHBP), lacks the transmembrane and intracellular regions of GHR and is secreted into the serum. The truncated protein is produced by one of two different processes, depending on the animal species. In mice and rats, alternative splicing of GHR precursor messenger RNA replaces the transmembrane and intracellular regions with a very short hydrophilic tail (encoded by exon 8A). In humans, cows, and pigs (among others), no alternative RNA splicing is apparent but instead the GHBP is produced by proteolysis of the GHR. The GHBP appears to be to modulate the level of circulating growth hormone (GH).

In one embodiment the GHR is a human GHR (hGHR) having a nucleotide sequence as shown in NM_000163.4 (SEQ ID NO:4) or NG_011688 (4852-302955) (SEQ ID NO:5).

The targeting process usually also includes determination of at least one target region, segment, or site within the target nucleic acid for the antisense interaction to occur such that the desired effect, for example, inhibition of expression, will result. The term "region" as used herein is defined as a portion of the target nucleic acid having at least one identifiable structure, function, or characteristic. Within regions of the target nucleic acids are segments. "Segments" are defined as smaller or sub-portions of regions within a target nucleic acid. "Sites" as used herein, means positions within the target nucleic acid.

Since the "translation initiation codon" is typically 5'-AUG (in transcribed mRNA molecules; 5'-ATG in the corresponding DNA molecule), the translation initiation codon is also referred to as the "AUG codon", the "start codon" or the "AUG start codon". A minority of genes have a translation initiation codon having the RNA sequence 5'-GUG, 5'-UUG, or 5'-CUG, and 5'-AUA, 5'-ACG and 5'-CUG have been shown to function in vivo. Thus, the terms "translation initiation codon" and "start codon" can encompass many codon sequences even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. The terms "start codon" and "translation initiation codon" as used herein refer to the codon or codons that are used in vivo to initiate translation of an mRNA transcribed from a gene encoding, for example, GHR, regardless of the sequence(s) of such codons.

A "translation termination codon" also referred to as a "stop codon" may have one of three RNA sequences: 5'-UAA, 5'-UAG and 5'-UGA (5'-TAA, 5'-TAG and 5'-TGA, respectively in the corresponding DNA molecule). The terms "translation termination codon" and "stop codon" as used herein refer to the codon or codons that are used in vivo to terminate translation of an mRNA transcribed from a gene encoding the GHR, regardless of the sequence(s) of such codons.

The terms "start codon region" and "translation initiation codon region" refer to a portion of the mRNA or gene that encompasses from about 25 to about 50 contiguous nucleotides in either direction (i.e., 5' or 3') from the translation initiation codon. Similarly, the terms and "stop codon region" and "translation termination codon region" refer to a portion of the mRNA or gene that encompasses from about 25 to about 50 contiguous nucleotides in either direction (i.e., 5' or 3') from the translation termination codon. Consequently, the "start codon region" or "translation initiation codon region" and the "stop codon region" or "translation termination codon region" are all regions which may be targeted effectively with the antisense compounds.

The "open reading frame" (ORF) or "coding region", which is known in the art to refer to the region between the translation initiation codon and the translation termination codon, is also a region which may be targeted effectively. In one embodiment, the intragenic region encompassing the translation initiation or termination codon of the ORF of a gene is targeted.

Other target regions include the 5' untranslated region (5'UTR), known in the art to refer to the portion of the mRNA in the 5' direction from the translation initiation codon, and thus including nucleotides between the 5' cap site and the translation initiation codon of the mRNA (or corresponding nucleotides on the gene), and the 3' untranslated region (3'UTR), known in the art to refer to the portion of the mRNA in the 3' direction from the translation termination codon, and thus including nucleotides between the translation termination codon and 3' end of the mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself, as well as the first 50 nucleotides adjacent to the cap site. In one embodiment, the 5' cap region is targeted.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA transcripts produced via the process of splicing of two (or more) mRNAs from different gene sources are known as "fusion transcripts". In one embodiment, introns, or splice sites, that is, intron-exon junctions or exon-intron junctions, or aberrant fusion junctions due to rearrangements or deletions are targeted.

Alternative RNA transcripts can be produced from the same genomic region of DNA. These alternative transcripts are generally known as "variants".

"Pre-mRNA variants" are transcripts produced from the same genomic DNA that differ from other transcripts produced from the same genomic DNA in either their start or stop position and contain both intronic and exonic sequence. Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

In mouse, rat and monkey, GHBP, which is the soluble shortened form of GHR, is produced by alternative splicing of the GHR primary transcript. In some embodiments it may be preferable to target regions of the transcript which are present in both the GHR transcript and in the shorter GHBP transcript. In other embodiments it may be preferable to target regions of the mRNA which are only present in the longer GHR transcript. In humans, cows, and pigs (among others), no alternative RNA splicing is apparent but instead the shorter GHBP is produced by proteolysis of the GHR. It will be understood that in the context of this disclosure, "nucleic acid encoding GHR" includes nucleic acid encoding GHBP.

Variants can be produced through the use of alternative signals to start or stop transcription, that is, through use of an alternative start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. In one embodiment, the pre-mRNA or mRNA variants are targeted. The human GHR has several transcript variants as can be identified from the National Center for Biotechnology Information http://www.ncbi.nlm.nih.gov/guide/and other web sites http://www.uniprot.org/uniprot/P10912#PRO_0000010958. There are additionally alternative sequences and natural variants sequences of these transcripts.

The location on the target nucleic acid to which the antisense compound hybridizes is referred to as the "target segment". As used herein, the term "target segment" is defined as at least an 8-nucleobase portion of a target region to which an antisense compound is targeted. While not wishing to be bound by theory, it is presently believed that these target segments represent portions of the target nucleic acid which are accessible for hybridization.

Once one or more target regions, segments or sites have been identified, antisense compounds are chosen which are sufficiently complementary to a target segment, that is, antisense compounds that hybridize sufficiently well and with sufficient specificity, to give the desired effect.

In a further embodiment, the target segment identified herein may be employed in a screen for additional compounds that modulate the expression of the GHR gene (and thus expression of GHR). "Modulators" are those compounds that decrease or increase the expression of a nucleic acid molecule encoding GHR and which comprise at least a 8 nucleobase portion which is complementary to a preferred target segment.

The screening method comprises the steps of contacting a target segment of the nucleic acid encoding GHR with one or more candidate modulators, and selecting for one or more candidate modulators which decrease or increase the expression of a nucleic acid encoding GHR. Once it is shown that the candidate modulator or modulators are capable of modulating (e.g., either decreasing or increasing) the expression of a nucleic acid encoding GHR, the modulator may then be employed in further investigative studies of the function of GHR, or for use as a research, diagnostic, or therapeutic agent.

The target segment may also be combined with its respective complementary antisense compound to form stabilized double-stranded (duplexed) oligonucleotides.

Such double stranded oligonucleotide moieties have been shown in the art to modulate target expression and regulate translation, as well as RNA processing via an antisense mechanism. Moreover, the double-stranded moieties may be subject to chemical modifications (Fire et al., 1998; Timmons and Fire, 1998; Timmons et al., 2001; Tabara et al., 1998; Montgomery et al., 1998; Tuschl et al., 1999; Elbashir et al., 2001a; Elbashir et al., 2001b). For example, such double-stranded moieties have been shown to inhibit the target by the classical hybridization of antisense strand of the duplex to the target, thereby triggering enzymatic degradation of the target (Tijsterman et al., 2002).

Exemplary Target Nucleic Acids
Exemplary target sequences are shown in Table 2.

TABLE 2

Sequence and position of preferred target segments identified in growth hormone receptor

| SITE ID | TARGET SEQ ID NO | TARGET SITE | SEQUENCE | REV COMP OF SEQ ID | ACTIVE IN | SEQ ID NO |
|---|---|---|---|---|---|---|
| 144070 | 4 | 332 | gaatggaaagaatgccctga | 6 | H. sapiens | 84 |
| 144071 | 4 | 337 | gaaagaatgccctgattatg | 7 | H. sapiens | 85 |
| 144082 | 4 | 947 | ccagttccaaagattaaagg | 8 | H. sapiens | 86 |
| 144086 | 4 | 1079 | attgagctagatattgatga | 9 | H. sapiens | 87 |
| 144087 | 4 | 1124 | gacacagacagacttctaag | 10 | H. sapiens | 88 |
| 144093 | 4 | 1514 | agcgacattacaccagcagg | 11 | H. sapiens | 89 |
| 144098 | 4 | 1724 | aaccaagaggacatttacat | 12 | H. sapiens | 90 |
| 144099 | 4 | 1729 | agaggacatttacatcacca | 13 | H. sapiens | 91 |
| 144100 | 4 | 1734 | acatttacatcaccacagaa | 14 | H. sapiens | 92 |
| 144101 | 4 | 1739 | tacatcaccacagaaagcct | 15 | H. sapiens | 93 |
| 144102 | 4 | 1744 | caccacagaaagccttacca | 16 | H. sapiens | 94 |
| 144106 | 4 | 1922 | tatgtgagcacagaccaact | 17 | H. sapiens | 95 |
| 144107 | 4 | 1927 | gagcacagaccaactgaaca | 18 | H. sapiens | 96 |
| 144108 | 4 | 1936 | ccaactgaacaaaatcatgc | 19 | H. sapiens | 97 |
| 144118 | 4 | 4043 | tctgctactttgctgctatg | 21 | H. sapiens | 98 |
| 144119 | 4 | 4183 | tttctatagccaaaaatagc | 22 | H. sapiens | 99 |
| 144120 | 4 | 4197 | aatagctaaatacctcaatc | 23 | H. sapiens | 100 |
| 188518 | 4 | 31 | aggtcctacaggtatggatc | 24 | H. sapiens | 101 |
| 188519 | 4 | 36 | ctacaggtatggatctctgg | 25 | H. sapiens | 102 |
| 188520 | 4 | 115 | cacagcagctatccttagca | 26 | H. sapiens | 103 |
| 188521 | 4 | 160 | taatccaggcctaaagacaa | 27 | H. sapiens | 104 |
| 188523 | 4 | 185 | tctaaggagcctaaattcac | 29 | H. sapiens | 105 |
| 188524 | 4 | 274 | gaacctaggacccatacagc | 30 | H. sapiens | 106 |
| 188525 | 4 | 362 | gctggggaaaacagctgtta | 31 | H. sapiens | 107 |
| 188526 | 4 | 439 | tggtggtacagtggatgaaa | 32 | H. sapiens | 108 |
| 188527 | 4 | 468 | ctgttgatgaaatagtgcaa | 33 | H. sapiens | 109 |
| 188528 | 4 | 480 | tagtgcaaccagatccaccc | 34 | H. sapiens | 110 |
| 188529 | 4 | 564 | gatgggaagcaccacgcaat | 35 | H. sapiens | 111 |
| 188530 | 4 | 652 | atggaaaatgatggaccctc | 36 | H. sapiens | 112 |
| 188531 | 4 | 684 | cagttccagtgtactcattg | 37 | H. sapiens | 113 |
| 188532 | 4 | 752 | tctggaaattatggcgagtt | 38 | H. sapiens | 114 |
| 188533 | 4 | 857 | atctttggaatatttgggct | 39 | H. sapiens | 115 |
| 188534 | 4 | 913 | gcaaaggattaaaatgctga | 40 | H. sapiens | 116 |
| 188535 | 4 | 979 | tctcctcaaggaaggaaaat | 41 | H. sapiens | 117 |
| 188536 | 4 | 1000 | agaggaggtgaacacaatct | 42 | H. sapiens | 118 |

TABLE 2-continued

Sequence and position of preferred target segments identified in growth hormone receptor

| SITE ID | TARGET SEQ ID NO | TARGET SITE | SEQUENCE | REV COMP OF SEQ ID | ACTIVE IN | SEQ ID NO |
|---|---|---|---|---|---|---|
| 188537 | 4 | 1053 | acagtgatgactcttgggtt | 43 | H. sapiens | 119 |
| 188538 | 4 | 1084 | gctagatattgatgagccag | 44 | H. sapiens | 120 |
| 188539 | 4 | 1110 | agactgaggaatcagacaca | 45 | H. sapiens | 121 |
| 188540 | 4 | 1236 | atttcaatgccaatgacata | 46 | H. sapiens | 122 |
| 188541 | 4 | 1302 | aagcagatctcttatgcctt | 47 | H. sapiens | 123 |
| 188542 | 4 | 1420 | tcctactgaaggagctgagt | 48 | H. sapiens | 124 |
| 188543 | 4 | 1560 | agaataaggcagggatgtcc | 49 | H. sapiens | 125 |
| 188544 | 4 | 1623 | acttccttatggacaatgcc | 50 | H. sapiens | 126 |
| 188545 | 4 | 1651 | tgaggcagatgccaaaaagt | 51 | H. sapiens | 127 |
| 188546 | 4 | 1656 | cagatgccaaaaagtgcatc | 52 | H. sapiens | 128 |
| 188547 | 4 | 1861 | cctcatactcaatgcgactg | 53 | H. sapiens | 129 |
| 188548 | 4 | 1884 | tgcccttgcctgacaaagag | 54 | H. sapiens | 130 |
| 188549 | 4 | 1913 | tcatgtggctatgtgagcac | 55 | H. sapiens | 131 |
| 188550 | 4 | 1949 | atcatgccttagcctttctt | 56 | H. sapiens | 132 |
| 188551 | 4 | 1973 | ttcccaagagctacgtattt | 57 | H. sapiens | 133 |
| 188552 | 4 | 2196 | ctgtttagtagcagtgattg | 58 | H. sapiens | 134 |
| 188554 | 4 | 2337 | ttgaatgcaaaccatagcac | 60 | H. sapiens | 135 |
| 188555 | 4 | 2454 | atagtttggatatgtaaaac | 61 | H. sapiens | 136 |
| 188556 | 4 | 2853 | tcaccaaatcttggttgatg | 62 | H. sapiens | 137 |
| 188557 | 4 | 2988 | gagataagatctatagcctc | 63 | H. sapiens | 138 |
| 188558 | 4 | 3271 | agaaactttctttctcacta | 64 | H. sapiens | 139 |
| 188559 | 4 | 3765 | acatcattcttgagagcatt | 65 | H. sapiens | 140 |
| 188560 | 4 | 3980 | gaaaagctagaattgagtgt | 66 | H. sapiens | 141 |
| 188562 | 4 | 4057 | gctatggttttctccaagag | 68 | H. sapiens | 142 |
| 188563 | 4 | 4097 | taaagtatcatcagtgtaga | 69 | H. sapiens | 143 |
| 188564 | 4 | 4120 | taattcaattcaaagctgtg | 70 | H. sapiens | 144 |
| 188565 | 4 | 4133 | agctgtgtgtttggaagact | 71 | H. sapiens | 145 |
| 188566 | 4 | 4156 | ttactatttcacaacagcct | 72 | H. sapiens | 146 |
| 188567 | 4 | 4170 | cagcctgacaacatttctat | 73 | H. sapiens | 147 |
| 188568 | 4 | 4218 | gtctcagaatgtcattttgg | 74 | H. sapiens | 148 |
| 188569 | 4 | 4245 | gtggccacataagccattat | 75 | H. sapiens | 149 |
| 188570 | 5 | 2571 | tcaatcagggtcacataact | 76 | H. sapiens | 150 |
| 188572 | 5 | 8405 | tttgaacctccagcctccat | 78 | H. sapiens | 151 |
| 188573 | 5 | 22712 | gtcttgaaagatggacccta | 79 | H. sapiens | 152 |
| 188574 | 5 | 25543 | gtttagattctatctggaga | 80 | H. sapiens | 153 |
| 188575 | 5 | 29755 | aaagtaccagaatatttgga | 81 | H. sapiens | 154 |

Compositions/Formulations

Antisense compounds useful in the methods of the present disclosure may be admixed, encapsulated, conjugated or otherwise associated with other molecules, molecule structures or mixtures of compounds, resulting in, for example, liposomes, receptor-targeted molecules, oral, rectal, topical or other formulations, for assisting in uptake, distribution and/or absorption.

Representative United States patents that teach the preparation of such uptake, distribution and/or absorption-assisting formulations include, but are not limited to, U.S. Pat. Nos. 5,108,921, 5,354,844, 5,416,016, 5,459,127, 5,521,291, 5,543,158, 5,547,932, 5,583,020, 5,591,721, 4,426,330, 4,534,899, 5,013,556, 5,108,921, 5,213,804, 5,227,170, 5,264,221, 5,356,633, 5,395,619, 5,416,016, 5,417,978, 5,462,854, 5,469,854, 5,512,295, 5,527,528, 5,534,259, 5,543,152, 5,556,948, 5,580,575, and 5,595,756.

The antisense compounds may be administered in a pharmaceutically acceptable carrier. The term "pharmaceutically acceptable carrier" refers to molecular entities that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, solvents, surfactants, excipients, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the disclosure.

The antisense compounds may be pharmaceutically acceptable salts, esters, or salts of the esters, or any other compounds which, upon administration are capable of providing (directly or indirectly) the biologically active metabolite.

The term "pharmaceutically acceptable salts" as used herein refers to physiologically and pharmaceutically acceptable salts of the antisense compounds that retain the desired biological activities of the parent compounds and do not impart undesired toxicological effects upon administration. Preferred examples of pharmaceutically acceptable salts and their uses are further described in U.S. Pat. No. 6,287,860.

The antisense compounds may be prodrugs or pharmaceutically acceptable salts of the prodrugs, or other bioequivalents.

The term "prodrugs" as used herein refers to therapeutic agents that are prepared in an inactive form that is converted to an active form (i.e., drug) upon administration by the action of endogenous enzymes or other chemicals and/or conditions. In particular, prodrug forms of the antisense compounds are prepared as SATE [(S acetyl-2-thioethyl) phosphate]derivatives according to the methods disclosed in WO 93/24510, WO 94/26764 and U.S. Pat. No. 5,770,713.

Formulations of the growth hormone (GH) variants for therapeutic administration are prepared for storage by mixing a GH variant having the desired degree of purity with an optional pharmaceutically acceptable carrier, excipient, or stabilizer (Remington's Pharmaceutical Sciences, 16th edition, A. Oslo, A (editor) (1980)) in the form of a lyophilized cake or an aqueous solution. Parenteral formulations can be prepared by mixing the GH variant in a unit dosage injectable form (solution, suspension, or emulsion) with a pharmaceutically acceptable carrier. Pharmaceutically acceptable carriers are non-toxic to recipients at the dosages and concentrations employed and are compatible with other ingredients of the formulation. For example, the formulation preferably does not include oxidizing agents and other compounds known to be deleterious to polypeptides. Suitable carriers include buffers containing phosphate, borate, HEPES, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates, including glucose, mannose, or dextrins; chelating agents such as EDTA; divalent metal ions such as zinc, cobalt, or copper; sugar alcohols such as mannitol or sorbitol; salt-forming counterions such as sodium; and/or nonionic surfactants such as Tween, Pluronics, or polyethylene glycol (PEG).

Additionally, the GH formulation set forth in WO 89/09614 can be employed, wherein the GH variant is contained in a composition comprising glycine, mannitol and a buffer, such as a phosphate buffer. An exemplary version of this formulation is: 0.68 g/L glycine, 18.0 g/L mannitol, 5 mM sodium phosphate, pH 7.4. Alternatively, the GH variant can be contained in a liquid formulation that does not necessarily contain mannitol or glycine and comprises 0.1 to 5% (w/v) of a non-ionic surfactant, such as polysorbate, or a poloxamer. An exemplary version of this formulation is: 5 mg/ml GH variant, 8.77 mg/ml NaCl, 2.5 mg/ml phenol, 2.0 mg/ml polysorbate 20, and 10 mM sodium citrate, pH 6.0.

The GH variant is also suitably administered by sustained-release systems. Suitable examples of sustained-release compositions include semi-permeable polymer matrices in the form of shaped articles, for example, films, or microcapsules. Sustained-release matrices include polylactides (U.S. Pat. No. 3,773,919; EP 58,481), copolymers of L-glutamic acid and gamma-ethyl-L-glutamate (Sidman et al., 1983), poly(2-hydroxyethyl methacrylate) (Langer et al., 1981; Langer, 1982), ethylene vinyl acetate (Langer et al., 1982) or poly-D-(−)-3-hydroxybutyric acid (EP 133,988). Sustained-release GH variant compositions also include liposomally entrapped GH variants. Liposomes containing GH variants are prepared by methods known in the art (see, DE 3,218,121; Epstein et al., 1985; Hwang et al., 1980; EP 52,322; EP 36,676; EP 88,046; EP 143,949; EP 142,641; JP 83-118008; U.S. Pat. No. 4,485,045; U.S. Pat. No. 4,544,545; and EP 102,324). Ordinarily, the liposomes are of the small (about 200-800 Angstroms) unilamellar type in which the lipid content is greater than about 30 mol. percent cholesterol, the selected proportion being adjusted for the optimal GH variant therapy.

The GH variant can also be formulated for local administration. Suitable formulations vary depending on the site of administration and do not differ from those known in the art. For example, GH can be formulated in a balanced salt solution for administration to the eye.

The GH variant formulation for therapeutic administration is sterile. Sterility is readily accomplished by filtration through sterile filtration membranes (e.g., 0.2 micron membranes). Therapeutic GH variant compositions generally are placed into a container having a sterile access port, for example, an intravenous solution bag or vial having a stopper pierceable by a hypodermic injection needle. GH variants ordinarily are stored in unit or multi-dose containers, for example, sealed ampoules or vials, as an aqueous solution or as a lyophilized formulation for reconstitution. As an example of a lyophilized formulation, 5-ml vials are filled with 2 ml of sterile-filtered 0.5% (w/v) aqueous GH variant solution, and the resulting mixture is lyophilized.

The infusion solution is prepared by reconstituting the lyophilized GH variant using bacteriostatic water-for-injection and the like.

The formulation of pegylated GH variants is carried out as described above for GH variants generally.

Administration

The methods of the present disclosure rely on the unsuspected synergy of combining a growth hormone (GH) variant having antagonistic activity with an oligonucleotide targeted to growth hormone receptor (GHR) to reduce insulin-like growth factor I (IGF-I) levels in a subject.

In a particular embodiment of the present disclosure, the GH variant the oligonucleotide are administered concomitantly. The GH variant and the oligonucleotide may be administered in the form of a composition comprising an admixture of both components. Alternatively, the GH variant and the oligonucleotide may be administered in separate compositions.

In one embodiment, the antisense oligonucelotide is administered systemically. As used herein "systemic administration" is a route of administration that is either enteral or parenteral.

As used herein "enteral" refers to any form of administration that involves any part of the gastrointestinal tract and includes oral administration of, for example, the antisense oligonucleotide in tablet, capsule or drop form; gastric feeding tube, duodenal feeding tube, or gastrostomy; and rectal administration of, for example, the antisense compound in suppository or enema form.

As used herein "parenteral" includes administration by injection or infusion. Examples include, intravenous (into a vein), intraarterial (into an artery), intramuscular (into a muscle), intracardiac (into the heart), subcutaneous (under the skin), intraosseous infusion (into the bone marrow), intradermal, (into the skin itself), intrathecal (into the spinal canal), intraperitoneal (infusion or injection into the peritoneum), intravesical (infusion into the urinary bladder). transdermal (diffusion through the intact skin), transmucosal (diffusion through a mucous membrane), inhalational.

The antisense oligonucleotide may be administered as single dose or as repeated doses on a periodic basis, for example, daily, once every two days, three, four, five, six seven, eight, nine, ten, eleven, twelve, thirteen or fourteen days, once weekly, twice weekly, three times weekly, or every two weeks, every three weeks, or every four weeks.

The antisense oligonucleotide to be used in the therapy is formulated and dosed in a fashion consistent with good medical practice, taking into account the specific condition being treated, the clinical condition of the individual patient, the site of delivery of the oligonucleotide, the method of administration, the scheduling of administration, and other factors known to practitioners. The "effective amount" of oligonucelotide for purposes herein is thus determined by such considerations. The term "effective amount" in this context refers to any dose of the antisense oligonucleotide sufficient to inhibit GHR expression, under the conditions of administration.

By way of example, a dose of 25-3400, more preferably 50-1600 mg oligonucelotide may be administered to a subject. A dose of 150-400 mg, for example, a dose of 250 mg is particularly contemplated for humans. In one embodiment, a dose of 250 mg per day is administered six times over 3 weeks, on days 1, 3, 5, 7, 14 and 21. In another embodiment, a dose of 250 mg is administered once weekly, or once a fortnight.

The GH variant may be administered by, for example, continuous infusion (using, for example, minipumps such as osmotic pumps), or by injection using, for example, intravenous or subcutaneous means. In one embodiment, the GH variant is administered subcutaneously. The administration can also be as a single bolus or by slow-release depot formulation.

The GH variant composition to be used in the therapy is formulated and dosed in a fashion consistent with good medical practice, taking into account the specific condition being treated, the clinical condition of the individual patient, the site of delivery of the GH variant composition, the method of administration, the scheduling of administration, and other factors known to practitioners. The "effective amount" of GH variant for purposes herein (including an antagonist effective amount to counteract, for example, acromegaly) is thus determined by such considerations. The term "effective amount" in this context refers to any dose of the GH variant sufficient to antagonize GH binding, under the conditions of administration.

As a general proposition, the total pharmaceutically effective amount of the GH variant administered parenterally per dose is in the range of about 1 µg/kg/day to about 100 mg/kg/day of patient body weight, although, as noted above, this is subject to therapeutic discretion. Usually, this dose is between about 0.01 and about 10 mg/kg/day, and more usually for humans between about 0.01 and about 1 µg/kg/day. If given continuously, the GH variant is typically administered at a dose rate of about 1 µg/kg/hour to about 50 µg/kg/hour, either by one to four injections per day or by continuous subcutaneous infusions, for example, using a mini-pump. An intravenous bag solution can also be employed. The key factor in selecting an appropriate dose is the result obtained, as measured for antagonists, for example, by reduction in serum GH, serum insulin-like growth factor I (IGF-I), and tumor growth, etc.

In general, a pegylated GH variant can be administered by any of the routes of administration described above. However, it is presently believed that a pegylated GH variant need not be administered as frequently as a non-pegylated GH variant. Non-pegylated GH and GH variants are typically administered at least three times a week and often daily. The pegylated forms of these proteins can be administered between about once every three days to about once a month, or more typically between about once every 6-7 days to once every two weeks. However, the pegylated GH variant Somavert is typically administered daily at doses ranging from 5 to 80 mg or more typically 10 to 30 mg per day after a loading dose of 40 mg on the first day. Somavert 30 mg/day is the highest approved daily dose regimen for acromegaly. Higher daily doses are desired in some acromegaly patients and in cancer.

The GH variant may be administered as single dose or as repeated doses on a periodic basis, for example, daily, once every two days, three, four, five, six seven, eight, nine, ten, eleven, twelve, thirteen or fourteen days, once weekly, twice weekly, three times weekly, or every two weeks, every three weeks, or every four weeks.

In one embodiment of the present disclosure, the GH variant is Somavert and the oligonucleotide is ATL1103 (SEQ ID NO:19) and the compounds are administered sequentially. In one embodiment, the ATL1103 oligonucleotide is first administered at a dose of 250 mg/day on days 1, 3, 5, 7, 14 and 21, and once weekly thereafter (for 5 to 12 weeks) and the GH variant Somavert is subsequently administered on the same days at 30 mg/day. Alternatively, the ATL1103 oligonucleotide may be administered once or twice weekly (for 8 to 12 weeks) at doses of 250 mg together with once or twice or three weekly Somavert doses of 30 mg.

After 5 to 12 weeks, treatment may be continued (cycle 2) with the same or increased or lower doses of Somavert, and with the same or increased or lower doses of ATL1103, and with the same or increased or lower dosing frequency to achieve the desired target IGF-I levels. Post 5 to 12 weeks, the Somavert dose modification may be in about 5 to 10 mg increments and monitored at about 1 to 4 weeks to assess IGF-I levels. Post 5 to 12 weeks, the ATL1103 dose modification may be in about 25 or 50 mg increments and monitored at about 1 to 8 weeks to assess IGF-I levels. Cycle 2 can be continued if the target IGF-I normalization is achieved or a new cycle started to further optimize dosing to achieve IGF-I normalization on a patient by patient basis.

In another embodiment, a repeat 21 day treatment cycle may be used, for cancer or retinopathy treatment. The ATL1103 oligonucleotide is first administered at a dose of 250 mg/day on days 1, 3, 5, 7, 14 and 21, and the GH variant Somavert is subsequently administered on the same days at 30 mg/day. Alternatively, in a repeat cycle, the ATL1103 oligonucleotide dosing may be once or twice weekly 250 mg together with once or twice weekly Somavert doses of 30 mg on the same days or once weekly 80 mg Somavert on the same day. Alternatively, treatments may be on different days.

After 5 to 12 weeks, treatment may be continued (cycle 2) with the same or increased or lower doses of Somavert, and with the same or increased or lower doses of ATL1103, and administered the same or increased or lower dosing frequency to achieve the desired target IGF-I levels and treatment outcomes in cancer or retinopathy. Post 5 to 12 weeks, the Somavert dose modification may be in about 5 to 10 mg increments and monitored at about 1 to 4 weeks to assess IGF-I levels. Post 5 to 12 weeks, the ATL1103 dose modification may be in about 25 or 50 mg increments and monitored at about 1 to 8 weeks to assess IGF-I levels. Cycle 2 can be continued if the target IGF-I normalization is achieved or a new cycle started to further optimize dosing to achieve IGF-I normalization on a patient by patient basis.

In another embodiment, the ATL1103 drug may be dosed once or twice weekly at doses of 100, 200, 250, 300, 350, or 400 mg/day and Somavert may be dosed daily, every other day, or once or twice weekly at 5, 10, 15, 20, 25, 30, 35, 40, 50, 60, 70 or 80 mg/day.

In another embodiment, the ATL1103 oligonucleotide is first administered at one of the above doses once every other week and the GH variant Somavert is subsequently administered on alternative weeks, so that the patient is on a once weekly alternative dosing regimen, first of ATL1103 and then of Somavert. In a similar embodiment, the patient is on a twice weekly dosing regimen, first of ATL1103 and then of Somavert, a few days apart, or one day apart. Somavert may also be given first and then ATL1103 dosing may follow. Somavert and ATL1103 may also be combined in a mixture and given on the same day. For example, the ATL1103 in a solution in a pre-filled syringe, may be added to the lyophilized Somavert, the Somavert reconstituted into solution, and the ATL1103 and Somavert mixture administered to the subject.

EXAMPLES

Phase I Trial of the GHR Targeting Drug ATL1103

The primary objective of the Phase I trial was to assess the safety, tolerability and pharmacokinetics (pK) of ATL1103.

The Phase I trial was a randomized, placebo controlled, double blind study of single ascending doses and multiple doses of ATL1103 in healthy adult male subjects aged between 18 and 45 years. In the single ascending dose stage of the trial, 24 subjects were administered four dose levels of ATL1103 as a single injection starting at 25 mg and escalating to 75, 250 and 400 mg or placebo. The multiple dose stage was undertaken in 12 subjects, 8 who were to receive six subcutaneous doses of 250 mg of ATL1103 and 4 subjects who received placebo administered on days 1, 3, 5, 7, 14 and 21. Subjects were monitored out to day 35.

Importantly, no serious adverse events were reported in this trial. Two subjects in the multiple dose arm withdrew from the study for reasons not related to safety. All adverse events were reported as "mild to moderate". Injection site reactions represented the majority of all the adverse events reported in the trial. There was one elevation in the liver enzyme ALT reported as an adverse event in the multiple dose stage. Importantly, the ALT levels in this subject returned to normal during the dosing phase, suggesting no residual or cumulative effect of the drug on this safety parameter.

A secondary objective of this study was to obtain data on the pharmacodynamic effects of ATL1103 on the IGF-I levels in the blood of the trial subjects. Reduction of increased levels of serum IGF-I to normal is the therapeutic endpoint in the treatment of the growth disorder acromegaly, and reducing the effects of IGF-I has a potential role in the treatment of diabetic retinopathy, nephropathy and certain forms of cancer.

As defined in the statistical analysis plan, the effect of ATL1103 on serum IGF-I was assessed as a change in IGF-I levels versus baseline (starting point) readings for those subjects who received treatment (ATL1103). Pre-dose baseline levels of IGF-I were recorded prior to the commencement of dosing and then measured at weekly intervals until the end of the monitoring period. This treated group showed a trend in reduction in IGF-I levels from day 14 to day 28, with a significant effect ($p=0.034$ one sided t-test) at day 21 with a 7% reduction in mean IGF-I levels versus baseline.

Other exploratory objectives of the study investigated the drug's mechanism of action and broader pharmacological profile, including the pharmacodynamic effects on levels of growth hormone binding protein (GHBP), insulin-like growth factor binding protein 3 (IGFBP-3), acid labile subunit of the insulin-like growth factor binding protein complex (ALS), and growth hormone (GH), as well as in vitro mitogenic and apoptotic parameters.

Notably, ATL1103 had a significant effect on reducing GHBP by 16% ($p=0.007$) at day 21 and 19% ($p<0.05$) at day 28, one week past the last dose. As circulating GHBP is produced by cleavage from the GHR, the reduction of circulating GHBP levels suggests that GHR expression is being reduced. ATL1103 also significantly reduced IGFBP-3 and ALS, both consistent with its effect on IGF-I and the fact that they are regulated by GH. There was no effect on GH levels. Specific trial details and outcomes are summarized in Tables 3-6.

TABLE 3

Summary of ATL1103 Phase I clinical trial

| | |
|---|---|
| Title | A randomised, placebo-controlled, double-blind, single ascending dose and multiple dose study to assess the safety, tolerability, pharmacokinetics and pharmacodynamics of subcutaneous doses of ATL1103 in healthy adult male subjects |
| Trial description | Phase I trial of subcutaneous administration of ATL1103 in healthy males |
| Objectives | Primary objectives:<br>To assess the safety and tolerability of single subcutaneous doses (Stage A) and multiple subcutaneous doses (Stage B) of ATL1103 in healthy male subjects.<br>To determine the single dose and multiple dose pharmacokinetic (PK) profiles of ATL1103 by the subcutaneous route of dosing<br>Secondary objective:<br>To assess the pharmacodynamic (PD) effects on IGF-I levels following subcutaneous administration of ATL1103<br>Exploratory objective:<br>To assess the PD effects on circulating levels of (i) growth hormone (GH), (ii) insulin-like growth factor binding protein 3 (IGF-BP3), (iii) insulin-like growth factor acid-labile subunit (ALS), (iv) insulin-like growth factor II (IGF-II) and (v) growth hormone binding protein (GHBP) and on (vi) mitogenic and apoptotic activity, following subcutaneous administration of ATL1103 |
| Main selection criteria; number of subjects | Males 18-45 years of age, BMI: 19 to 30 kg/m2, healthy (determined by medical and drug history, physical examination and ECG). IGF-I levels in the normal range<br>Stage A: 24 subjects (four groups of six subjects): randomized for 4 on ATL1103, 2 placebo<br>Stage B: 12 subjects (one group): randomized for 8 active, 4 placebo |
| Test Drug, Dose and Mode of administration | Subcutaneous administration of ATL1103 in the following doses:<br>Stage A (single dose): 0 mg (placebo); 25, 75, 250, 400 mg.<br>Stage B (multiple doses): 0 mg (placebo); 250 mg. Six doses administered over 3 weeks (on days 1, 3, 5, 7, 14, 21). |
| Criteria for assessment | Safety and tolerability: Physical examinations, vital signs, adverse event monitoring and ECGs. Blood sampling for clinical safety (haematology, biochemistry), coagulation (PT, APTT and TT), urinalysis and complement assessments (Bb)<br>Pharmacokinetic: Blood sampling for plasma ATL1103 levels at various time points over 7 days (Stage A) and 35 days (Stage B)<br>Pharmacodynamic:<br>IGF-I: Serum samples collected at least weekly to day 35. Exploratory PD: Blood sampling for GH, and the following for Stage B only: IGF-BP3, ALS, IGF-II, GHBP and in vitro mitogenic and apoptotic parameters on Days 1, 7, 21 and 28 of the study |
| Subject withdrawals | Two subjects withdrew from the study after the fifth dose of ATL1103 due to 1) withdrawal of consent 2) subject lost to follow up. No subject withdrew or was withdrawn for safety reasons. |
| Outcomes | Primary objective outcomes<br>ATL1103 was considered safe and generally well tolerated at the doses used in the study<br>There were no serious adverse events reported<br>There were 24 treatment-emergent adverse events (TEAE) in Stage A (19 in the 16 ATL1103-treated subjects, 5 in the 8 placebo-treated subjects), all reported as mild or moderate. In the ATL1103-treated subjects most common adverse events reported were pain at injection site (6), headache (5), influenza-like illness (2).<br>There were 25 TEAEs in Stage B (18 in the 8 ATL1103-treated subjects; 7 in the 4 placebo-treated subjects). All were reported as mild. In ATL1103-treated subjects the most commonly reported adverse events were injection site reactions (13).<br>Notably, although influenza-like illness (inc muscle aching and fever) was seen in two subjects after single doses of 400 mg ATL1103, this was not seen after repeated doses of 250 mg.<br>Increased ALT levels were reported for one subject in Stage B at Day 11. ALT levels returned to the normal range by pre-dose day 21 and remained within normal range throughout the rest of the study period.<br>A summary of the pharmacokinetic parameters is shown in Table 1.<br>Secondary & Exploratory objectives outcomes<br>The effect of ATL1103 on serum IGF-I levels and on the exploratory PD markers were determined as change from baseline levels.<br>For IGF-I there was a clear trend for mean levels to be lower than baseline on days D14, 21, 28, 35 of the study with a statistically significant effect reached by day 21 (Table 2)<br>No treatment-related effects were apparent in growth hormone levels (data not shown)<br>The inhibitory effect of ATL1103 on other exploratory PD markers is shown in Table 3. Of particular note is the ATL1103-related inhibition of circulating GHBP. GHBP is produced by cleavage from the GHr receptor, so reduction of circulating GHBP levels suggests that GHr expression is reduced. This provides support for ATL1103 working via an antisense mechanism of action.<br>IGF-BP3 and ALS reductions are consistent with the effect of ATL1103 on IGF-I (Table 3). |

TABLE 4

Summary of pharmacokinetic parameters (mean ± SD)

| | n | Cmax (ng/mL) | Tmax (hr) | AUClast (hr * ng/mL) |
|---|---|---|---|---|
| Single Dose | | | | |
| 25 mg | 4 | 466 ± 136 | 3.25 ± 0.5 | 3711 ± 822 |
| 75 mg | 4 | 3139 ± 1576 | 3.25 ± 0.96 | 21342 ± 4755 |
| 250 mg | 4 | 12383 ± 3000 | 2.5 ± 1.29 | 88942 ± 11295 |
| 400 mg | 4 | 14343 ± 2823 | 3.25 ± 0.96 | 151123 ± 29434 |
| Multiple dose (250 mg; Pharmacokinetic population) | | | | |
| Day 1 | 6 | 8318 ± 2623 | 3.84 ± 1.49 | 58400 ± 11220 |
| Day 21 | 6 | 8557 ± 1431 | 3.00 ± 0.63 | 91870 ± 16795 |

TABLE 5

Serum IGF-I levels in ATL1103-treated subjects in Stage B
Pre-dose IGF-I: 36.57 ± 13.16 nmol/L: mean ± SD

| Study day | Change from pre-dose Mean ± SD (% change from pre-dose) | Probability < (−t)[a] |
|---|---|---|
| Day 3  | +2.65 ± 9.47 (12%) | >0.500 |
| Day 5  | +0.32 ± 7.42 (6%)  | >0.500 |
| Day 7  | +0.77 ± 7.51 (6%)  | >0.500 |
| Day 14 | −1.43 ± 7.19 (−2%) | 0.323 |
| Day 21 | −3.40 ± 3.59 (−7%) | 0.034 |
| Day 28 | −3.43 ± 7.53 (−7%) | 0.157 |
| Day 35 | −1.9 ± 5.08 (−1%)  | 0.201 |

[a]1-sided t-test on change from pre-dose at each time point; alternate hypothesis is suppression Per protocol population; (n = 6 at each time point)

TABLE 6

Exploratory PD assessments of ATL1103 subjects in Stage B

Pre-dose value/Mean change from pre-dose (% change from pre-dose)

| | GHBP (pmol/L) | IGF-BP3 (ng/ml) | IGF-II (ng/ml) | ALS (mU/ml) |
|---|---|---|---|---|
| Pre-dose | 1053.8 ± 664    | 2906.2 ± 320.8   | 722.3 ± 113.8     | 1710.2 ± 305.4   |
| Day 7    | −31.2 (0%)      | −310.5** (−10%)  | −101.8*** (−14%)  | −115.3 (−5%)     |
| Day 21   | −169.5** (−16%) | −228.3* (−8%)    | −57.5 (−8%)       | −160.7 (−9%)     |
| Day 28   | −233.3* (−19%)  | −160.5 (−5%)     | −29.2 (−5%)       | −188.7* (−10%)   |

*P < 0.050,
**P < 0.010,
***p < 0.001;
1-sided t-test on change from pre-dose at each time point; alternate hypothesis is suppression Per protocol population; (n = 6 at each time point)

Example 2

Co-Administration of an Antisense Oligonucleotide and Somavert Including in Subjects in Need of Serum IGF-I Reduction ATL1103 is to be subcutaneously administered at 250 mg per day, six times over 3 weeks on days 1, 3, 5, 7, 14 and 21.

Somavert will be dosed subcutaneously at 20 mg per day for 7 days starting on day 1 or day 24.

Although not wishing to be limited to theory, ATL1103 is cleared from the blood after each dose and accumulates in the liver and other organs because of its long tissue half life. ATL1103 will be working to decrease GHR protein on the cell surface of hepatocytes and other liver cells and other organs and decrease the resultant soluble form of GHR in the blood (GHBP) which is cleaved from the cell surface GHR protein.

Control groups: Somavert is to be administered alone for a similar 7 or 24 day period or ATL1103 is to be administered for a similar 21 day period to normal volunteers or subjects in need of reduction of serum IGF-I.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I levels, and optionally, GH levels.

Example 3

Co-Administration of an Antisense Oligonucleotide and Somavert for the Treatment of Acromegaly Groups of 15 acromegalics are to be dosed with ATL1103 as described in Example 1 and with additional once weekly dosing for 6 weeks and either (i) 30 mg once weekly Somavert or (ii) 80 mg once weekly Somavert for 6 weeks, starting on day 24.

Control groups: ATL1103 or Somavert is to be administered alone for a similar 9 week period or 6 week period, respectively, to acromegalic patients. It has previously been shown that serum IGF-I was reduced by 16% and 31% and 12.5% and 26.7% of patients were normalized for serum IGF-I levels when administered Somavert alone at 30 and 80 mg, respectively for 6 weeks at these doses. Somavert once weekly dosing was abandoned for daily dosing for acromegalics to normalize the serum IGF-I of a greater number of acromegalics.

Treatment is to be continued with the same or increased or lower doses of Somavert, and with the same or increased or lower doses of ATL1103, and administered with the same or increased or lower dosing frequency to achieve the desired target serum IGF-I levels.

Example 4

Co-Administration of an Antisense Oligonucleotide and Somavert for the Treatment of Acromegaly Groups of 15 acromegalics are to be dosed with 200 mg ATL1103 once weekly dosing for 13 weeks and either (i) 30 mg once weekly Somavert or (ii) 80 mg once weekly Somavert for 13 weeks on the same days as ATL1103.

Control groups: ATL1103 or Somavert is to be administered alone for a similar 13 week period to acromegalic patients.

Treatment is to be continued with the same or increased or lower doses of Somavert, and with the same or increased or lower doses of ATL1103, and administered with the same or increased or lower dosing frequency to achieve the desired target serum IGF-I levels.

Example 5

Co-Administration of an Antisense Oligonucleotide and Somavert for the Treatment of Acromegaly Groups of 15 acromegalics are to be dosed with 200 mg ATL1103 once or twice weekly dosing for 13 weeks and either (i) 30 mg once weekly Somavert or (ii) 30 mg twice weekly Somavert for 13 weeks on the same days as ATL1103.

Control groups: ATL1103 or Somavert is to be administered alone for a similar 13 week period to acromegalic patients.

Treatment is to be continued with the same or increased or lower doses of Somavert, and with the same or increased or lower doses of ATL1103, and administered with the same or increased or lower dosing frequency to achieve the desired target serum IGF-I levels.

Example 6

Co-Administration of an Antisense Oligonucleotide and Somavert for the Treatment of Diabetic Retinopathy Groups of 15 patients with diabetic retinopathy are to be dosed with 200 mg ATL1103 once or twice weekly dosing for 13 weeks and either (i) 30 mg once weekly Somavert or (ii) 30 mg twice weekly Somavert for 13 weeks on the same days as ATL1103.

Control groups: ATL1103 or Somavert is to be administered alone for a similar 13 week period to diabetic retinopathy patients.

Treatment is to be continued with the same or increased or lower doses of Somavert, and with the same or increased or lower doses of ATL1103, and administered with the same or increased or lower dosing frequency to achieve the desired target IGF-I levels, and optionally GH levels and outcomes in retinal disease.

Example 7

Co-Administration of an Antisense Oligonucleotide and Somavert for the Treatment of Cancer Groups of 15 patients with cancer associated with increased IGF-I are to be dosed with 200 mg ATL1103 once or twice weekly dosing for 13 weeks and either (i) 30 mg once weekly Somavert or (ii) 30 mg twice weekly Somavert for 13 weeks or (iii) 80 mg once weekly or (iv) 80 mg twice weekly Somavert.

Control groups: ATL1103 or Somavert is to be administered alone, with patients standard medication, for a similar 13 week period to cancer patients.

Treatment is to be continued with the same or increased or lower doses of Somavert, and with the same or increased or lower doses of ATL1103, and administered with the same or increased or lower dosing frequency to achieve the desired target IGF-I levels, and optinally GH levels and outcomes in cancer.

Example 8

Co-Administration of an Antisense Oligonucleotide and Somavert for the Treatment of Acromegaly Somavert will be dosed subcutaneously at the doses acromegaly patients are currently using for their treatment, for example, 10, 15, 20, 25, 30, 35, 40, 45, 50 mg/day or more.

ATL1103 is to be subcutaneously administered at, 250 mg per day, six times over 3 weeks on days 1, 3, 5, 7, 14 and 21.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I and, optionally, GH levels.

Example 9

Co-Administration of an Antisense Oligonucleotide and Somavert for the Treatment of Acromegaly Somavert will be dosed subcutaneously at the doses acromegaly patients are currently using for their treatment, for example, 10, 15, 20, 25, 30, 35, 40, 45, 50 mg/day or more.

ATL1103 is to be subcutaneously administered at 100, 150, 200, 250, 300, 350 or 400 mg over 3 weeks once or twice weekly or until a cumulative dose of ~1200-1800 mg.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I and, optionally, GH levels.

Example 10

Co-Administration of an Antisense Oligonucleotide and Somavert for the Treatment of Acromegaly Somavert will be dosed subcutaneously at the doses acromegaly patients are currently using for their treatment, for example, 10, 15, 20, 25, 30, 35, 40, 45, 50 mg/day or more.

ATL1103 is to be subcutaneously administered at 100, 150, 200, 250, 300, 350 or 400 mg over 4 weeks once or twice weekly, or over 6 weeks once or twice weekly, or over 8 weeks once or twice weekly, or over 12 weeks once or twice weekly.

Pharmacodynamic and pharmacological effects will be assessed as described in Example 1 with similar assays and additional assays where useful, for example, for serum IGF-I and GH.

Treatment is to be continued with the same or increased or lower doses of Somavert, and with the same or increased or lower doses of ATL1103, and administered with the same or increased or lower dosing frequency to achieve the desired target serum IGF-I and, optionally, GH levels.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Altschul et al., J. Mol. Biol. (1990) 215:403-410
Barnes and Sato, Cell (1980) 22:649
Buckmann and Merr, Makromol. Chem. (1981) 182:1379-1384
Carter et al., Nucl. Acids. Res. (1986) 13: 4331
Chen et al., J. Biol. Chem. (1997) 272:5133-5140
Crea et al., Proc. Natl. Acad. Sci. USA (1978) 75:5765
Cunningham et al., Science (1991) 254:821-825
de Vos et al., Science (1992) 255:306-312
Elbashir et al., Nature (2001a) 411:494-498
Elbashir et al., Genes Dev. (2001b) 15:188-200
Englisch et al., Angewandte Chemie, International Edition (1991) 30:613
Epstein et al., Proc. Natl. Acad. Sci. U.S.A. (1985) 82:3688-3692
Fire et al., Nature (1998) 391:806-811
Giustina et al., Pituitary (2011) 14:125-133
Goeddel et al., Nature (1979) 281:544
Gray et al., Gene (1985) 39:247
Guo and Kempheus, Cell (1995) 81:611-620
Hwang et al., Proc. Natl. Acad. Sci. U.S.A. (1980) 77:4030-4034
Langer et al., J. Biomed. Mater. Res (1981) 15:167-277
Langer, Chem. Tech. (1982) 12:98-105
Martin et al., Helv. Chim. Acta (1995) 78:486-504
Mandel et al., J. Mol. Biol. (1970) 53:154
Montgomery et al., Proc. Natl. Acad. Sci. USA. (1998) 95:15502-15507
Nielsen et al., Science (1991) 254, 1497-1500
Putski et al., Eur. Neurol. (2010) 63:311-317
Sidman et al., Biopolymers (1983) 22:547-556
Spencer et al., J. Biol. Chem. (1988) 263:7862-7867
Tabara et al., Science (1998) 282:430-431
Tijsterman et al., Science (2002) 295:694-697
Timmons et al., Gene (2001) 263:102-112
Timmons and Fire, Nature (1998) 395:854
Tuschl et al., Genes Dev. (1999) 13:3191-3197
Ultsch et al., J. Mol. Biol. (1991) 222:865-8
Ultsch M et al., J. Mol. Biol. (1993) 231:1133-36
Ultsch et al., J. Mol. Biol. (1994) 236:286-99
van der Lely et al., The Lancet (2001) 358:1754-1759
Vos et al. (1992)
Vieira and Messing, Meth. Enzymol. (1987) 153:3-11
Wells et al., Gene (1985) 34:315
Wells et al., Philos. Trans. R. Soc. London SerA (1986) 317:415
Zhang and Madden, Genome Res. (1997) 7:649-656
Zoller et al., Nucl. Acids Res., (1987) 10: 6487

---

The invention claimed is:

1. A method of reducing the level of insulin-like growth factor I (IGF-I) in a subject, the method comprising administering a growth hormone (GH) variant having GH antagonistic activity and comprising the following amino acid substitutions: H18D, H21N, G120K, R167N, K168A, D171S, K172R, E174S, I179T compared with the native GH amino acid sequence shown in SEQ ID NO:2, in combination with an oligonucleotide 15 to 30 nucleobases in length comprising at least one modified internucleoside linkage, sugar moiety, or nucleobase, targeted to a nucleic acid encoding human growth hormone receptor (GHR) so as to inhibit expression of the GHR, thereby reducing the level of IGF-I in the subject.

2. The method of claim 1, wherein the nucleic acid is as shown in SEQ ID NO:4 or SEQ ID NO:5.

3. The method of claim 1, wherein the oligonucleotide is a DNA oligonucleotide.

4. The method of claim 1, wherein the oligonucleotide is a RNA oligonucleotide.

5. The method of claim 4, wherein the oligonucleotide is a short interfering RNA (siRNA).

6. The method of claim 1, wherein the oligonucleotide is a chimeric oligonucleotide.

7. The method of claim 1, wherein the oligonucleotide has at least 70% complementarity with the nucleic acid encoding human GHR.

8. The method of claim 1, wherein the oligonucleotide has at least 80% complementarity with the nucleic acid encoding human GHR.

9. The method of claim 1, wherein the oligonucleotide has at least 90% complementarity with the nucleic acid encoding human GHR.

10. The method of claim 1, wherein the oligonucleotide has at least 95% complementarity with the nucleic acid encoding human GHR.

11. The method claim 1, wherein the oligonucleotide comprises at least an 8 consecutive nucleobase portion of SEQ ID NO: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 78, 79, 80, or 81.

12. The method of claim 1, wherein the oligonucleotide consists of the nucleobase sequence of SEQ ID NOs: 6, 7, 8, 9, 10, 11, 12, 13, 14, 15, 16, 17, 18, 19, 21, 22, 23, 24, 25, 26, 27, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 60, 61, 62, 63, 64, 65, 66, 68, 69, 70, 71, 72, 73, 74, 75, 76, 7 8, 79, 80, or 81.

13. The method of claim 12, wherein the oligonucleotide consists of the nucleobase sequence of SEQ ID NO:6.

14. The method of claim 1, wherein the oligonucleotide specifically hybridizes with a region encoding human GHR, wherein the region comprises a translation initiation codon, a termination codon, a coding region, a 5' untranslated region, a 3' untranslated region, an intron:exon junction or an exon:intron junction.

15. The method of claim 14, wherein the region comprises at least an 8 consecutive nucleobase portion of a sequence selected from SEQ ID NOs: 84-154.

16. The method of claim 1, wherein the oligonucleotide comprises at least an 8 consecutive nucleobase portion complementary to a region of SEQ ID NO:4 selected from the group consisting of nucleotides 260-339, 332-351 and 344-423 of SEQ ID NO:4.

17. The method of claim 1, wherein the oligonucleotide inhibits the expression of GHR and/or growth hormone binding protein (GHBP) by at least 15%.

18. The method of claim 1, wherein the oligonucleotide comprises at least one 2'-0-methoxyethyl sugar moiety.

19. The method of claim 1, wherein the oligonucleotide comprises at least one phosphorothioate internucleoside linkage.

20. The method of claim 1, wherein the oligonucleotide comprises at least one 5-methylcytosine.

21. The method of claim 1, wherein the oligonucleotide consists of 20 linked nucleosides, wherein the oligonucleotide consists of a nucleobase of SEQ ID NO:6; and wherein the oligonucleotide consists of a ten deoxynucleotide region flanked on both the 5' end and the 3' end of said ten deoxynucleotide region with five 2'-O-(2-methoxyethyl) nucleotides, and wherein each internucleoside linkage in the oligonucleotide is a phosphorothioate linkage, and wherein each cytosine in said oligonucleotide is a 5-methylcytosine.

* * * * *